United States Patent
Kuo et al.

(10) Patent No.: US 7,678,786 B2
(45) Date of Patent: Mar. 16, 2010

(54) BENZOAZEPIN-OXY-ACETIC ACID DERIVATIVES AS PPAR-DELTA AGONISTS USED FOR THE INCREASE OF HDL-C, LOWER LDL-C AND LOWER CHOLESTEROL

(75) Inventors: Gee-Hong Kuo, Scotch Plains, NJ (US); Yan Zhang, Fort Washington, PA (US); Lan Shen, Thousand Oaks, CA (US); Songfeng Lu, Raritan, NJ (US); Keith T. Demarest, Flemington, NJ (US); Patricia Pelton, Long Valley, NJ (US)

(73) Assignee: Janssen Pharmaceutica NV (BE)

( * ) Notice: Subject to any disclaimer, the term of this patent is extended or adjusted under 35 U.S.C. 154(b) by 15 days.

(21) Appl. No.: 11/736,221

(22) Filed: Apr. 17, 2007

(65) Prior Publication Data

US 2007/0244094 A1 Oct. 18, 2007

Related U.S. Application Data

(60) Provisional application No. 60/793,001, filed on Apr. 18, 2006.

(51) Int. Cl.
*A61P 1/18* (2006.01)
*A61P 3/06* (2006.01)
*A61P 3/10* (2006.01)
*A61K 31/55* (2006.01)
*C07D 223/16* (2006.01)

(52) U.S. Cl. .......................... 514/217.01; 514/217.02; 540/594; 540/595

(58) Field of Classification Search ............ 514/217.01, 514/217.02; 540/594, 595
See application file for complete search history.

(56) References Cited

U.S. PATENT DOCUMENTS

| | | | |
|---|---|---|---|
| 4,737,495 | A | 4/1988 | Bomhard et al. |
| 4,820,867 | A | 4/1989 | Belanger et al. |
| 2004/0143006 | A1 | 7/2004 | Jeppesen et al. |
| 2005/0124698 | A1 | 6/2005 | Kuo et al. |
| 2006/0058382 | A1 | 3/2006 | Kuo et al. |
| 2006/0058393 | A1 | 3/2006 | DeAngelis et al. |
| 2006/0257987 | A1 | 11/2006 | Gonzalez Valcarcel et al. |
| 2007/0060649 | A1 | 3/2007 | Abdel-Magid et al. |

FOREIGN PATENT DOCUMENTS

| | | | |
|---|---|---|---|
| EP | 0204349 | A3 | 12/1986 |
| WO | WO 03/011807 | | 2/2003 |
| WO | WO 03/074495 | | 9/2003 |
| WO | WO 2005/030694 | | 4/2005 |

OTHER PUBLICATIONS

Leibowitz, M. D., et al., "Activation of PPARδ alters lipid metabolism in db/db mice." FEBS Letters, 2000, pp. 333-336, vol. 473, No. 3.
Oliver, W. R., "A selective peroxisome proliferator-activated receptor δ agonist promotes reverse cholesterol transport." PNAS, 2001, pp. 5306-5311. vol. 98, No. 9.
Auboeuf et al., 1997, Diabetes 46(8):1319-1327.
Braissant et al., 1996, Endocrinology 137(1): 354-366.
Barak et al, 2002, Proc. Natl. Acad. Sci. USA 99(1):303-308.
Lawn et al., 1999, J. Clin. Investigation 104(8): R25-R31.
Tanaka et al, 2003, Proc. Natl. Acad. Sci. USA 100(26):15924-15929.
Wang et al., 2003, Cell 113:159-170.
Gould P.L., "Salt Selection for Basic Drugs.", International J. Pharm., 1986 vol. 33, pp. 201-217.
Berge et al., "Pharmaceutical Salts.", J. Pharm. Sci., 1977, vol. 66(1), pp. 1-19.
Ohsumi, K. et al. "Pyrazole-O-Glucosides as Novel Na+ -Glucose Cotransporter (SGLT) Inhibitors" Bioorganic & Medicinal Chemistry Letters,2003 vol. 13, pp. 2269-2272.
Pomerantz et al., "Formaldehyde Semicarbazone.", J. Org. Chem.,1982, vol. 47 (11), pp. 2217-2218.
Spinelli et al., "Application of the Hammett relationship to a series of tetrasubstituted thiophens. Kinetics of piperidino-debromination of some 2-bromo-3-nitro-5-X-thiophens and 2-bromo-4-methyl-3-nitro-5-Xthiophens in methanol.", J. Chem. Soc., Perkin Trans. 2, 1972 pp. 1866-1869. DOI: 10.1039/P29720001866.
Still et al., "Rapid Chromatographic Technique for Preparative Separations with Moderate Resolution.", J. Org. Chem., 1978 vol. 43(14), pp. 2923-2925.
Sznaidman et al., "Novel Selective Small Molecule Agonists for Peroxisome Proliferator-Activated Receptor ẟ (PPARẟ)-Synthesis and Biological Activity.", Bioorganic & Medicinal Chemistry Letters, 2003, 13(9), 1517-1521.

*Primary Examiner*—Brenda L Coleman

(57) ABSTRACT

The invention is directed to compounds of Formula (I) useful as PPAR agonists. Pharmaceutical compositions and methods of treating one or more conditions including, but not limited to, diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof, using compounds of the invention are also described.

24 Claims, No Drawings

BENZOAZEPIN-OXY-ACETIC ACID DERIVATIVES AS PPAR-DELTA AGONISTS USED FOR THE INCREASE OF HDL-C, LOWER LDL-C AND LOWER CHOLESTEROL

CROSS-REFERENCE TO RELATED APPLICATIONS

This application claims the benefit of U.S. Provisional Application 60/793,001, filed on Apr. 18, 2006, which is incorporated by reference herein in its entirety.

STATEMENT REGARDING FEDERALLY SPONSORED RESEARCH OR DEVELOPMENT

The research and development of the invention described below was not federally sponsored.

BACKGROUND OF THE INVENTION

The peroxisome proliferator-activated receptors (PPARs) are considered to be metabolic sensors regulating the expression of genes involved in glucose and lipid homeostasis. They are members of nuclear receptor superfamily of RXR heterodimers and are ligand-activated transcription factors. Agonists of the PPARα (e.g. Gemfibrozil) and PPARγ (e.g., Avandia®) subtypes are used for the treatment of dyslipidemias and diabetes, respectively. Each receptor has a distinct tissue distribution with PPARα showing highest expression in liver, PPARγ in adipose tissue and PPARδ having the widest distribution being ubiquitously expressed in adult rat (Braissant et al., 1996) and in humans, expression was found in many different tissues involved in lipid metabolism including liver, kidney, abdominal adipose and skeletal muscle (Auboeuf et al., 1997).

Recently, potent ligands for PPARδ have been published allowing a better understanding of its function in lipid metabolism (Barak et al, 2002; Oliver et al., 2001; Tanaka et al, 2003; Wang et al., 2003). The main effect of these compounds in db/db mice (Leibowitz et al., 2000) and obese rhesus monkeys (Oliver et al., 2001) was an increase of high density lipoprotein cholesterol (HDL-C) and a decrease in triglycerides with little effect on glucose (although insulin levels were decreased in monkeys). HDL-C serves to remove cholesterol from peripheral cells through a process called reverse cholesterol transport. The first and rate-limiting step, which is a transfer of cellular cholesterol and phospholipids to the apolipoprotein A-I component of HDL, is mediated by the ATP binding cassette transporter A1 (ABCA1) (Lawn et al., 1999). PPARδ activation appears to increase HDL-C through transcriptional regulation of ABCA1 (Oliver et al., 2001). Therefore, by inducing ABCA1 mRNA in macrophages, PPARδ agonists could increase HDL-C levels in patients and remove excess cholesterol from lipid-laden macrophages, one of the major players in atherosclerotic lesion development. This would be an alternative therapy to the statin drugs, which show little effect on HDL-C and mainly decrease LDL-C or the fibrates, the only marketed PPARα agonists, having low potency and inducing only modest HDL-C elevations. In addition, like the fibrates, PPARδ agonists have the potential to also reduce triglycerides, an additional risk factor for cardiovascular disease.

Examples of known PPAR delta agonists variously useful for hyperlipidemia, diabetes, or atherosclerosis include L-165041 (Leibowitz et al., 2000) and GW501516 (Oliver et al., 2001). There is a continuing need for new PPAR delta agonists. There is a further need for new PPAR delta agonists that increase HDL-C, lower LDL-C, and/or lower cholesterol. There is a further need for new PPAR delta agonists for the treatment of diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

SUMMARY OF THE INVENTION

The present invention is directed to a compound of Formula (I):

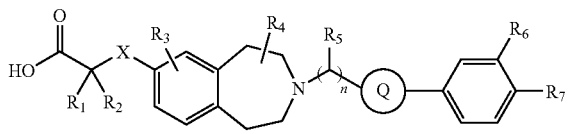

Formula (I)

wherein:

X is a covalent bond, O, or S;

$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;

$R_3$ is H;

$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$ alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, cyano substituted $C_{1-4}$alkyl, and hydroxy substituted $C_{1-4}$alkyl;

$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;

n is 1; and

Q is selected from the group consisting of

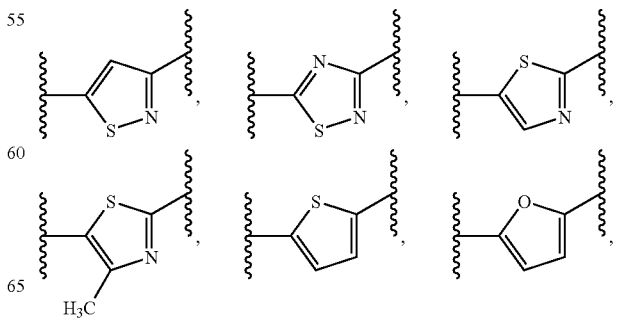

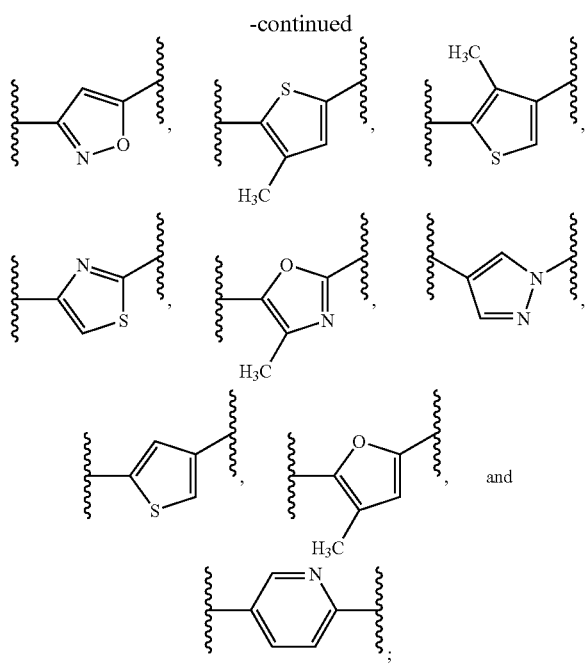

and enantiomers, diastereomers, tautomers, solvates, or pharmaceutically acceptable salts thereof.

The present invention is further directed to pharmaceutical compositions containing one or more compounds of Formula (I), and to use of such compounds and compositions to treat a condition directly or indirectly mediated by PPAR delta.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$) alkyl, with ($C_1$-$C_3$) being particularly preferred. Cyclic alkyl can be, for example, $C_{3-10}$alkyl; preferably, cycloalkyl is $C_{3-7}$cycloalkyl.

"Alkanyl" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and "heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—)$_7$ biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or ($C_1$-$C_6$) alkyl.

"Aryl" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_{5-20}$) aryl, with ($C_{5-10}$) being particularly preferred. Particularly preferred aryl groups are phenyl and naphthyl groups.

"Arylalkyl" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthyl methyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is $(C_{6-26})$ arylalkyl, e.g., the alkanyl, alkenyl or alkynyl moiety of the arylalkyl group is $(C_{1-6})$ and the aryl moiety is $(C_{5-20})$. In particularly preferred embodiments the arylalkyl group is $(C_{6-13})$, e.g., the alkanyl, alkenyl or alkynyl moiety of the arylalkyl group is $(C_{1-3})$ and the aryl moiety is $(C_{5-10})$. Even more preferred arylalkyl groups are phenylalkanyls.

"Alkanyloxy" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy ($CH_3CH_2CH_2O$—), propan-2-yloxy (($CH_3)_2CHO$—), cyclopropan-1-yloxy, etc.; butanyloxy groups such as butan-1 yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are $(C_{1-8})$ alkanyloxy groups, with $(C_{1-3})$ being particularly preferred.

"Heteroaryl" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl" refers to a saturated or unsaturated monocyclic or bicyclic alkyl radical in which one carbon atom is replaced with N, O or S. In certain specified embodiments the cycloheteroalkyl may contain up to four heteroatoms independently selected from the group consisting of N, O and S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl" refers to a saturated monocyclic or bicyclic alkanyl radical in which one carbon atom is replaced with N, O or S. In certain specified embodiments the cycloheteroalkanyl may contain up to four heteroatoms independently selected from the group consisting of N, O and S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl" refers to a saturated monocyclic or bicyclic alkenyl radical in which one carbon atom is replaced with N, O or S. In certain specified embodiments the cycloheteroalkenyl may contain up to four heteroatoms independently selected from the group consisting of N, O and S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

The term "substituted" refers to a radical in which one or more hydrogen atoms are each independently replaced with the same or different substituent(s). Typical substituents include, but are not limited to, —X, —R, —O⁻, =O, —OR, —O—OR, —SR, —S⁻, =S, —NRR, =NR, —CX₃, —CN, —OCN, —SCN, —NCO, —NCS, —NO, —NO₂, =N₂, —N₃, —NHOH, —S(O)₂O⁻, —S(O)₂OH, —S(O)₂R, —P(O)(O—)₂, —P(O)(OH)₂, —C(O)R, —C(O)X, —C(S) R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, ($C_{1-8}$alkylamino)carbonyl, (arylamino)carbonyl and aryl($C_{1-8}$alkyl)carbonyl With reference to substituents, the term "independenly" means that when more than one of such substituent is possible, such substituents may be the same or different from each other.

In any structure that contains the symbol ξ that symbol designates the location(s) of the open valence(s) where the partial structure attaches to the rest of the molecule.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$-alkyl" substituent refers to a group of the formula:

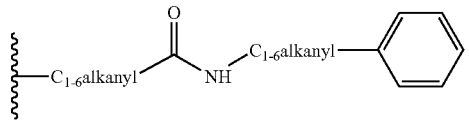

The present invention is directed to compositions comprising a compound of Formula (I) for uses as PPAR delta agonists:

wherein:

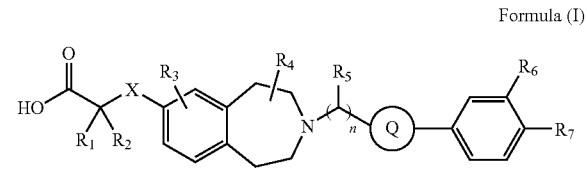

Formula (I)

wherein:
  X is a covalent bond, O, or S;
  $R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;
  $R_3$ is H;
  $R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$ alkyl, $C_{6-10}$aryl, heteroaryl, halo substituted $C_{1-4}$alkyl, amino substituted $C_{1-4}$alkyl, C$_{6-10}$aryl substituted CO$_{1-4}$alkyl, cyano substituted C$_{1-4}$alkyl, and hydroxy substituted C$_{1-4}$alkyl;

R$_6$ and R$_7$ are independently selected from the group consisting of H, halo, C$_{1-3}$alkyl, halo substituted C$_{1-3}$alkyl, C$_{1-3}$alkoxy, and halo substituted C$_{1-3}$alkoxy;

n is 1; and

Q is selected from the group consisting of

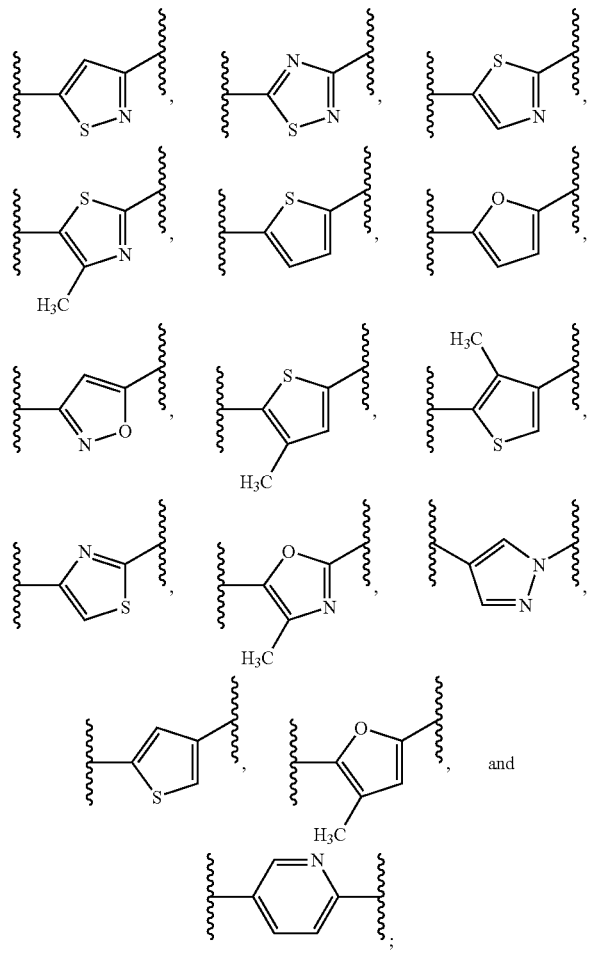

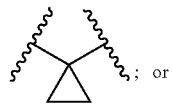

and enantiomers, diastereomers, tautomers, solvates, or pharmaceutically acceptable salts thereof.

In particular, the present invention is directed to a compound of Formula (I) wherein:

X is O; or

R$_1$ and R$_2$ are independently selected from the group consisting of H and C$_{1-8}$alkyl, or R$_1$, R$_2$ and the carbon atom to which they are attached together may form C$_{3-5}$cycloalkyl, and more particularly R$_1$ and R$_2$ are independently selected from the group consisting of H and CH$_3$, or R$_1$, R$_2$ and the carbon atom to which they are attached together may form R$_4$ and R$_5$ are independently selected from the group consisting of H and C$_{1-8}$alkyl, and more particularly R$_5$ is H, CH$_3$, or —CH$_2$CH$_3$; or R$_6$ and R$_7$ are independently selected from the group consisting of H, halo, halo substituted C$_{1-3}$alkyl, C$_{1-3}$alkoxy, and halo substituted C$_{1-3}$alkoxy, and more particularly R$_6$ is H and R$_7$ is selected from the group consisting of halo, halo substituted C$_{1-3}$alkyl, and halo substituted C$_{1-3}$alkoxy, and more particularly R$_7$ is selected from the group consisting of F, CF$_3$, and —O—CF$_3$; or Q is selected from the group consisting of

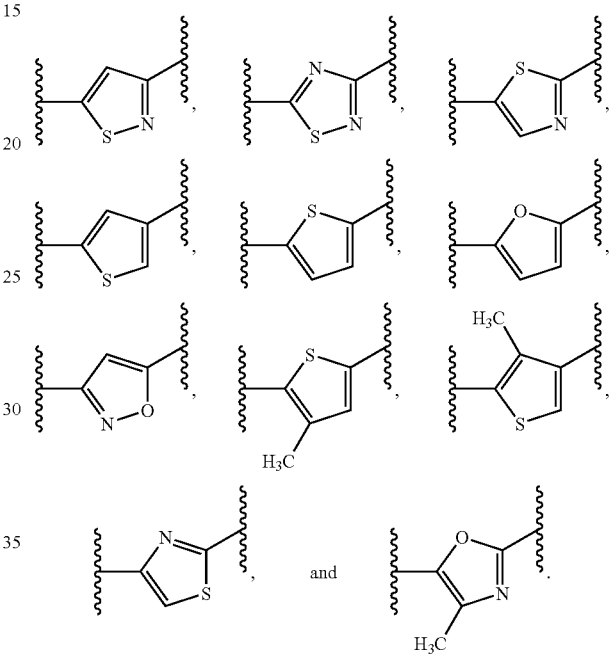

and more particularly Q is selected from the group consisting of

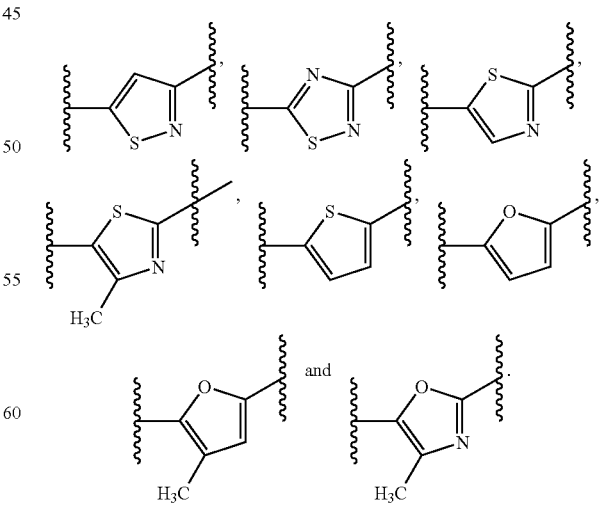

More particularly, the present invention is directed to a compound of Formula (I) as shown above wherein:

X is O;

R$_1$, R$_2$, R$_4$, and R$_5$ are independently selected from the group consisting of H and C$_{1-3}$alkyl, or R$_1$, R$_2$ and the carbon atom to which they are attached together may form C$_{3-5}$cycloalkyl; and R$_6$ and R$_7$ are independently selected from the group consisting of H, halo, C$_{1-3}$alkoxy, halo substituted C$_{1-3}$alkyl, and halo substituted C$_{1-3}$alkoxy;

and enantiomers, diastereomers, tautomers, solvates, or pharmaceutically acceptable salts thereof.

In another aspect, the present invention is directed to pharmaceutical compositions containing one or more compounds, salts or solvates of Formula (I) as described herein admixed with a pharmaceutically acceptable carrier, excipient or diluent, wherein the compositions can be used to treat a condition directly or indirectly mediated by PPAR delta.

The present invention is also directed to a method of treating or preventing a disease or condition in a subject, particularly a mammal and more particularly a human, which disease or condition is affected by the modulation of PPAR delta.

Therefore, in yet another aspect, the present invention is directed to a method of treating or preventing a disease or condition in a mammal which disease or condition is affected by the modulation of PPAR delta receptors, which method comprises administering to a mammal in need of such treatment or prevention a therapeutically effective amount of a compound, salt or solvate of Formula (I) as described herein. More particularly, the therapeutically effective amount comprises a dose range of from about 0.1 mg to about 15,000 mg. More particularly, the therapeutically effective amount comprises a dose range of from about 50 mg to about 1000 mg. More particularly, the therapeutically effective amount comprises a dose range of from about 100 mg to about 1000 mg.

In a further aspect, the present invention is directed to a method for treating or preventing a disease or condition selected from the group consisting of diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, and obesity, said method comprising the step of administering to a mammal in need of such treatment a therapeutically effective amount of a compound, salt or solvate of Formula (I). More particularly, the therapeutically effective amount comprises a dose range of from about 0.1 mg to about 15,000 mg. More particularly, the therapeutically effective amount comprises a dose range of from about 50 mg to about 1000 mg. More particularly, the therapeutically effective amount comprises a dose range of from about 100 mg to about 1000 mg.

In still a further aspect, the present invention is directed to a kit comprising in one or more containers an amount of the composition of Formula (I) effective to treat or prevent a disease or condition selected from the group consisting of diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, and obesity. More particularly, the therapeutically effective amount comprises a dose range of from about 0.1 mg to about 15,000 mg. More particularly, the therapeutically effective amount comprises a dose range of from about 50 mg to about 1000 mg. More particularly, the therapeutically effective amount comprises a dose range of from about 100 mg to about 1000 mg.

In another embodiment, the present invention is directed to a compound of Formula (Ia)

Formula (Ia)

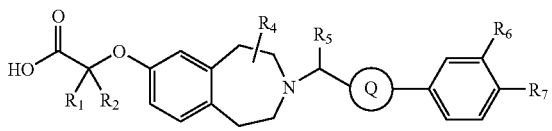

wherein

R$_1$ and R$_2$ are independently selected from the group consisting of H and C$_{1-8}$alkyl, or R$_1$, R$_2$ and the carbon atom to which they are attached together may form C$_{3-5}$cycloalkyl;

R$_4$ and R$_5$ are independently selected from the group consisting of H and C$_{1-8}$alkyl;

R$_6$ and R$_7$ are independently selected from the group consisting of H, C$_{1-3}$alkyl, halo, and halo substituted C$_{1-3}$alkyl; and Q is selected from the group consisting of

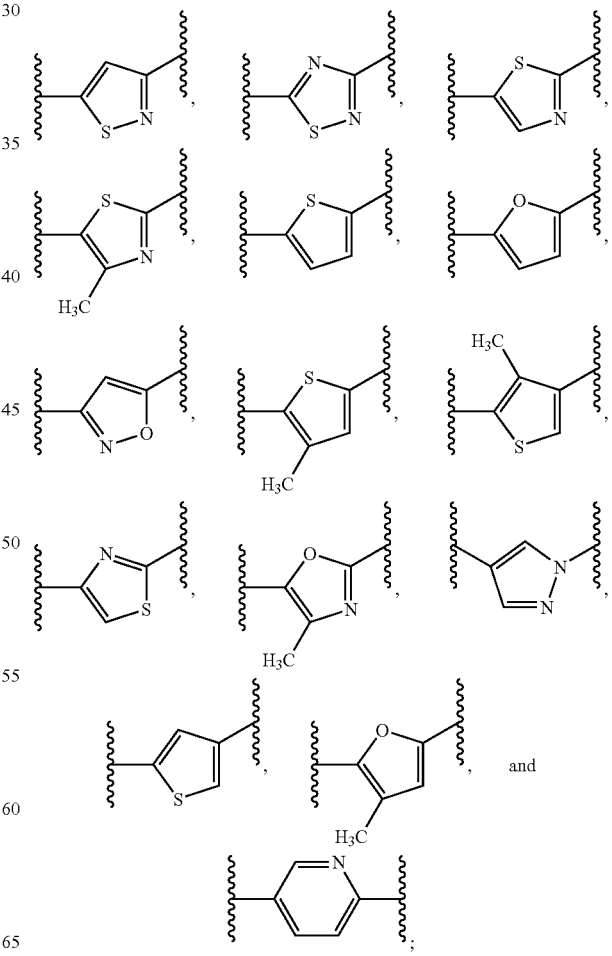

and enantiomers, diastereomers, tautomers, solvates, or pharmaceutically acceptable salts thereof.

In yet another embodiment, the present invention is directed to a compound of Formula (Ib)

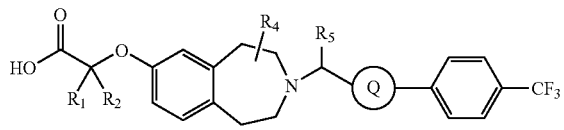

Formula (Ib)

wherein $R_1$ and $R_2$ are independently selected from the group consisting of H and $CH_3$, or $R_1$, $R_2$ and the carbon atom to which they are attached together may form

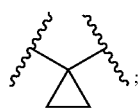

$R_4$ and $R_5$ are independently selected from the group consisting of H, $CH_3$, and $-CH_2CH_3$; and Q is selected from the group consisting of

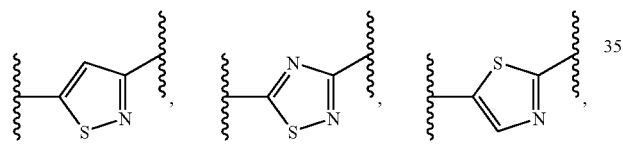

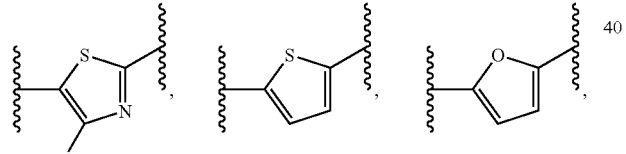

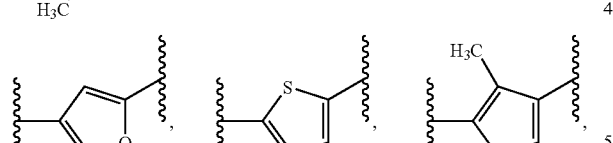

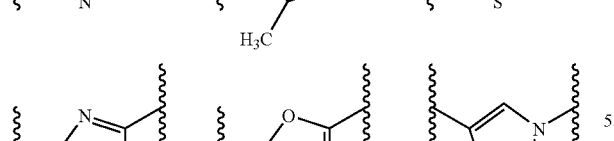

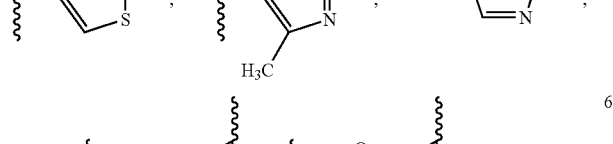

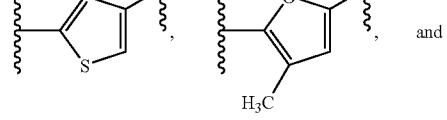
and

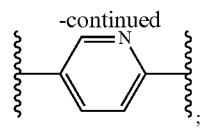

and enantiomers, diastereomers, tautomers, solvates, or pharmaceutically acceptable salts thereof.

In yet another embodiment, the present invention is directed to a compound of Formula (Ic)

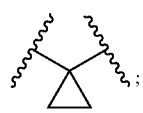

Formula (Ic)

$R_1$, $R_2$, and $R_4$, are independently selected from the group consisting of H and $CH_3$, or $R_1$, $R_2$ and the carbon atom to which they are attached together may form $R_5$ is selected from the group consisting of H, $CH_3$, and $-CH_2CH_3$;

$R_7$ is halo or halo substituted $C_{1-3}$alkyl; and

Q is selected from the group consisting of and enantiomers, diastereomers, tautomers, solvates, or pharmaceutically acceptable salts thereof.

In particular, the present invention is directed to compounds of Formula (Ic) hereinabove wherein:
(a) $R_1$ or $R_2$ is H;
(b) $R_1$ and $R_2$ are both H;
(c) $R_1$ or $R_2$ is $CH_3$;
(d) $R_1$ and $R_2$ are both $CH_3$;

(e) $R_1$, $R_2$ and the carbon atom to which they are attached together form

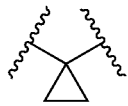

(f) $R_4$ is H or $CH_3$;
(g) $R_5$ is H, $CH_3$, or —$CH_2CH_3$;
(h) $R_1$ or $R_2$ is H and $R_4$ is H or $CH_3$;
(i) $R_1$ and $R_2$ are both H and $R_4$ is H or $CH_3$;
(j) $R_1$ or $R_2$ is H and $R_5$ is H, $CH_3$, or —$CH_2CH_3$;
(k) $R_1$ and $R_2$ are both H and $R_5$ is H, $CH_3$, or —$CH_2CH_3$;
(l) $R_1$ or $R_2$ is $CH_3$ and $R_5$ is H, $CH_3$, or —$CH_2CH_3$;
(m) $R_1$ and $R_2$ are both $CH_3$ and $R_5$ is H, $CH_3$, or —$CH_2CH_3$;
(n) $R_1$ or $R_2$ is H, $R_4$ is H, and $R_5$ is H, $CH_3$ or —$CH_2CH_3$;
(o) $R_1$ and $R_2$ are both H, $R_4$ is H, and $R_5$ is H, $CH_3$, or —$CH_2CH_3$;
(p) $R_1$ or $R_2$ is $CH_3$, $R_4$ is H, and $R_5$ is H, $CH_3$, or —$CH_2CH_3$;
(q) $R_1$ and $R_2$ are both $CH_3$, $R_4$ is H, and $R_5$ is H, $CH_3$, or —$CH_2CH_3$;
(r) $R_1$, $R_2$ and the carbon atom to which they are attached together form

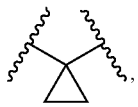

$R_4$ is H, and $R_5$ is H, $CH_3$, or —$CH_2CH_3$;
(s) $R_7$ is $CF_3$;
(t) $R_7$ is Cl;
(u) $R_1$ or $R_2$ is H, $R_7$ is $CF_3$, and $R_4$ is H or $CH_3$;
(v) $R_1$ and $R_2$ are both H, $R_7$ is $CF_3$, and $R_4$ is H or $CH_3$;
(w) $R_1$ or $R_2$ is H, $R_7$ is $CF_3$, and $R_5$ is H, $CH_3$, or —$CH_2CH_3$;
(x) $R_1$ and $R_2$ are both H, $R_7$ is $CF_3$, and $R_5$ is H, $CH_3$, or —$CH_2CH_3$;
(y) $R_1$ or $R_2$ is $CH_3$, $R_7$ is $CF_3$, and $R_5$ is H, $CH_3$, or —$CH_2CH_3$;
(z) $R_1$ and $R_2$ are both $CH_3$, $R_7$ is $CF_3$, and $R_5$ is H, $CH_3$, or —$CH_2CH_3$;
(aa) $R_1$ or $R_2$ is H, $R_4$ is H, $R_7$ is $CF_3$, and $R_5$ is H, $CH_3$, or —$CH_2CH_3$;
(bb) $R_1$ and $R_2$ are both H, $R_4$ is H, $R_7$ is $CF_3$, and $R_5$ is H, $CH_3$, or —$CH_2CH_3$;
(cc) $R_1$ or $R_2$ is $CH_3$, $R_4$ is H, $R_7$ is $CF_3$, and $R_5$ is H, $CH_3$, or —$CH_2CH_3$;
(dd) $R_1$ and $R_2$ are both $CH_3$, $R_4$ is H, $R_7$ is $CF_3$, and $R_5$ is H, $CH_3$, or —$CH_2CH_3$;
(ee) $R_1$, $R_2$ and the carbon atom to which they are attached together form

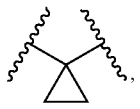

$R_4$ is H, $R_7$ is $CF_3$, and $R_5$ is H, $CH_3$, or —$CH_2CH_3$;
(ff) Q is selected from the group consisting of

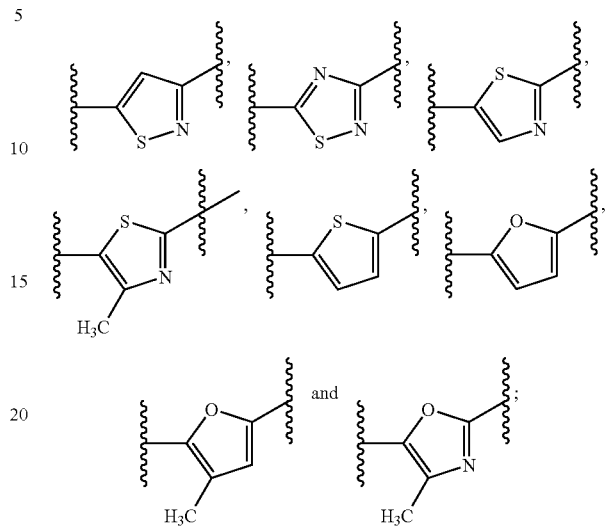

(gg) $R_1$ or $R_2$ is H and Q is selected from the group consisting of

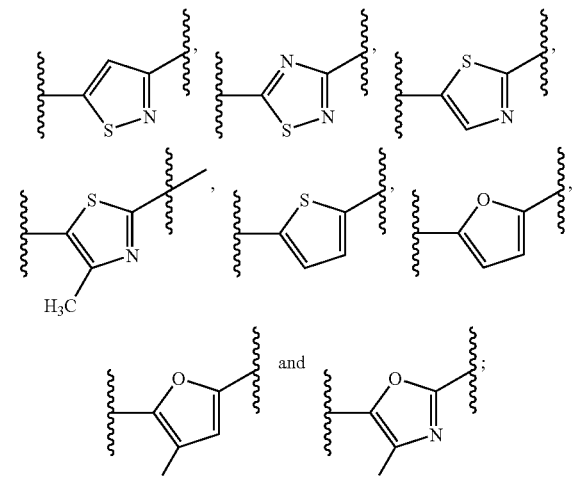

(hh) $R_1$ and $R_2$ are both H and Q is selected from the group consisting of

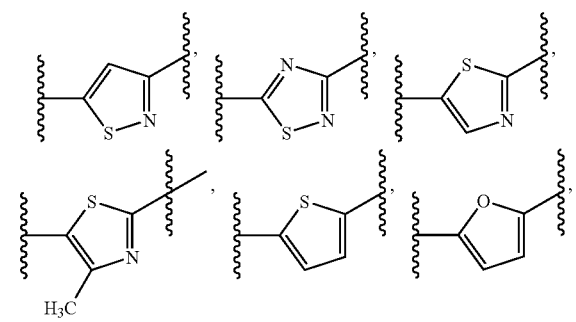

-continued

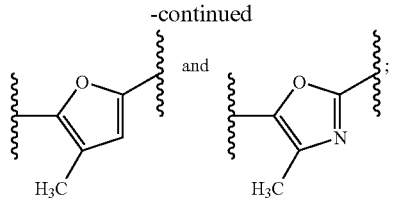
and (ii) $R_1$ or $R_2$ is $CH_3$ and Q is selected from the group consisting of

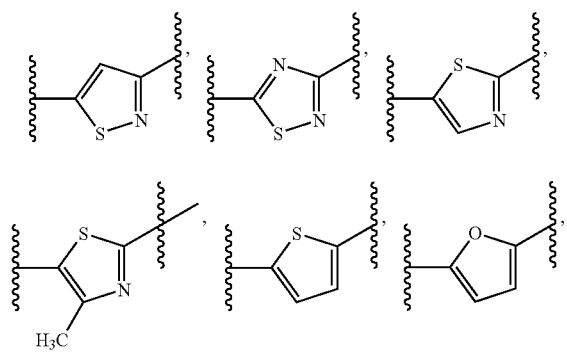

(jj) $R_1$ and $R_2$ are both $CH_3$ and Q is selected from the group consisting of

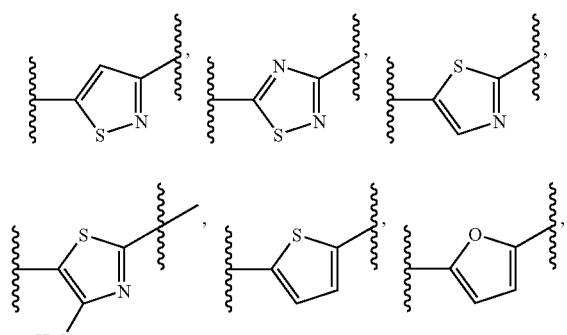

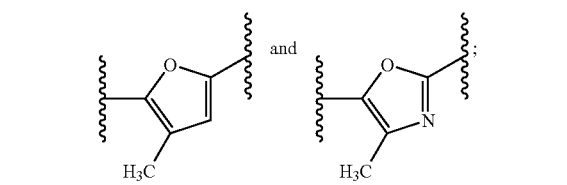
and (kk) $R_4$ is H or $CH_3$ and Q is selected from the group consisting of

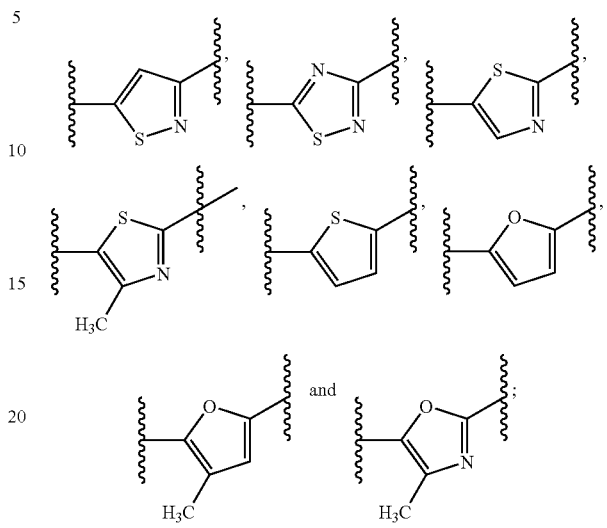

and (ll) $R_5$ is H, $CH_3$, or —$CH_2CH_3$ and Q is selected from the group consisting of

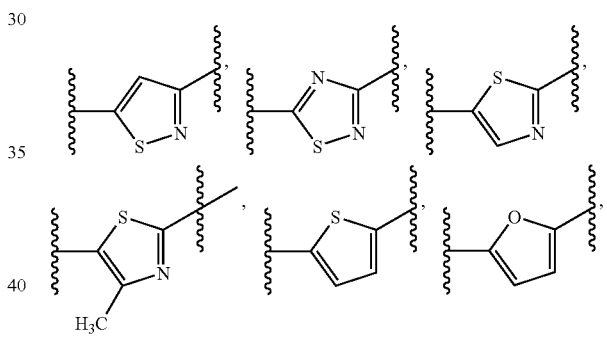

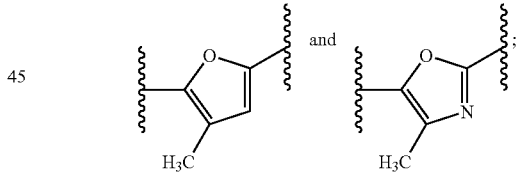
and (mm) $R_1$ or $R_2$ is H and $R_4$ is H or $CH_3$ and Q is selected from the group consisting of

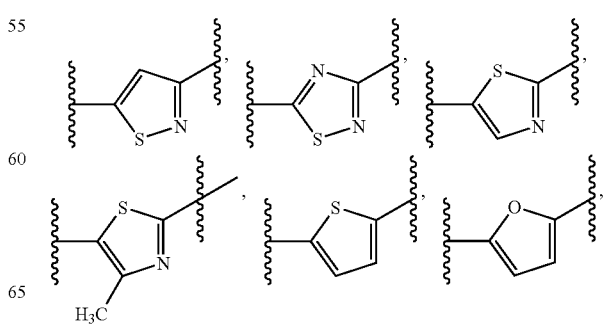

-continued

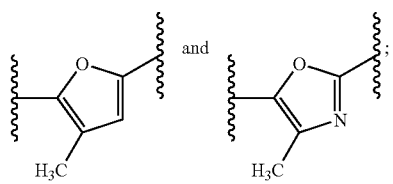

(nn) $R_1$ and $R_2$ are both H and $R_4$ is H or $CH_3$ and Q is selected from the group consisting of

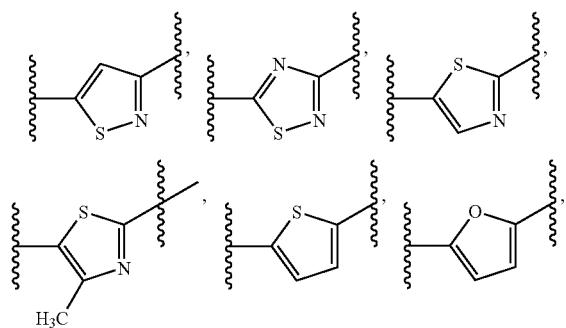

(oo) $R_1$ or $R_2$ is H and $R_5$ is H, $CH_3$, or $-CH_2CH_3$ and Q is selected from the group consisting of

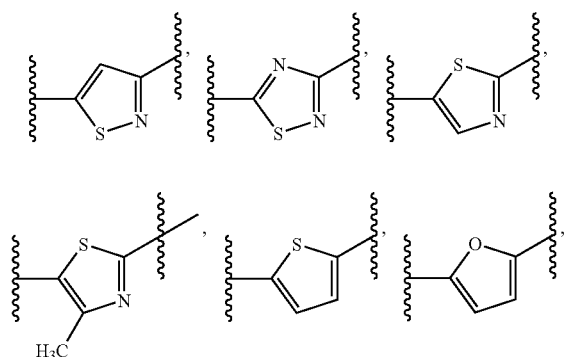

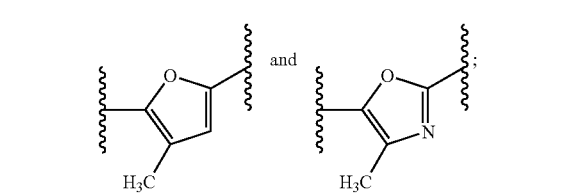

(pp) $R_1$ and $R_2$ are both H and $R_5$ is H, $CH_3$, or $-CH_2CH_3$ and Q is selected from the group consisting of

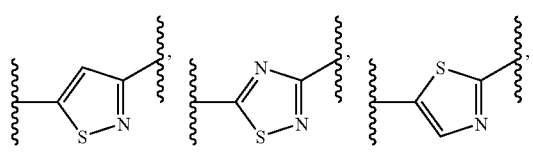

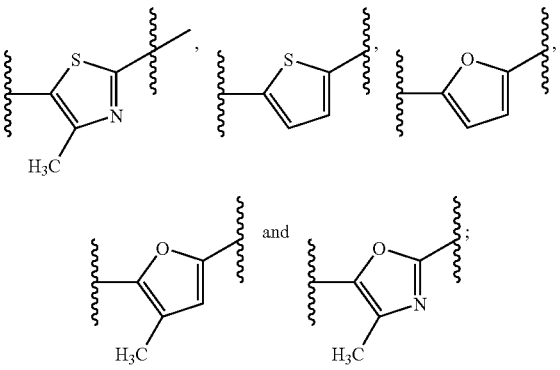

(qq) $R_1$ or $R_2$ is $CH_3$ and $R_5$ is H, $CH_3$, or $-CH_2CH_3$ and Q is selected from the group consisting of

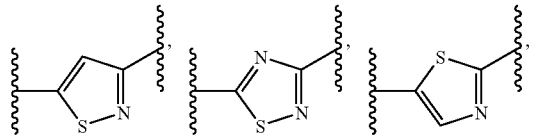

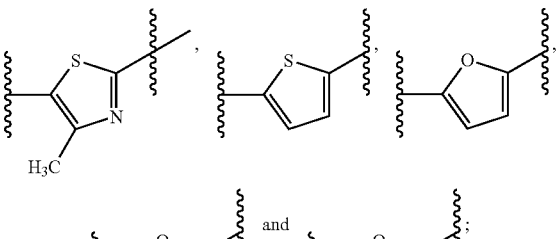

(rr) $R_1$ and $R_2$ are both $CH_3$, $R_5$ is H, $CH_3$, or $-CH_2CH_3$, and Q is selected from the group consisting of

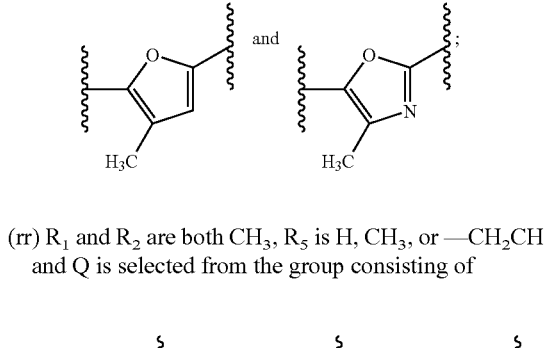

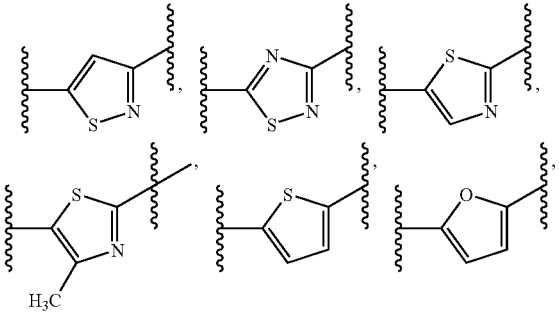

-continued

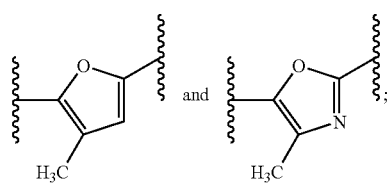

(ss) $R_1$ or $R_2$ is H, $R_4$ is H, $R_5$ is H, $CH_3$, or $-CH_2CH_3$, and Q is selected from the group consisting of

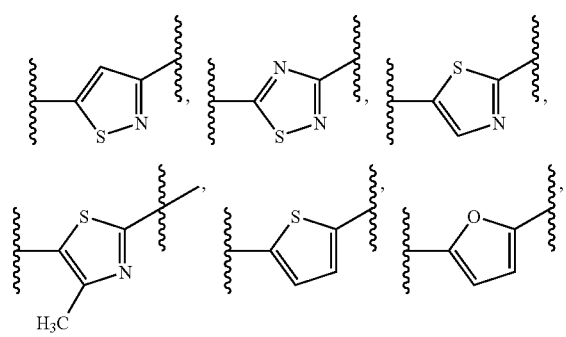

(tt) $R_1$ and $R_2$ are both H, $R_4$ is H, $R_5$ is H, $CH_3$, or $-CH_2CH_3$, and Q is selected from the group consisting of

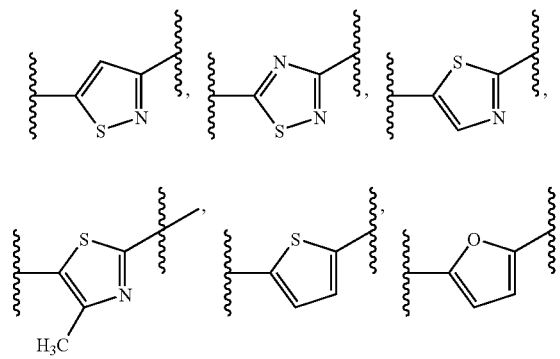

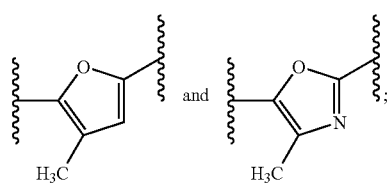

(uu) $R_1$ or $R_2$ is $CH_3$, $R_4$ is H, $R_5$ is H, $CH_3$, or $-CH_2CH_3$, and Q is selected from the group consisting of

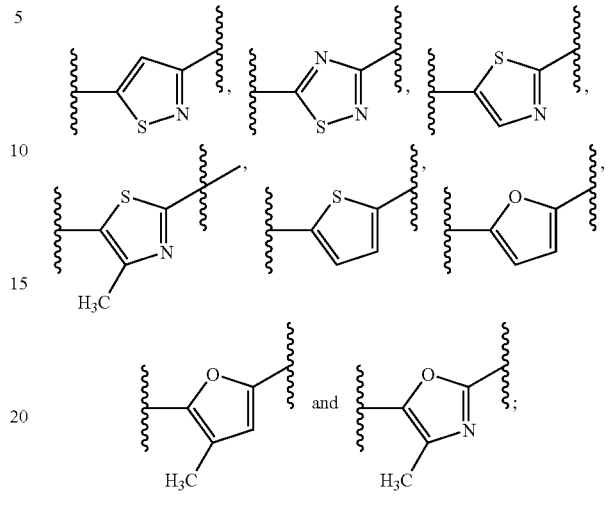

(vv) $R_1$ and $R_2$ are both $CH_3$, $R_4$ is H, $R_5$ is H, $CH_3$, or $-CH_2CH_3$, and Q is selected from the group consisting of

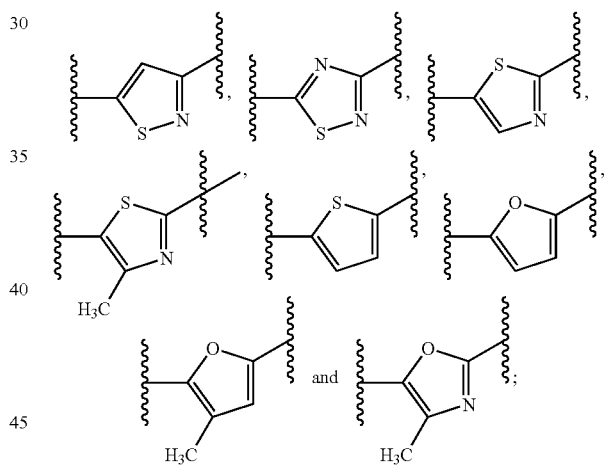

(ww) $R_1$, $R_2$ and the carbon atom to which they are attached together form

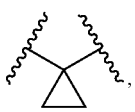

$R_4$ is H, $R_5$ is H, $CH_3$, or $-CH_2CH_3$, and Q is selected from the group consisting of

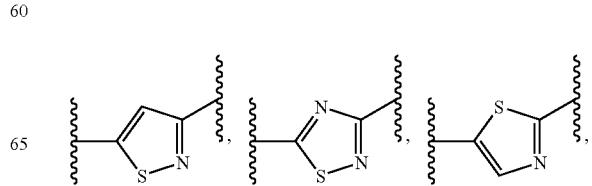

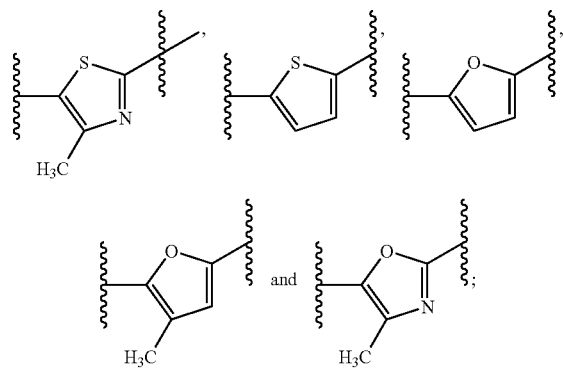

$R_7$ is $CF_3$ and Q is selected from the group consisting of

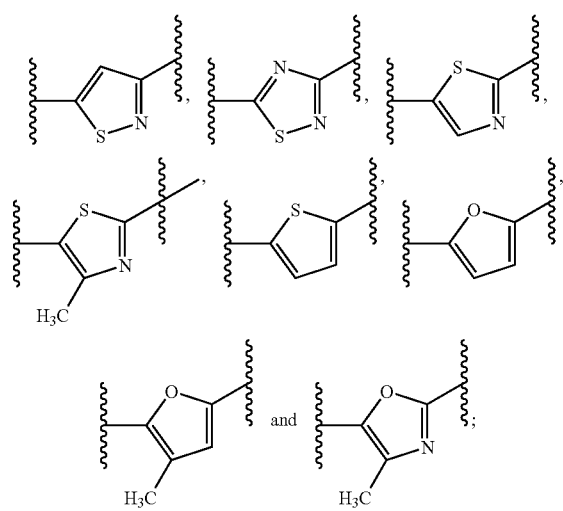

(xx) $R_7$ is Cl and Q is selected from the group consisting of

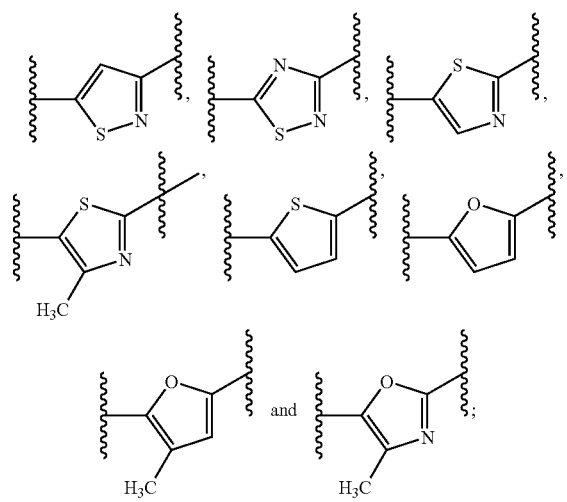

(yy) $R_1$ or $R_2$ is H, $R_7$ is $CF_3$, $R_4$ is H or $CH_3$, and Q is selected from the group consisting of

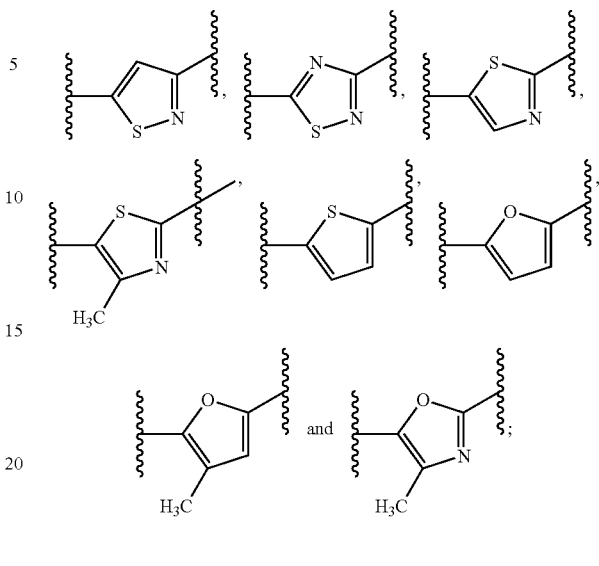

(zz) $R_1$ and $R_2$ are both H, $R_7$ is $CF_3$, $R_4$ is H or $CH_3$, and Q is selected from the group consisting of

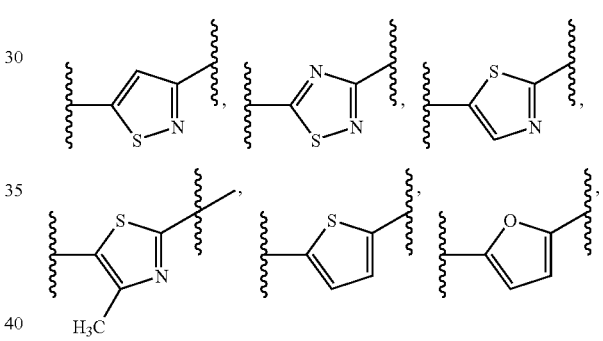

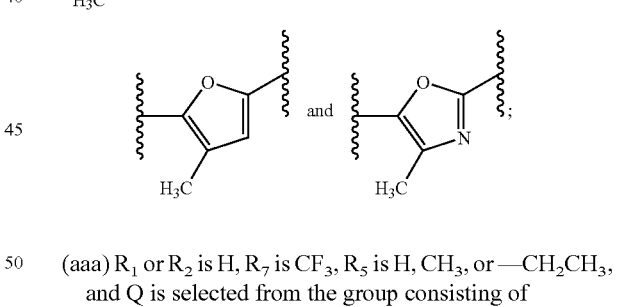

(aaa) $R_1$ or $R_2$ is H, $R_7$ is $CF_3$, $R_5$ is H, $CH_3$, or $-CH_2CH_3$, and Q is selected from the group consisting of

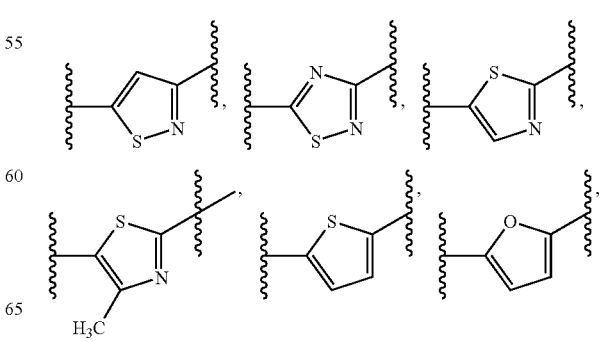

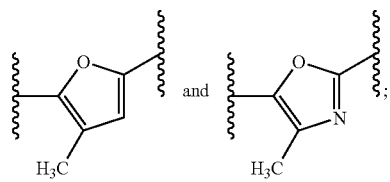

(bbb) R₁ and R₂ are both H, R₇ is CF₃, R₅ is H, CH₃, or —CH₂CH₃, and Q is selected from the group consisting of

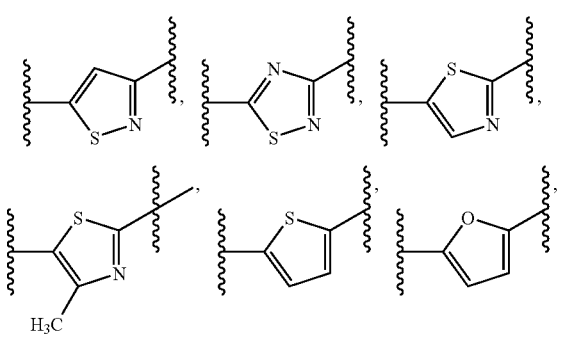

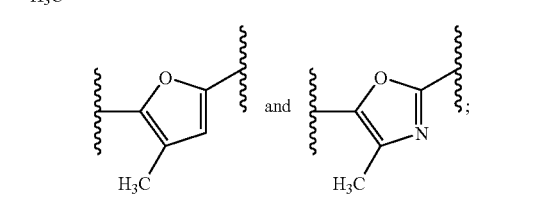

(ccc) R₁ or R₂ is CH₃, R₇ is CF₃, R₅ is H, CH₃, or —CH₂CH₃, and Q is selected from the group consisting of

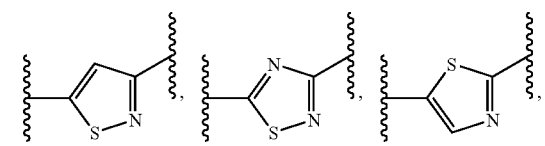

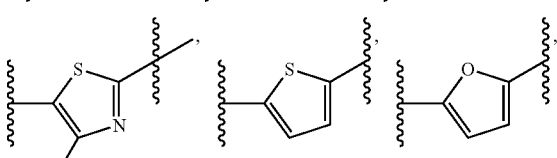

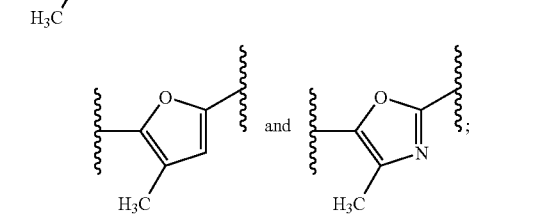

(ddd) R₁ and R₂ are both CH₃, R₇ is CF₃, R₅ is H, CH₃, or —CH₂CH₃, and Q is selected from the group consisting of

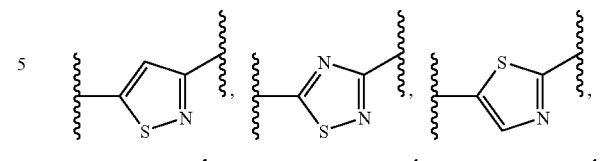

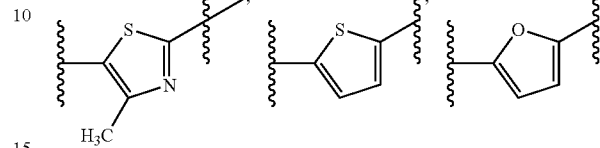

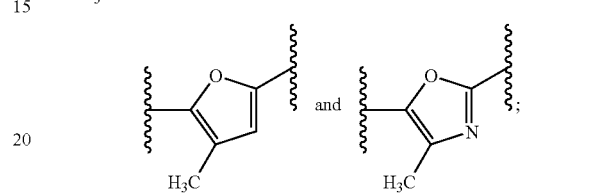

R₁ or R₂ is H, R₄ is H, R₇ is CF₃, R₅ is H, CH₃, or —CH₂CH₃, and Q is selected from the group consisting of

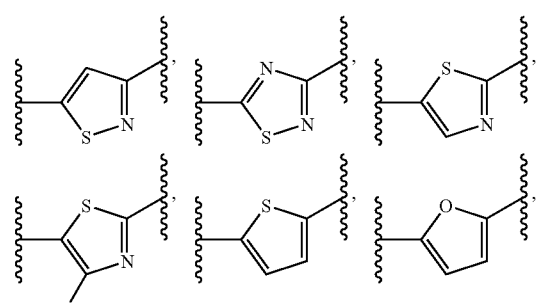

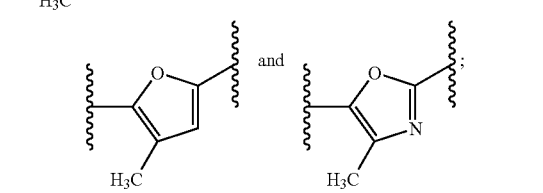

(eee) R₁ and R₂ are both H, R₄ is H, R₇ is CF₃, R₅ is H, CH₃, or —CH₂CH₃, and Q is selected from the group consisting of

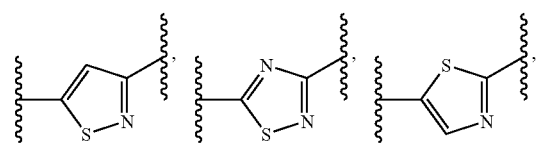

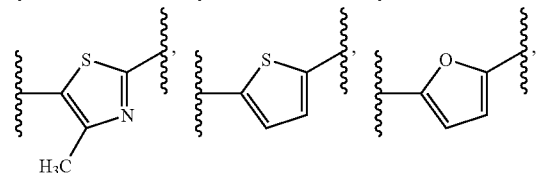

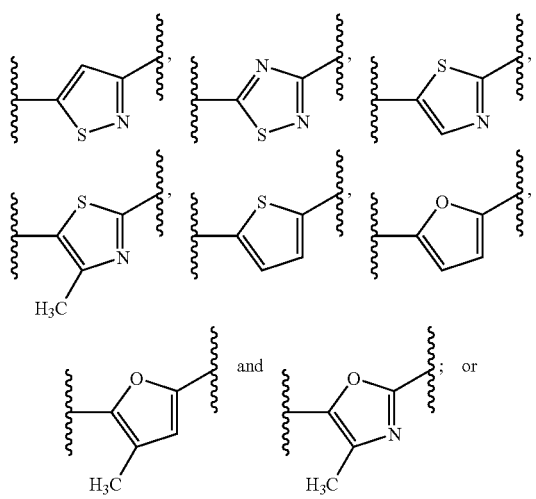

(fff) $R_1$ or $R_2$ is $CH_3$, $R_4$ is H, $R_7$ is $CF_3$, $R_5$ is H, $CH_3$, or —$CH_2CH_3$, and Q is selected from the group consisting of

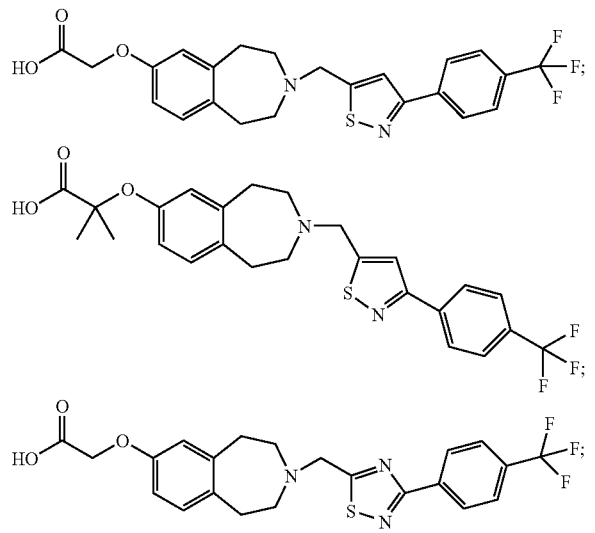

(a) $R_1$ and $R_2$ are both $CH_3$, $R_4$ is H, $R_7$ is $CF_3$, $R_5$ is H, $CH_3$, or —$CH_2CH_3$, and Q is selected from the group consisting of and enantiomers, diastereomers, tautomers, solvates, or pharmaceutically acceptable salts thereof.

In yet another embodiment, the present invention is directed to a compound selected from the group consisting of

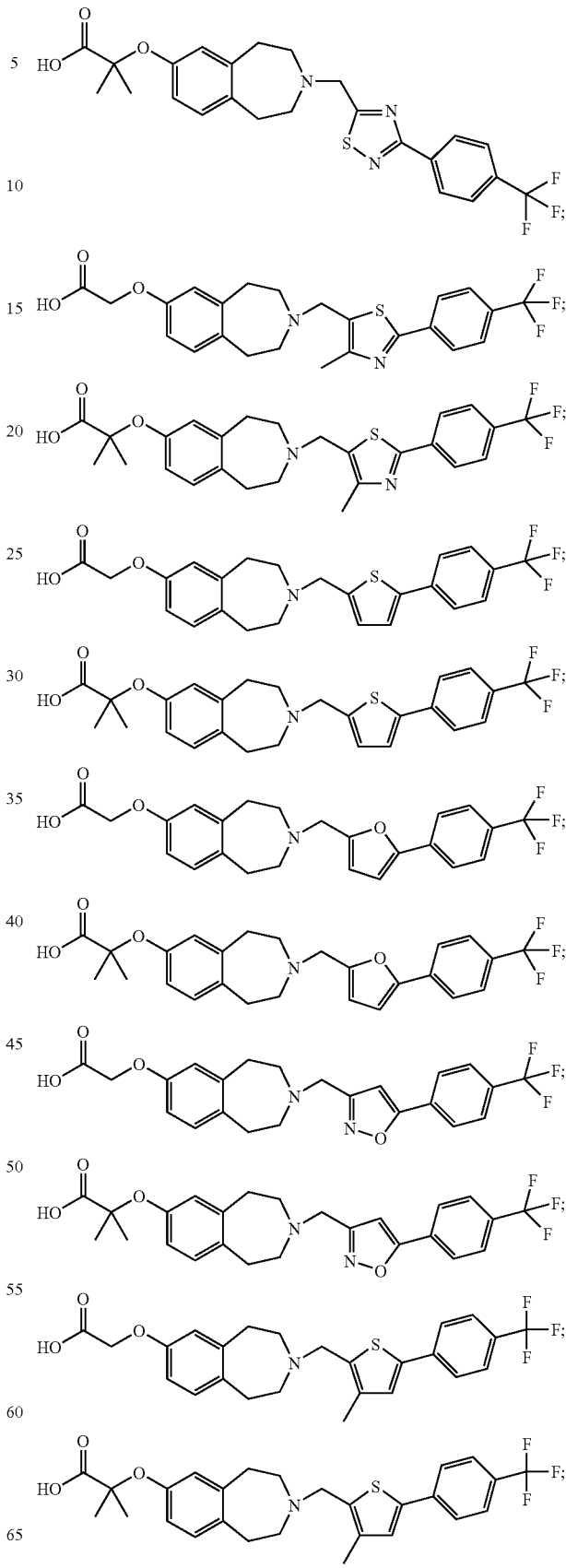

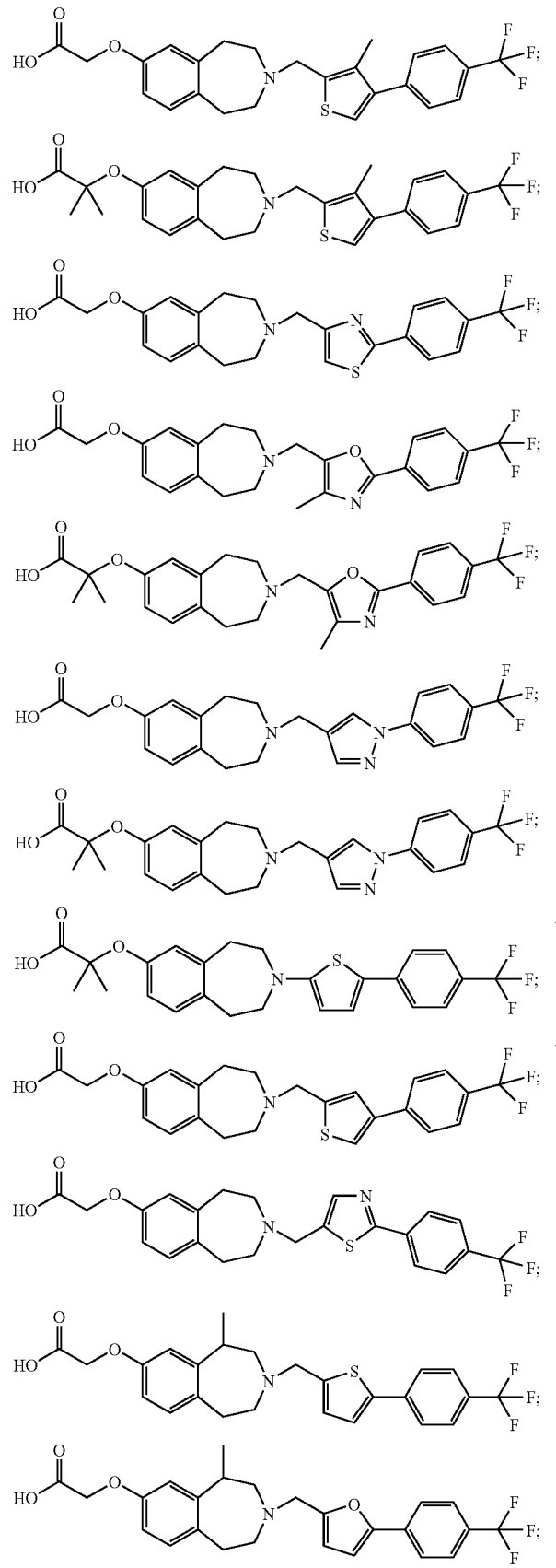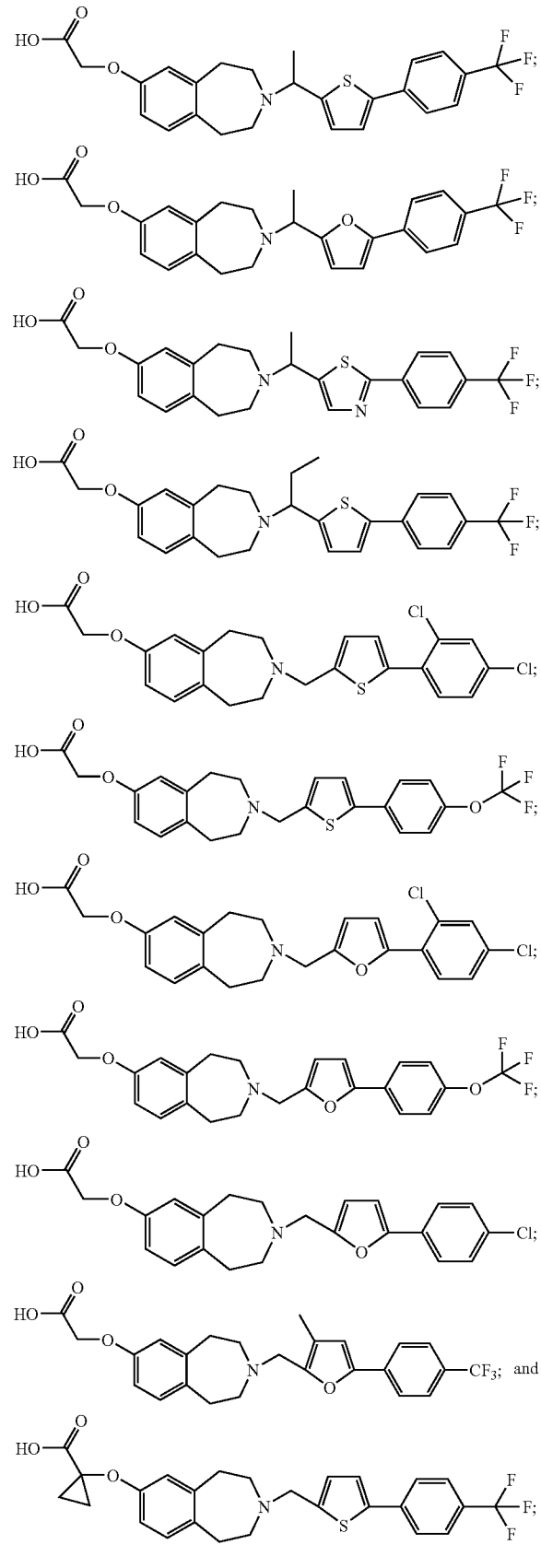

and enantiomers, diastereomers, tautomers, solvates, or pharmaceutically acceptable salts thereof. Specifically, the compound of formula (I) is

[Chemical structure]

The present invention is further directed to a compound of Formula (I)

Formula (I)

[Chemical structure]

wherein:
X is a covalent bond, O, or S;
$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;
$R_3$ is H;
$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$ alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, heteroaryl substituted $C_{1-4}$alkyl, cyano substituted $C_{1-4}$alkyl, and hydroxy substituted $C_{1-4}$alkyl;
$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;
n is 1; and
Q is $C_{6-10}$aryl;

and enantiomers, diastereomers, tautomers, solvates, or pharmaceutically acceptable salts thereof.

The present invention is also directed to a compound of Formula (I)

Formula (I)

[Chemical structure]

wherein:
X is a covalent bond, O, or S;
$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;
$R_3$ is H;
$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, heteroaryl substituted $C_{1-4}$alkyl, cyano substituted $C_{1-4}$alkyl, and hydroxy substituted $C_{1-4}$alkyl;
$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;
n is 1 or 2; and
Q is selected from the group consisting of

[Chemical structures of heterocycles], and and enantiomers, diastereomers, tautomers, solvates, or pharmaceutically acceptable salts thereof.

The present invention is also directed to a compound of Formula (I)

Formula (I)

[Chemical structure]

wherein:
X is a covalent bond, O, or S;
$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;
$R_3$ is H;
$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, cyano substituted $C_{1-4}$alkyl, and hydroxy substituted $C_{1-4}$alkyl;
$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;
n is 2; and
Q is selected from the group consisting of

[Chemical structures of heterocycles]

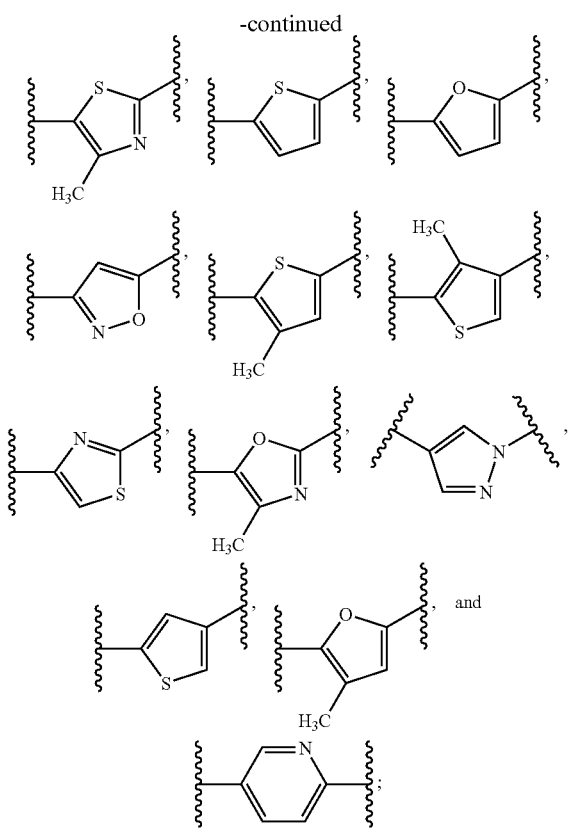

and enantiomers, diastereomers, tautomers, solvates, or pharmaceutically acceptable salts thereof.

In yet another embodiment, the present invention is directed to a compound selected from the group consisting of

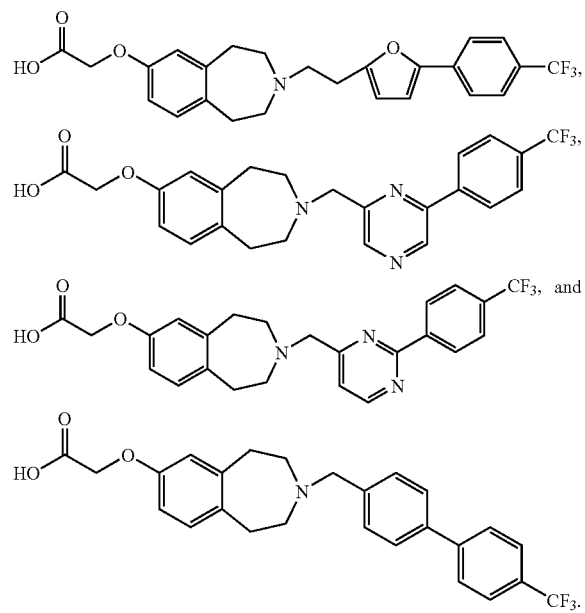

and enantiomers, diastereomers, tautomers, solvates, or pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. Representative hydroxy group prodrug forms include, but are not limited to, $C_{1-4}$alkanylethers, substituted $C_{1-4}$alkanylethers, and $C_{1-4}$alkanyl esters.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Thus, another embodiment of the present invention is a composition comprising the dextrorotatory enantiomer of a compound of Formula (I), wherein said composition is substantially free from the levorotatory isomer of said compound. In the present context, substantially free means less than 25%, preferably less than 10%, more preferably less than 5%, even more preferably less than 2% and even more preferably less than 1% of the dextrorotatory isomer calculated as $$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

For example, the present invention is also directed to a compound selected from the group consisting of

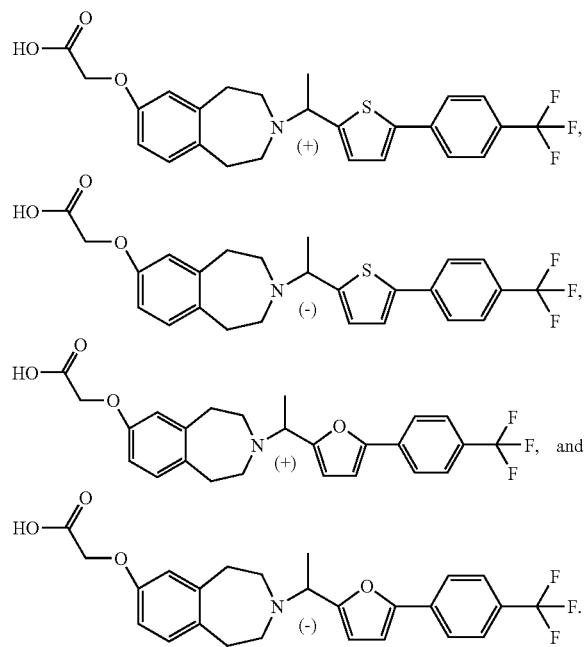

wherein the compound is substantially free from the corresponding other enantiomer.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention is required for a subject in need thereof.

The invention also provides a pharmaceutical pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of condition intended to be within the scope of the present invention include, but are not limited to, diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

Compounds of the present invention are also useful as PPAR delta agonists for treating, preventing, or inhibiting the progression of, a condition directly or indirectly mediated by PPAR delta.

The compounds of the present invention are particularly useful in treating diabetes, nephropathy, neuropathy, retinopathy, polycystic ovary syndrome, hypertension, ischemia, stroke, irritable bowel disorder, inflammation, cataract, cardiovascular diseases, Metabolic X Syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

In regard to the use of the present compounds in treatment of the diseases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below as well as the illustrative examples that follow. Since the schemes are an illustration, the invention should not be construed as being limited by the chemical reactions and conditions expressed. The preparation of the various starting materials used in the schemes is well within the skill of persons versed in the art.

Scheme 1.
General methods for the synthesis of Compounds of formula (Id)

Method 1.

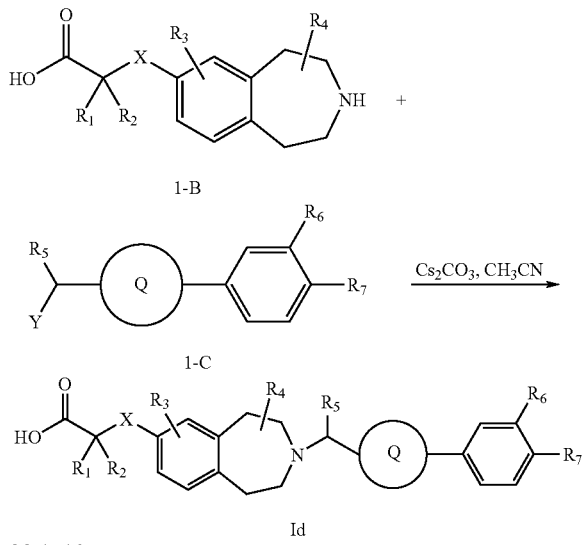

Method 2.

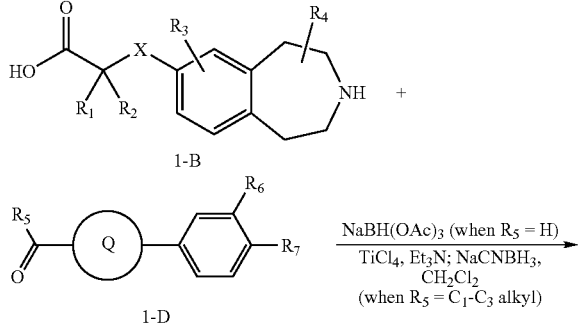

-continued

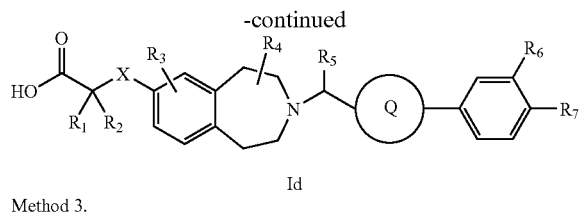

Method 3.

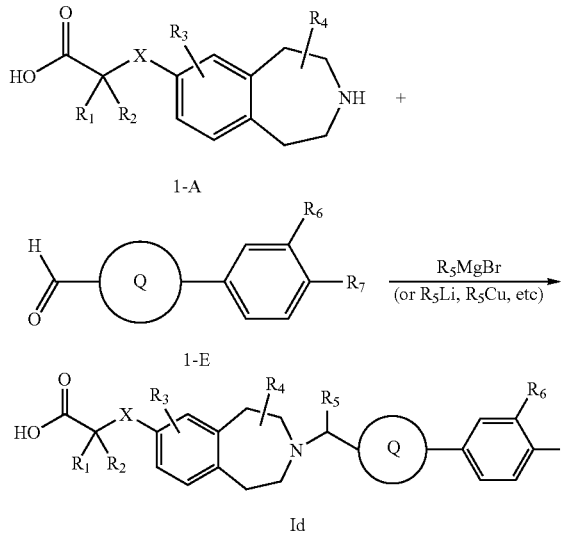

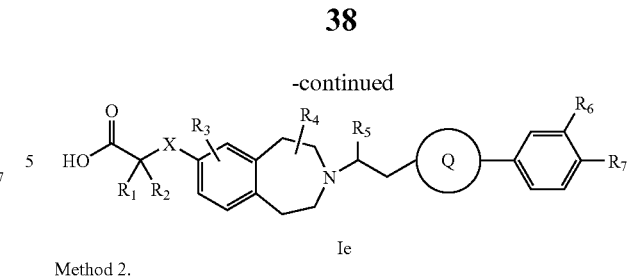

Method 2.

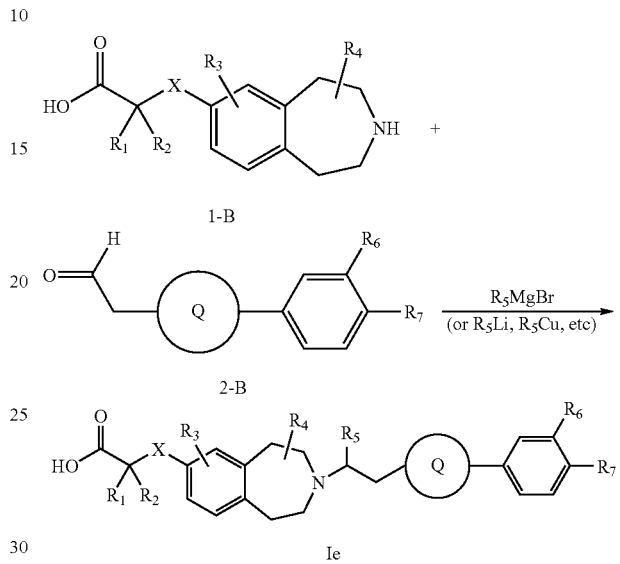

Scheme 1, wherein $R_1$, $R_2$, $R_3$, $R_4$, $R_5$, $R_6$, $R_7$, X and Q are as described above, describes several general methods for the synthesis of compounds of Formula Id. For example, in Method 1, alkylation of the substituted benzoazepine 1-B with a compound of Formula 1-C where Y can be a leaving group such as Br, Cl, 1, mesylate, etc. under a basic condition, such as $Cs_2CO_3$ in $CH_3CN$, can generate the corresponding compound of Id. In Method 2, reductive amination of 1-B with aryl aldehyde 1-D (e.g. $R_5$=H) by using $NaBH(OAc)_3$ will generate Id; or reaction of 1-B with aryl ketone (e.g. $R_5$=$C_1$-$C_3$ alkyl) to give the shiff-base followed by reduction with $NaCNBH_3$ will generate Id. In Method 3, reaction of 1-B with aryl aldehyde 1-E to give the shiff-base followed by reaction with organo-alkyl reagents such as Grignard reagents, $CH_3Li$ or organo-cupper reagent, will also provide Id.

Scheme 2.
General methods for the synthesis of Compound of formula (Ie)

Method 1.

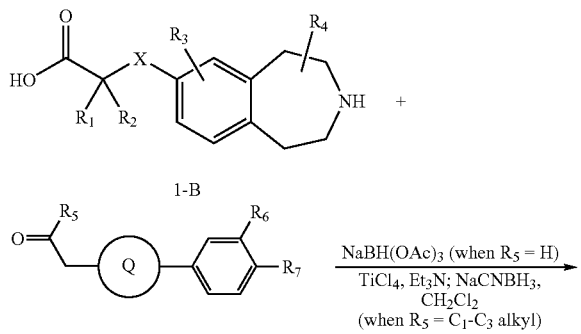

Scheme 2, wherein $R_1$, $R_2$, $R_3$, $R_4$, $R_5$, $R_6$, $R_7$, X and Q are as described above, describes several general methods for the synthesis of compounds of Formula Ie. For example, in Method 1, reductive amination of 1-B with aryl aldehyde 2-A (e.g. $R_5$=H) by using $NaBH(OAc)_3$ will generate Ie; or reaction of 1-B with aryl ketone (e.g. $R_6$=$C_1$-$C_3$ alkyl) to give the shiff-base followed by reduction with $NaCNBH_3$ will generate Ie. In Method 2, reaction of 1-B with aryl aldehyde 2-B to give the shiff-base followed by reaction with organo-alkyl reagents such as Grignard reagents, $CH_3Li$ or organo-cupper reagent, will also provide Ie.

Compounds of Formula (I) that are chiral may be separated into their enantiomers by chromatography on a chiral stationary phase. Alternatively, the basic compounds of the present invention may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

| Abbreviations | |
|---|---|
| Ac= | CH₃C(O)— |
| Aq= | aqueous |
| Cpd= | Compound |
| con= | concentration |
| DCE= | dichloroethane |
| DMF= | N,N-dimethylformamide |
| DMSO= | dimethylsulfoxide |
| dppf= | diphenylphosphinoferrocene |
| Et= | ethyl |
| EtOAc= | ethyl acetate |
| h or hr= | hour(s) |
| HATU= | N-[(dimethylamino)(3H-1,2,3-triazolo(4,5-b) pyridine-3-yloxy)methylene]-N-methylmethanaminium hexafluorophosphate |
| LAH= | lithium aluminum hydride |
| Me= | methyl |
| min= | minute(s) |
| Ph= | phenyl |
| PPA= | polyphosphoric acid |
| psi= | pascal per square inch |
| t-Boc= | tert-butoxycarbonyl |
| t-Bu= | tert-butyl |
| TEA= | triethylamine |
| TFA= | trifluoroacetic acid |
| THF= | tetrahydrofuran |
| TLC= | (thin layer chromatography) |
| LiN(TMS)₂= | Lithium bis(trimethylsilyl)amide |
| Tol= | toluene |

EXAMPLES

Example A

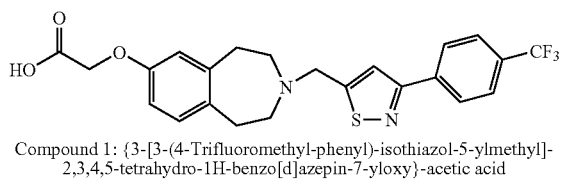

Compound 1: {3-[3-(4-Trifluoromethyl-phenyl)-isothiazol-5-ylmethyl]-2,3,4,5-tetrahydro-1H-benzo[d]azepin-7-yloxy}-acetic acid The title compound was made according to Schemes A1 and A2.

Scheme A1

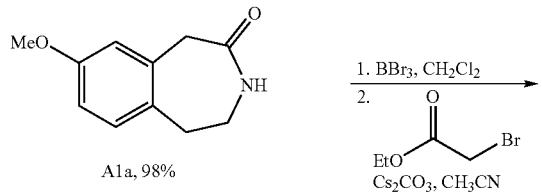

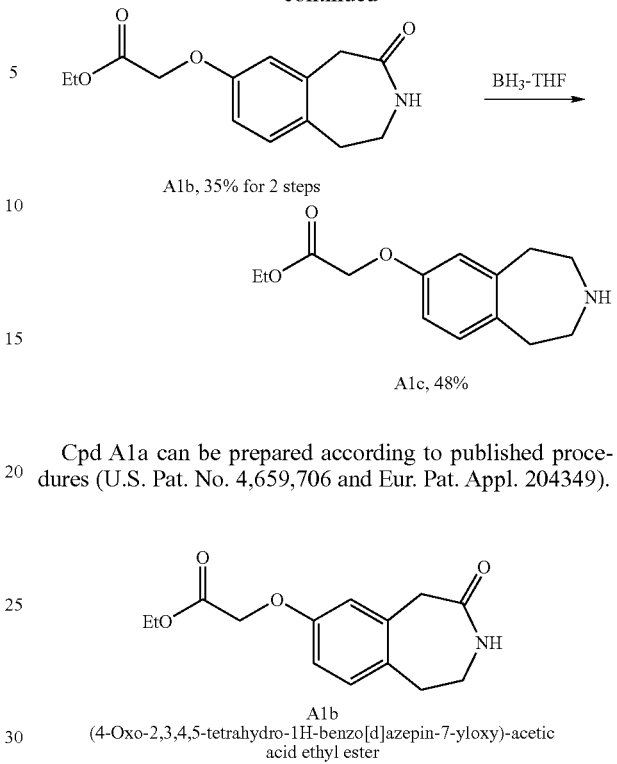

Cpd A1a can be prepared according to published procedures (U.S. Pat. No. 4,659,706 and Eur. Pat. Appl. 204349).

A1b
(4-Oxo-2,3,4,5-tetrahydro-1H-benzo[d]azepin-7-yloxy)-acetic acid ethyl ester To a solution of A1a (725 mg, 3.8 mmol) in CH₂Cl₂ (10 mL) at −78° C. was added BBr₃ (1 M in CH₂Cl₂, 11.4 mL, 11.4 mmol). The reaction mixture was allowed to warm to room temperature and stirred at room temperature for 5 h. MeOH (5 mL) was added slowly to quench the reaction. The reaction mixture was then concentrated to give a yellow solid.

A mixture of the above crude phenol, ethyl bromoacetate (950 mg, 5.69 mmol) and Cs₂CO₃ (2.47 g, 7.58 mmol) in CH₃CN (15 mL) was stirred at 80° C. for 20 h. After cooling to room temperature, the mixture was partitioned between EtOAc and H₂O and the aqueous layer was extracted with EtOAc. The combined organic phases were dried (Na₂SO₄), concentrated and purified by column chromatography to give 350 mg (35%) of Cpd A1b as a white solid: ¹H NMR (300 MHz, CDCl₃) δ 7.04 (d, J=8.4 Hz, 1H), 7.77 (dd, J=8.4, 2.7 Hz, 1H), 6.69 (d, J=2.5 Hz, 1H), 5.83 (bs, 1H), 4.59 (s, 2H), 4.27 (q, J=7.1 Hz, 2H), 3.80 (s, 2H), 3.58-3.52 (m, 2H), 3.06 (t, J=6.0 Hz, 2H), 1.30 (t, J=7.1 Hz, 3H); MS (ES) m/z: 286 (M+Na⁺).

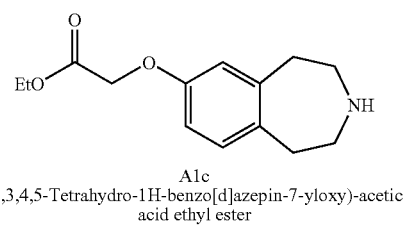

A1c
(2,3,4,5-Tetrahydro-1H-benzo[d]azepin-7-yloxy)-acetic acid ethyl ester

1 M borane-THF solution (1 mL, 1.02 mmol) was added dropwise to an ice-cooled and stirred solution of A1b (90 mg, 0.342 mmol) in THF (5 mL). The stirring was continued at 0° C. for 1 h and then room temperature for 20 min. The solution was cooled back to 0° C. and 1N HCl (2 mL) was added slowly to destroy the excess borane. After stirring at room temperature for 15 min, the solution was concentrated to remove THF. The aqueous solution was washed with EtOAc and then basified with $Na_2CO_3$ until pH>10 and then extracted with EtOAc. The combined organic phases were dried ($Na_2SO_4$), concentrated and vacuum dried to give 43 mg (48%) of A1c as a yellow jelly oil: $^1$H NMR (300 MHz, $CDCl_3$) δ 6.99 (d, J=8.4 Hz, 1H), 6.70 (s, 1H), 6.60 (d, J=8.4 Hz, 1H), 4.59 (s, 2H), 4.28 (q, J=7.1 Hz, 2H), 297 (bm, 4H), 2.84 (bm, 4H), 2.67 (s, 1H), 1.30 (t, J=7.1 Hz, 3H); MS (ES) m/z: 250 (M+H$^+$).

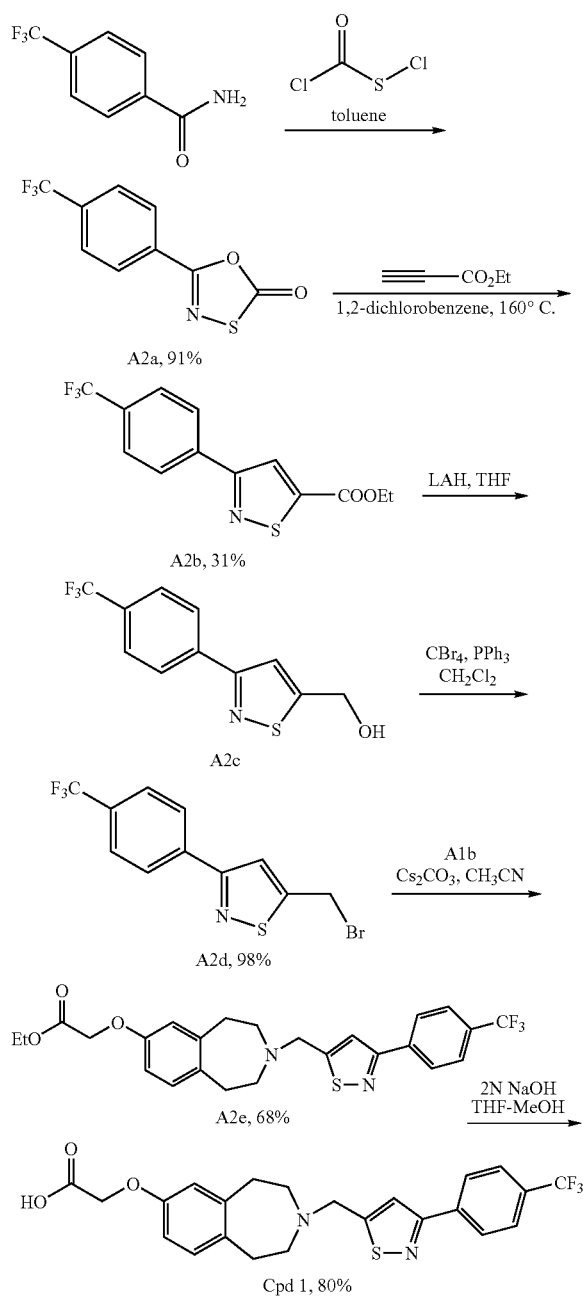

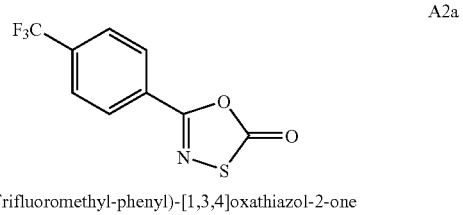

5-(4-Trifluoromethyl-phenyl)-[1,3,4]oxathiazol-2-one

The reaction mixture of 4-trifluoromethylbenzamide (11.3 g, 59.8 mmol), chlorocarbonylsulfenyl chloride (10.1 mL, 119.6 mmol) in toluene (120 mL) was heated at 80° C. for 15 h, cooled and concentrated. The solid was transferred to a sintered funnel, washed with a small amount of ethanol and dried under vacuum to give 13.4 g (91%) of A2a as white crystals: $^1$H NMR (300 MHz, $CDCl_3$) δ 8.11 (d, J=8.2 Hz, 2H), 7.77 (d, J=8.3 Hz, 2H).

A2b
3-(4-Trifluoromethyl-phenyl)-isothiazole-5-carboxylic acid ethyl ester

The reaction mixture of A2a (608 mg, 2.46 mmol) and ethyl propiolate (726 mg, 7.41 mmol) in chlorobenzene (10 mL) was heated at 135° C. for 20 h. TLC showed some of the starting material A2a still remained. More ethyl propiolate (726 mg, 7.41 mmol) and 1,2-dichlorobenzene (10 mL) were added and the solution was heated at 160° C. for 7 h. After cooling to room temperature, the reaction mixture was purified by column chromatography to give 229 mg (31%) of A2b as a white solid: $^1$H NMR (300 MHz, $CDCl_3$) δ 8.15 (s, 1H), 8.09 (d, J=8.1 Hz, 2H), 7.73 (d, J=8.2 Hz, 2H), 4.44 (q, J=7.1 Hz, 2H), 1.43 (t, J=7.1 Hz, 3H); MS (ES) m/z: 302 (M+H$^+$).

A2c
[3-(4-Trifluoromethyl-phenyl)-isothiazol-5-yl]-methanol

To the solution of A2b (104 mg, 0.345 mmol) in THF (2 mL) at −78° C. was added 1.0 M $LiAlH_4$ (0.21 mL, 0.21 mmol) in THF. After stirring at −78° C. for 30 min, water was slowly added and the mixture was allowed to warm up to room temperature. The precipitated solid was filtered and rinsed with $CH_2Cl_2$. The filtrate was washed with saturated $NH_4Cl$, and the aqueous solution was back extracted with $CH_2Cl_2$. The combined organic phases were dried and concentrated to give 98 mg of crude A2c as a yellow solid: $^1$H NMR (300 MHz, $CDCl_3$) δ 8.04 (d, J=8.3 Hz, 2H), 7.70 (d, J=8.4 Hz, 2H), 7.51 (s, 1H), 5.06 (s, 2H); MS (ES) m/z: 260 (M+H$^+$).

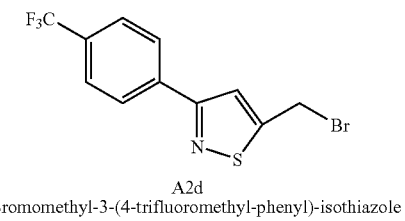

A2d
5-Bromomethyl-3-(4-trifluoromethyl-phenyl)-isothiazole

To the solution of A2c (1.0 g, 3.86 mmol) in CH$_2$Cl$_2$ (25 mL) at 0° C. was added PPh$_3$ (1.3 g, 5.01 mmol) and CBr$_4$ (1.7 g, 5.01 mmol). The reaction mixture was allowed to warm up to room temperature and stirred for 4 h at room temperature. The reaction mixture was concentrated and purified through column chromatography to get 1.36 g (98%) A2d as a white solid:

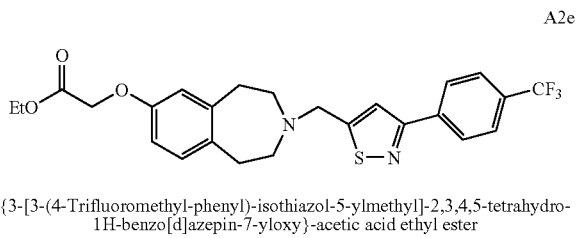

A2e

{3-[3-(4-Trifluoromethyl-phenyl)-isothiazol-5-ylmethyl]-2,3,4,5-tetrahydro-1H-benzo[d]azepin-7-yloxy}-acetic acid ethyl ester A mixture of A1e (15 mg, 0.060 mmol), A2d (23 mg, 0.072 mmol) and Et$_3$N (20 mg, 0.18 mmol) in CH$_3$CN (1 mL) was stirred for 5 hours. EtOAc and H$_2$O were added and the aqueous layer was extracted with EtOAc. The combined organic phases were dried (Na$_2$SO$_4$), concentrated and purified through column chromatography to get 20 mg (68%) Cpd A2e as a white solid: $^1$H NMR (300 MHz, CDCl$_3$) δ 8.05 (d, J=8.4 Hz, 2H), 7.69 (d, J=8.4 Hz, 2H), 7.45 (s, 1H), 7.00 (d, J=8.2 Hz, 1H), 6.70 (d, J=2.5 Hz, 1H), 6.62 (dd, J=8.2, 2.5 Hz, 1H), 4.59 (s, 2H), 4.27 (q, J=7.1 Hz, 2H), 3.98 (s, 2H), 2.90 (m, 4H), 2.70 (m, 4H), 1.30 (t, J=7.1 Hz, 3H); MS (ES) m/z: 491 (M+H$^+$).

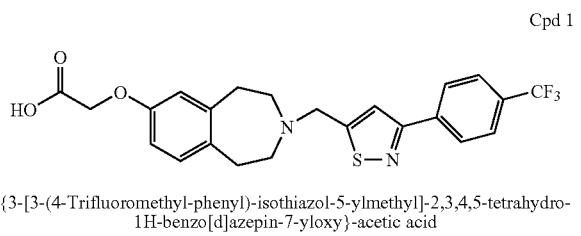

Cpd 1

{3-[3-(4-Trifluoromethyl-phenyl)-isothiazol-5-ylmethyl]-2,3,4,5-tetrahydro-1H-benzo[d]azepin-7-yloxy}-acetic acid A mixture of A2e (20 mg, 0.041 mmol) and 2 M NaOH (41 µL, 0.082 mmol) in THF-MeOH (0.6 mL-0.2 mL) was stirred under N$_2$ for 2 h and concentrated. CH$_2$Cl$_2$ and water were added, and the mixture was acidified with concentrated HCl. The organic phase was separated and the aqueous phase was extracted with CH$_2$Cl$_2$. The combined organic layers were dried (Na$_2$SO$_4$), concentrated, and purified by column chromatography to give 15 mg (80%) of Cpd 1 as a white solid: $^1$H NMR (300 MHz, CDCl$_3$) δ 8.05 (d, J=8.0 Hz, 2H), 7.90 (s, 1H), 7.71 (d, J=8.4 Hz, 2H), 6.95 (d, J=8.3 Hz, 1H), 6.75 (dd, J=8.1, 2.6 Hz, 1H), 6.65 (d, J=2.6 Hz, 1H), 4.65 (s, 2H), 4.38 (s, 2H), 3.07 (m, 4H), 2.93 (m, 4H); MS (ES) m/z: 463 (M+H$^+$).

Example B

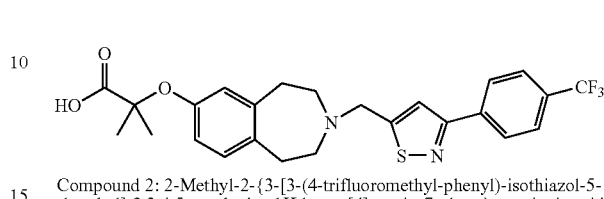

Compound 2: 2-Methyl-2-{3-[3-(4-trifluoromethyl-phenyl)-isothiazol-5-ylmethyl]-2,3,4,5-tetrahydro-1H-benzo[d]azepin-7-yloxy}-propionic acid The title compound was made according to Scheme B.

Scheme B

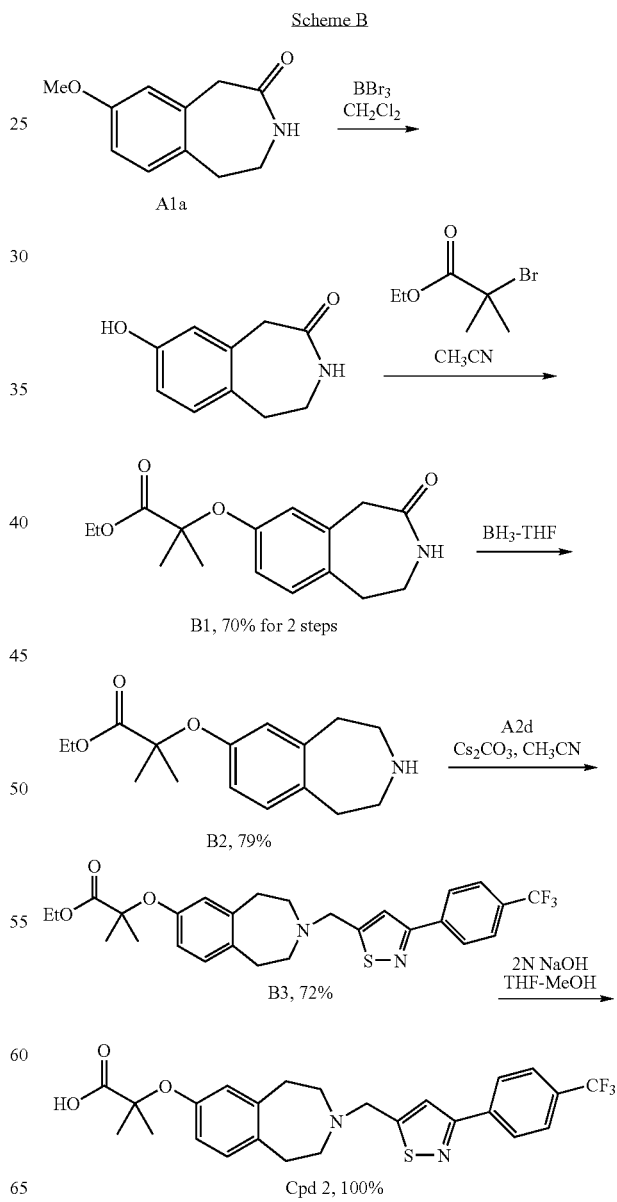

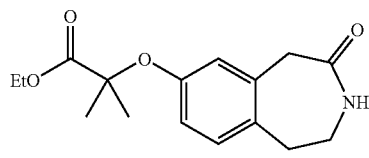

2-Methyl-2-(4-oxo-2,3,4,5-tetrahydro-1H-benzo[d]
azepin-7-yloxy)-propionic acid ethyl ester To a solution of A1a (4.0 g, 20.9 mmol) in CH$_2$Cl$_2$ (20 mL) at −78° C. was added BBr$_3$ (1 M in CH$_2$Cl$_2$, 62.8 mL, 62.8 mmol). The mixture was allowed to warm to room temperature and stirred at room temperature for 5 h. MeOH (5 mL) was added slowly to quench the reaction. The reaction mixture was then concentrated to give a yellow solid.

A mixture of the above crude phenol, ethyl bromoisobutyrate (6.1 g, 31.4 mmol) and Cs$_2$CO$_3$ (20.8 g, 63.8 mmol) in CH$_3$CN (200 mL) was stirred at 80° C. for 20 h. After cooling to room temperature, the mixture was partitioned between EtOAc and H$_2$O and the aqueous layer was extracted with EtOAc. The combined organic phases were dried (Na$_2$SO$_4$), concentrated and purified by column chromatography to give 4.2 g (70%) of B1 as a white solid: $^1$H NMR (300 MHz, CD$_3$OD) δ 7.03 (d, J=8.4 Hz, 1H), 6.68 (dd, J=8.3, 2.6 Hz, 1H), 6.63 (d, J=2.6 Hz, 1H), 4.21 (q, J=7.1 Hz, 2H), 3.76 (s, 2H), 3.57-3.52 (m, 2H), 3.04 (t, J=6.0 Hz, 2H), 1.53 (s, 6H), 1.24 (t, J=7.1 Hz, 3H); MS (ES) m/z: 314 (M+Na$^+$).

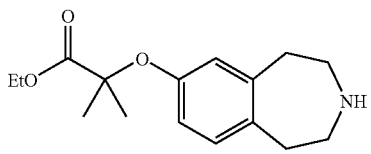

2-Methyl-2-(2,3,4,5-tetrahydro-1H-benzo[d]azepin-7-yloxy)-propionic acid ethyl ester The 1 M borane-THF solution (20.5 mL, 20.5 mmol) was added dropwise to an ice-cooled and stirred solution of B1 (2.0 g, 6.85 mmol) in THF (20 mL). The stirring was continued at room temperature for 1 h. The solution was cooled back to 0° C. and 1N HCl (25 mL) was added slowly to destroy the excess borane. After stirring at room temperature for 15 min, the solution was concentrated to remove THF. The aqueous solution was washed with EtOAc, basified with Na$_2$CO$_3$ until pH>10 and then extracted with EtOAc. The combined organic phases were dried (Na$_2$SO$_4$) and concentrated to give 1.5 g (79%) of B2 as a colorless jelly oil: $^1$H NMR (300 MHz, CDCl$_3$) δ 6.95 (d, J=8.4 Hz, 1H), 6.64 (d, J=2.5 Hz, 1H), 6.55 (dd, J=8.4, 2.6 Hz, 1H), 4.22 (q, J=7.1 Hz, 2H), 2.99 (m, 2H), 2.88 (m, 2H), 1.59 (s, 6H), 1.25 (t, J=7.1 Hz, 3H); MS (ES) m/z: 278 (M+H$^+$).

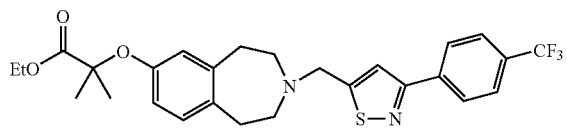

2-Methyl-2-{3-[3-(4-trifluoromethyl-phenyl)-isothiazol-5-ylmethyl]-2,3,4,5-tetrahydro-1H-benzo[d]azepin-7-yloxy}-propionic acid ethyl ester Cpd B3 was prepared using same procedure as for cpd A2e by replacing A1b with B2 (white solid, 72%): $^1$H NMR (300 MHz, CDCl$_3$) δ 8.05 (d, J=8.4 Hz, 2H), 7.69 (d, J=8.4 Hz, 2H), 7.55 (s, 1H), 6.93 (d, J=8.2 Hz, 1H), 6.64 (d, J=2.5 Hz, 1H), 6.57 (dd, J=8.2, 2.5 Hz, 1H), 4.23 (q, J=7.1 Hz, 2H), 4.05 (s, 2H), 2.92 (m, 4H), 2.80 (m, 4H), 1.57 (s, 6H), 1.25 (t, J=7.1 Hz, 3H); MS (ES) m/z: 519 (M+H$^+$).

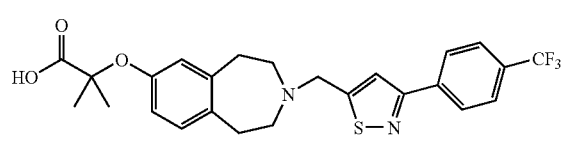

2-Methyl-2-{3-[3-(4-trifluoromethyl-phenyl)-isothiazol-5-ylmethyl]-2,3,4,5-tetrahydro-1H-benzo[d]azepin-7-yloxy}-propionic acid Cpd 2 was prepared using similar procedure as for cpd 1. Cpd 2 was obtained as a white solid (100%): $^1$H NMR (300 MHz, CD$_3$OD) δ 8.21 (d, J=8.1 Hz, 2H), 8.06 (s, 1H), 7.80 (d, J=8.2 Hz, 2H), 7.09 (d, J=82 Hz, 1H), 6.78 (d, J=2.5 Hz, 1H), 6.72 (dd, J=8.2, 2.5 Hz, 1H), 4.74 (s, 2H), 3.33 (m, 4H), 3.11 (m, 4H), 1.54 (s, 6H); MS (ES) m/z: 491 (M+H$^+$).

Example C

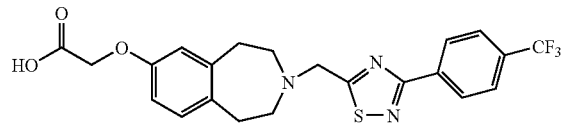

Compound 3: {3-[3-(4-Trifluoromethyl-phenyl)-[1,2,4]thiadiazol-5-ylmethyl]-2,3,4,5-tetrahydro-1H-benzo[d]azepin-7-yloxy}-acetic acid The title compound was made according to Scheme C.

Scheme C

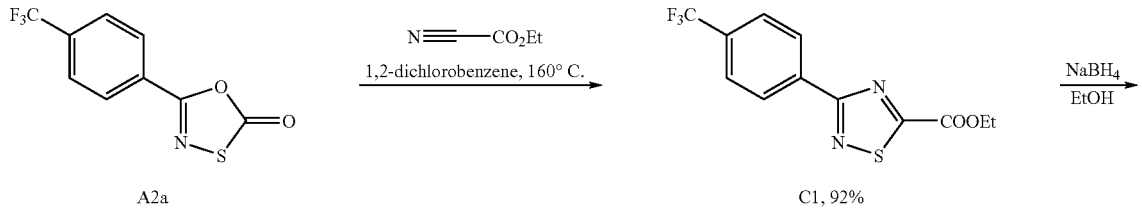

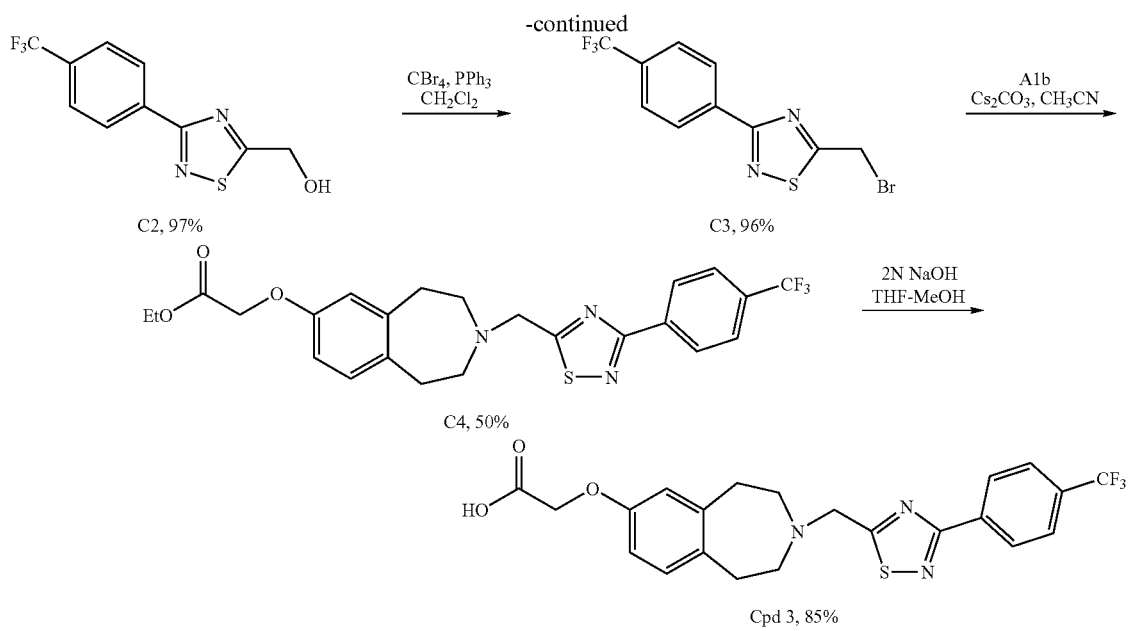

C2, 97%

C3, 96%

C4, 50%

Cpd 3, 85%

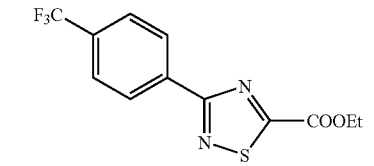

3-(4-Trifluoromethyl-phenyl)-[1,2,4]thiadiazole-5-carboxylic acid ethyl ester

A reaction mixture of A2a (448 mg, 1.81 mmol) and ethyl cyanoformate (722 mg, 7.29 mmol) in 1,2-dichlorobenzene (7 mL) was heated at 160° C. for 20 h. After cooling to room temperature, the reaction mixture was purified by column chromatography to give 505 mg (92%) of C1 as a yellow solid: $^1$H NMR (300 MHz, CDCl$_3$) δ 8.50 (d, J=8.1 Hz, 2H), 7.76 (d, J=82 Hz, 2H), 4.57(q, J=7.1 Hz, 2H), 1.49 (t, J=7.1 Hz, 3H); MS (ES) m/z: 303 (M+H$^+$).

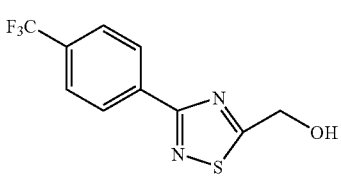

[3-(4-Trifluoromethyl-phenyl)-[1,2,4]thiadiazol-5-yl]-methanol

To a solution of C1 (200 mg, 0.662 mmol) in EtOH (10 mL) at room temperature was added NaBH$_4$ (64 mg, 1.7 mmol). After stirring for 2 h, a few drops of water were added to quench excess of hydride. EtOH was evaporated, and the residue was partitioned between CH$_2$Cl$_2$ and water. The organic phase was dried (Na$_2$SO$_4$) and concentrated to provide 167 mg (97%) of C2 as off-white crystals: $^1$H NMR (300 MHz, CDCl$_3$) δ 8.40 (d, J=8.1 Hz, 2H), 7.74 (d, J=8.2 Hz, 2H), 5.20 (s, 2H), 2.65 (br, 1H); MS (ES) m/z: 261 (M+H$^+$).

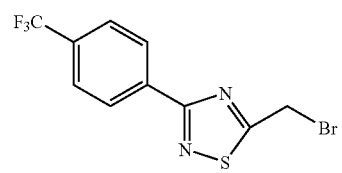

5-Bromomethyl-3-(4-trifluoromethyl-phenyl)-[1,2,4]thiadiazole

Cpd C3 was prepared according to a similar procedure as for cpd A2d. Cpd C3 was obtained as a white solid (96%): $^1$H NMR (300 MHz, CDCl$_3$) δ 8.40 (d, J=8.1 Hz, 2H), 7.74 (d, J=8.3 Hz, 2H), 4.83(s, 2H); MS (ES) m/z: 321 (M−H$^+$).

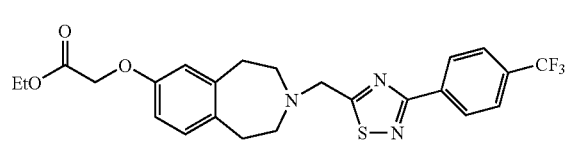

{3-[3-(4-Trifluoromethyl-phenyl)-[1,2,4]thiadiazol-5-ylmethyl]-2,3,4,5-tetrahydro-1H-benzo[d]azepin-7-yloxy}-acetic acid ethyl ester Cpd C4 was prepared according to a similar procedure as for cpd A2e. Cpd C4 was obtained as a white solid (50%): $^1$H NMR (300 MHz, CDCl$_3$) δ 8.40 (d, J=8.1 Hz, 2H), 7.73 (d, J=8.3 Hz, 2H), 7.02 (d, J=8.2 Hz, 1H), 6.72 (d, J=2.6 Hz, 1H), 6.65 (dd, J=8.2, 2.7 Hz, 1H), 4.59 (s, 2H), 4.27 (q, J=7.1 Hz, 2H), 4.11 (s, 2H), 2.95-2.83 (m, 8H), 1.30 (t J=7.1 Hz, 3H); MS (ES) m/z: 492 (M+H$^+$).

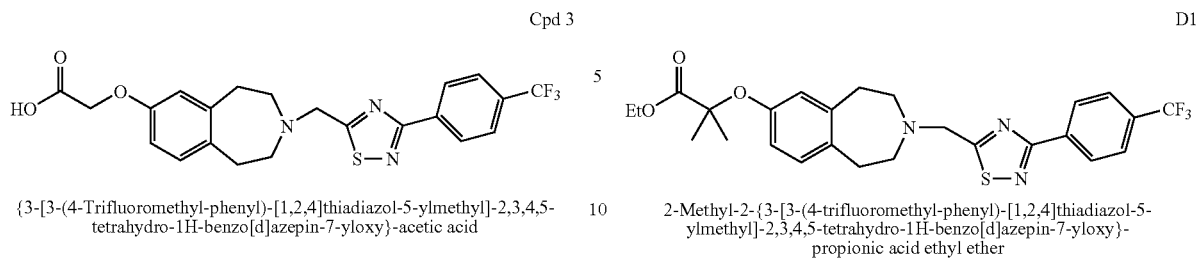

Cpd 3

{3-[3-(4-Trifluoromethyl-phenyl)-[1,2,4]thiadiazol-5-ylmethyl]-2,3,4,5-tetrahydro-1H-benzo[d]azepin-7-yloxy}-acetic acid Cpd 3 was prepared according to a similar procedure as for cpd 1. Cpd 3 was obtained as a white solid (85%): $^1$H NMR (300 MHz, CD$_3$OD) δ 8.48 (d, J=7.7 Hz, 2H), 7.83 (d, J=6.8 Hz, 2H), 7.07 (d, J=8.5 Hz, 1H), 6.79 (s, 1H), 6.73 (d, J=7.1 Hz, 1H), 463 (s, 2H), 4.58 (s, 2H), 3.22 (m, 4H), 3.07 (m, 4H); MS (ES) m/z: 464 (M+H$^+$).

D1

2-Methyl-2-{3-[3-(4-trifluoromethyl-phenyl)-[1,2,4]thiadiazol-5-ylmethyl]-2,3,4,5-tetrahydro-1H-benzo[d]azepin-7-yloxy}-propionic acid ethyl ether Cpd D1 was prepared according to a similar procedure as for cpd B3. Cpd B3 was obtained as a white solid (76%): $^1$H NMR (300 MHz, CDCl$_3$) δ 8.39 (d, J=8.2 Hz, 2H), 7.72 (d, J=8.4 Hz, 2H), 6.95 (d, J=8.2 Hz, 1H), 6.66 (d, J=2.5 Hz, 1H), 6.58 (dd, J=8.1, 2.6 Hz, 1H), 4.24 (q, J=7.1 Hz, 2H), 4.12 (s, 2H), 2.91 (m, 4H), 2.88 (m, 4H), 1.58 (s, 6H), 1.26 (t, J=7.1 Hz, 3H); MS (ES) m/z: 520 (M+H$^+$).

Example D

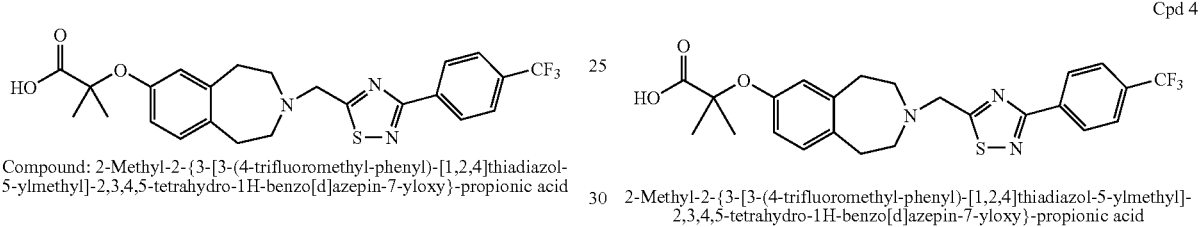

Compound: 2-Methyl-2-{3-[3-(4-trifluoromethyl-phenyl)-[1,2,4]thiadiazol-5-ylmethyl]-2,3,4,5-tetrahydro-1H-benzo[d]azepin-7-yloxy}-propionic acid Cpd 4

2-Methyl-2-{3-[3-(4-trifluoromethyl-phenyl)-[1,2,4]thiadiazol-5-ylmethyl]-2,3,4,5-tetrahydro-1H-benzo[d]azepin-7-yloxy}-propionic acid The title compound was made according to Scheme D.

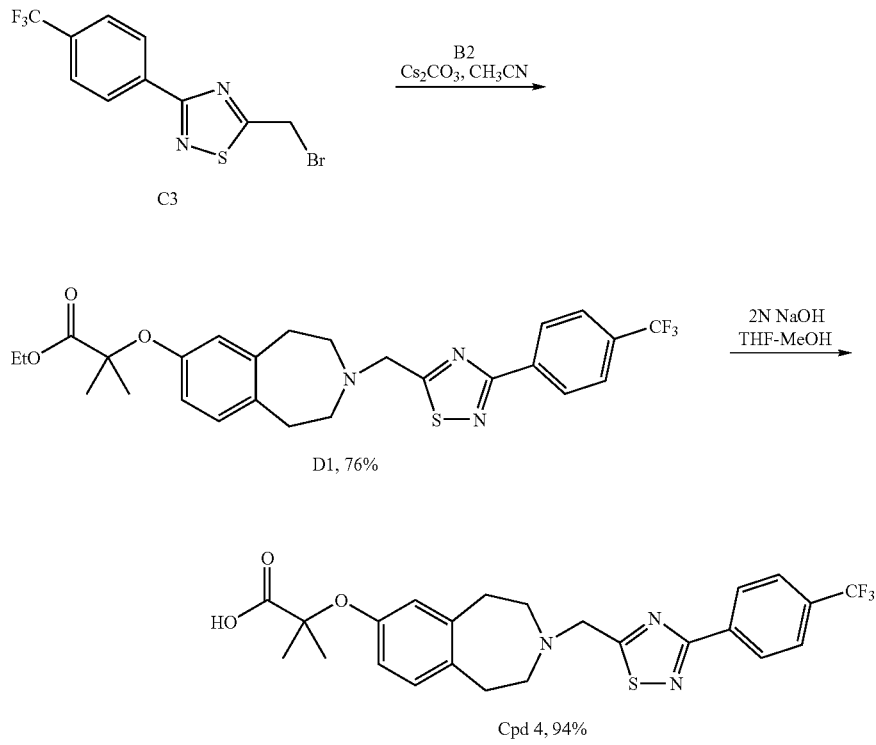

Scheme D

Cpd 4 was prepared according to a similar procedure as for cpd 2. Cpd 4 was obtained as a white solid (94%): ¹H NMR (300 MHz, CD₃OD) δ 8.50 (d, J=8.2 Hz, 2H), 7.84 (d, J=8.3 Hz, 2H), 7.09 (d, J=8.2 Hz, 1H), 6.78 (d, J=2.5 Hz, 1H), 6.72 (dd, J=8.2, 2.6 Hz, 1H), 4.84 (s, 2H), 3.46 (m, 4H), 3.16 (m, 4H), 1.55 (s, 6H); MS (ES) m/z: 492 (M+H⁺).

Example E

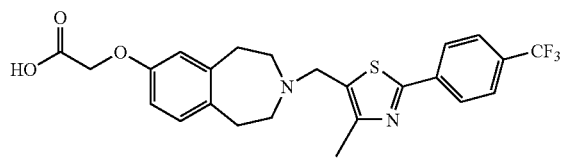

Compound 5: {3-[4-Methyl-2-(4-trifluoromethyl-phenyl)-thiazol-5-ylmethyl]-2,3,4,5-tetrahydro-1H-benzo[d]azepin-7-yloxy}-acetic acid The title compound was made according to Scheme E.

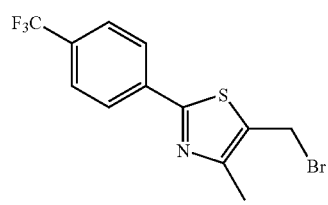

5-Bromomethyl-4-methyl-2-(4-trifluoromethyl-phenyl)-thiazole

Cpd E2 was prepared from cpd E1 (*Bioorg & Med. Chem. Lett.*, 2003, 13 (9), 1517-1521) following a similar procedure as for cpd A2d. Cpd E2 was obtained as a white solid (96%): ¹H NMR (300 MHz, CDCl₃) δ 8.01 (d, J=8.7 Hz, 2H), 7.68 (d, J=8.6 Hz, 2H), 4.72 (s, 2H), 2.48 (s, 3H).

Scheme E

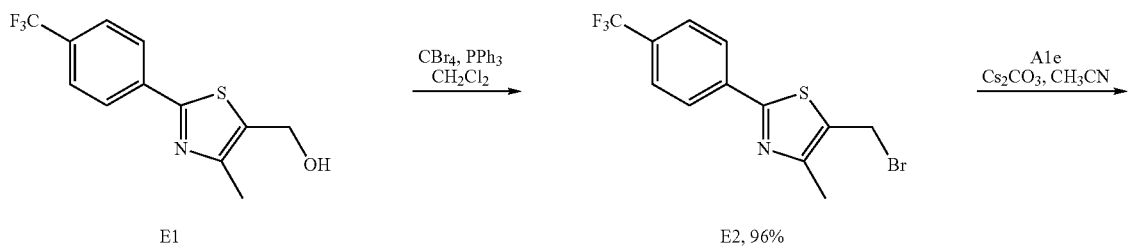

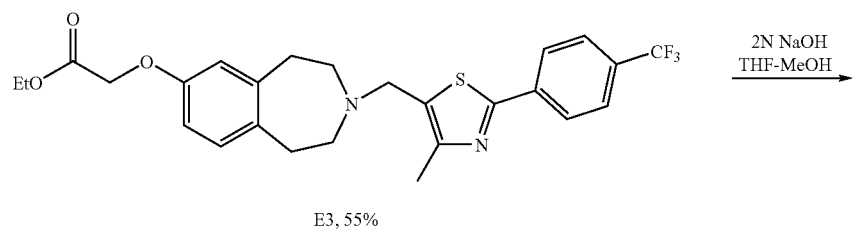

E3, 55%

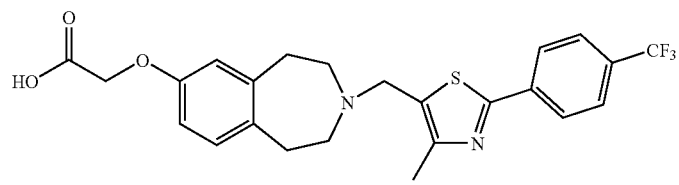

Cpd 5, 85%

53

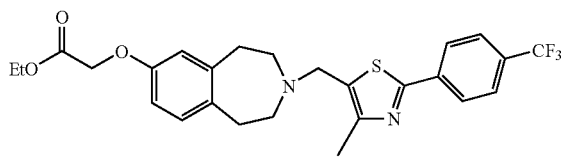

{3-[4-Methyl-2-(4-trifluoromethyl-phenyl)-thiazol-5-ylmethyl]-2,3,4,5-tetrahydro-1H-benzo[d]azepin-7-yloxy}-acetic acid ethyl ester Cpd E3 was prepared according to a similar procedure as for cpd A2e. Cpd E3 was obtained as a white solid (53%): $^{1}$H NMR (300 MHz, CDCl$_{3}$) δ 8.02 (d, J=8.2 Hz, 2H), 7.68 (d, J=8.3 Hz, 2H), 7.00 (d, J=8.2 Hz, 1H), 6.70 (d, J=2.5 Hz, 1H), 6.62 (dd, J=8.2, 2.5 Hz, 1H), 4.59 (s, 2H), 4.27 (q, J=7.1 Hz, 2H), 3.76 (s, 2H), 2.90-2.83 (m, 4H), 2.72-2.64 (m, 4H), 2.42 (s, 3H), 1.30 (t, J=7.1 Hz, 3H); MS (ES) m/z: 505 (M+H$^{+}$).

54

Cpd 5 was prepared according to a similar procedure as for cpd 1. Cpd 1 was obtained as a white solid (85%): $^{1}$H NMR (300 MHz, CDCl$_{3}$) δ 8.01 (d, J=8.2 Hz, 2H), 7.68 (d, J=8.4 Hz, 2H), 6.97 (d, J=8.3 Hz, 1H), 6.71 (dd, J=8.3, 2.5 Hz, 1H), 6.66 (d, J=2.4 Hz, 1H), 4.63 (s, 2H), 4.52 (s, 2H), 3.40-2.85 (m, 8H), 2.49 (s, 3H); MS (ES) m/z: 477 (M+H$^{+}$).

Example F

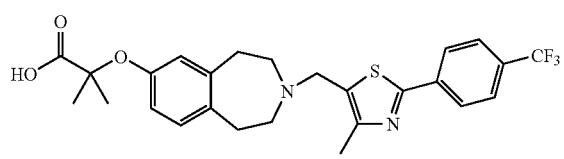

Compound 6: 2-Methyl-2-{3-[4-methyl-2-(4-trifluoromethyl-phenyl)-thiazol-5-ylmethyl]-2,3,4,5-tetrahydro-1H-benzo[d]azepin-7-yloxy}-propionic acid The title compound was made according to Scheme F.

Scheme F

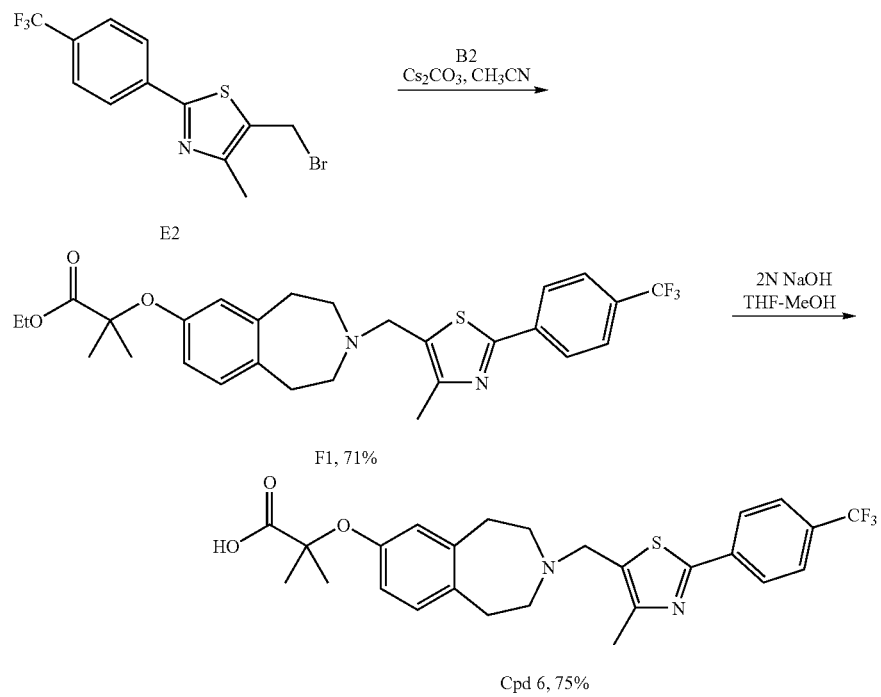

Cpd 5

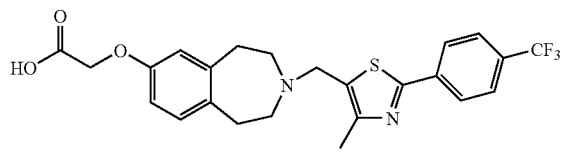

{3-[4-Methyl-2-(4-trifluoromethyl-phenyl)-thiazol-5-ylmethyl]-2,3,4,5-tetrahydro-1H-benzo[d]azepin-7-yloxy}-acetic acid

F1

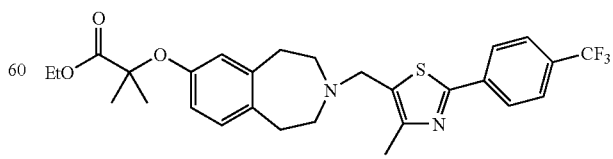

2-Methyl-2-{3-[4-methyl-2-(4-trifluoromethyl-phenyl)-thiazol-5-ylmethyl]-2,3,4,5-tetrahydro-1H-benzo-[d]azepin-7-yloxy}-propionic acid ethyl ester Cpd F1 was prepared using a similar procedure as for cpd B3. Cpd F1 was obtained as a white solid (71%): $^1$H NMR (300 MHz, CDCl$_3$) δ 8.02 (d, J=8.2 Hz, 2H), 7.65 (d, J=8.3 Hz, 2H), 6.93 (d, J=8.2 Hz, 1H), 6.63 (d, J=2.4 Hz, 1H), 6.56 (dd, J=8.1, 2.5 Hz, 1H), 4.23 (q, J=7.1 Hz, 2H), 3.75 (s, 2H), 2.85 (m, 4H), 2.68 (m, 4H), 2.47 (s, 3H), 1.57 (s, 6H), 1.25 (t, J=7.1 Hz, 3H); MS (ES) m/z: 533 (M+H$^+$).

Cpd 6

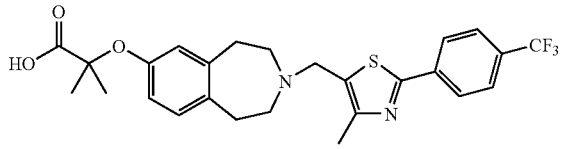

2-Methyl-2-{3-[4-methyl-2-(4-trifluoromethyl-phenyl)-thiazol-5-ylmethyl]-2,3,4,5-tetrahydro-1H-benzo[d]azepin-7-yloxy}-propionic acid Cpd 6 was prepared using a similar procedure as for cpd 2. Cpd 6 was obtained as a white solid (75%): $^1$H NMR (300 MHz, CD$_3$OD) δ 8.13 (d, J=8.2 Hz, 2H), 7.80 (d, J=8.3 Hz, 2H), 7.04 (d, J=8.2 Hz, 1H), 6.75 (d, J=2.4 Hz, 1H), 6.71 (dd, J=8.2, 2.5 Hz, 1H), 4.50 (s, 2H), 3.31-3.24 (m, 4H), 3.01-2.97 (m, 4H), 2.52 (s, 3H), 1.56 (s, 6H); MS (ES) m/z: 505 (M+H$^+$).

Example G

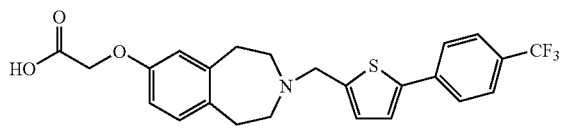

Compound 7: {3-[5-(4-Trifluoromethyl-phenyl)-thiophen-2-ylmethyl]-2,3,4,5-tetrahydro-1H-benzo[d]azepin-7-yloxy}-acetic acid The title compound was made according to Schemes G1 or G2.

Scheme G1

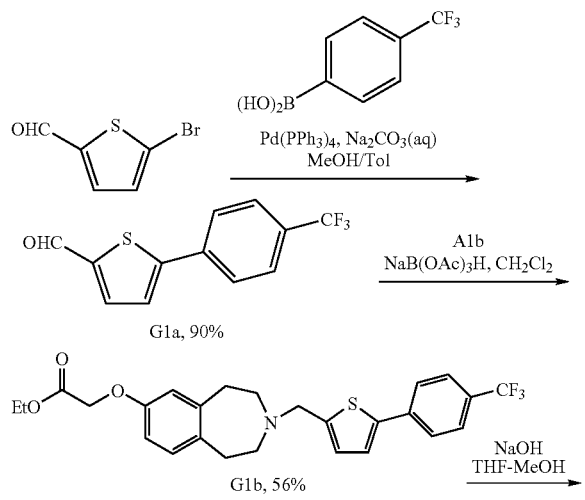

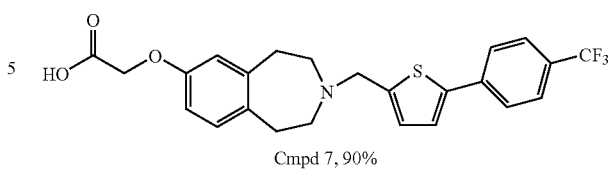

Cmpd 7, 90%

G1a

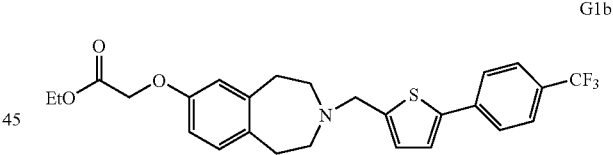

5-(4-Trifluoromethyl-phenyl)-thiophene-2-carbaldehyde

A mixture of 5-bromothiophene-2-carboxyaldehyde (2 g, 10.5 mmol), 4-trifluoromethyl-benzeneboronic acid (2.19 g, 11.5 mmol), Pd(PPh$_4$)$_3$ (605 mg, 0.52 mmol) and 2N Na$_2$CO$_3$ (21 mL, 42 mmol) in toluene/MeOH (30 mL/15 mL) was degassed with N$_2$ and then stirred at 80° C. for 18 h. After cooling to room temperature, the reaction mixture was partitioned between EtOAc and H$_2$O and the aqueous layer was extracted with EtOAc. The combined organic phases were dried (Na$_2$SO$_4$), concentrated and purified by column chromatography to give G1a (2.4 g, 90%) as a white solid: $^1$H NMR (300 MHz, CDCl$_3$) δ 9.92 (s, 1H), 7.79-7.77 (m, 3H), 7.70 (d, J=8.4 Hz, 2H), 7.48 (d, J=3.9 Hz, 1H); MS (ES) m/z: 279 (M+Na$^+$).

G1b

{3-[5-(4-Trifluoromethyl-phenyl)-thiophen-2-ylmethyl]-2,3,4,5-tetrahydro-1H-benzo[d]azepin-7-yloxy}-acetic acid ethyl ester A mixture of A1b (100 mg, 0.401 mmol) and G1a (113 mg, 0.442 mmol) in dichloromethane (4 mL) was stirred at room temperature for 1.5 h. Na(OAc)$_3$BH (170 mg, 0.803 mmol) was added and the resulting mixture was then stirred for 17 h. Saturated NaHCO$_3$ was added and the solution was extracted with CH$_2$Cl$_2$. The combined organic phases were dried (Na$_2$SO$_4$), concentrated and purified by column chromatography to give cpd G1b (110 mg, 56%) as a white solid: $^1$H NMR (300 MHz, CDCl$_3$) δ 7.67 (d, J=8.2 Hz, 2H), 7.60 (d, J=8.3 Hz, 2H), 7.23 (d, J=3.6 Hz, 1H), 6.99 (d, J=8.2 Hz, 1H), 6.89 (d, J=3.6 Hz, 1H), 6.69 (d, J=2.7 Hz, 1H), 6.62 (dd, J=8.2, 2.7 Hz, 1H), 4.58 (s, 2H), 4.26 (q, J=7.1 Hz, 2H), 3.85 (s, 2H), 2.91-2.87 (m, 4H), 2.71-2.67 (m, 4H), 1.29 (t, J=7.1 Hz, 3H); MS (ES) m/z: 490 (M+H$^+$).

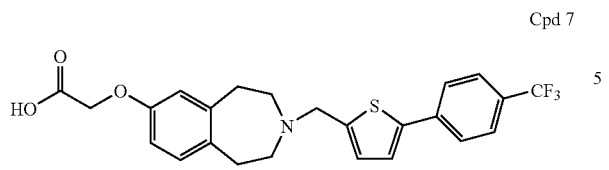

Cpd 7

{3-[5-(4-Trifluoromethyl-phenyl)-thiophen-2-ylmethyl]-2,3,4,5-tetrahydro-1H-benzo[d]azepin-7-yloxy}-acetic acid Cpd 7 was prepared using a similar procedure as for cpd 1. Cpd 7 was obtained as a white solid (90%): $^1$H NMR (300 MHz, CD$_3$OD) δ 7.85 (d, J=8.2 Hz, 2H), 7.72 (d, J=8.4 Hz, 2H), 7.56 (d, J=3.7 Hz, 1H), 7.36 (d, J=3.7 Hz, 1H), 7.10 (d, J=8.2 Hz, 1H), 6.80 (d, J=2.5 Hz, 1H), 6.76 (dd, J=8.2, 2.5 Hz, 1H), 4.63 (s, 2H), 4.58 (s, 2H), 3.35-3.28 (m, 4H), 3.13-3.07 (m, 4H); MS (ES) m/z: 462 (M+H$^+$).

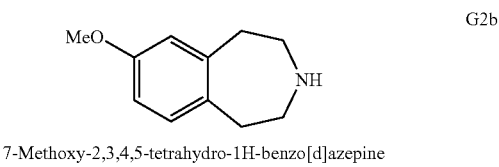

G2b

7-Methoxy-2,3,4,5-tetrahydro-1H-benzo[d]azepine

1 M borane-THF solution (1 mL, 1.02 mmol) was added dropwise to an ice-cooled and stirred solution of A1a (1.91 g, 10 mmol, in THF (50 mL). A1a was prepared according to published procedures (Eur. Pat. Appl. 204349). The ice bath was removed and the solution was heated at reflux for 3 h. Upon cooling back to 0° C., MeOH (2 mL) was added and the reaction mixture was stirred at room temperature for 35 min and concentrated. The white solid residue was treated with 6 N HCl (50 mL) and the mixture was heated at reflux for 1 h

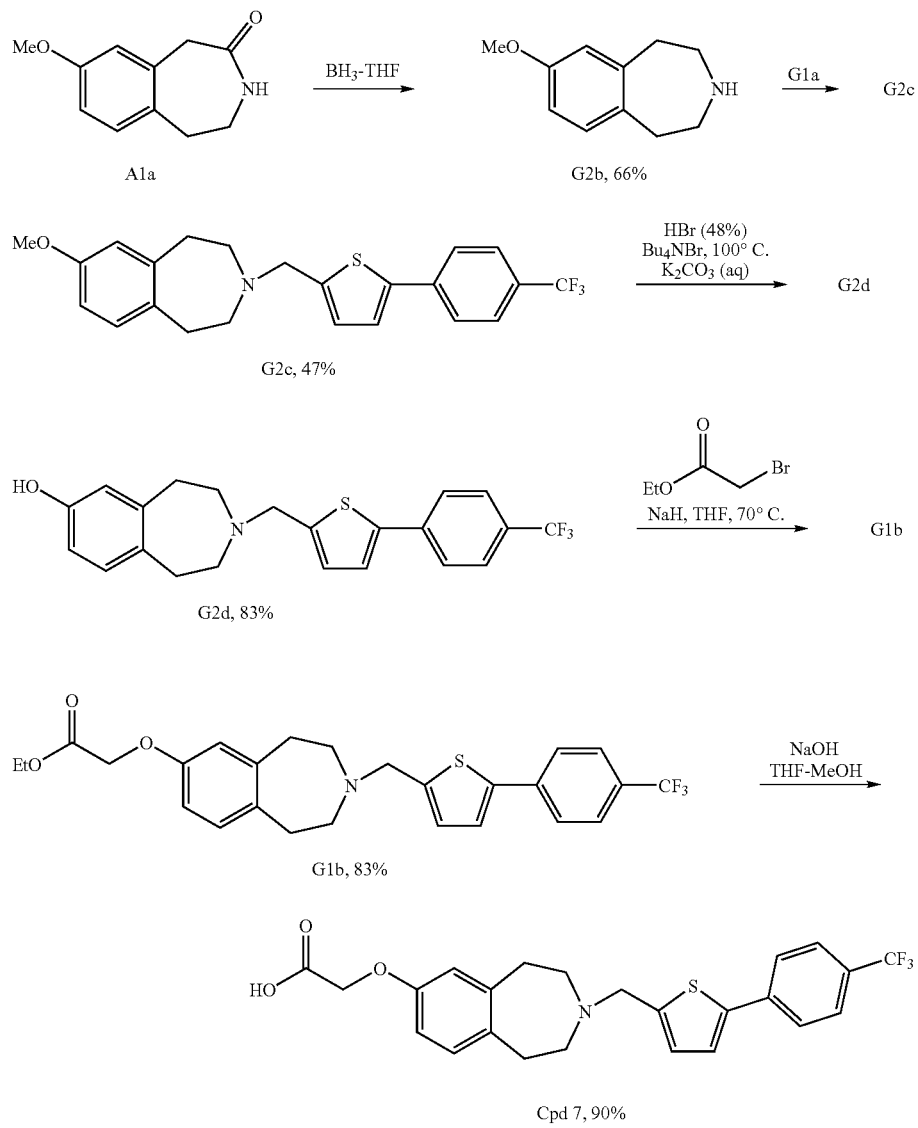

Scheme G2 and then room temperature overnight. The aqueous solution was washed with Et₂O and then basified with 5 N NaOH until pH>10 and extracted with EtOAc. The combined organic phases were washed with brine, dried (Na₂SO₄), concentrated and vacuum dried to give G2b (1.17 g, 66%) as a clear yellow oil: ¹H NMR (300 MHz, CDCl₃) δ 7.01 (d, J=8.1 Hz, 1H), 6.70-6.60 (m, 2H), 3.78 (s, 3H), 3.01-2.83 (m, 8H), 2.34 (br, 1H).

A mixture of G2c (2.21 g, 5.30 mmol), HBr (48%, 6.0 mL, 53.0 mmol) and Bu₄NBr (171 mg, 0.53 mmol) in AcOH (6 mL) was stirred at 100° C. for 16.5 h. Saturated K₂CO₃ was added till pH~10 and the solution extracted with EtOAc. The combined organic phases were dried (Na₂SO₄) and concentrated to give G2d (1.77 g, 83%) as a beige solid: ¹H NMR (400 MHz, CDCl₃) δ 7.66 (d, J=8.4 Hz, 2H), 7.61 (d, J=8.4 Hz, 2H), 7.25 (d, J=3.6 Hz, 1H), 6.97 (d, J=3.3 Hz, 1H), 6.94 (d, J=7.7 Hz, 1H), 6.60-6.57 (m, 2H), 4.01 (s, 2H), 2.94 (m, 4H), 2.82 (m, 4H); MS (ES) m/z: 404 (M+H⁺).

G2c

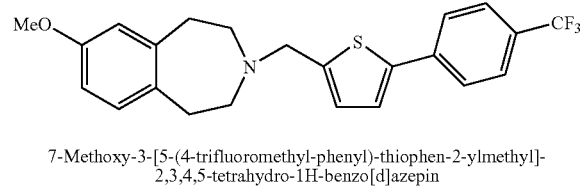

7-Methoxy-3-[5-(4-trifluoromethyl-phenyl)-thiophen-2-ylmethyl]-2,3,4,5-tetrahydro-1H-benzo[d]azepin To a solution of G2b (2.02 g, 11.4 mmol) and G1a (2.92 g, 11.4 mmol) in dichloromethane (50 mL) was added AcOH (0.65 mL, 11.4 mmol). The reaction mixture was stirred for 1.5 h. Na(OAc)₃BH (3.62 g, 17.1 mmol) was added and the reaction mixture was then stirred for another 20 h. 2 N NaOH was added (pH~11) and the solution was extracted with EtOAc. The combined organic phases were dried (Na₂SO₄), concentrated and purified by column chromatography to give G2c (2.23 g, 47%) as a yellow solid: ¹H NMR (300 MHz, CDCl₃) δ 7.68 (d, J=8.2 Hz, 2H), 7.61 (d, J=8.5 Hz, 2H), 7.24 (d, J=3.8 Hz, 1H), 7.01 (d, J=3.8 Hz, 1H), 6.91 (m, 1H), 6.66-6.62 (m, 2H), 3.88 (s, 2H), 3.77 (s, 3H), 2.91 (m, 4H), 2.72 (m, 4H); MS (ES) m/z: 418 (M+H⁺).

G1b

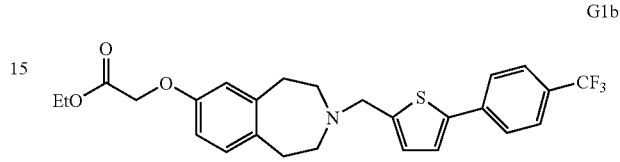

{3-[5-(4-Trifluoromethyl-phenyl)-thiophen-2-ylmethyl]-2,3,4,5-tetrahydro-1H-benzo[d]azepin-7-yloxy}-acetic acid ethyl ester To a solution of NaH (60% in mineral oil, 317 mg, 7.93 mmol) in THF (12 mL) was added G2d (1.07 g, 2.64 mmol) in THF (5 mL) followed by ethyl bromoacetate (0.35 mL, 3.17 mmol). After stirring at reflux for 1 h, the reaction mixture was cooled, quenched with saturated NH₄Cl solution and partitioned between ether and water. The organic phase was dried (Na₂SO₄), concentrated and purified by column chromatography to give G1b (1.02 g, 79%), which was further converted to Compound 7 as described above.

Example H

G2d

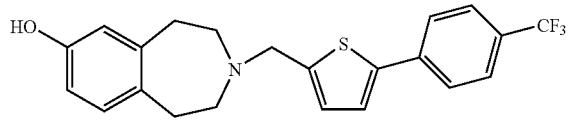

3-[5-(4-Trifluoromethyl-phenyl)-thiophen-2-ylmethyl]-2,3,4,5-tetrahydro-1H-benzo[d]azepin-7-ol

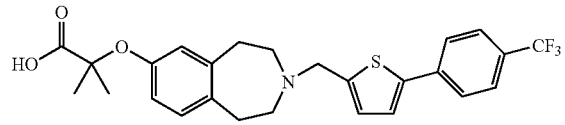

Compound 8: 2-Methyl-2-{3-[5-(4-trifluoromethyl-phenyl)-thiophen-2-ylmethyl]-2,3,4,5-tetrahydro-1H-benzo[d]azepin-7-yloxy}-propionic acid The title compound was made according to Scheme H.

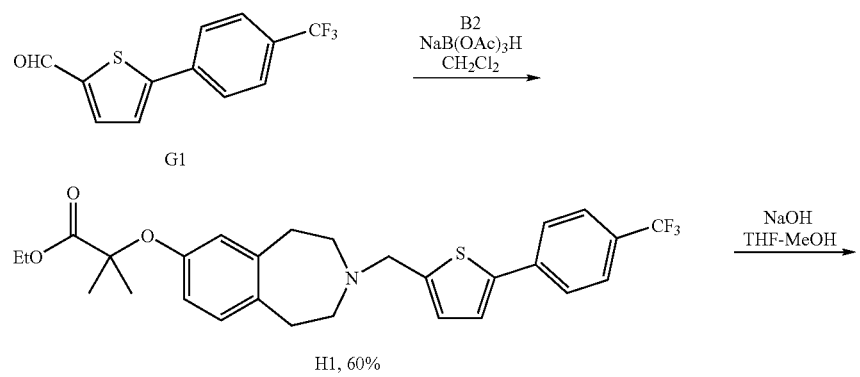

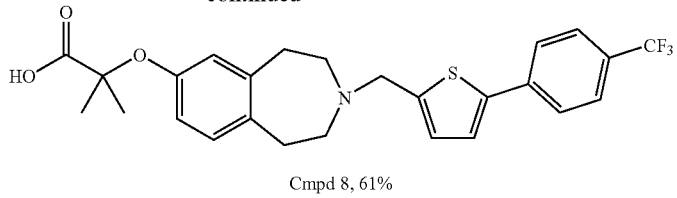

Cmpd 8, 61%

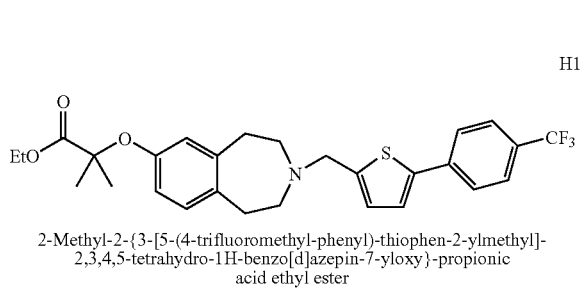

2-Methyl-2-{3-[5-(4-trifluoromethyl-phenyl)-thiophen-2-ylmethyl]-2,3,4,5-tetrahydro-1H-benzo[d]azepin-7-yloxy}-propionic acid ethyl ester Cpd H1 was prepared according to a similar procedure as for cpd G2. Cpd H1 was obtained as a white solid (60%): $^1$H NMR (300 MHz, CDCl$_3$) δ 7.67 (d, J=8.4 Hz, 2H), 7.60 (d, J=8.5 Hz, 2H), 7.24 (d, J=3.6 Hz, 1H), 6.94-6.91 (m, 2H), 6.62 (d, J=2.5 Hz, 1H), 6.55 (dd, J=8.2, 2.6 Hz, 1H), 4.23 (q, J=7.1 Hz, 2H), 3.90 (s, 2H), 2.90 (m, 4H), 2.74 (m, 4H), 1.57 (s, 6H), 1.24 (t, J=7.1 Hz, 3H); MS (ES) m/z: 518 (M+H$^+$).

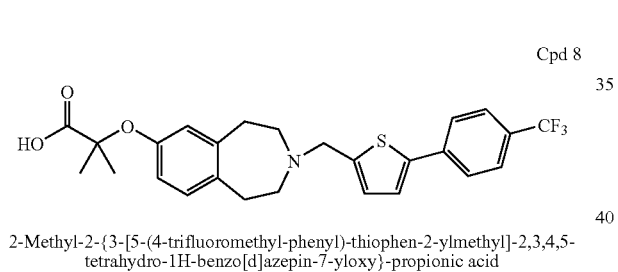

2-Methyl-2-{3-[5-(4-trifluoromethyl-phenyl)-thiophen-2-ylmethyl]-2,3,4,5-tetrahydro-1H-benzo[d]azepin-7-yloxy}-propionic acid Cpd 8 was prepared according to a similar procedure as for cpd 2. Cpd 8 was obtained as a white solid (61%): $^1$H NMR (300 MHz, CD$_3$OD) δ 7.86 (d, J=7.9 Hz, 2H), 7.73 (d, J=8.3 Hz, 2H), 758 (d, J=2.7 Hz, 1H), 7.38 (d, J=3.7 Hz, 1H), 7.11 (d, J=3.7 Hz, 1H), 6.80 (d, J=2.5 Hz, 1H), 6.73 (dd, J=8.2, 2.5 Hz, 1H), 4.68 (s, 2H), 3.21-3.00 (m, 8H), 1.54 (s, 6H); MS (ES) m/z: 490 (M+H$^+$).

Example I

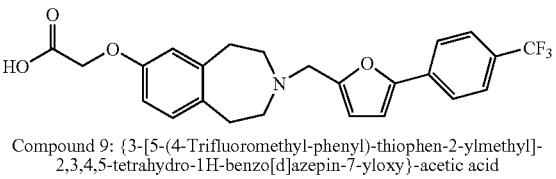

Compound 9: {3-[5-(4-Trifluoromethyl-phenyl)-thiophen-2-ylmethyl]-2,3,4,5-tetrahydro-1H-benzo[d]azepin-7-yloxy}-acetic acid The title compound was made according to Scheme I.

Scheme I

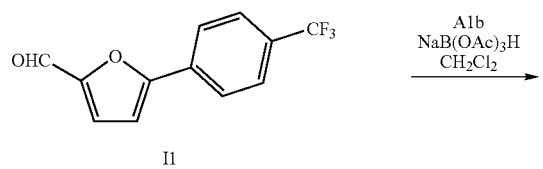

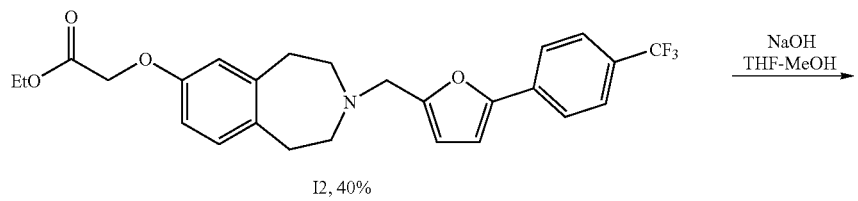

-continued

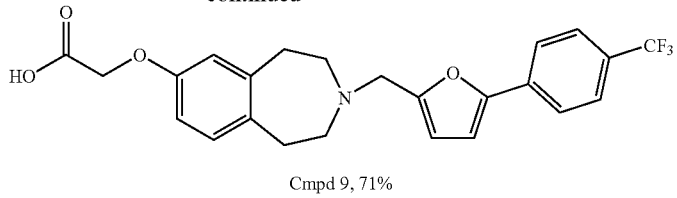

Cmpd 9, 71%

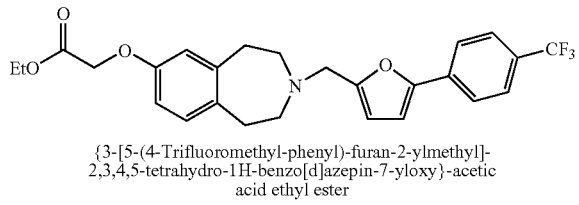

{3-[5-(4-Trifluoromethyl-phenyl)-furan-2-ylmethyl]-2,3,4,5-tetrahydro-1H-benzo[d]azepin-7-yloxy}-acetic acid ethyl ester Cpd I2 was prepared from cpd I1 (*Bioorg. & Med. Chem. Lett.* 2003, 13(13), 2159-2161) using a similar procedure as for cpd G2. Cpd I2 was obtained as a white solid (40%): $^1$H NMR (300 MHz, CDCl$_3$) δ 7.72 (d, J=8.2 Hz, 2H), 7.60 (d, J=8.5 Hz, 2H), 6.98 (d, J=8.2 Hz, 1H), 6.68 (m, 2H), 6.60 (dd, J=8.2, 2.6 Hz, 1H), 6.30 (d, J=3.3 Hz, 1H), 4.56 (s, 2H), 4.26 (q, J=7.1 Hz, 2H), 3.79 (s, 2H), 2.92-2.87 (m, 4H), 2.73-2.67 (m, 4H), 1.28 (t, J=7.1 Hz, 3H); MS (ES) m/z: 474 (M+H$^+$).

Cpd 9

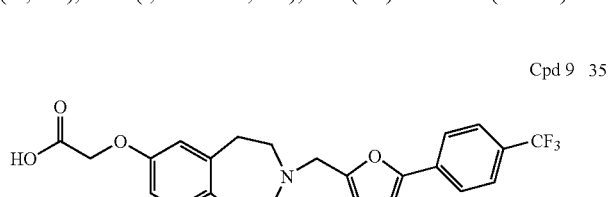

{3-[5-(4-Trifluoromethyl-phenyl)-thiophen-2-ylmethyl]-2,3,4,5-tetrahydro-1H-benzo[d]azepin-7-yloxy}-acetic acid Cpd 9 was prepared according to a similar procedure as for cpd 1. Cpd 9 was obtained as a white solid (71%): $^1$H NMR (300 MHz, CD$_3$OD) δ 7.89 (d, J=8.2 Hz, 2H), 7.69 (d, J=8.3 Hz, 2H), 6.98-6.94 (m, 2H), 6.75-6.69 (m, 3H), 4.44 (s, 2H), 4.33 (s, 2H), 3.14 (m, 4H), 2.82 (m, 4H); MS (ES) m/z: 446 (M+H$^+$).

Example J

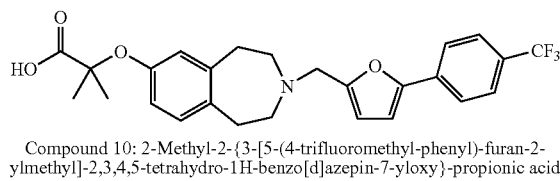

Compound 10: 2-Methyl-2-{3-[5-(4-trifluoromethyl-phenyl)-furan-2-ylmethyl]-2,3,4,5-tetrahydro-1H-benzo[d]azepin-7-yloxy}-propionic acid The title compound was made according to Scheme J.

Scheme J

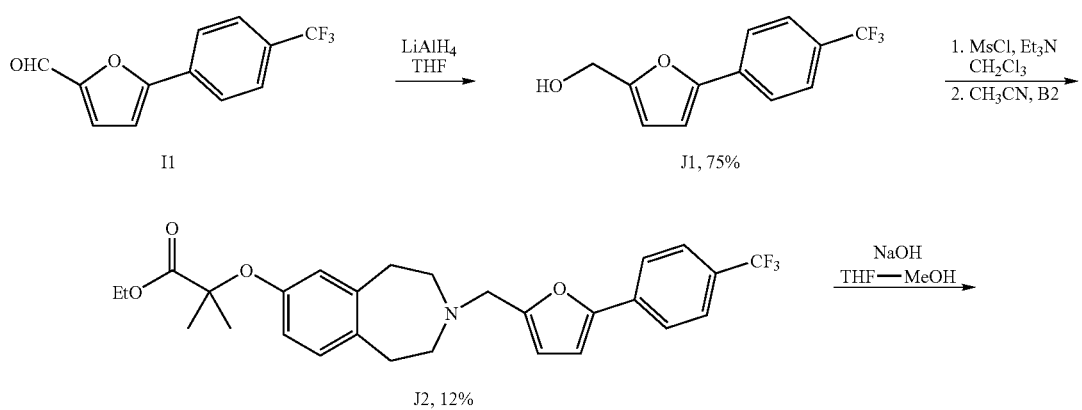

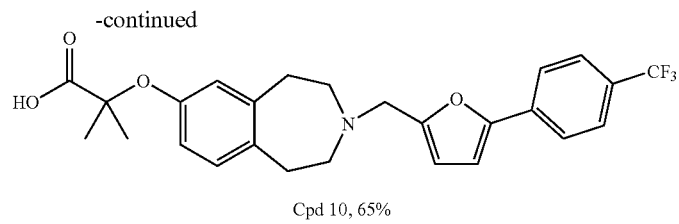

Cpd 10, 65%

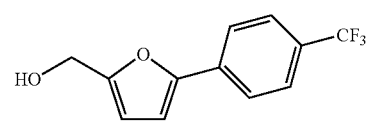

[5-(4-Trifluoromethyl-phenyl)-furan-2-yl]-methanol

Cpd J1 was prepared according to a similar procedure as for cpd E1. Cpd J1 was obtained as a white solid (75%): $^1$H NMR (300 MHz, CDCl$_3$) δ 7.76 (d, J=8.4 Hz, 2H), 7.62 (d, J=8.5 Hz, 2H), 6.73 (d, J=3.3 Hz, 1H), 6.42 (d, J=3.2 Hz, 1H), 4.69 (d, J=5.9 Hz, 2H), 1.75 (t, J=6.0 Hz, 1H); MS (ES) m/z: 225 (M−OH).

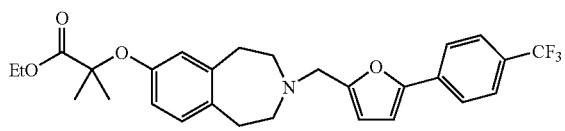

2-Methyl-2-{3-[5-(4-trifluoromethyl-phenyl)-furan-2-ylmethyl]-2,3,4,5-tetrahydro-1H-benzo[d]azepin-7-yloxy}-propionic acid ethyl ester A mixture of J1 (80 mg, 0.33 mmol), methanesulfonyl chloride (38 mg, 0.33 mmol) and triethylamine (230 μL, 1.65 mmol) in CH$_2$Cl$_2$ (2 mL) was stirred at room temperature for 1.5 h. Cpd B2 (50 mg, 0.165 mmol) in CH$_3$CN (1 mL) was added and the solution was stirred overnight under N$_2$. The resulting mixture was concentrated and purified by column chromatography (EtOAc/hexane) to give 10 mg (12%, 2 steps) of J2 as a white solid: $^1$H NMR (300 MHz, CDCl$_3$) δ 7.72 (d, J=8.2 Hz, 2H), 7.60 (d, J=8.4 Hz, 2H), 6.91 (d, J=8.2 Hz, 1H), 6.69 (d, J=3.3 Hz, 1H), 6.61 (d, J=2.3 Hz, 1H), 6.54 (dd, J=8.1, 2.2 Hz, 1H), 6.30 (d, J=3.2 Hz, 1H), 4.21 (q, J=7.1 Hz, 2H), 3.79 (s, 2H), 2.87 (m, 4H), 2.71 (m, 4H), 1.56 (s, 6H), 1.23 (t, J=7.1 Hz, 3H); MS (ES) m/z: 502 (M+H$^+$).

Cpd 10

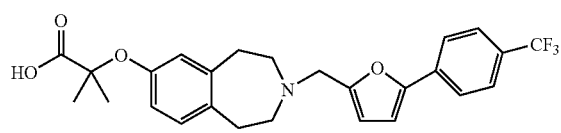

2-Methly-2-{3-[5-(4-trifluoromethyl-phenyl)-furan-2-ylmethyl]-2,3,4,5-tetrahydro-1H-benzo[d]azepin-7-yloxy}-propionic acid Cpd 10 was prepared using a similar procedure as for cpd 2. Cpd 2 was obtained as a white solid (65%): $^1$H NMR (300 MHz, CD$_3$OD) δ 7.94 (d, J=8.1 Hz, 2H), 7.73 (d, J=8.2 Hz, 2H), 7.10-7.05 (m, 2H), 6.87 (d, J=3.2 Hz, 1H), 6.78 (d, J=2.5 Hz, 1H), 6.72 (dd, J=8.1, 2.5 Hz, 1H), 4.54 (s, 2H), 3.40 (m, 4H), 3.11 (m, 4H), 1.54 (s, 6H); MS (ES) m/z: 474 (M+H$^+$).

Example K

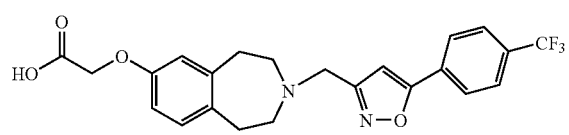

Compound 11: {3-[5-(4-Trifluoromethyl-phenyl)-isoxazol-3-ylmethyl]-2,3,4,5,-tetrahydro-1H-benzo[d]azepin-7-yloxy}-acetic acid The title compound was made according to Schemes K1 and K2.

Scheme K1

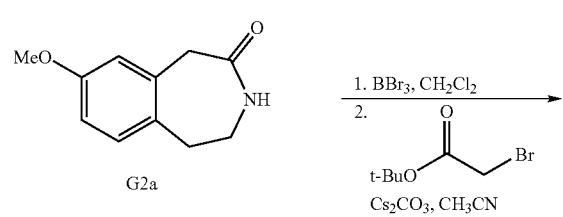

K1a, 28% for 2 steps

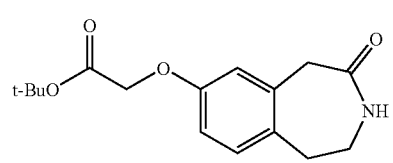

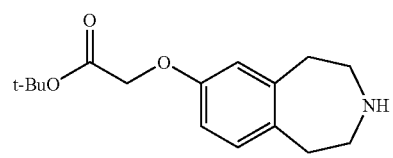

K1b, 52%

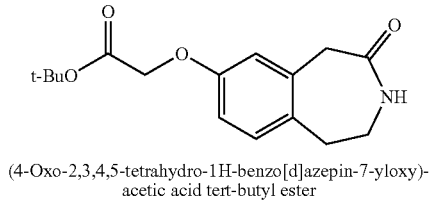

(4-Oxo-2,3,4,5-tetrahydro-1H-benzo[d]azepin-7-yloxy)-acetic acid tert-butyl ester Cpd K1a was prepared according to a similar procedure as for cpd A1b. Cpd K1a was obtained as a white solid (28% over 2 steps): $^1$H NMR (300 MHz, CDCl$_3$) δ 7.03 (d, J=8.4 Hz, 1H), 6.76 (dd, J=8.4, 2.7 Hz, 1H), 6.67 (d, J=2.6 Hz, 1H), 5.79 (brs, 1H), 4.48 (s, 2H), 3.79 (s, 2H), 358-3.52 (m, 2H), 3.06 (t, J=6.6 Hz, 2H), 1.49 (s, 9H); MS (ES) m/z: 314 (M+Na$^+$).

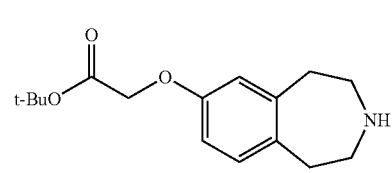

(2,3,4,5,-Tetrahydro-1H-benzo[d]azepin-7-yloxy}-acetic acid tert-butyl ester

Cpd K1b was prepared using a similar procedure as for cpd A1c. Cpd K1b was obtained as a yellow oil (52%): $^1$H NMR (300 MHz, CDCl$_3$) δ 6.98 (d, J=8.3 Hz, 1H), 6.68 (d, J=2.6 Hz, 1H), 6.63 (dd, J=8.2, 2.6 Hz, 1H), 4.48 (s, 2H), 2.93-2.84 (m, 8H), 1.49 (s, 9H); MS (ES) m/z: 278 (M+H$^+$).

Scheme K2

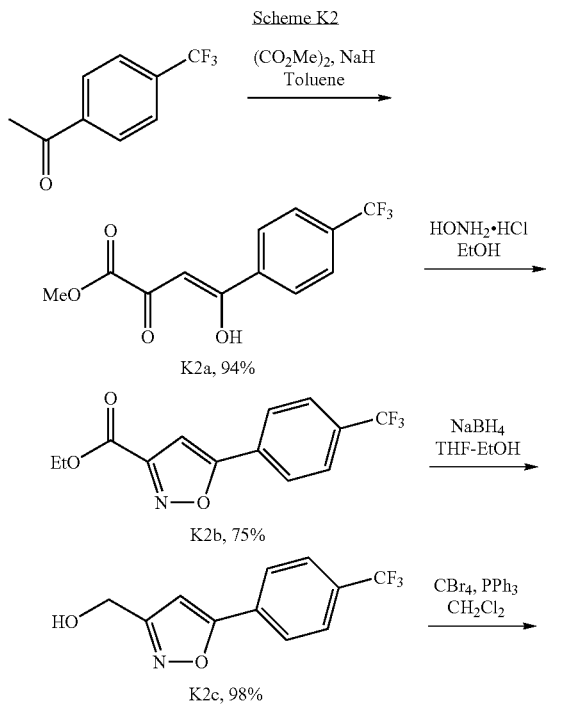

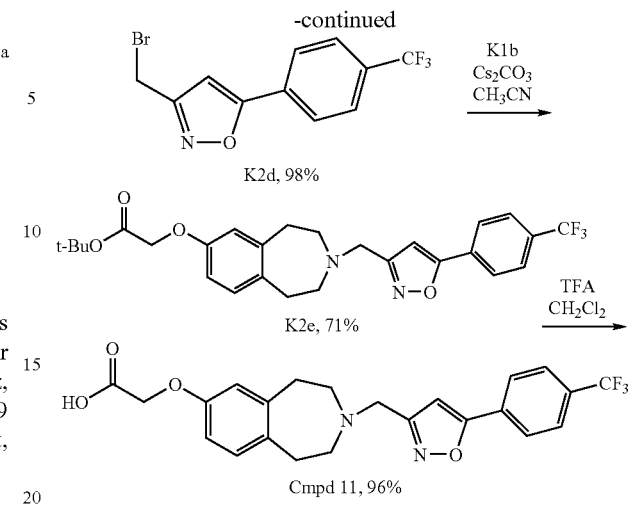

To a solution of 1-(4-trifluoromethyl-phenyl)ethanone (2.0 g, 10.6 mmol) and dimethyl oxylate (1.63 g, 13.8 mmol) in toluene (50 mL) at 0° C. was added NaH portionwise (60%, 636 mg, 15.9 mmol). The mixture was stirred at room temperature for 1 h and then 60° C. for 2 h. After cooling to room temperature, H$_2$O was added slowly to quench the reaction. The mixture was acidified with 1 N HCl and extracted with EtOAc. The combined organic phases were dried (Na$_2$SO$_4$), concentrated and purified by column chromatography to give 2.74 g (94%) of K2a as a white solid: $^1$H NMR (300 MHz, CDCl$_3$) δ 8.11 (d, J=8.3 Hz, 2H), 7.77 (d, J=8.3 Hz, 2H), 7.10 (s, 2H), 3.97 (s, 3H); MS (ES) m/z: 297 (M+Na$^+$).

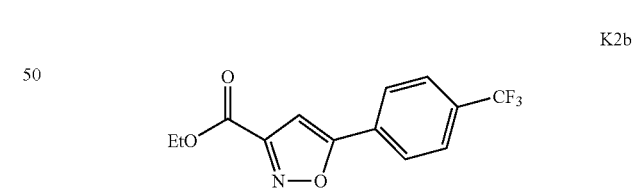

5-(4-Trifluoromethyl-phenyl)-isoxazole-3-carboxylic acid ethyl ester

To a solution of K2a (2.7 g, 9.85 mmol) in EtOH (40 mL) was added hydroxylamine hydrogen chloride (2.05 g, 29.5 mmol). The mixture was stirred at room temperature for 1 h and then 80° C. for 2 h. After cooling to room temperature, the precipitate was filtered and washed with EtOH. The white solid was dried under vacuum to give 2.0 g (75%) of K2b: $^1$H NMR (300 MHz, CDCl$_3$) δ 7.94 (d, J=8.2 Hz, 2H), 7.76 (d, J=8.3 Hz, 2H), 7.03 (s, 1H), 4.49 (d, J=7.1 Hz, 2H), 1.45 (d, J=7.1 Hz, 3H); MS (ES) m/z: 286 (M+H$^+$).

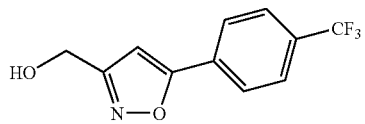

[5-(4-Trifluoromethyl-phenyl)-isoxazole-3-yl]-methanol

Cpd K2c was prepared according to a similar procedure as for cpd C2. Cpd K2c was obtained as a white solid (98%): $^1$H NMR (300 MHz, CDCl$_3$) δ 7.90 (d, J=8.2 Hz, 2H), 7.73 (d, J=8.5 Hz, 2H), 6.70 (s, 1H), 4.84 (s, 2H); MS (ES) m/z: 244 (M+H$^+$).

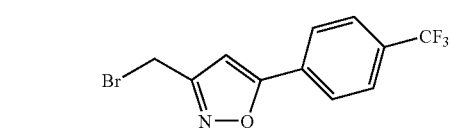

3-Bromomethyl-5-(4-trifluoromethyl-phenyl)-isoxazole

Cpd K2d was prepared according to a similar procedure as for cpd A2d. Cpd K2d was obtained as a white solid (98%); $^1$H NMR (300 MHz, CDCl$_3$) δ 7.91 (d, J=8.3 Hz, 2H), 7.75 (d, J=8.3 Hz, 2H), 6.73 (s, 2H), 4.49 (s, 2H); MS (ES) m/z: 306 (M+H$^+$).

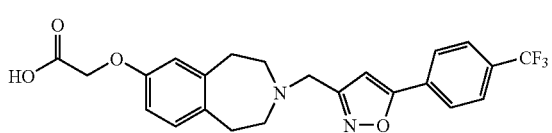

{3-[5-(4-Trifluoromethyl-phenyl)-isoxazol-3-ylmethyl]-2,3,4,5-tetrahydro-1H-benzo[d]azepin-7-yloxy}-acetic acid tert-butyl ester Cpd K2e was prepared according to a similar procedure as for cpd A2e. Cpd K2e was obtained as a white solid (71%): $^1$H NMR (300 MHz, CDCl$_3$) δ 7.90 (d, J=8.4 Hz, 2H), 7.72 (d, J=8.4 Hz, 2H), 6.98 (d, J=8.2 Hz, 1H), 6.69 (s, 1H), 6.68 (d, J=2.6 Hz, 1H), 6.61 (dd, J=8.2, 2.6 Hz, 1H), 4.47 (s, 2H), 3.79 (s, 2H), 2.90-2.86 (m, 4H), 2.72-2.67 (m, 4H), 1.48 (s, 9H); MS (ES) m/z: 503 (M+H$^+$).

Cmpd 11

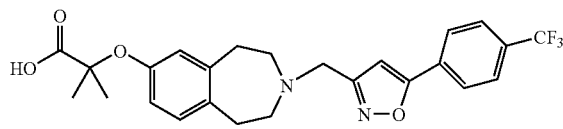

{3-[5-(4-Trifluoromethyl-phenyl)-isoxazol-3-ylmethyl]-2,3,4,5-tetrahydro-1H-benzo[d]azepin-7-yloxy}-acetic acid To a solution of K2e (38.5 mg, 0.076 mmol) in CH$_2$Cl$_2$ (1 mL) was added trifluoroacetic acid (0.1 mL). The mixture was stirred at room temperature for 15 h, concentrated and purified by column chromatography to give 30 mg (96%) of compound 11 as a white solid: $^1$H NMR (300 MHz, CD$_3$OD) δ 8.08 (d, J=8.2 Hz, 2H), 7.86 (d, J=8.3 Hz, 2H), 7.17-7.13 (m, 2H), 6.85 (d, J=2.5 Hz, 1H), 6.78 (dd, J=8.2, 2.6 Hz, 1H), 4.64 (s, 4H), 3.5 (m, 4H), 3.18 (m, 4H); MS (ES) m/z: 447 (M+H$^+$).

Example L

Compound 12: 2-Methyl-2-{3-[5-(4-trifluoromethyl-phenyl)-isoxazol-3-ylmethyl]-2,3,4,5,-tetrahydro-1H-benzo[d]azepin-7-yloxy}-propionic acid The title compound was made according to Scheme L.

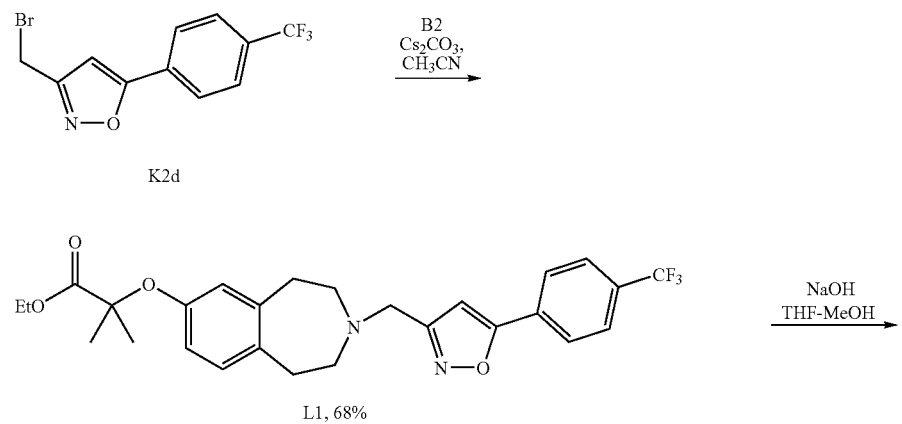

Scheme L

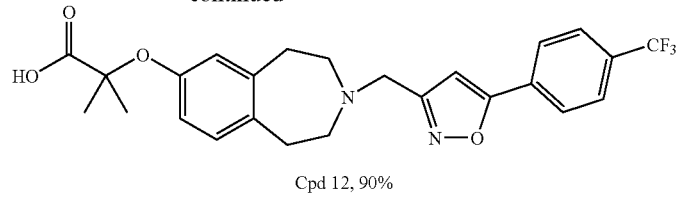

Cpd 12, 90%

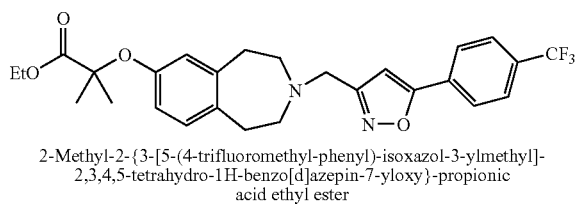

L1

2-Methyl-2-{3-[5-(4-trifluoromethyl-phenyl)-isoxazol-3-ylmethyl]-2,3,4,5-tetrahydro-1H-benzo[d]azepin-7-yloxy}-propionic acid ethyl ester Cpd L1 was prepared following the same procedure as for cpd B3. Cpd L1 was obtained as a white solid (68%): $^1$H NMR (300 MHz, CDCl$_3$) δ 7.90 (d, J=8.3 Hz, 2H), 7.72 (d, J=8.4 Hz, 2H), 6.93 (d, J=8.2 Hz, 1H), 6.71 (s, 1H), 6.63 (d, J=2.5 Hz, 1H), 6.55 (dd, J=8.1, 2.6 Hz, 1H), 4.23 (q, J=7.1 Hz, 2H), 3.81 (s, 2H), 2.88-2.86 (m, 4H), 2.73-2.70 (m, 4H), 1.57 (s, 6H), 1.25 (t, J=7.1 Hz, 3H); MS (ES) m/z: 503 (M+H$^+$).

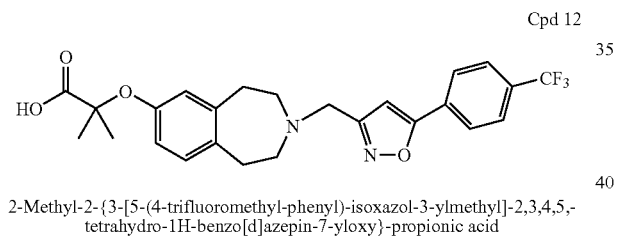

Cpd 12

2-Methyl-2-{3-[5-(4-trifluoromethyl-phenyl)-isoxazol-3-ylmethyl]-2,3,4,5,-tetrahydro-1H-benzo[d]azepin-7-yloxy}-propionic acid Cpd 12 was prepared following the same procedure as for cpd 2. Cpd 12 was obtained as a white solid 90%): $^1$H NMR (300 MHz, CD$_3$OD) δ 8.08 (d, J=8.0 Hz, 2H), 7.86 (d, J=8.4 Hz, 2H), 7.16 (s, 1H), 7.11 (d, J=8.3 Hz, 1H), 6.80 (d, J=2.5 Hz, 1H), 6.73 (dd, J=8.2, 2.6 Hz, 1H), 4.62 (s, 2H), 3.54 (m, 4H), 3.16 (m, 4H), 1.55 (s, 6H); MS (ES) m/z: 475 (M+H$^+$).

Example M

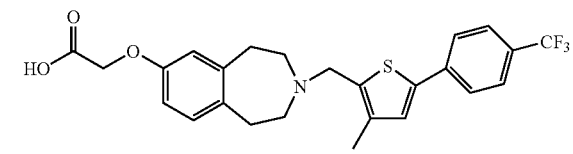

Compound 13: {3-[3-Methyl-5-(4-trifluoromethyl-phenyl)-thiophen-2-ylmethyl]-2,3,4,5,-tetrahydro-1H-benzo[d]azepin-7-yloxy}-acetic acid The title compound was made according to Scheme M.

Scheme M

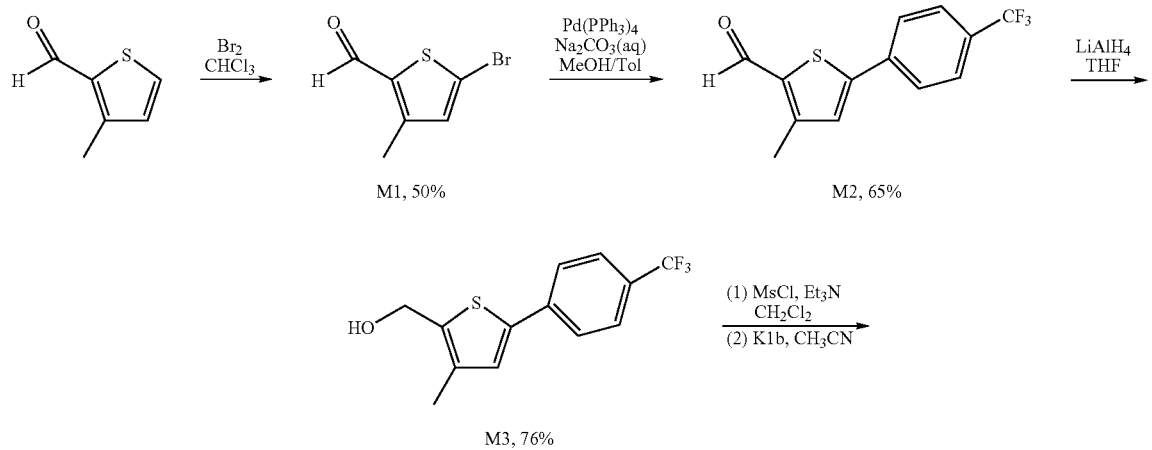

-continued

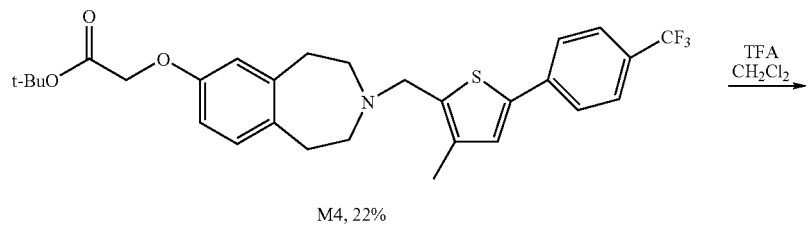

M4, 22%

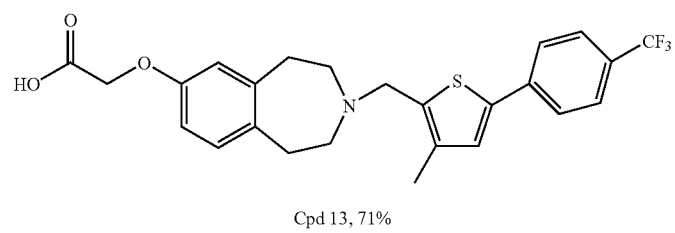

Cpd 13, 71%

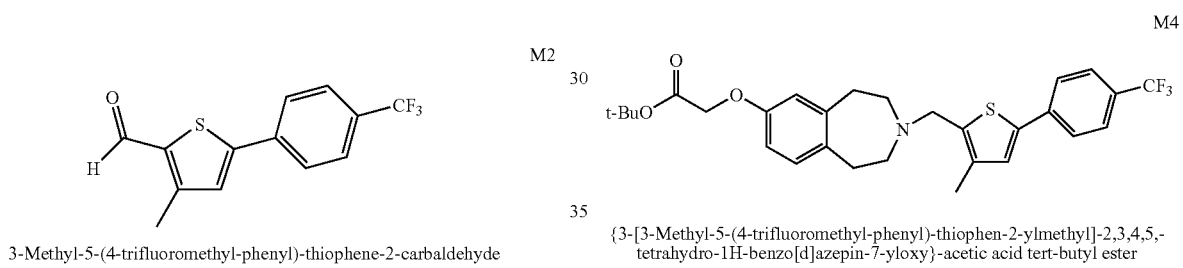

[3-Methyl-5-(4-trifluoromethyl-phenyl)-thiophene-2-carbaldehyde]       {3-[3-Methyl-5-(4-trifluoromethyl-phenyl)-thiophen-2-ylmethyl]-2,3,4,5,-tetrahydro-1H-benzo[d]azepin-7-yloxy}-acetic acid tert-butyl ester Cpd M2 was prepared from cpd M1 (*J. Chem. Soc.*, Perkin Trans 2, 1972, 1866) following the same procedure as for cpd G1a. Cpd M2 was obtained as a white crystalline solid (65%): $^1$H NMR (300 MHz, CDCl$_3$) δ 10.05 (s, 1H), 7.75 (d, J=8.5 Hz, 2H), 7.67 (d, J=8.5 Hz, 2H), 7.26 (s, 1H), 2.61 (s, 3H); MS (ES) m/z: 293 (M+Na$^+$).

Cpd M4 was prepared following the same procedure as for cpd J2. Cpd M4 was obtained as a white solid (22%): $^1$H NMR (300 MHz, CDCl$_3$) δ 7.65 (d, J=8.2 Hz, 2H), 7.58 (d, J=8.4 Hz, 2H), 7.11 (s, 1H) 6.99 (d, J=8.2 Hz, 1H), 6.68 (d, J=2.6 Hz, 1H), 6.61 (dd, J=8.2, 2.7 Hz, 1H), 4.48 (s, 2H), 3.74 (s, 2H), 2.88 (m, 4H), 2.69 (m, 4H), 2.20 (s, 3H), 1.48 (s, 9H); MS (ES) m/z: 532 (M+H$^+$).

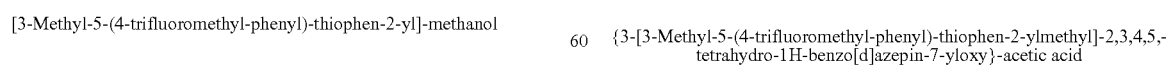

[3-Methyl-5-(4-trifluoromethyl-phenyl)-thiophen-2-yl]-methanol       {3-[3-Methyl-5-(4-trifluoromethyl-phenyl)-thiophen-2-ylmethyl]-2,3,4,5,-tetrahydro-1H-benzo[d]azepin-7-yloxy}-acetic acid Cpd M3 was prepared according to the same procedure as for cpd E1. Cpd M3 was obtained as a white solid (76%): $^1$H NMR (300 MHz, CDCl$_3$) δ 7.65 (d, J=8.6 Hz, 2H), 7.60 (d, J=8.5 Hz, 2H), 7.14 (s, 1H), 4.79 (s, 2H), 2.27 (s, 3H), 1.68 (brs, 1H); MS (ES) m/z: 255 (M−OH).

Cpd 13 was prepared following the same procedure as for cpd 11. Cpd 13 was obtained as a white solid (71%): $^1$H NMR (300 MHz, CD$_3$OD) δ 7.79 (d, J=8.2 Hz, 2H), 7.67 (d, J=8.4 Hz, 2H), 7.36 (s, 1H), 6.98 (d, J=9.0 Hz, 1H), 6.73-6.70 (m, 2H), 4.45 (s, 2H), 4.36 (s, 2H), 3.17 (m, 4H), 2.84 (m, 4H), 2.29 (s, 3H); MS (ES) m/z: 476 (M+H$^+$).

Example N

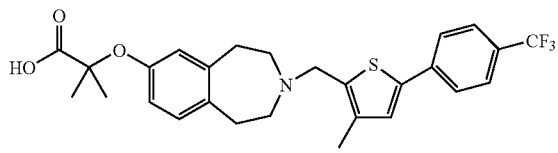

Compound 14: 2-Methyl-2-{3-[3-methyl-5-(4-trifluoromethyl-phenyl)-thiophen-2-ylmethyl]-2,3,4,5,-tetrahydro-1H-benzo[d]azepin-7-yloxy}-propionic acid The title compound was made according to Scheme N.

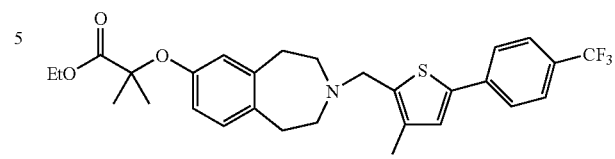

2-Methyl-2-{3-[3-methyl-5-(4-trifluoromethyl-phenyl)-thiophen-2-ylmethyl]-2,3,4,5-tetrahydro-1H-benzo[d]azepin-7-yloxy}-propionic acid ethyl ester Cpd N1 was prepared following the same procedure as for cpd M4. Cpd N1 was obtained as a white solid (17%): $^1$H NMR (300 MHz, CDCl$_3$) δ 7.65 (d, J=8.2 Hz, 2H), 7.59 (d, J=8.3 Hz, 2H), 7.10 (s, 1H), 6.92 (d, J=8.2 Hz, 1H), 6.62 (d, J=2.6 Hz, 1H), 6.55 (dd, J=8.2, 2.7 Hz, 1H), 4.22 (q, J=7.1 Hz, 2H), 3.72 (s, 2H), 2.86 (m, 4H), 2.70 (m, 4H), 2.20 (s, 3H), 1.58 (s, 6H), 1.25 (t, J=7.1 Hz, 3H); MS (ES) m/z: 532 (M+H$^+$).

Scheme N

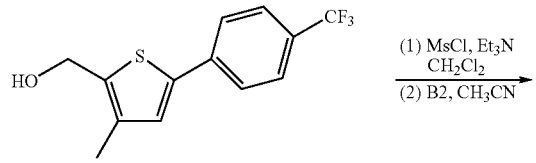

M3

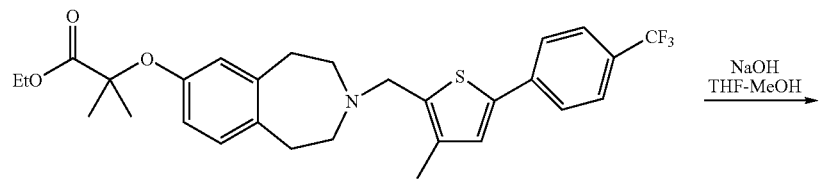

N1, 17%

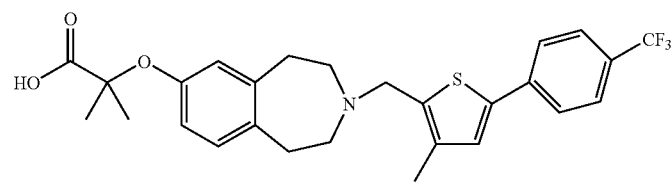

Cpd 14, 80%

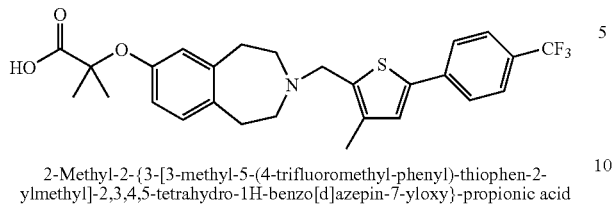

2-Methyl-2-{3-[3-methyl-5-(4-trifluoromethyl-phenyl)-thiophen-2-ylmethyl]-2,3,4,5-tetrahydro-1H-benzo[d]azepin-7-yloxy}-propionic acid Cpd 14 was prepared following the same procedure as for cpd 2. Cpd 14 was obtained as a white solid (80%): $^1$H NMR (300 MHz, CD$_3$OD) δ 7.84 (d, J=8.2 Hz, 2H), 7.71 (d, J=8.3 Hz, 2H), 7.45 (s, 1H), 7.11 (d, J=8.3 Hz, 1H), 6.80 (d, J=2.5 Hz, 1H), 6.74 (dd, J=8.2, 2.6 Hz, 1H), 4.60 (s, 2H), 3.29 (m, 4H), 3.13 (m, 4H), 2.35 (s, 3H), 1.55 (s, 6H); MS (ES) m/z: 504 (M+H$^+$).

Example O

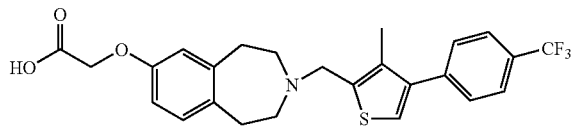

Compound 15: {3-[3-Methyl-4-(4-trifluoromethyl-phenyl)-thiophen-2-ylmethyl]-2,3,4,5-tetrahydro-1H-benzo[d]azepin-7-yloxy}-acetic acid The title compound was made according to Scheme O.

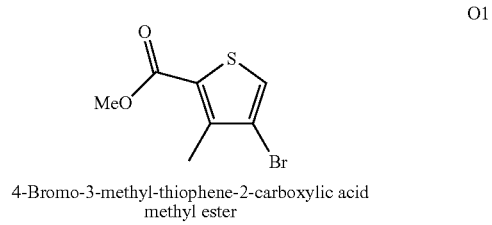

4-Bromo-3-methyl-thiophene-2-carboxylic acid methyl ester

To a solution of 3-methylthiophene-2-carboxylic acid methyl ester (2.0 g, 12.8 mmol) in CH$_2$Cl$_2$ (10 mL) and acetic acid (10 mL) was added Br$_2$ (0.79 mL, 15.3 mmol). The mixture was stirred at room temperature for 20 h and then partitioned between CH$_2$Cl$_2$ and H$_2$O. The aqueous layer was extracted with CH$_2$Cl$_2$. The combined organic phases were washed with saturated sodium thiosulfate solution, dried (Na$_2$SO$_4$), concentrated and purified by column chromatography to give 1.4 g (46%) of O1 as a white solid: $^1$H NMR (300 MHz, CD$_3$OD) δ 7.41 (s, 1H), 3.88 (s, 3H), 2.52 (s, 3H).

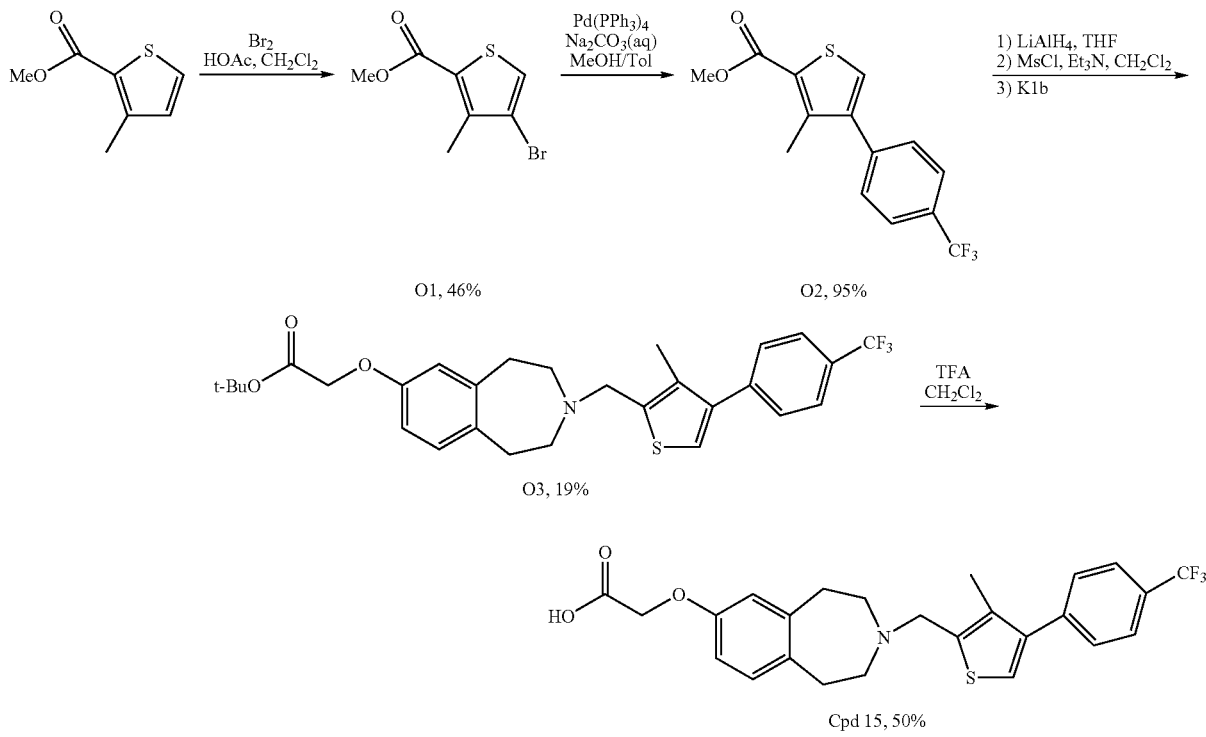

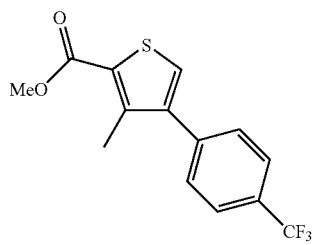

3-Methyl-4-(4-trifluoromethyl-phenyl)-thiophene-2-carboxylic acid methyl ester

Cpd O2 was prepared following the same procedure as for cpd G1. Cpd O2 was obtained as a white solid (95%): $^1$H NMR (300 MHz, CDCl$_3$) δ 7.71 (d, J=8.2 Hz, 2H), 7.65 (d, J=8.2 Hz, 2H), 7.40 (s, 1H), 3.90 (s, 3H), 2.51 (s, 3H).

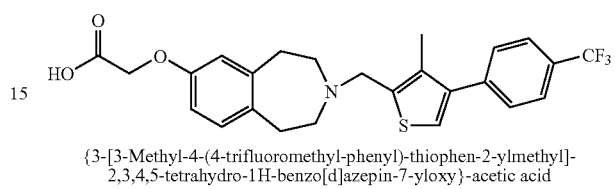

{3-[3-Methyl-4-(4-trifluoromethyl-phenyl)-thiophen-2-ylmethyl]-2,3,4,5-tetrahydro-1H-benzo[d]azepin-7-yloxy}-acetic acid tert-butyl ester To the solution of O2 (590 mg, 2.0 mmol) in THF (10 mL) at 0° C. was added 1.0 M LiAlH$_4$ (2.16 mL, 2.16 mmol) in THF. The mixture was allowed to warm up to room temperature and stirred at room temperature for 1 h. Water was slowly added and the precipitated solid was filtered and rinsed with CH$_2$Cl$_2$. The filtrate was washed with saturated NH$_4$Cl and the aqueous solution was back extracted with CH$_2$Cl$_2$. The combined organic phases were dried (Na$_2$SO$_4$) and concentrated to give a crude solid. It was used to carry through a similar procedure as for preparing cpd J2 and gave compound O3 as a white solid (19%): $^1$H NMR (300 MHz, CDCl$_3$) δ 7.65 (d, J=8.2 Hz, 2H), 7.47 (d, J=8.2 Hz, 2H), 7.16 (s, 1H), 6.99 (d, J=8.2 Hz, 1H), 6.69 (d, J=2.5 Hz, 1H), 6.61 (dd, J=8.1, 2.4 Hz, 1H), 4.48 (s, 2H), 3.81 (s, 2H), 2.90 (m, 4H), 2.73 (m, 4H), 2.15 (s, 3H), 1.48 (s, 9H); MS (ES) m/z: 532 (M+H$^+$).

Cpd 15

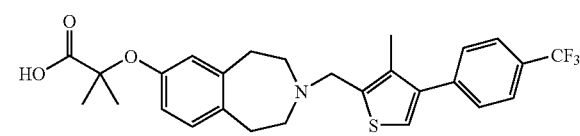

{3-[3-Methyl-4-(4-trifluoromethyl-phenyl)-thiophen-2-ylmethyl]-2,3,4,5-tetrahydro-1H-benzo[d]azepin-7-yloxy}-acetic acid Cpd 15 was prepared following the same procedure as for cpd 11. Cpd 15 was obtained as a white solid (50%): $^1$H NMR (300 MHz, CD$_3$OD) δ 7.71 (d, J=8.3 Hz, 2H), 7.57 (d, J=8.1 Hz, 2H), 7.46 (s, 1H), 6.97 (d, J=8.9 Hz, 1H), 6.72-6.67 (m, 2H), 4.40 (s, 2H), 4.22 (s, 2H), 3.01 (m, 4H), 2.84 (m, 4H), 2.21 (s, 3H), MS (ES) m/z: 476 (M+H$^+$).

Example P

Compound 16: 2-Methyl-2-{3-[3-methyl-4-(4-trifluoromethyl-phenyl)-thiophen-2-ylmethyl]-2,3,4,5-tetrahydro-1H-benzo[d]azepin-7-yloxy}-propionic acid The title compound was made according to Scheme P.

Scheme P

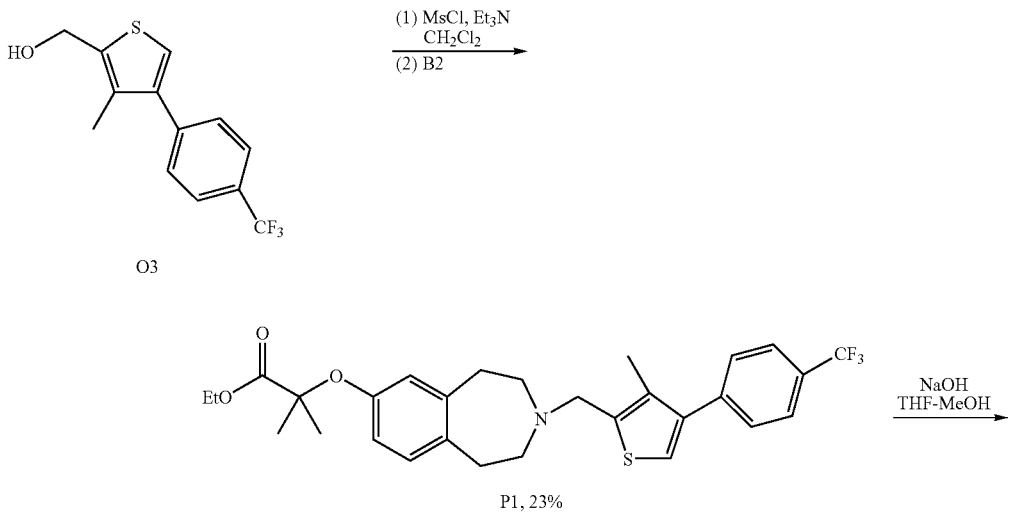

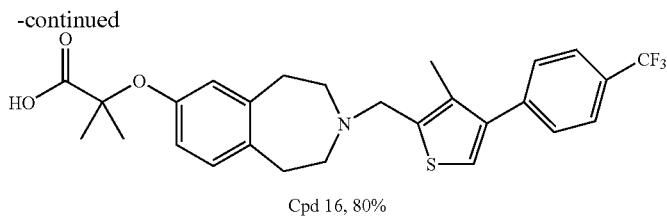

Cpd 16, 80%

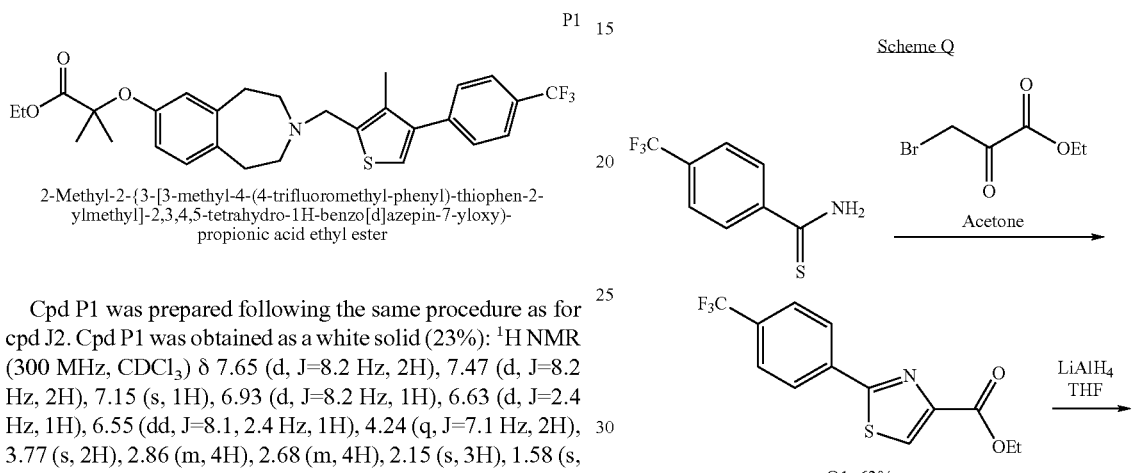

P1

2-Methyl-2-{3-[3-methyl-4-(4-trifluoromethyl-phenyl)-thiophen-2-ylmethyl]-2,3,4,5-tetrahydro-1H-benzo[d]azepin-7-yloxy)-propionic acid ethyl ester Cpd P1 was prepared following the same procedure as for cpd J2. Cpd P1 was obtained as a white solid (23%): $^1$H NMR (300 MHz, CDCl$_3$) δ 7.65 (d, J=8.2 Hz, 2H), 7.47 (d, J=8.2 Hz, 2H), 7.15 (s, 1H), 6.93 (d, J=8.2 Hz, 1H), 6.63 (d, J=2.4 Hz, 1H), 6.55 (dd, J=8.1, 2.4 Hz, 1H), 4.24 (q, J=7.1 Hz, 2H), 3.77 (s, 2H), 2.86 (m, 4H), 2.68 (m, 4H), 2.15 (s, 3H), 1.58 (s, 6H), 1.25 (t, J=7.1 Hz, 3H); MS (ES) m/z: 532 (M+H$^+$).

Cpd 16

2-Methyl-2-{3-[3-methyl-4-(4-trifluoromethyl-phenyl)-thiophen-2-ylmethyl]-2,3,4,5-tetrahydro-1H-benzo[d]azepin-7-yloxy}-propionic acid Cpd 16 was prepared following the same procedure as for cpd 2. Cpd 16 was obtained as a white solid (80%): $^1$H NMR (300 MHz, CD$_3$OD) δ 7.73 (d, J=8.2 Hz, 2H), 7.72-7.56 (m, 3H), 6.98 (d, J=8.2 Hz, 1H), 6.73-6.68 (m, 2H), 4.47 (s, 2H), 3.30-3.12 (m, 4H), 2.95-2.89 (m, 4H), 2.24 (s, 3H), 1.57 (s, 6H); MS (ES) m/z: 504 (M+H$^+$).

Example Q

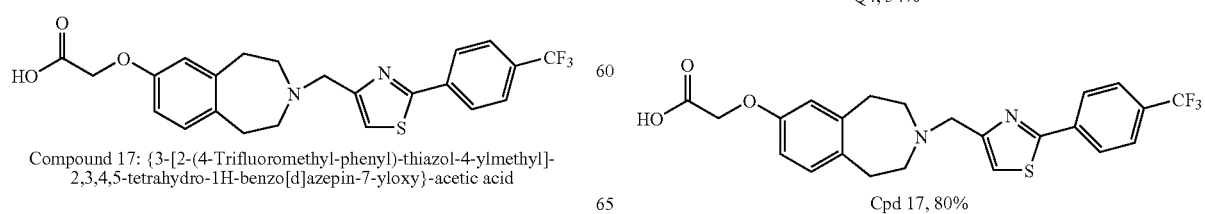

Compound 17: {3-[2-(4-Trifluoromethyl-phenyl)-thiazol-4-ylmethyl]-2,3,4,5-tetrahydro-1H-benzo[d]azepin-7-yloxy}-acetic acid The title compound was made according to Scheme Q.

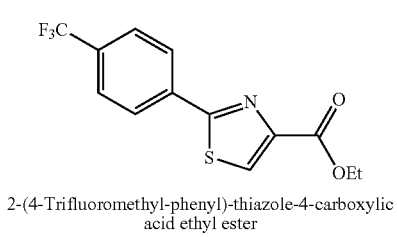

Q1

2-(4-Trifluoromethyl-phenyl)-thiazole-4-carboxylic acid ethyl ester

To a stirred solution of 4-trifluoromethylthiobenzamide (205 g, 10 mmol) in acetone (10 mL) was added ethyl bromopyruvate (1.95 g, 10 mmol) in acetone (10 mL) dropwise. The mixture was stirred under reflux for 3 h. After cooling to room temperature, the solution was concentrated and purified by column chromatography to give 1.9 g (63%) of cpd Q1 as a white solid: $^1$H NMR (300 MHz, CDCl$_3$) δ 8.23 (s, 1H), 8.14 (d, J=8.4 Hz, 2H), 7.72 (d, J=8.4 Hz, 2H), 4.46 (q, J=7.1 Hz, 2H) 1.44 (t, J=7.1 Hz, 3H); MS (ES) m/z: 302 (M+H$^+$).

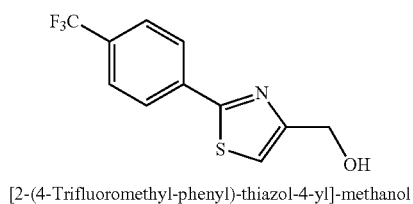

Q2

[2-(4-Trifluoromethyl-phenyl)-thiazol-4-yl]-methanol

Cpd Q2 was prepared following the same procedure as for cpd E1. Cpd Q2 was obtained as a white solid (51%): $^1$H NMR (300 MHz, CDCl$_3$) δ 8.07 (d, J=8.1 Hz, 2H), 7.70 (d, J=8.2 Hz, 2H), 7.27 (s, 1H), 4.86 (d, J=6.0 Hz, 2H), 2.21 (t, J=6.0 Hz, 1H); MS (ES) m/z: 260 (M+H$^+$).

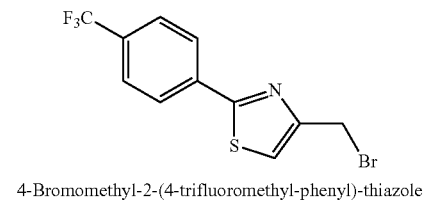

Q3

4-Bromomethyl-2-(4-trifluoromethyl-phenyl)-thiazole

Cpd Q3 was prepared following the same procedure as for cpd A2d. Cpd Q3 was obtained as a white solid (89%): $^1$H NMR (300 MHz, CDCl$_3$) δ 8.07 (d, J=8.1 Hz, 2H), 7.70 (d, J=8.2 Hz, 2H), 7.38 (s, 1H), 4.64 (s, 2H).

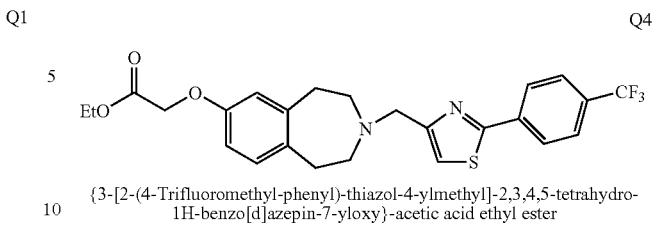

Q4

{3-[2-(4-Trifluoromethyl-phenyl)-thiazol-4-ylmethyl]-2,3,4,5-tetrahydro-1H-benzo[d]azepin-7-yloxy}-acetic acid ethyl ester Cpd Q4 was prepared following the same procedure as for cpd A2e. Cpd Q4 was obtained as a white solid (54%): $^1$H NMR (300 MHz, CDCl$_3$) δ 8.05 (d, J=8.2 Hz, 2H), 7.68 (d, J=8.3 Hz, 2H), 7.25 (s, 1H), 6.99 (d, J=8.2 Hz, 1H), 6.70 (d, J=2.6 Hz, 1H), 6.61 (dd, J=8.2, 2.6 Hz, 1H), 4.58 (s, 2H), 4.26 (q, J=7.1 Hz, 2H), 3.91 (s, 2H), 2.94-2.88 (m, 4H), 2.79-2.71 (m, 4H), 1.29 (t, J=7.1 Hz, 3H); MS (ES) m/z: 491 (M+H$^+$).

Cmpd 17

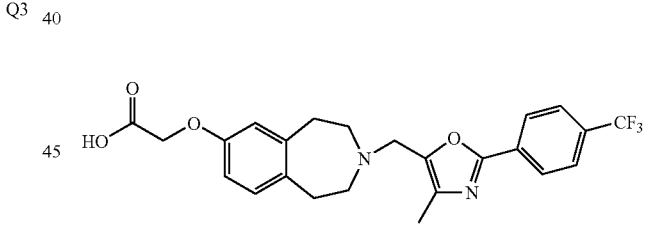

{3-[2-(4-Trifluoromethyl-phenyl)-thiazol-4-ylmethyl]-2,3,4,5-tetrahydro-1H-benzo[d]azepin-7-yloxy}-acetic acid Cpd 17 was prepared following the same procedure as for cpd A2e. Cpd 17 was obtained as a white solid (80%): $^1$H NMR (300 MHz, CD$_3$OD) δ 8.15 (d, J=8.2 Hz, 2H), 7.81 (s, 1H), 7.77 (d, J=8.3 Hz, 2H), 6.96 (d, J=9.0 Hz, 1H), 6.71-6.68 (m, 2H), 4.41 (s, 2H), 4.33 (s, 2. H), 3.14 (m, 4H), 2.84 (m, 4H); MS (ES) m/z: 463 (M+H$^+$).

Example R

Compound 18: {3-[4-Methyl-2-(4-trifluoromethyl-phenyl)-oxazol-5-ylmethyl]-2,3,4,5-tetrahydro-1H-benzo[d]azepin-7-yloxy}-acetic acid The title compound was made according to Scheme R.

Scheme R

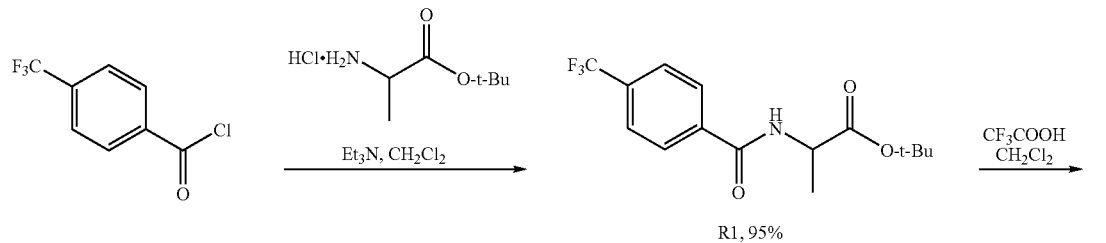

R1, 95%

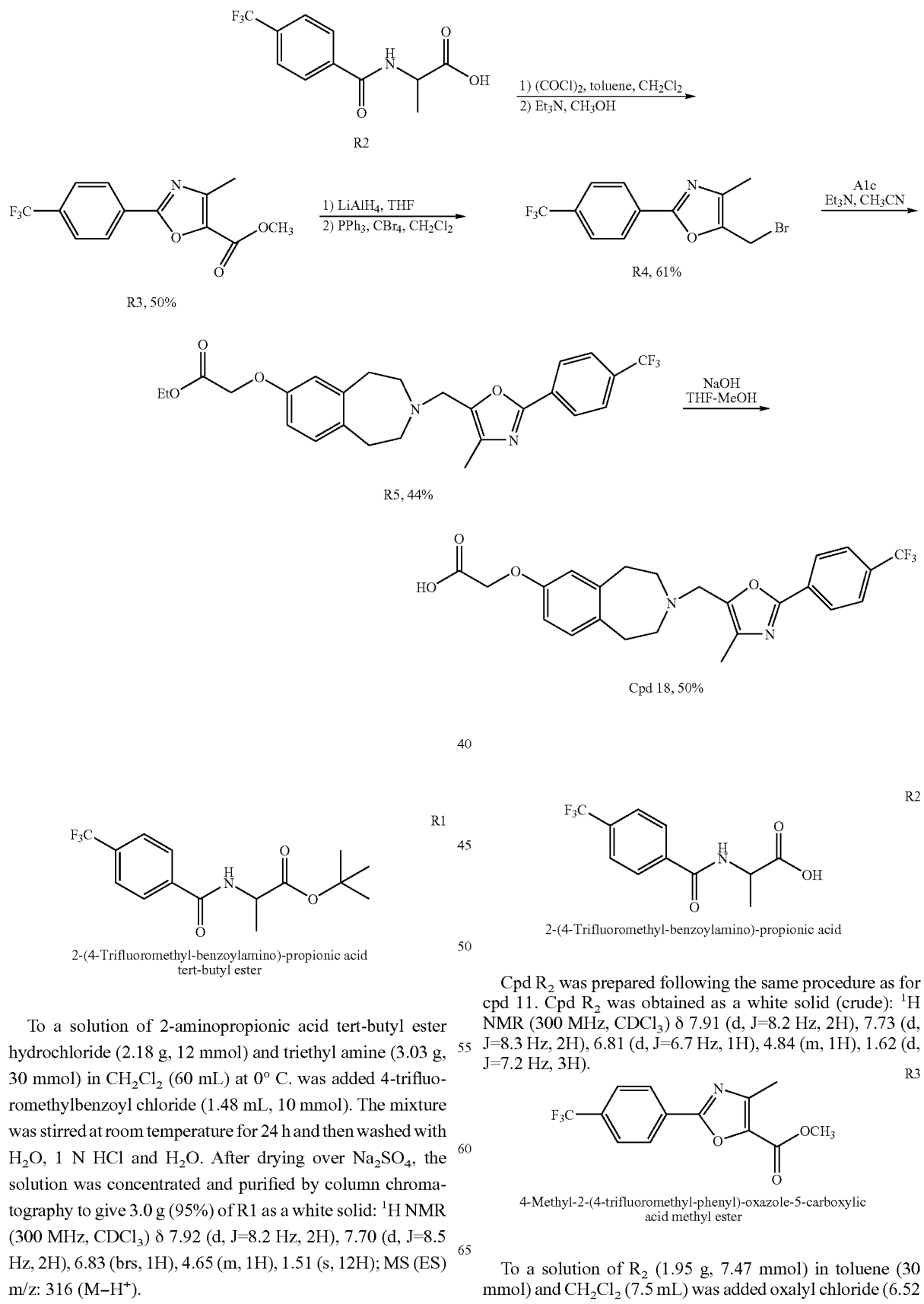

2-(4-Trifluoromethyl-benzoylamino)-propionic acid tert-butyl ester

To a solution of 2-aminopropionic acid tert-butyl ester hydrochloride (2.18 g, 12 mmol) and triethyl amine (3.03 g, 30 mmol) in $CH_2Cl_2$ (60 mL) at 0° C. was added 4-trifluoromethylbenzoyl chloride (1.48 mL, 10 mmol). The mixture was stirred at room temperature for 24 h and then washed with $H_2O$, 1 N HCl and $H_2O$. After drying over $Na_2SO_4$, the solution was concentrated and purified by column chromatography to give 3.0 g (95%) of R1 as a white solid: $^1H$ NMR (300 MHz, $CDCl_3$) δ 7.92 (d, J=8.2 Hz, 2H), 7.70 (d, J=8.5 Hz, 2H), 6.83 (brs, 1H), 4.65 (m, 1H), 1.51 (s, 12H); MS (ES) m/z: 316 (M–H$^+$).

2-(4-Trifluoromethyl-benzoylamino)-propionic acid

Cpd $R_2$ was prepared following the same procedure as for cpd 11. Cpd $R_2$ was obtained as a white solid (crude): $^1H$ NMR (300 MHz, $CDCl_3$) δ 7.91 (d, J=8.2 Hz, 2H), 7.73 (d, J=8.3 Hz, 2H), 6.81 (d, J=6.7 Hz, 1H), 4.84 (m, 1H), 1.62 (d, J=7.2 Hz, 3H).

4-Methyl-2-(4-trifluoromethyl-phenyl)-oxazole-5-carboxylic acid methyl ester To a solution of $R_2$ (1.95 g, 7.47 mmol) in toluene (30 mmol) and $CH_2Cl_2$ (7.5 mL) was added oxalyl chloride (6.52 mL, 74.7 mmol). The mixture was stirred at room temperature for 24 h and concentrated.

To the above crude intermediate at 0° C. was added Et₃N (1.53 mL, 11.2 mmol) followed by MeOH (56 mL). The mixture was stirred at room temperature for 3 h, concentrated and purified by column chromatography to give 1.06 g (50%) of R3 as a white solid: ¹H NMR (300 MHz, CDCl₃) δ 8.24 (d, J=8.2 Hz, 2H), 7.74 (d, J=8.3 Hz, 2H), 3.96 (s, 3H), 2.56 (s, 3H); MS (ES) m/z: 286 (M+H⁺).

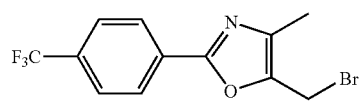

R4

5-Bromomethyl-4-methyl-2-(4-trifluoromethyl-phenyl)-oxazole

Cpd R3 was reduced to give a crude alcohol intermediate following the same procedure as in the preparation of compound E1. Cpd R4 was prepared following the same procedure as for cpd A2d. Cpd R4 was obtained as a white solid (61%): ¹H NMR (300 MHz, CDCl₃) δ 8.14 (d, J=8.6 Hz, 2H), 7.71 (d, J=8.4 Hz, 2H), 4.60 (s, 2H), 2.26 (s, 3H).

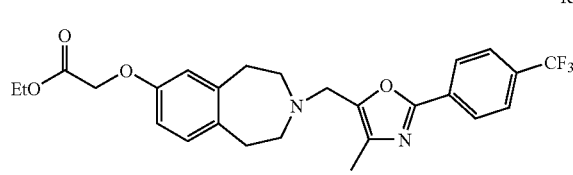

R5

{3-[4-Methyl-2-(4-trifluoromethyl-phenyl)-oxazol-5-ylmethyl]-2,3,4,5-tetrahydro-1H-benzo[d]azepin-7-yloxy}-acetic acid ethyl ester Cpd R5 was prepared following the same procedure as for cpd A2e. Cpd R5 was obtained as a white solid (44%): ¹H NMR (300 MHz, CDCl₃) δ 8.12 (d, J=8.4 Hz, 2H), 7.69 (d, J=8.5 Hz, 2H), 6.99 (d, J=8.2 Hz, 1H), 6.69 (d, J=2.6 Hz, 1H), 6.61 (dd, J=8.2, 2.6 Hz, 1H), 4.57 (s, 2H), 4.26 (q, J=7.1 Hz, 2H), 3.77 (s, 2H), 2.92-2.87 (m, 4H), 2.72-2.68 (m, 4H), 2.23 (s, 3H), 1.29 (t, J=7.1 Hz, 3H); MS (ES) m/z: 489 (M+H⁺).

Cpd 18

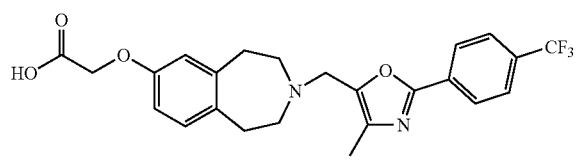

{3-[4-Methyl-2-(4-trifluoromethyl-phenyl)-oxazol-5-ylmethyl]-2,3,4,5-tetrahydro-1H-benzo[d]azepin-7-yloxy}-acetic acid Cpd 18 was prepared following the same procedure as for cpd A2e. Cpd 18 was obtained as a white solid (50%): ¹H NMR (300 MHz, CD₃OD) δ 8.19 (d, J=8.1 Hz, 2H), 7.81 (d, J=8.3 Hz, 2H), 6.98 (d, J=8.0 Hz, 1H), 6.70-6.67 (m, 2H), 4.42 (s, 2H), 4.17 (s, 2H), 3.05-2.95 (m, 4H), 2.90-2.80 (m, 4H), 2.27 (s, 3H); MS (ES) m/z: 461 (M+H⁺).

Example S

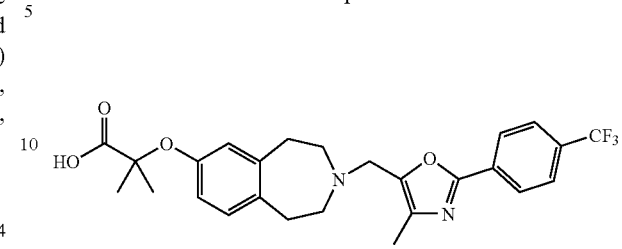

Compound 19: 2-Methyl-2-{3-[4-methyl-2-(4-trifluoromethyl-phenyl)-oxazol-5-ylmethyl]-2,3,4,5-tetrahydro-1H-benzo[d]azepin-7-yloxy}-propionic acid The title compound was made according to Scheme S.

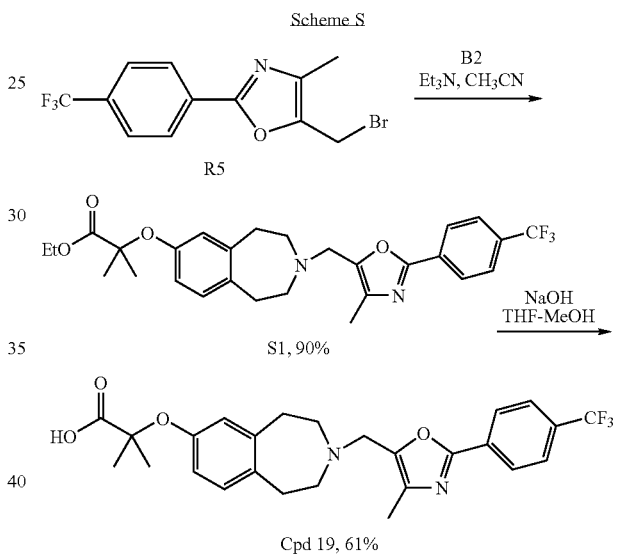

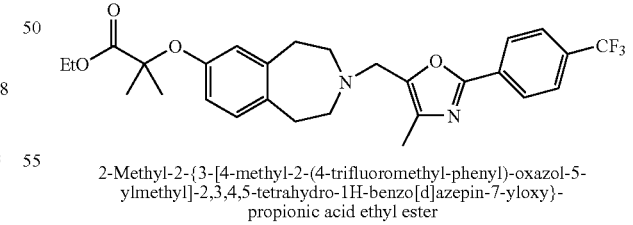

S1

2-Methyl-2-{3-[4-methyl-2-(4-trifluoromethyl-phenyl)-oxazol-5-ylmethyl]-2,3,4,5-tetrahydro-1H-benzo[d]azepin-7-yloxy}-propionic acid ethyl ester Cpd S1 was prepared following the same procedure as for cpd B3. Cpd S1 was obtained as a white solid (90%); ¹H NMR (300 MHz, CDCl₃) δ 8.12 (d, J=8.3 Hz, 2H), 7.68 (d, J=8.4 Hz, 2H), 6.92 (d, J=8.2 Hz, 1H), 6.62 (d, J=2.5 Hz, 1H), 6.54 (dd, J=8.1, 2.5 Hz, 1H), 4.22 (q, J=7.1 Hz, 2H), 3.76 (s, 2H), 2.90-2.82 (m, 4H), 2.70-2.63 (m, 4H), 2.23 (s, 3H), 1.56 (s, 6H), 1.23 (t, J=7.1 Hz, 3H), MS (ES) m/z: 517 (M+H⁺).

Cpd 19

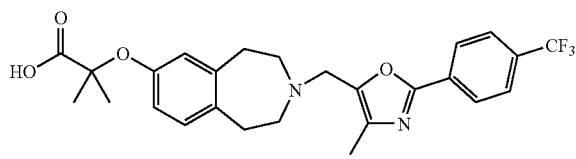

2-Methyl-2-{3-[4-methyl-2-(4-trifluoromethyl-phenyl)-oxazol-5-ylmethyl]-2,3,4,5-tetrahydro-1H-benzo[d]azepin-7-yloxy}-propionic acid Cpd 19 was prepared following the same procedure as for cpd 2. Cpd 19 was obtained as a white solid (61%): $^1$H NMR (300 MHz, CD$_3$OD) δ 8.24 (d, J=8.3 Hz, 2H), 7.85 (d, J=8.4 Hz, 2H), 7.12 (d, J=8.2 Hz, 1H), 6.80 (d, J=2.5 Hz, 1H), 6.73 (dd, J=8.2, 2.5 Hz, 1H), 4.64 (s, 2H), 3.85-3.75 (m, 2H), 3.25-3.02 (m, 6H), 2.34 (s, 3H), 1.54 (s, 6H); MS (ES) m/z: 489 (M+H$^+$).

Example 20

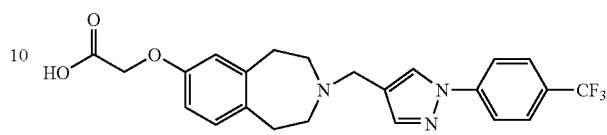

Compound 20: {3-[1-(4-Trifluoromethyl-phenyl)-1H-pyrazol-4-ylmethyl]-2,3,4,5-tetrahydro-1H-benzo[d]azepin-7-yloxy}-acetic acid The title compound was made according to Scheme T.

Scheme T

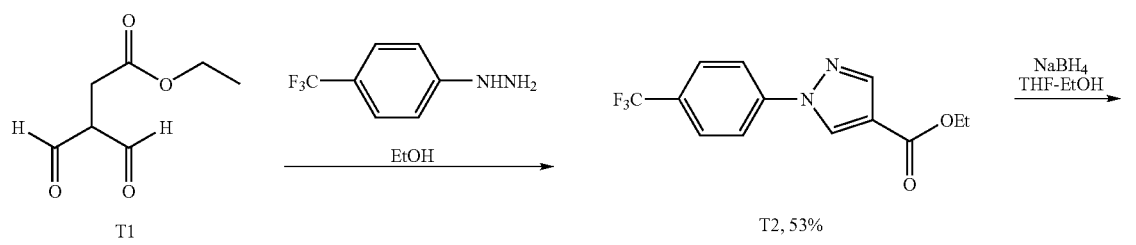

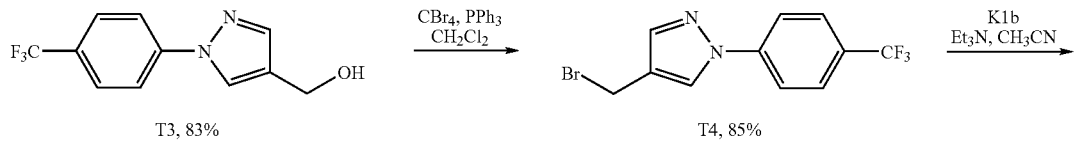

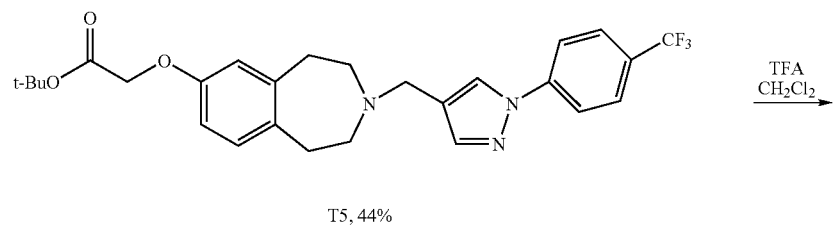

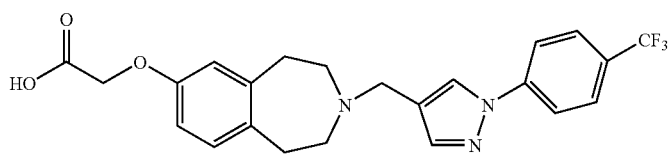

Cpd 20, 50%

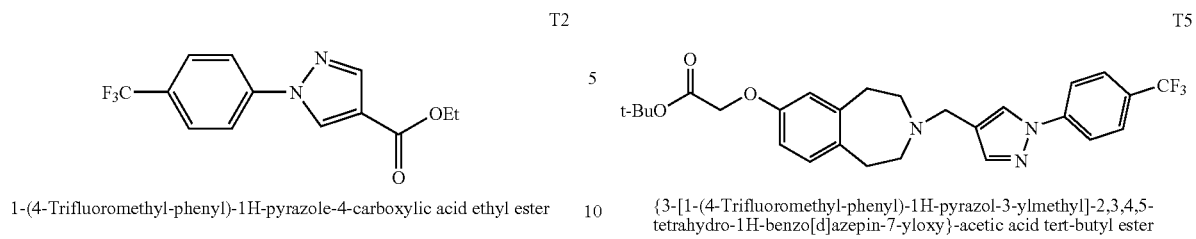

1-(4-Trifluoromethyl-phenyl)-1H-pyrazole-4-carboxylic acid ethyl ester

To a solution of T1 (864 mg, 6 mmol, *J. Org. Chem.*, 1982, 47, 2217-2218) in EtOH (6 mL) at 0° C. was added (4-trifluoromethylphenyl)hydrazine (1.06 g, 6 mmol) in EtOH (30 mL). The mixture was stirred at room temperature for 2 days and then washed with $H_2O$, 1 N HCl and $H_2O$. After drying over $Na_2SO_4$, the solution was concentrated and purified by column chromatography to give 3.0 g (95%) of R1 as a white solid: $^1$H NMR (300 MHz, CDCl$_3$) δ 8.47 (s, 1H), 8.13 (s, 1H), 7.86 (d, J=8.6 Hz, 2H), 7.75 (d, J=8.6 Hz, 2H), 4.36 (q, J=7.1 Hz, 2H), 1.36 (t, J=7.1 Hz, 3H).

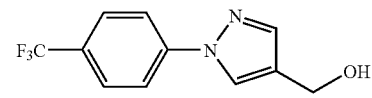

[1-(4-Trifluoromethyl-phenyl)-1H-pyrazol-4-yl]-methanol

Cpd T3 was prepared following the same procedure as in the preparation of K2c. Cpd T3 was obtained as a white solid (83%): $^1$H NMR (300 MHz, CDCl$_3$) δ 7.99 (s, 1H), 7.81 (d, J=8.8 Hz, 2H), 7.75 (s, 1H), 7.71 (d, J=8.8 Hz, 2H), 4.70 (d, J=5.4 Hz, 2H), 1.66 (t, J=5.5 Hz, 1H); MS (ES) m/z: 243 (M+H$^+$).

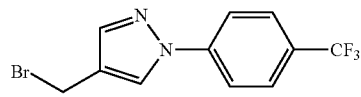

4-Bromomethyl-1-(4-trifluoromethyl-phenyl)-1H-pyrzole

Cpd T4 was prepared following the same procedure as for cpd A2d. Cpd T4 was obtained as a white solid (85%): $^1$H NMR (300 MHz, CDCl$_3$) δ 7.95 (s, 1H), 7.75-7.60 (m, 5H), 4.43 (s, 2H).

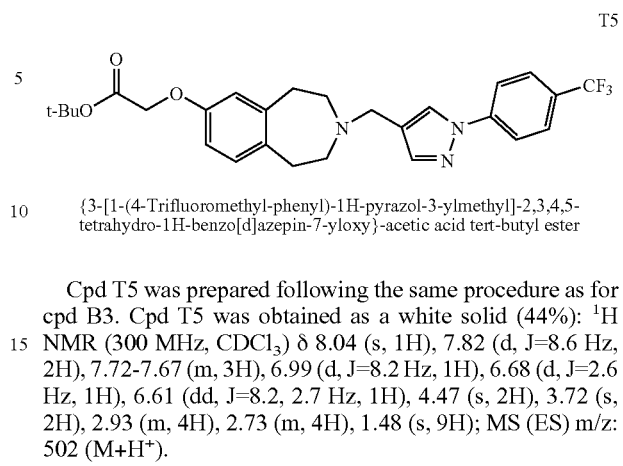

{3-[1-(4-Trifluoromethyl-phenyl)-1H-pyrazol-3-ylmethyl]-2,3,4,5-tetrahydro-1H-benzo[d]azepin-7-yloxy}-acetic acid tert-butyl ester Cpd T5 was prepared following the same procedure as for cpd B3. Cpd T5 was obtained as a white solid (44%): $^1$H NMR (300 MHz, CDCl$_3$) δ 8.04 (s, 1H), 7.82 (d, J=8.6 Hz, 2H), 7.72-7.67 (m, 3H), 6.99 (d, J=8.2 Hz, 1H), 6.68 (d, J=2.6 Hz, 1H), 6.61 (dd, J=8.2, 2.7 Hz, 1H), 4.47 (s, 2H), 3.72 (s, 2H), 2.93 (m, 4H), 2.73 (m, 4H), 1.48 (s, 9H); MS (ES) m/z: 502 (M+H$^+$).

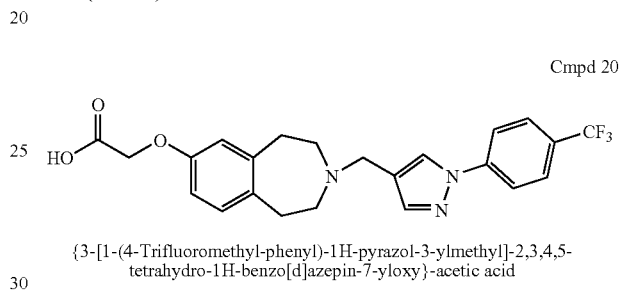

{3-[1-(4-Trifluoromethyl-phenyl)-1H-pyrazol-3-ylmethyl]-2,3,4,5-tetrahydro-1H-benzo[d]azepin-7-yloxy}-acetic acid Cpd 20 was prepared following the same procedure as in the preparation of cpd 11. Cpd 20 was obtained as a white solid (50%): $^1$H NMR (300 MHz, CD$_3$OD) δ 8.59 (s, 1H), 8.02 (d, J=8.5 Hz, 2H), 7.93 (m, 1H), 7.83 (d, J=8.6 Hz, 2H), 7.14 (d, J=8.3 Hz 1H), 6.83 (d, J=2.6 Hz, 1H), 6.77 (dd, J=8.3, 2.6 Hz, 1H), 4.64 (s, 2H), 4.42 (s, 2H), 3.84-3.78 (m, 2H), 3.25-2.99 (m, 6H); MS (ES) m/z: 446 (M+H$^+$).

Example U

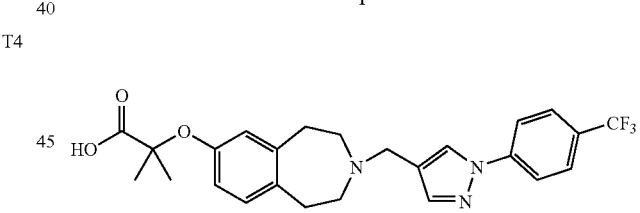

Compound 21: 2-Methyl-2-{3-[1-(4-trifluoromethyl-phenyl)-1H-pyrazol-3-ylmethyl]-2,3,4,5-tetrahydro-1H-benzo[d]azepin-7-yloxy}-propionic acid The title compound was made according to Scheme U.

Scheme U

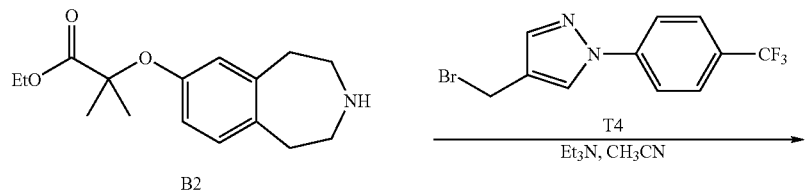

-continued

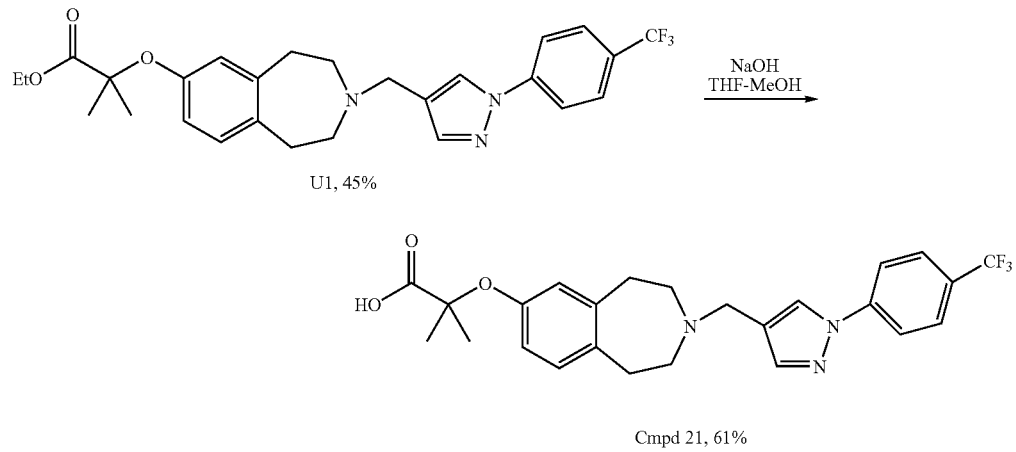

U1, 45%

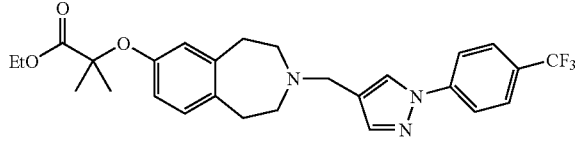

Cmpd 21, 61%

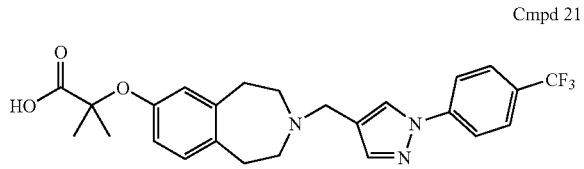

2-Methyl-2-{3-[1-(4-trifluoromethyl-phenyl)-1H-pyrazol-3-ylmethyl]-2,3,4,5-tetrahydro-1H-benzo[d]azepin-7-yloxy}-propionic acid ethyl ester Cpd U1 was prepared following the same procedure as for cpd B3. Cpd U1 was obtained as a white solid (45%): $^1$H NMR (300 MHz, CDCl$_3$) δ 8.44 (s, 1H), 7.86 (d, J=8.6 Hz, 2H), 7.75-7.68 (m, 3H), 6.95 (d, J=8.2 Hz, 1H), 6.65 (d, J=2.6 Hz, 1H), 6.59 (dd, J=8.2, 2.6 Hz, 1H), 4.23 (q, J=7.1 Hz, 2H), 3.91 (s, 2H), 3.10 (m, 4H), 2.96 (m, 4H), 1.58 (s, 6H), 1.25 (t, J=7.1 Hz, 3H); MS (ES) m/z: 502 (M+H$^+$).

Cmpd 21

2-Methyl-2-{3-[1-(4-trifluoromethyl-phenyl)-1H-pyrazol-3-ylmethyl]-2,3,4,5-tetrahydro-1H-benzo[d]azepin-7-yloxy}-propionic acid Cpd 21 was prepared following the same procedure as for cpd 2. Cpd 21 was obtained as a white solid (61%): $^1$H NMR (300 MHz, CD$_3$OD) δ 8.54 (s, 1H), 7.99 (d, J=8.6 Hz, 2H), 7.87 (s, 1H), 7.81 (d, J=8.7 Hz, 2H), 6.93 (d, J=7.6 Hz, 1H), 6.75-6.67 (m, 2H), 4.27 (s, 2H), 3.30-3.10 (m, 4H), 2.81 (m, 4H), 1.57 (s, 6H); MS (ES) m/z: 474 (M+H$^+$).

Example V

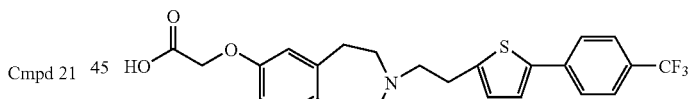

Compound 22: (3-{2-[5-(4-Trifluoromethyl-phenyl)-thiophen-2-yl]-ethyl}-2,3,4,5-tetrahydro-1H-benzo[d]azepin-7-yloxy)-acetic acid The title compound was made according to Scheme V.

Scheme V

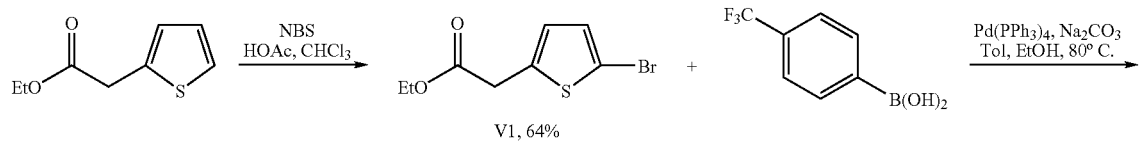

V1, 64%

-continued

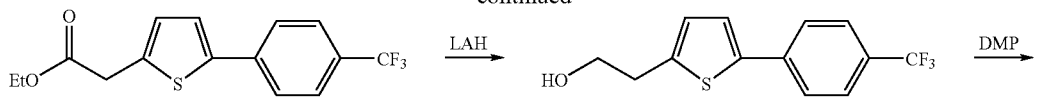
V2, 64%

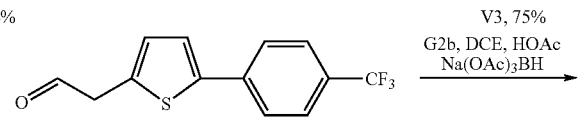
V3, 75%

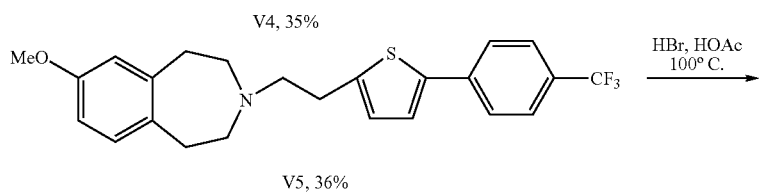
V4, 35%

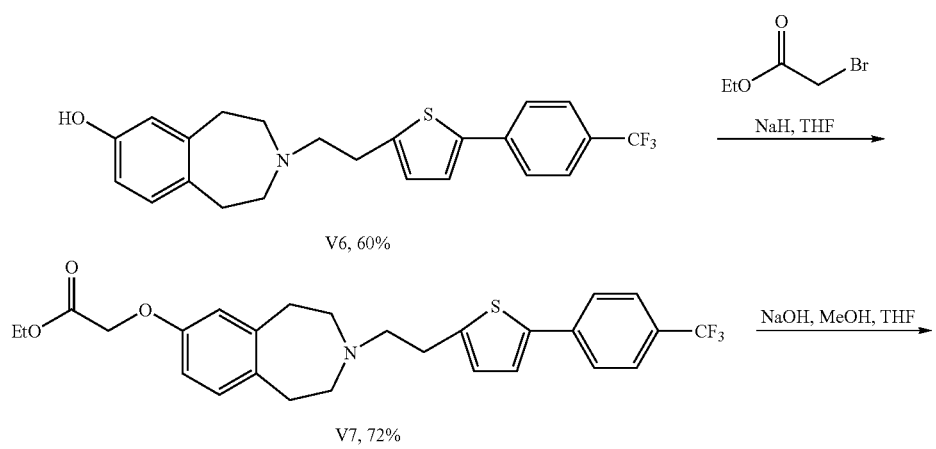

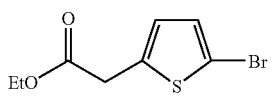
(5-Bromo-thiophen-2-yl)-acetic acid ethyl ester

A mixture of 2-thiophene acetate (1.380 g, 8.107 mmol), CHCl$_3$ (40 mL) and HOAc (40 mL) was cooled in ice bath. N-bromosuccinamide (1.472 g, 8.269 mmol) was added. The resulting mixture was stirred at r.t. for 18 h and then poured into water (100 mL). The layers were separated and the aqueous phase was extracted with chloroform (2×30 mL). The combined organic layers were washed with water, brine, dried (Na$_2$SO$_4$) and concentrated. The residue was purified by column chromatography eluting with EtOAc/Hexane to give cpd V1 as yellow oil (1.301 g, 64%): $^1$H NMR (300 MHz, CDCl$_3$) δ 6.89 (d, J=3.7 Hz, 1H), 6.68-6.69 (m, 1H), 4.15-4.22 (q, J=7.2 Hz, 2H), 3.75(d, J=0.7 Hz, 2H), 1.30(t, J=7.1 Hz, 3H).

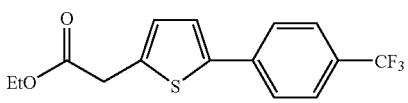
[5-(4-Trifluoromethyl-phenyl)-thiophen-2-yl]-acetic acid ethyl ester Cpd V2 (430 mg, 64%) was prepared using a similar procedure as for cpd G1. $^1$H NMR (300 MHz, CDCl$_3$) δ 7.59-7.68 (m, 4H), 7.24 (d, J=3.7 Hz, 1H), 6.94 (d, J=3.6 Hz, 1H), 4.18-4.25 (q, J=7.1 Hz, 2H), 3.84 (s, 2H), 1.28-1.32 (t, J=7.1 Hz, 3H).

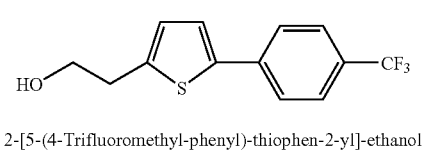

2-[5-(4-Trifluoromethyl-phenyl)-thiophen-2-yl]-ethanol

To a THF (5 mL) solution of V2 (423 mg, 1.347 mmol) was added a THF solution of LAH (1.0 M, 1.62 mmol) at 0° C. After stirring for 30 min, the mixture was quenched with aqueous NH$_4$Cl and then extracted with Et$_2$O. The organic extracts were concentrated and the residue purified by column chromatography eluting with EtOAc/Hexane to give cpd V3 as yellow solid (276 mg, 75%): $^1$H NMR (300 MHz, CDCl$_3$) δ 7.59-7.67 (m, 4H), 7.25 (d, J=3.6 Hz, 1H), 6.88 (d, J=3.6 Hz, 1H), 3.92 (t, J=6.2 Hz, 2H), 3.10 (t, J=6.2 Hz, 2H).

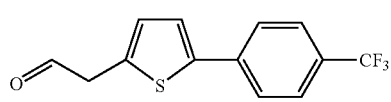

[5-(4-Trifluoromethyl-phenyl)-thiophen-2-yl]-acetaldehyde

To a mixture of V3 (194 mg, 0.713 mmol) in CH$_2$Cl$_2$ (7 mL) at 0° C. was added Dess-Martin reagent (333 mg, 0.784 mmol). The mixture was stirred for 30 min and then washed with a mixture of aqueous NaHCO$_3$ and aqueous Na$_2$S$_2$O$_3$, followed by brine. After drying over Na$_2$SO$_4$, the mixture was concentrated and the resulting residue purified by column chromatography eluting with EtOAc/hexane to give cpd V4 as yellow solid (82 mg, 35%): $^1$H NMR (300 MHz, CDCl$_3$) δ 9.78 (t, J=1.9 Hz, 1H), 7.60-7.68 (m, 4H), 7.29 (d, J=3.6 Hz, 1H), 6.94 (d, J=3.6 Hz, 1H), 3.92 (d, J=1.2 Hz, 2H).

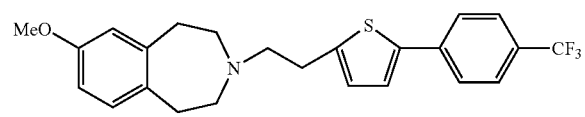

7-Methoxy-3-{2-[5-(4-trifluoromethyl-phenyl)-thiophen-2-yl]-ethyl}-2,3,4,5-tetrahydro-1H-benzo[d]azepine Cpd V5 (40 mg, 36%) was prepared according to the same procedure as for cpd G2c. $^1$H NMR (300 MHz, DMSO-d$_6$) δ 7.71-7.82 (m, 4H), 7.49 (d, J=3.6 Hz, 1H), 7.02 (d, J=8.1 Hz, 1H), 6.96 (d, J=3.6 Hz, 1H), 6.71 (d, J=2.5 Hz, 1H), 6.62-6.66 (dd, J=2.5, 8.1 Hz, 1H), 3.70 (s, 3H), 2.98 (m, 2H), 2.83 (m, 4H), 2.74 (m, 2H), 2.64 (m, 4H); MS (ES) m/z: 432.1 (M+H$^+$).

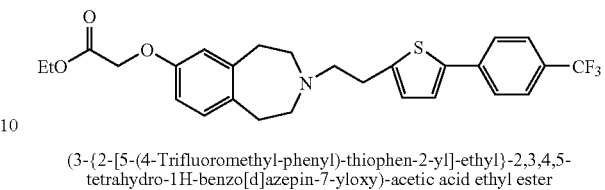

(3-{2-[5-(4-Trifluoromethyl-phenyl)-thiophen-2-yl]-ethyl}-2,3,4,5-tetrahydro-1H-benzo[d]azepin-7-yloxy)-acetic acid ethyl ester Cpd V7 (13 mg, 72%) was prepared according to the same procedure as for cpd G1b. $^1$H NMR (300 MHz, CDCl$_3$) δ 7.58-7.66 (m, 4H), 7.22 (d, J=3.6 Hz, 1H), 7.03 (d, J=7.5 Hz, 1H), 6.88 (d, J=3.7 Hz, 1H), 6.72 (s, 1H), 6.67 (br, 1H), 4.60 (s, 2H), 4.24-4.31 (q, J=7.1 Hz, 2H), 2.72-2.91 (m, 12H), 1.30 (t, J=7.1 Hz, 3H); MS (ES) m/z: 504.0 (M+H$^+$).

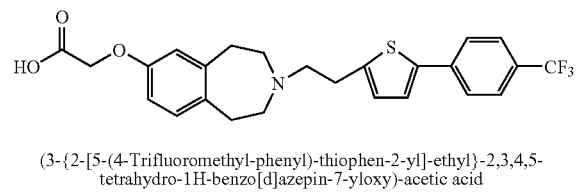

(3-{2-[5-(4-Trifluoromethyl-phenyl)-thiophen-2-yl]-ethyl}-2,3,4,5-tetrahydro-1H-benzo[d]azepin-7-yloxy)-acetic acid Cpd 22 (6 mg, 60%) was prepared according to the same procedure as for cpd 7. $^1$H NMR (400 MHz, DMSO-d$_6$) δ 7.83 (d, J=8.3 Hz, 2H), 7.75 (d, J=8.5 Hz, 2H), 7.56 (d, J=3.6 Hz, 1H), 7.11 (d, J=8.3 Hz, 1H), 7.04 (d, J=3.5 Hz, 1H), 6.81 (d, J=1.9 Hz, 1H), 6.68-6.71 (dd, J=2.5, 8.1 Hz, 1H), 4.64 (s, 2H), 3.03-3.20 (br, 12H); MS (ES) m/z: 476 (M+H$^+$), 474 (M−H$^+$).

Example W

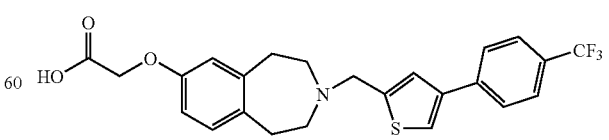

Compound 23: {3-[4-(4-Trifluoromethyl-phenyl)-thiophen-2-ylmethyl]-2,3,4,5-tetrahydro-1H-benzo[d]azepin-7-yloxy}-acetic acid The title compound was made according to Scheme W.

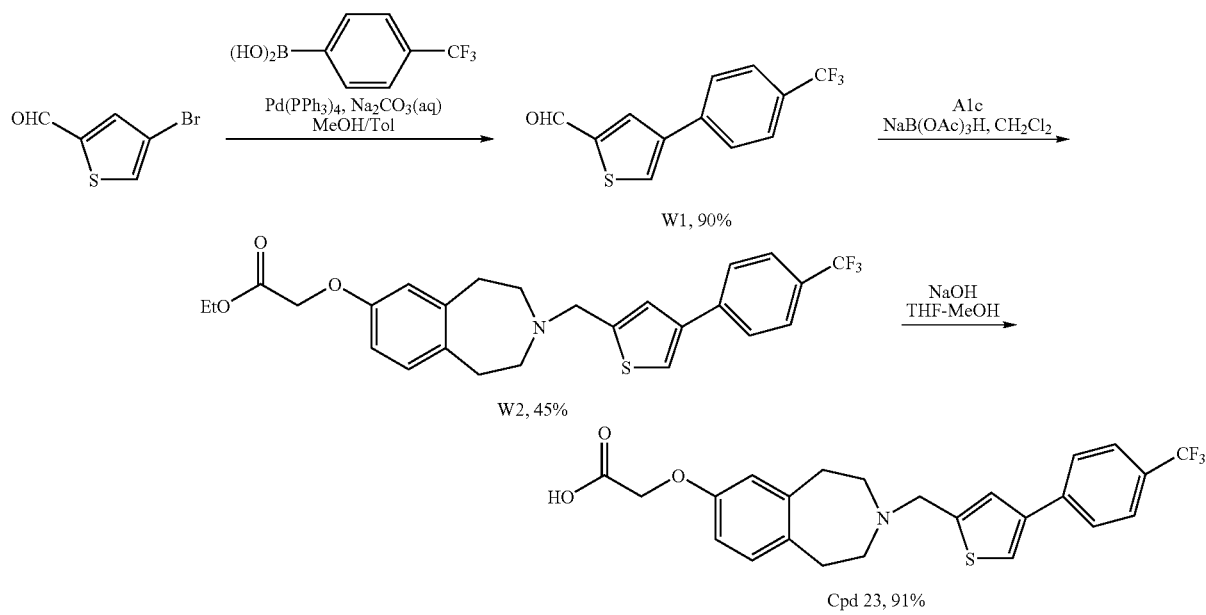

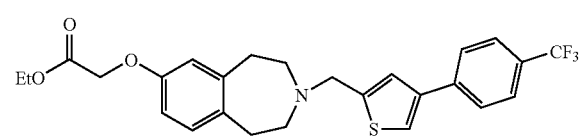

4-(4-Trifluoromethyl-phenyl)-thiophene-2-carbaldehyde

Cpd W1 was prepared following the same procedure as for cpd G1

Cpd W1 was obtained as a white solid (90%): $^1$H NMR (300 MHz, CDCl$_3$) δ 10.00 (s, 1H), 8.07 (s, 1H), 7.92 (s, 1H), 7.71 (s, 4H).

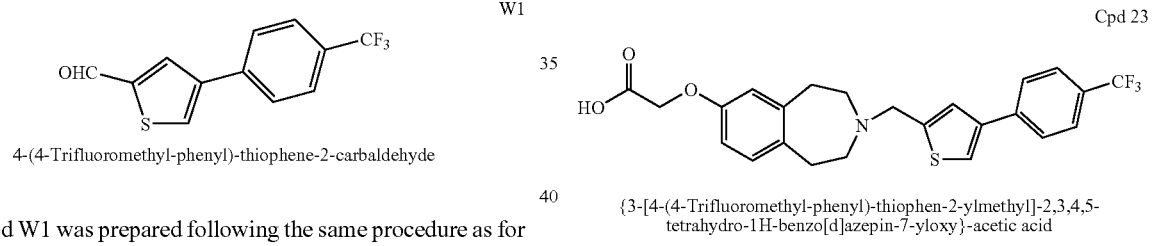

{3-[4-(4-Trifluoromethyl-phenyl)-thiophen-2-ylmethyl]-2,3,4,5-tetrahydro-1H-benzo[d]azepin-7-yloxy}-acetic acid ethyl ester Cpd W2 was prepared following the same procedure as for cpd G2. Cpd W2 was obtained as a white solid (45%): $^1$H NMR (300 MHz, CDCl$_3$) δ 7.66 (d, J=8.8 Hz, 2H), 7.62 (d, J=8.7 Hz, 2H), 7.43 (s, 1H), 7.20 (s, 1H), 6.99 (d, J=8.2 Hz, 1H), 6.69 (d, J=2.6 Hz, 1H), 6.62 (dd, J=8.2, 2.6 Hz, 1H), 4.58 (s, 2H), 4.26 (q, J=7.1 Hz, 2H), 3.87 (s, 2H), 2.92-2.84 (m, 4H), 2.73-2.65 (m, 4H), 1.29 (t, J=7.1 Hz, 3H); MS (ES) m/z: 490 (M+H$^+$).

{3-[4-(4-Trifluoromethyl-phenyl)-thiophen-2-ylmethyl]-2,3,4,5-tetrahydro-1H-benzo[d]azepin-7-yloxy}-acetic acid Cpd 23 was prepared following the same procedure as for cpd A2e. Cpd 23 was obtained as a white solid (91%): $^1$H NMR (300 MHz, CD$_3$OD) δ 7.88 (s, 1H), 7.83 (d, J=8.1 Hz, 2H), 7.70-7.65 (m, 3H), 6.96 (d, J=8.9 Hz, 1H), 6.72-6.68 (m, 2H), 4.46 (s, 2H), 4.42 (s, 2H), 3.15-3.03 (m, 4H), 2.89-2.75 (m, 4H); MS (ES) m/z: 462 (M+H$^+$).

Example X

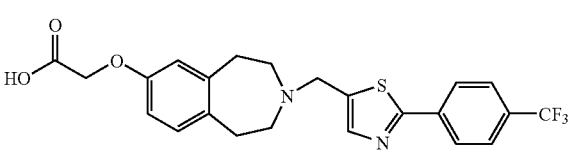

Compound 24: {3-[2-(4-Trifluoromethyl-phenyl)-thiazol-5-ylmethyl]-2,3,4,5-tetrahydro-1H-benzo[d]azepin-7-yloxy}-acetic acid The title compound was made according to Scheme X.

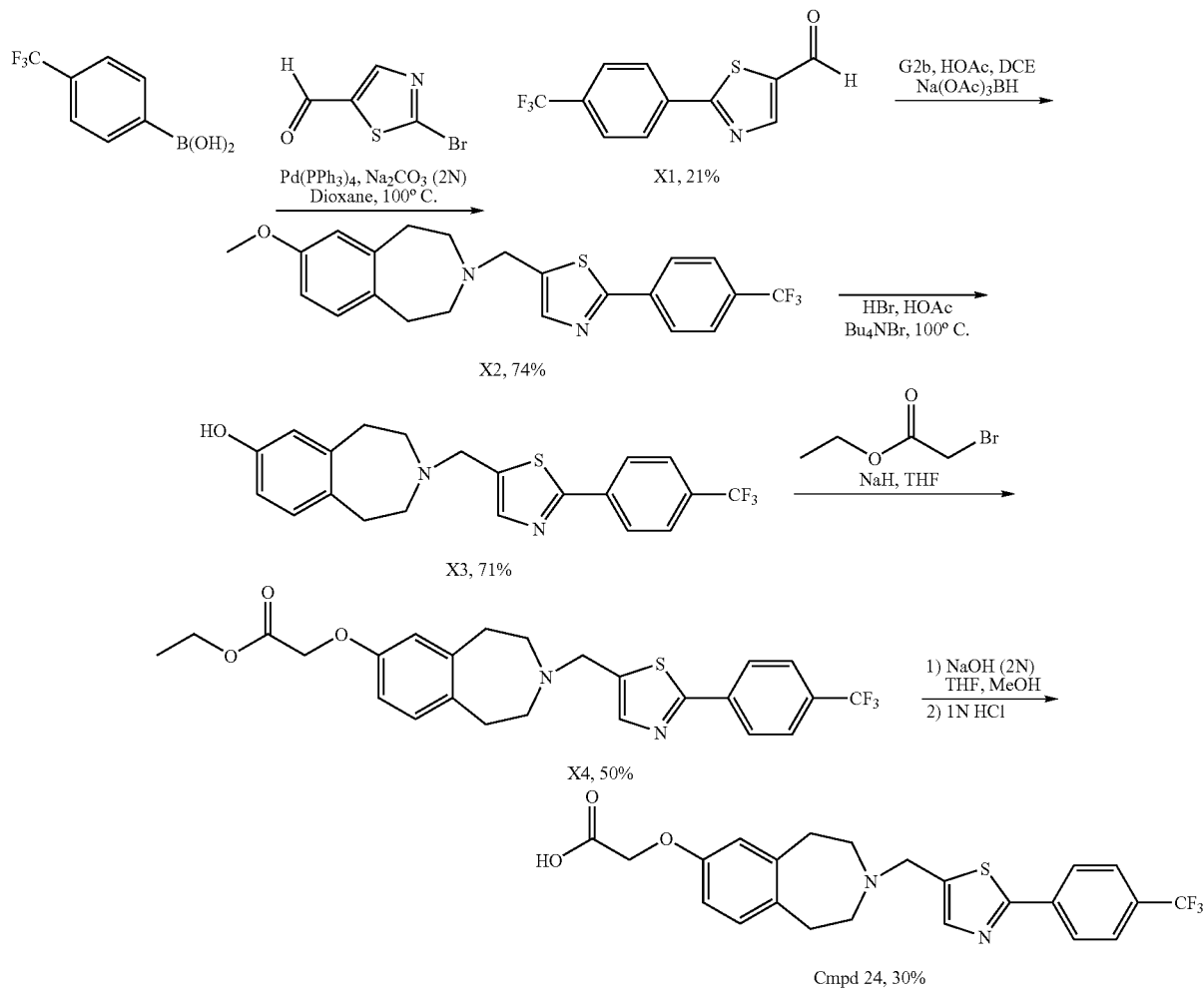

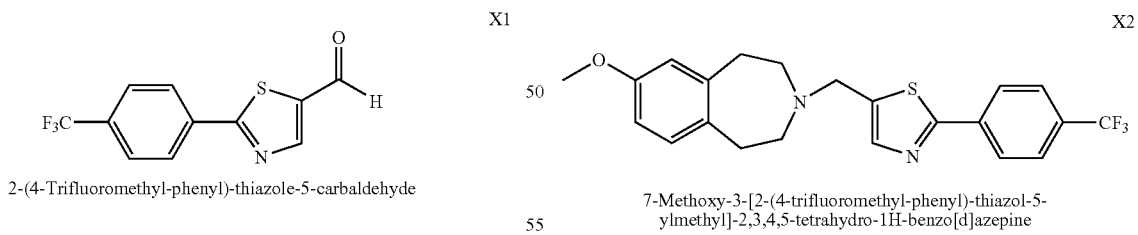

2-(4-Trifluoromethyl-phenyl)-thiazole-5-carbaldehyde

7-Methoxy-3-[2-(4-trifluoromethyl-phenyl)-thiazol-5-ylmethyl]-2,3,4,5-tetrahydro-1H-benzo[d]azepine A mixture of 2-bromo-5-formylthioazole (525 mg, 2.73 mmol), (4-trifluoromethyl)phenylboronic acid (519 mg, 2.73 mmol), tetrakis(triphenylphosphine)palladium(0) (95 mg, 0.082 mmol) and 2 N aqueous $Na_2CO_3$ (5.5 mL, 10.94 mmol) were refluxed in dioxane (8 mL) for 20 h. It was cooled and partitioned between EtOAc and water. After separating layers, the organic phase was washed with water and brine. It was dried over $Na_2SO_4$ and concentrated under reduced pressure. The crude product was purified by column chromatography eluting with EtOAc/Hexane. The title compound was obtained in yellow solids (145 mg, 21%).

Cpd X1 (139 mg, 0.541 mmol) and cpd A1a (96 mg, 0.541 mmol) were mixed with dichloroethane (2 mL) and glacial acetic acid (0.031 mL, 0.541 mmol) was added. After the resulting mixture was stirred at r.t. for 3 h, $Na(OAc)_3BH$ (172 mg, 0.811 mmol) was added and the mixture was stirred for another 21 h. It was then basified with 2N aq. NaOH and extracted with EtOAc. The organic extracts were concentrated under reduced pressure. Purification by column chromatography gave cpd X2 as a white solid (168 mg, 74%). $^1$H NMR (300 MHz, $CDCl_3$) δ 8.04 (d, J=8.2 Hz, 2H), 7.69 (d, J=8.4 Hz, 2H), 7.67 (s, 1H), 7.00 (d, J=7.8 Hz, 1H), 6.66-6.63 (m, 2H), 3.90 (s, 2H), 3.77 (s, 3H), 2.88 (m, 4H), 2.87 (m, 4H); MS (ES) m/z: 419 (M+H$^+$).

X3

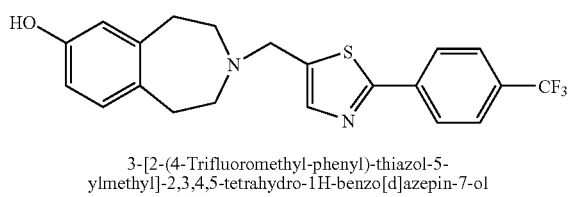

3-[2-(4-Trifluoromethyl-phenyl)-thiazol-5-ylmethyl]-2,3,4,5-tetrahydro-1H-benzo[d]azepin-7-ol A mixture of cpd X2 (145 mg, 0.347 mmol), HBr (48%, 0.8 mL, 6.94 mmol), $^n$Bu$_4$NBr (12 mg, 0.035 mmol) and HOAc (0.4 mL) were stirred at 100° C. for 18 h. After the mixture was cooled, it was diluted with water then basified with saturated aq. K$_2$CO$_3$ and extracted with EtOAc. The organic extracts were dried with Na$_2$SO$_4$ and concentrated under reduced pressure. The residue was purified by column chromatography eluting with dichloromethane/acetone (10:1) to give cpd X3 as a white solid (100 mg, 71%). $^1$H NMR (300 MHz, CD$_3$OD) δ 8.11 (d, J=8.4 Hz, 2H), 7.77 (d, J=8.4 Hz, 2H), 7.75 (s, 1H), 6.88 (d, J=8.0 Hz, 1H), 6.54 (d, J=2.4 Hz, 1H), 6.50 (dd, J=8.0, 2.5 Hz, 1H), 3.95 (s, 2H), 2.83 (m, 4H), 2.68 (m, 4H); MS (ES) m/z: 405 (M+H$^+$).

X4

{3-[2-(4-Trifluoromethyl-phenyl)-thiazol-5-ylmethyl]-2,3,4,5-tetrahydro-1H-benzo[d]azepin-7-yloxy}-acetic acid ethyl ester Cpd X3 (101 mg, 0.250 mmol) was dissolved in THF (3.0 mL). NaH (60%, 30 mg, 0.749 mmol) was added and followed by ethyl bromoacetate (0.033 mL, 0.297 mmol). The mixture was refluxed for 1 h. After cooling, it was treated with saturated aq. NH$_4$Cl and partitioned between water and Et$_2$O. The organic layers were washed with brine and concentrated under reduced pressure. The resulting residue was purified by column chromatography eluting with EtOAc/Hexane to give Cpd X4 as colorless oil (60 mg, 50%). $^1$H NMR (300 MHz, CDCl$_3$) δ 8.04 (d, J=8.2 Hz, 2H), 7.69 (d, J=8.5 Hz, 2H), 7.67 (s, 1H), 7.00 (d, J=8.2 Hz, 1H), 6.69 (d, J=2.6 Hz, 1H), 6.62 (dd, J=8.2, 2.6 Hz, 1H), 4.58 (s, 2H), 4.26 (q, J=7.1 Hz, 2H), 3.89 (s, 2H), 2.87 (m, 4H), 2.68 (m, 4H), 1.27 (t, J=7.1 Hz, 3H); MS (ES) m/z: 491 (M+H$^+$).

Cpd 24

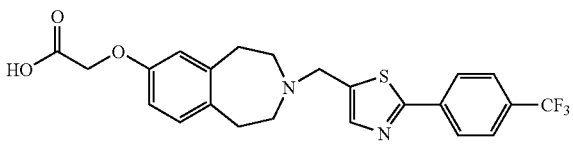

{3-[2-(4-Trifluoromethyl-phenyl)-thiazol-5-ylmethyl]-2,3,4,5-tetrahydro-1H-benzo[d]azepin-7-yloxy}-acetic acid A mixture of cpd X4 (50 mg, 0.102 mmol) in THF (0.3 mL) and methanol (0.3 mL) was treated with 2N aqueous NaOH (0.080 mL, 0.153 mmol). After stirring for 4 h, the mixture was acidified with 1N HCl and extracted with dichloromethane. The organic extracts were dried over Na$_2$SO$_4$ and concentrated under reduced pressure to give cpd 24 (14 mg, 30%). $^1$H NMR (300 MHz, CD$_3$OD) δ 8.18 (d, J=8.3 Hz, 2H), 8.04 (s, 1H), 7.82 (d, J=8.3 Hz, 2H), 7.12 (d, J=8.1 Hz, 1H), 6.81 (s, 1H), 6.76 (dd, J=8.5, 2.6 Hz, 1H), 4.67 (s, 2H), 4.61 (s, 2H), 3.37 (m, 4H), 3.10 (m, 4H); MS (ES) m/z: 463 (M+H$^+$).

Example Y

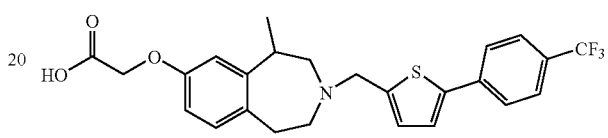

Compound 25: {5-Methyl-3-[5-(4-trifluoromethyl-phenyl)-thiophen-2-ylmethyl]-2,3,4,5-tetrahydro-1H-benzo[d]azepin-7-yloxy}-acetic acid The title compound was made according to Schemes Y1 and Y2.

Scheme Y1

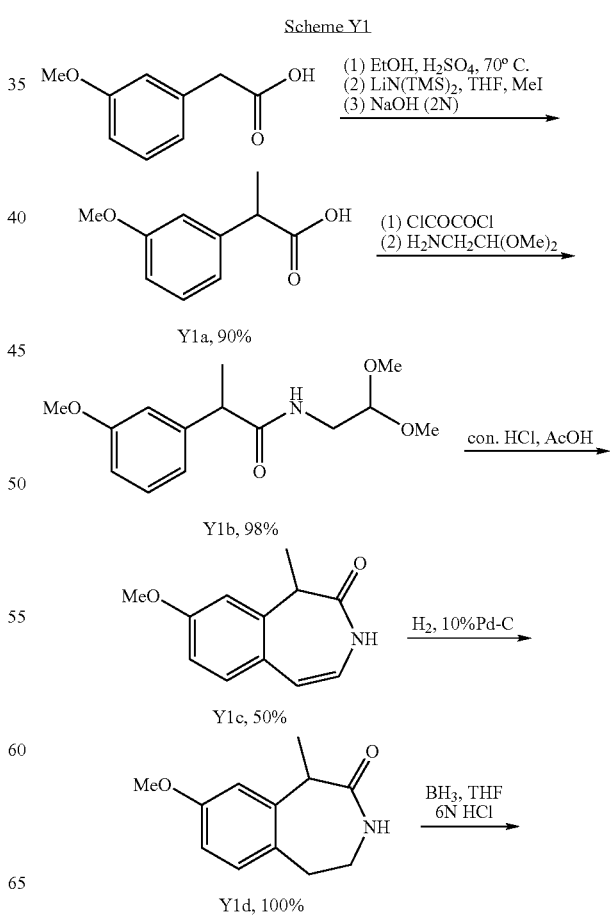

-continued

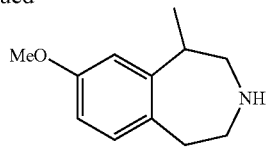

Y1e, 72%

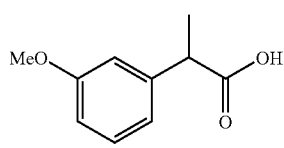

Y1a 2-(3-Methoxy-phenyl)-propionic acid (3-methoxy)phenylacetic acid (4.164 g, 25.06 mmol) was refluxed in EtOH in presence of catalytic amount of conc. $H_2SO_4$. The mixture was concentrated in vacuo, diluted with EtOAc, washed with saturated aqueous $NaHCO_3$ and brine. It was dried over $Na_2SO_4$ and concentrated to give colorless oil (4.69 g, 97%).

The above oil (1.060 g, 5.466 mmol) was dissolved in THF (20 mL) and cooled to −70° C. It was treated with a THF solution of $LiN(TMS)_2$ (1M, 6.56 mL). After stirring at −70° C. for 30 min, MeI was added and the resulting mixture was stirred for 3 h and then quenched with saturated aqueous $NH_4Cl$. The mixture was diluted with water and extracted with EtOAc. The organic extracts were dried over $Na_2SO_4$ and concentrated in vacuo to give red oil (1.046 g, 92%).

The above oil (1.00 g, 4.807 mmol) was mixed with MeOH (3 mL) and THF (6 mL). 2N aqueous NaOH was added. The mixture was stirred for 4 h and then acidified with 6N HCl till pH=1. Extraction with dichloromethane and subsequent concentration in vacuo gave cpd Y1a as yellow oil (869 mg, 100%). $^1$H NMR (400 MHz, $CDCl_3$) δ 7.29-7.22 (m, 1H), 6.91 (d, J=7.7 Hz, 1H), 6.86 (s, 1H), 6.81 (d, J=7.6 Hz, 1H), 3.80 (s, 3H), 3.71 (q, J=7.2 Hz, 1H), 1.50 (d, J=7.2 Hz, 3H); MS (ES) m/z: 181 ($M+H^+$).

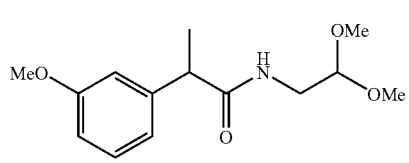

Y1b

N-(2,2-Dimethoxy-ethyl)-2-(3-methoxy-phenyl)-propionamide

Cpd Y1a (822 mg, 4.567 mmol) was mixed with dichloromethane (20 mL). Oxalyl chloride (0.60 mL, 6.85 mmol) and 2 drops of DMF were added. The mixture was stirred at r.t. for 15 h and then concentrated in vacuo. The resulting crude residue was added to a mixture of triethylamine (0.96 mL, 6.850 mmol), (2,2-dimethoxy)ethylamine (480 mg, 4.567 mmol) in dichloromethane (20 mL) and the resulting mixture was stirred at r.t. for 18 h. It was partitioned between $CH_2Cl_2$ and water. The organic layer was dried ($Na_2SO_4$) and concentrated in vacuo. The crude was purified by column chromatography eluting with EtOAc/Hexane to give cpd Y1b as colorless oil (1.015 g, 83%): $^1$H NMR (300 MHz, $CDCl_3$) δ 7.30-7.21 (m, 1H), 6.90-6.79 (m, 3H), 5.54 (brs, 1H), 4.28 (t, J=5.4 Hz, 1H), 3.81 (s, 3H), 3.53 (q, J=7.1 Hz, 1H), 3.38-3.29 (m, 8H), 1.51 (d, J=7.2 Hz, 3H).

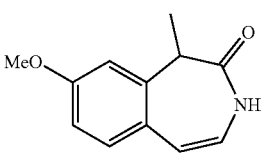

Y1c

8-Methoxy-1-methyl-1,3-dihydro-benzo[d]azepin-2-one

A mixture of cpd Y1b (3.875 g, 14.495 mmol) in conc. HCl (20 mL) and HOAc (20 mL) was stirred at room temperature for 17 h. It was then poured onto ice (66 g). The precipitates were collected by filtration and dried under vacuum at 70° C. to give cpd Y1c (1.464 g, 50%) as a yellow solid: $^1$H NMR (300 MHz, DMSO-$d_6$) δ 9.53 (d, J=3.6 Hz, 1H), 7.23 (d, J=8.5 Hz, 1H), 6.88 (dd, J=8.5, 2.5 Hz, 1H), 6.76 (d, J=2.3 Hz, 1H), 6.32 (d, J=9.0 Hz, 1H), 6.20 (dd, J=9.0, 4.7 Hz, 1H), 3.77 (s, 3H), 3.15 (m, 1H), 1.43 (d, J=7.0 Hz, 3H).

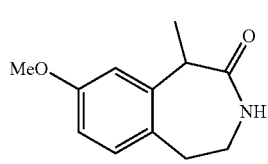

Y1d

8-Methoxy-1-methyl-1,3,4,5-tetrahydro-benzo[d]azepin-2-one

Cpd Y1c (1.44 g, 7.085 mmol) was mixed with EtOAc (30 mL) and MeOH (30 mL). Pd/C (10%, 75 mg, 0.071 mmol) was added. The mixture was shaken under $H_2$ atmosphere (45 psi) for 17 h. After filtration through celite, the solution was concentrated to give cpd Y1d (1.44 g, 100%) as a white solid: $^1$H NMR (300 MHz, DMSO-$d_6$) δ 7.33 (brs, 1H), 7.06 (d, J=8.3 Hz, 1H), 6.75 (dd, J=8.3, 2.5 Hz, 1H), 6.68 (d, J=2.4 Hz, 1H), 4.22 (q, J=13.8, 6.8 Hz, 1H), 3.73-3.64 (m, 4H), 3.18-3.10 (m, 2H), 2.91-2.84 (m, 1H), 1.33 (d, J=6.9 Hz, 3H); MS (ES) m/z: 206 ($M+H^+$).

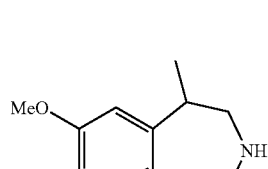

Y1e

8-Methoxy-1-methyl-2,3,4,5-tetrahydro-1H-benzo[d]azepine

To a solution of cpd Y1d (286 mg, 1.393 mmol) in THF (7 mL) was added $BH_3$-THF (1M, 4.18 mmol) at 0° C. The mixture was stirred at reflux for 4 h and then cooled. MeOH (2 mL) was added to quench excessive $BH_3$ at 0° C. and the mixture was stirred at room temperature for another 30 min. After concentration, the residue was taken up with 6N HCl and stirred at 100° C. for 1 h. The mixture was extracted with $Et_2O$ and the organic layer was discarded. The remaining aqueous phase was basified with 5N NaOH and then extracted with EtOAc. The organic extracts were dried over $Na_2SO_4$ and concentrated in vacuo to give cpd Y1e (191 mg, 72%) as colorless oil: $^1$H NMR (300 MHz, CDCl$_3$) δ 7.00 (d, J=8.2 Hz, 1H), 6.74 (d, J=2.6 Hz, 1H), 6.63 (dd, J=8.2, 2.7 Hz, 1H), 3.79 (s, 3H), 3.05-2.86 (m, 6H), 2.74 (dd, J=13.4, 7.6 Hz, 1H), 2.04 (brs, 1H), 1.33 (d, J=7.2 Hz, 3H); MS (ES) m/z: 192 (M+H$^+$).

basified with 5N NaOH, the mixture was extracted with EtOAc. The organic extracts were dried (Na$_2$SO$_4$) and concentrated. The residue was purified by column chromatography to give cpd Y2a (154 mg, 81%) as a yellow oil: $^1$H NMR (300 MHz, CDCl$_3$) δ 7.67 (d, J=8.1 Hz, 2H), 7.60 (d, J=8.5 Hz, 2H), 7.23 (d, J=3.6 Hz, 1H), 6.99 (d, J=8.2 Hz, 1H), 6.88

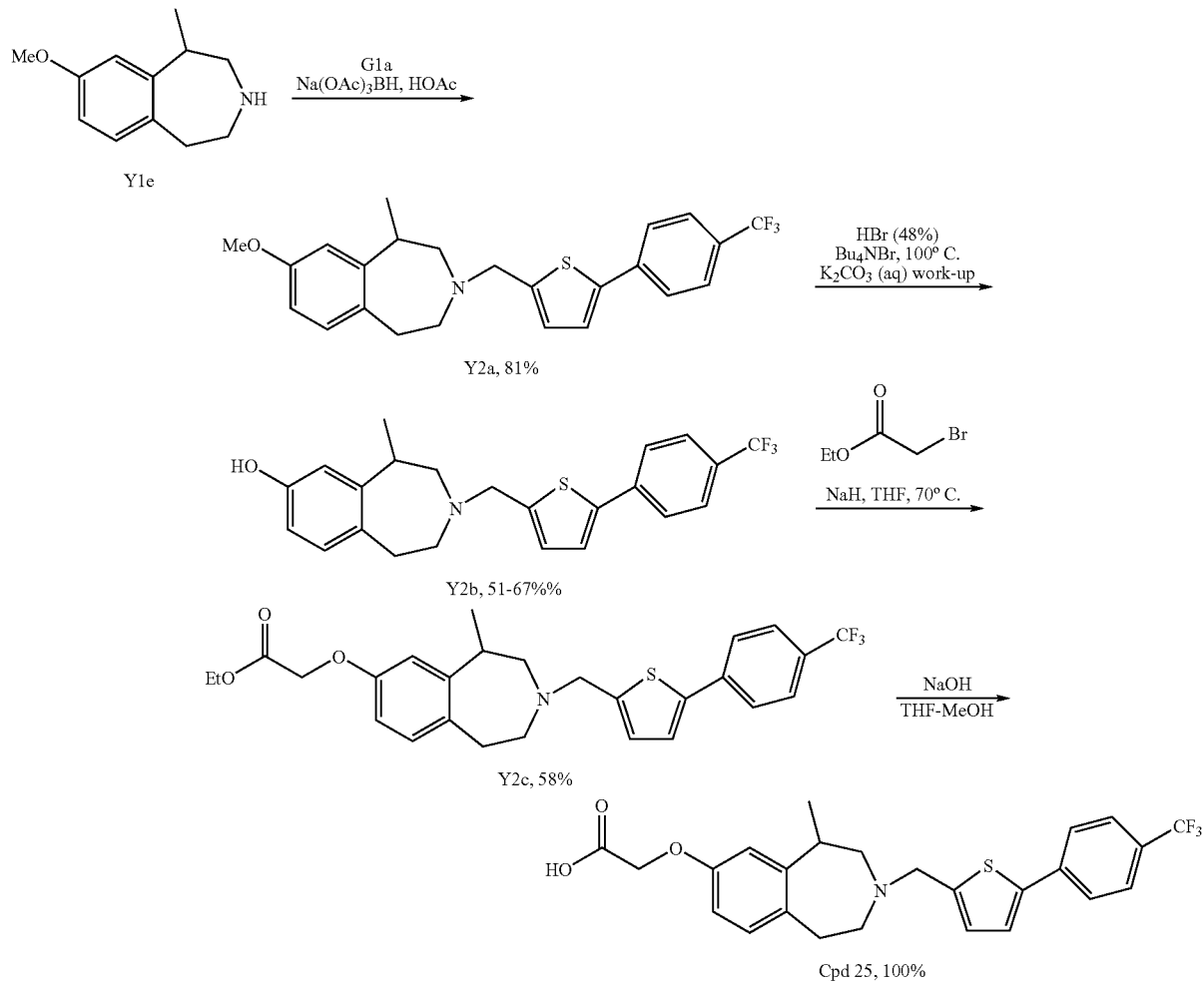

Scheme Y2

(m, 1H), 6.73 (d, J=2.5 Hz, 1H), 6.64 (dd, J=8.2, 2.6 Hz, 1H), 3.83 (d, J=4.7 Hz, 2H), 3.78 (s, 3H), 3.19-3.06 (m, 1H), 2.99-2.70 (m, 4H), 2.61-2.42 (m, 2H), 1.36 (d, J=7.2 Hz, 3H); MS (ES) m/z: 432 (M+H$^+$).

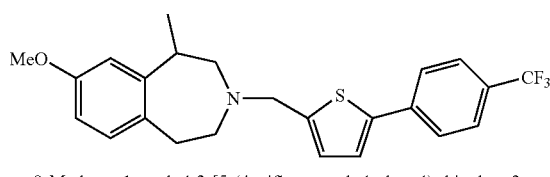

8-Methoxy-1-methyl-3-[5-(4-trifluoromethyl-phenyl)-thiophen-2-ylmethyl]-2,3,4,5-tetrahydro-1H-benzo[d]azepine A mixture of cpd Y1e (84.6 mg, 0.443 mmol), cpd G1a (113 mg, 0.443 mmol), dichloroethane (2 mL) and HOAc (0.025 mL, 0.443 mmol) was stirred at room temperature for 1 h. Na(OAc)$_3$BH (141 mg, 0.664 mmol) was added. The mixture was continued stirring for another 20 h. After it was

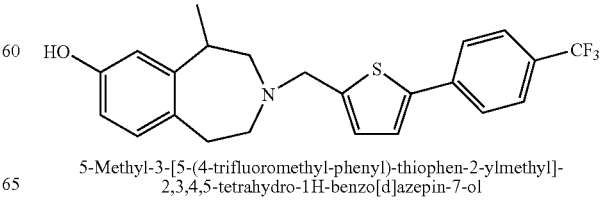

5-Methyl-3-[5-(4-trifluoromethyl-phenyl)-thiophen-2-ylmethyl]-2,3,4,5-tetrahydro-1H-benzo[d]azepin-7-ol A mixture of cpd Y2a (150 mg, 0.348 mmol), HBr (48%, 0.5 mL), HOAc (0.5 mL) and "Bu₄NBr (22 mg, 0.070 mmol) was stirred at 100° C. for 17 h. After it was cooled to room temperature, the mixture was basified with 5N NaOH and extracted with EtOAc. The organic extracts were washed with water, brine, dried (Na₂SO₄) and concentrated. The resulting residue was purified by column chromatography to give cpd Y2b (98 mg, 67%) as brown oil:

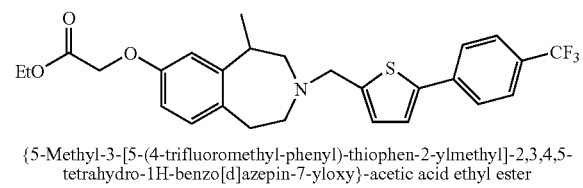

Y2c

{5-Methyl-3-[5-(4-trifluoromethyl-phenyl)-thiophen-2-ylmethyl]-2,3,4,5-tetrahydro-1H-benzo[d]azepin-7-yloxy}-acetic acid ethyl ester To a mixture of cpd Y2b (89 mg, 0.213 mmol) in THF (1.5 mL) was added NaH (60%, 43 mg, 1.07 mmol) and ethyl bromoacetate (0.047 mL, 0.426 mmol) subsequently. After it was stirred at reflux for 50 min, the mixture was cooled to room temperature and quenched with aqueous NH₄Cl. The resulting mixture was partitioned between water and Et₂O. The layers were separated and the organic phase was dried (Na₂SO₄) and concentrated. The resulting residue was purified by column chromatography to give cpd Y2c (62 mg, 58%) as a yellow solid: ¹H NMR (300 MHz, CDCl₃) δ 7.67 (d, J=8.2 Hz, 2H), 7.60 (d, J=8.6 Hz, 2H), 7.24 (d, J=3.6 Hz, 1H), 6.98 (d, J=8.3 Hz, 1H), 6.89 (m, 1H), 6.78 (d, J=2.4 Hz, 1H), 6.59 (dd, J=8.2, 2.6 Hz, 1H), 4.58 (s, 2H), 4.27 (q, J=7.2 Hz, 2H), 3.83 (s, 2H), 3.19-3.05 (m, 1H), 3.01-2.67 (m, 4H), 2.59-2.40 (m, 2H), 1.35 (d, J=7.2 Hz, 3H), 1.30 (t, J=7.1 Hz, 3H); MS (ES) m/z: 504 (M+H⁺).

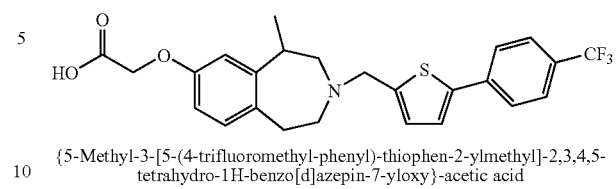

Cpd 25

{5-Methyl-3-[5-(4-trifluoromethyl-phenyl)-thiophen-2-ylmethyl]-2,3,4,5-tetrahydro-1H-benzo[d]azepin-7-yloxy}-acetic acid A mixture of cpd Y2c (56 mg, 0.111 mmol), THF (0.5 mL), MEOH (0.5 mL) and NaOH (2N, 0.11 mL, 0.22 mmol) was stirred at room temperature for 6 h. The solution was acidified with 1N HCl and extracted with dichloromethane. The organic extracts were dried and concentrated to give cpd 25 (57 mg, 100%) as a pale pink solid: ¹H NMR (300 MHz, CD₃OD) δ 7.86 (d, J=8.2 Hz, 2H), 7.72 (d, J=8.3 Hz, 2H), 7.57 (d, J=3.7 Hz, 1H), 7.38 (d, J=3.8 Hz, 1H), 7.15 (d, J=8.3 Hz, 1H), 6.89 (d, J=2.5 Hz, 1H), 6.77 (dd, J=8.3, 2.6 Hz, 1H), 4.67-4.65 (m, 4H), 3.76-3.41 (m, 4H), 3.25 (m, 1H), 3.17-3.00 (m, 2H), 1.46 (d, J=7.2 Hz, 3H); MS (ES) m/z: 476 (M+H⁺).

Example Z

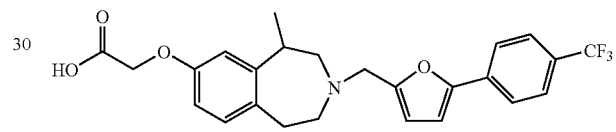

Compound 26: {5-Methyl-3-[5-(4-trifluoromethyl-phenyl)-furan-2-ylmethyl]-2,3,4,5-tetrahydro-1H-benzo[d]azepin-7-yloxy}-acetic acid The title compound was made according to Scheme Z.

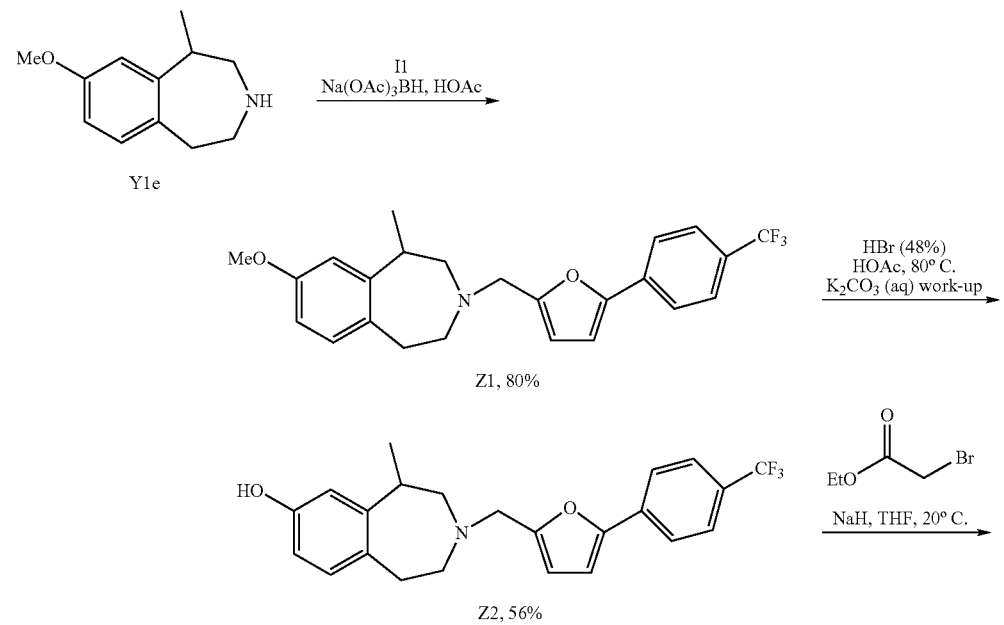

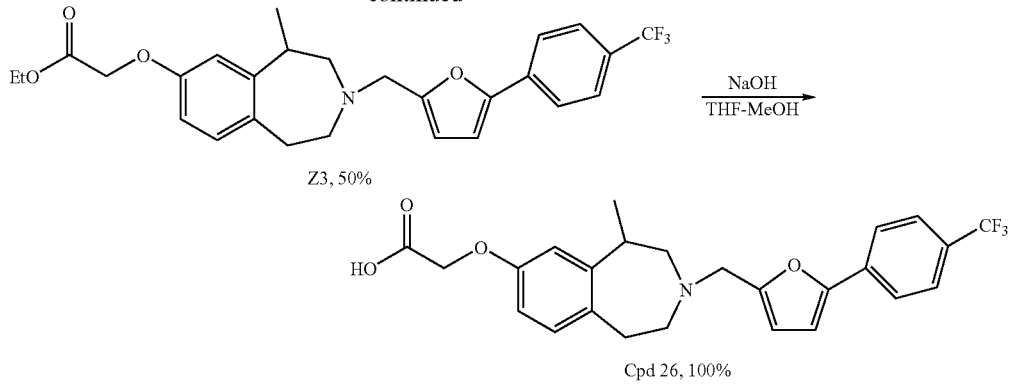

Z3, 50%

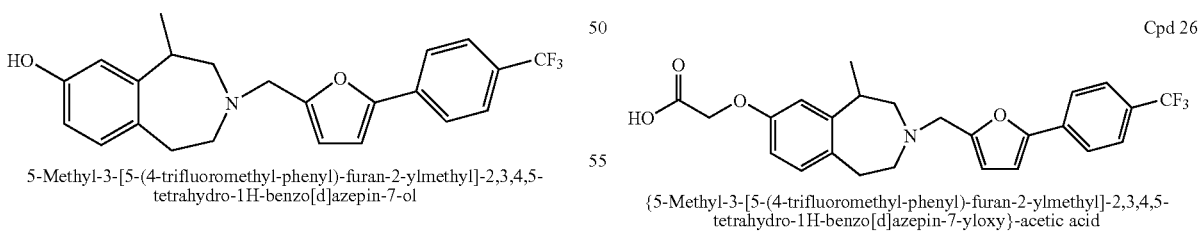

Cpd 26, 100%

Z1

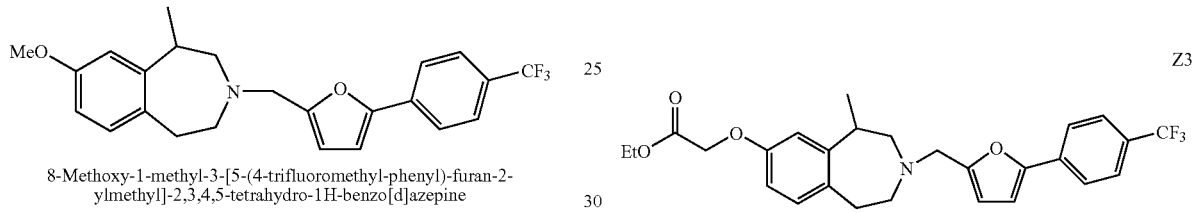

8-Methoxy-1-methyl-3-[5-(4-trifluoromethyl-phenyl)-furan-2-ylmethyl]-2,3,4,5-tetrahydro-1H-benzo[d]azepine A mixture of cpd Y1e (89 mg, 0.466 mmol), cpd I1 (112 mg, 0.466 mmol), dichloroethane (2 mL) and HOAc (0.027 mL, 0.466 mmol) was stirred at room temperature for 16 h. Na(OAc)$_3$BH (148 mg, 0.699 mmol) was added. The resulting mixture was continued stirring for another 24 h, basified with 2N NaOH and extracted with EtOAc. The organic extracts were dried (Na$_2$SO$_4$) and concentrated. The residue was purified by column chromatography to give cpd Z1 (153 mg, 79%): $^1$H NMR (300 MHz, CDCl$_3$) δ 7.72 (d, J=8.1 Hz, 2H), 7.60 (d, J=8.5 Hz, 2H), 6.98 (d, J=8.1 Hz, 1H), 6.72 (d, J=2.5 Hz, 1H), 6.68 (d, J=3.3 Hz, 1H), 6.62 (dd, J=8.2, 2.6 Hz, 1H), 6.29 (d, J=3.1 Hz, 1H), 3.77 (s, 5H), 3.11-3.16 (m, 1H), 2.78-2.99 (m, 4H), 2.40-2.54 (m, 2H), 1.35 (d, J=7.2 Hz, 3H); MS (ES) m/z: 416 (M+H$^+$).

Z2

5-Methyl-3-[5-(4-trifluoromethyl-phenyl)-furan-2-ylmethyl]-2,3,4,5-tetrahydro-1H-benzo[d]azepin-7-ol A mixture of cpd Z1 (140 mg, 0.337 mmol), HOAc (1 mL) and HBr (48%, 1 mL) was stirred at 80° C. for 17 h. Upon cooling, the mixture was diluted with EtOAc and basified with saturated aqueous K$_2$CO$_3$ till pH 9. It was then extracted with EtOAc. The organic extracts were dried (Na$_2$SO$_4$) and concentrated to provide cpd Z2 (137 mg, 100%) as brown oil: $^1$H NMR (300 MHz, CDCl$_3$) δ 7.71 (d, J=8.2 Hz, 2H), 7.59 (d, J=8=3 Hz, 2H), 6.90 (d, J=8.0 Hz, 1H), 6.68 (d, J=3.3 Hz, 1H), 6.65 (d, J=2.5 Hz, 1H), 6.53-6.57 (dd, J=8.0, 2.6 Hz, 1H), 6.32 (s, 1H), 3.75-3.80 (s, br, 2H), 2.81-3.16 (m, 5H), 2.37-2.51 (m, 2H), 1.34 (d, J=7.2 Hz, 3H); MS (ES) m/z: 402 (M+H$^+$), 400 (M−H$^+$).

Z3

{5-Methyl-3-[5-(4-trifluoromethyl-phenyl)-furan-2-ylmethyl]-2,3,4,5-tetrahydro-1H-benzo[d]azepin-7-yloxy}-acetic acid ethyl ester To a solution of cpd Z2 (108 mg, 0.269 mmol) in THF (1.5 mL) was added NaH (95%, 14 mg, 0.539 mmol) and ethyl bromoacetate (0.045 mL, 0.403 mmol). After it was stirred at room temperature for 4 h, it was quenched with aqueous NH$_4$Cl and extracted with Et$_2$O. The organic extracts were dried, concentrated and the residue was purified by column chromatography to provide cpd Z3 (65 mg, 50%): $^1$H NMR (300 MHz, CDCl$_3$) δ 7.72 (d, J=8.2 Hz, 2H), 7.60 (d, J=8.3 Hz, 2H), 6.98 (d, J=8.2 Hz, 1H), 6.78 (d, J=2.6 Hz, 1H), 6.68 (d, J=3.3 Hz, 1H), 6.56-6.60 (dd, J=2.7, 8.2 Hz, 1H), 6.30 (s, 1H), 4.58 (s, 2H), 4.23-4.29 (q, J=7.2 Hz, 2H), 3.78 (s, 2H), 2.78-3.15 (m, 5H), 2.38-2.51 (m, 2H), 1.35 (d, J=7.2 Hz, 3H), 1.26-1.31 (t, J=7.1 Hz, 3H); MS (ES) m/z: 488 (M+H$^+$).

Cpd 26

{5-Methyl-3-[5-(4-trifluoromethyl-phenyl)-furan-2-ylmethyl]-2,3,4,5-tetrahydro-1H-benzo[d]azepin-7-yloxy}-acetic acid To a solution of cpd Z3 (60 mg, 0.123 mmol) in THF (0.5 ml) and MeOH (0.5 mL) was added NaOH (2N, 0.12 mL). The mixture was stirred at room temperature for 2 h and then acidified with aqueous tartaric acid to pH 3-4. The mixture was extracted with EtOAc and the organic extracts were concentrated after drying over Na$_2$SO$_4$ to give cpd 26 (60 mg, 100%) as a white powder: $^1$H NMR (300 MHz, CDCl$_3$) δ 7.61-7.71 (m, 4H), 6.91 (d, J=8.2 Hz, 1H), 6.75 (s, 3H), 6.66-6.69 (dd, J=2.3, 8.2 Hz, 1H), 4.62 (s, 2H), 4.27-4.44 (m, 2H), 3.32-3.58 (m, 4H), 2.60-2.76 (m, 3H), 1.32 (d, J=6.9 Hz, 3H); MS (ES) m/z: 460 (M+H⁺).
Example AA
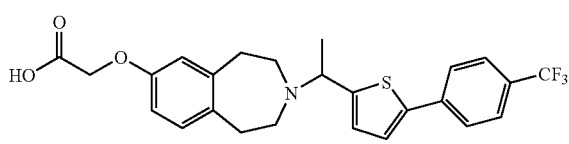
Compound 27: (3-{1-[5-(4-Trifluoromethyl-phenyl)-thiophen-2-yl]-ethyl}-2,3,4,5-tetrahydro-1H-benzo[d]azepin-7-yloxy)-acetic acid
The title compound was made according to Scheme AA.
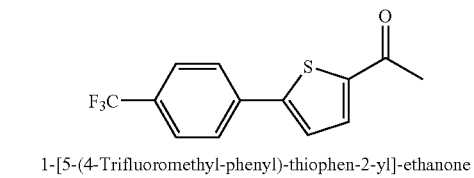
1-[5-(4-Trifluoromethyl-phenyl)-thiophen-2-yl]-ethanone
Cpd AA1 was prepared following a similar procedure as for cpd X1. Cpd AA1 was obtained (3.84 g, 84%) as a pale yellow solid:
Scheme AA
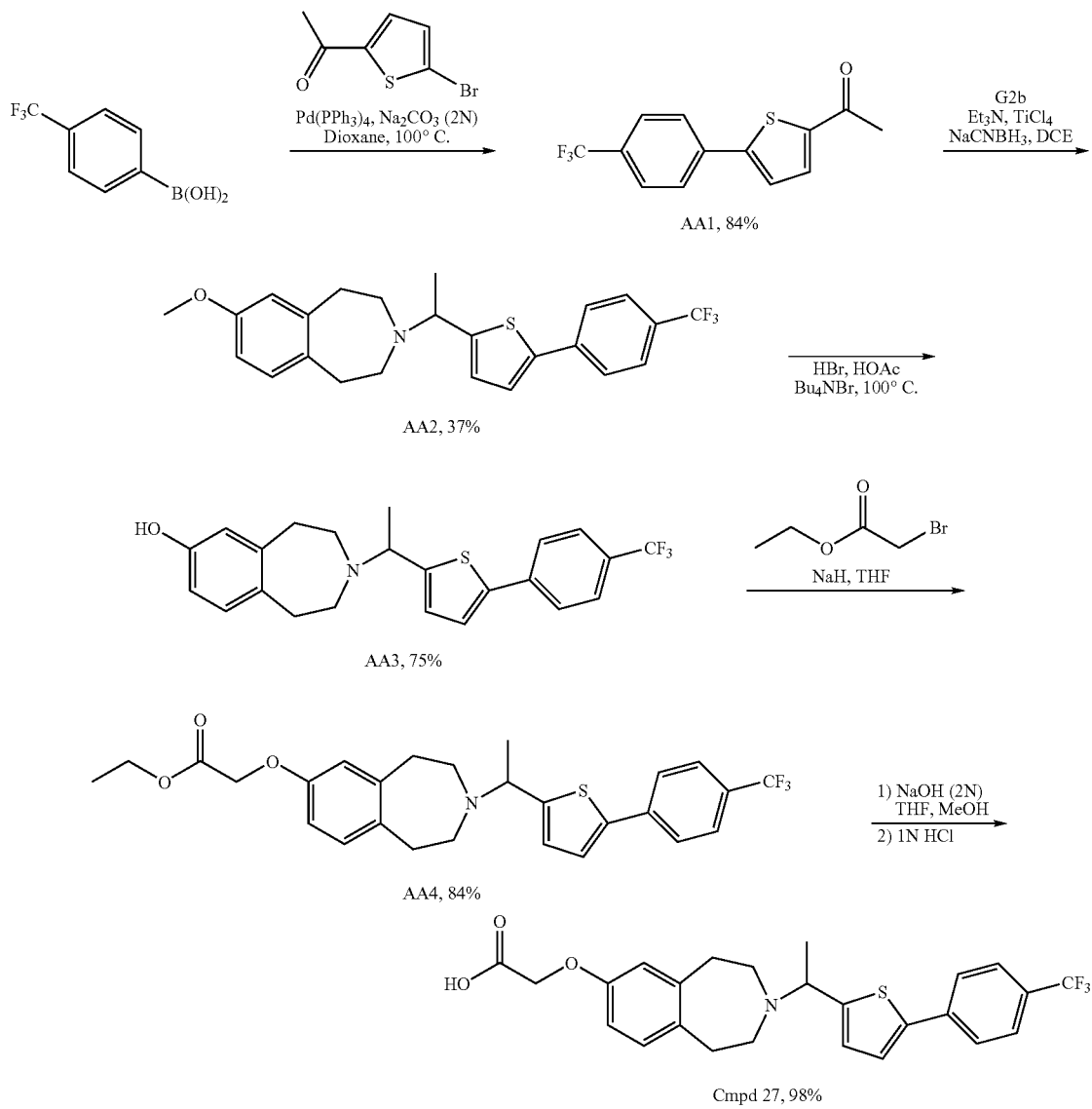

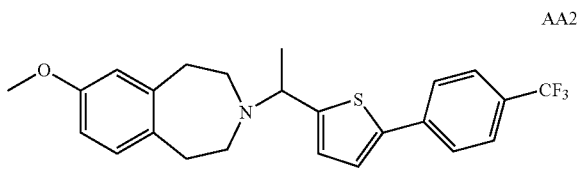

7-Methoxy-3-{1-[5-(4-trifluoromethyl-phenyl)-thiophen-2-yl]-ethyl}-2,3,4,5-tetrahydro-1H-benzo[d]azepine To a mixture of cpd G2b (582 mg, 3.288 mmol), cpd AA1 (888 mg, 3.288 mmol) and dichloroethane (30 mL) was added triethylamine (1.37 mL, 9.864 mmol) and TiCl$_4$ (1M in dichloromethane, 1.60 mL, 1.644 mmol). The resulting mixture was stirred at room temperature for 16 h. A solution of NaBH$_3$CN (310 mg, 4.932 mmol) in MeOH (2 mL) was added and stirring was continued for another 5.5 h. The mixture was then basified with 2N NaOH and extracted with EtOAc. The organic extracts were dried and concentrated. The residue was purified by column chromatography to give cpd AA2 (487 mg, 34%) as a reddish slurry: $^1$H NMR (300 MHz, CDCl$_3$) δ 7.67 (d, J=8.9 Hz, 2H), 7.59 (d, J=8.3 Hz, 2H), 7.23 (d, J=3.6 Hz, 1H), 6.99 (d, J=8.0 Hz, 1H), 6.84 (d, J=3.6 Hz, 1H), 6.66-6.61 (m, 2H), 4.15 (q, J=7.4 Hz, 1H), 3.77 (s, 3H), 2.89 (m, 4H), 2.70 (m, 4H), 1.41 (d, J=6.7 Hz, 3H); MS (ES) m/z: 432 (M+H$^+$).

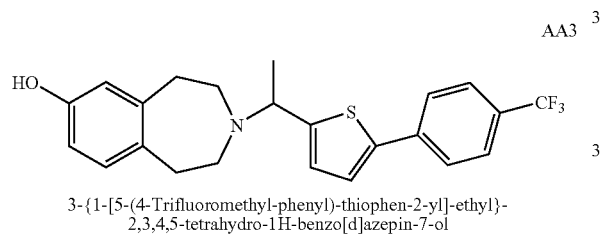

3-{1-[5-(4-Trifluoromethyl-phenyl)-thiophen-2-yl]-ethyl}-2,3,4,5-tetrahydro-1H-benzo[d]azepin-7-ol Cpd AA3 was prepared according to a similar procedure as for cpd Y2b. Cpd AA3 was obtained (249 mg, 53%) as a foam solid: $^1$H NMR (300 MHz, CDCl$_3$) δ 7.67 (d, J=8.3 Hz, 2H), 7.59 (d, J=8.5 Hz, 2H), 7.23 (d, J=3.7 Hz, 1H), 6.94 (d, J=7.9 Hz, 1H), 6.84 (d, J=3.5 Hz, 1H), 6.59-6.54 (m, 2H), 4.49 (brs, 1H), 2.86 (m, 4H), 2.71 (m, 4H), 1.41 (d, J=6.8 Hz, 3H); MS (ES) m/z: 418 (M+H$^+$).

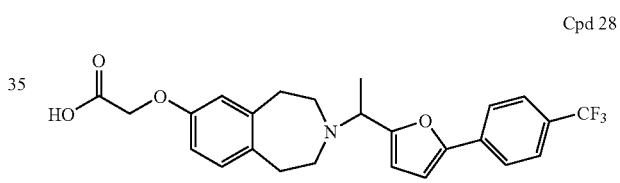

(3-{1-[5-(4-Trifluoromethyl-phenyl)-thiophen-2-yl]-ethyl}-2,3,4,5-tetrahydro-1H-benzo[d]azepin-7-yloxy)-acetic acid ethyl ester Cpd AA4 was prepared according to a similar procedure as for cpd Y2c. Cpd AA4 was obtained (222 mg, 74%) as brown oil: $^1$H NMR (300 MHz, CDCl$_3$) δ 7.67 (d, J=8.2 Hz, 2H), 7.59 (d, J=8.3 Hz, 2H), 7.23 (d, J=3.6 Hz, 1H), 6.99 (d, J=8.2 Hz, 1H), 6.84 (d, J=3.5 Hz, 1H), 6.69 (d, J=2.6 Hz, 1H), 6.61 (dd, J=8.2, 2.6 Hz, 1H), 4.57 (s, 2H), 4.26 (q, J=7.1 Hz, 2H), 4.12 (q, J=7.1 Hz, 1H), 2.88 (m, 4H), 2.69 (m, 4H), 1.41 (d, J=6.7 Hz, 3H), 1.29 (t, J=7.2 Hz, 3H); MS (ES) m/z: 504 (M+H$^+$).

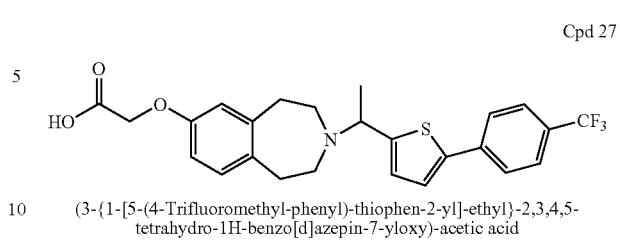

(3-{1-[5-(4-Trifluoromethyl-phenyl)-thiophen-2-yl]-ethyl}-2,3,4,5-tetrahydro-1H-benzo[d]azepin-7-yloxy)-acetic acid Cpd 27 was prepared according to a similar procedure as for cpd 25. Cpd 27 was obtained (220 mg) in 100% yield: $^1$H NMR (300 MHz, CDCl$_3$) δ 7.62 (s, 4H), 7.26 (m, 1H), 7.17 (d, J=3.5 Hz, 1H), 6.90 (d, J=8.2 Hz, 1H), 6.72 (dd, J=8.1, 2.4 Hz, 1H), 6.61 (d, J=2.2 Hz, 1H), 4.98 (m, 1H), 4.60 (s, 2H), 3.40-2.55 (m, 8H), 1.92 (d, J=6.9 Hz, 3H); MS (ES) m/z: 476 (M+H$^+$).

Cpd 27 racemates were separated by chiral HPLC. Condition used: column AD 25 cm, λ 302 nm, flow 1 ml/min; eluents: 70% of (Heptane+0.1% TFA) and 30% of ((MeOH+EtOH) 13/1+0.1% TFA); For cpd 27a: α=(−)45.0° (c=1, MeOH); For cpd 27b: α=(+)57.7° (c=1, MeOH/CHCl3).

Example BB

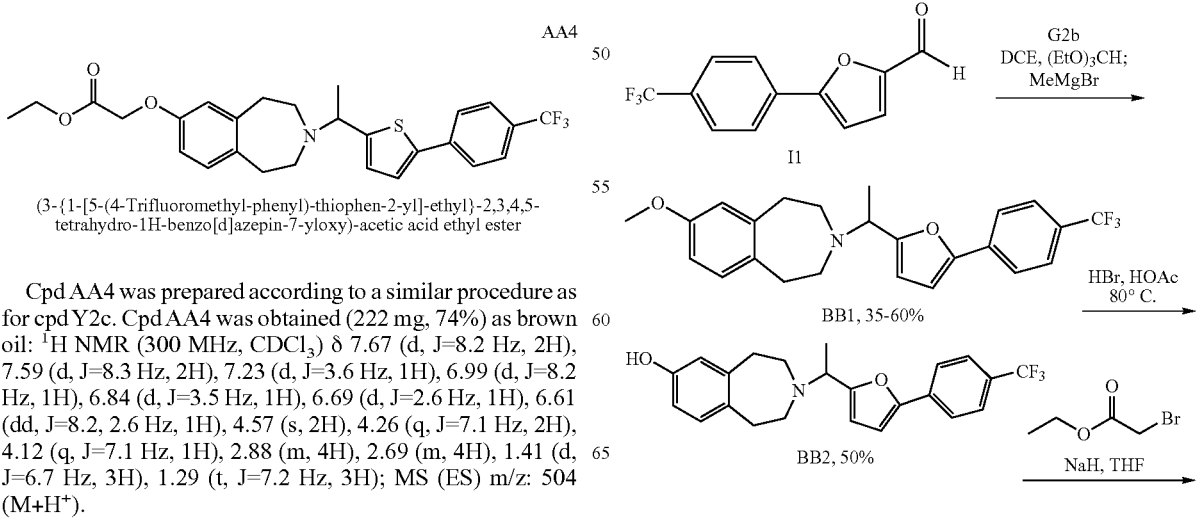

Compound 28: (3-{1-[5-(4-Trifluoromethyl-phenyl)-furan-2-yl]-ethyl}-2,3,4,5-tetrahydro-1H-benzo[d]azepin-7-yloxy)-acetic acid; compound with methane The title compound was made according to Scheme BB.

-continued

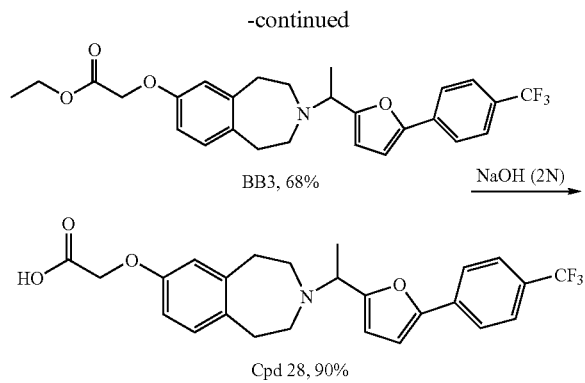

BB3, 68%

NaOH (2N) →

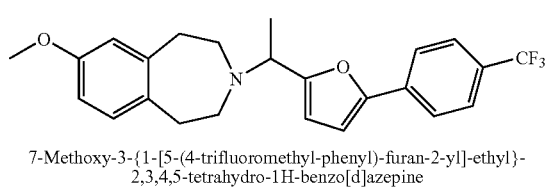

Cpd 28, 90%

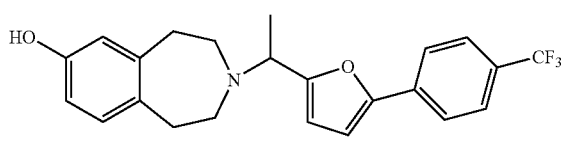

BB1

7-Methoxy-3-{1-[5-(4-trifluoromethyl-phenyl)-furan-2-yl]-ethyl}-2,3,4,5-tetrahydro-1H-benzo[d]azepine To a mixture of cpd I1 (750 mg, 3.124 mmol), cpd G2b (553 mg, 3.124 mmol) and dichloroethane (10 mL) was added triethyl orthoformate (0.52 mL, 3.124 mmol). After stirring at room temperature for 16 h, the resulting mixture was treated with MeMgBr (1.4 M in Toluene and THF, 4.5 mL, 6.25 mmol) with slow addition. The mixture was quenched with aqueous NH4Cl after stirring for another 10 min and then partitioned between EtOAc and water. The organic layers were separated, dried and concentrated. The crude product was purified by column chromatography to provide cpd BB1 (646 mg, 50%) as yellow oil: $^1$H NMR (300 MHz, CDCl$_3$) δ 7.68 (d, J=8.2 Hz, 2H), 7.58 (d, J=8.4 Hz, 2H), 6.97 (d, J=8.1 Hz, 1H), 6.59-6.66 (m, 3H), 6.22 (s, 1H), 4.02-4.04 (m, 1H), 3.74 (s, 3H), 2.78-2.87 (m, 6H), 2.56-2.58 (m, 2H), 1.49 (d, J=6.6 Hz, 3H); MS (ES) m/z: 416 (M+H$^+$).

BB2

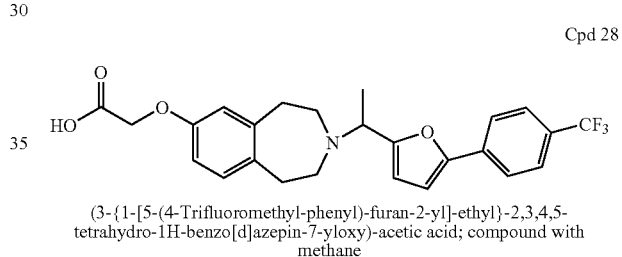

3-{1-[5-(4-Trifluoromethyl-phenyl)-furan-2-yl]-ethyl}-2,3,4,5-tetrahydro-1H-benzo[d]azepin-7-ol Cpd BB2 was prepared according to a similar procedure as for cpd Z2. Cpd BB2 was obtained (157 mg) in 54% yield: $^1$H NMR (300 MHz, CDCl$_3$) δ 7.68 (d, J=8.4 Hz, 2H), 7.58 (d, J=8.4 Hz, 2H), 6.91 (d, J=7.9 Hz, 1H), 6.66 (d, J=3.3 Hz, 1H), 6.51-6.57 (m, 2H), 6.23 (d, J=3.2 Hz, 1H), 4.01-4.09 (m, 1H), 2.78-2.86 (m, 6H), 2.57-2.68 (m, 2H), 1.50 (d, J=6.9 Hz, 3H); MS (ES) m/z: 402 (M+H$^+$).

BB3

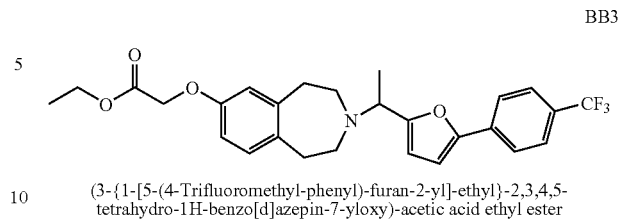

(3-{1-[5-(4-Trifluoromethyl-phenyl)-furan-2-yl]-ethyl}-2,3,4,5-tetrahydro-1H-benzo[d]azepin-7-yloxy)-acetic acid ethyl ester Cpd BB3 was prepared according to a similar procedure as for cpd Z3. Cpd BB3 was obtained (546 mg, 68%) as light brown oil: $^1$H NMR (300 MHz, CDCl$_3$) δ 7.68 (d, J=8.3 Hz, 2H), 7.59 (d, J=8.3 Hz, 2H), 6.96 (d, J=8.2 Hz, 1H), 6.60-6.67 (m, 2H), 6.56-6.59 (m, 1H), 6.21 (s, 1H), 4.55 (s, 2H), 4.21-4.28 (q, J=7.2 Hz, 2H), 4.00-4.11 (m, 1H), 2.76-2.87 (m, 6H), 2.55-2.58 (m, 2H), 1.47-1.50 (d, J=6.8 Hz, 3H), 1.23-1.28 (m, 3H); MS (ES) m/z: 488 (M+H$^+$). Cpd DD3 racemates were separated by chiral HPLC: column AD 500 g, flow rate 80 ml/min, λ 220 nm, eluent: CH$_3$CN. One enantiomer BB3a shows optical rotation α=(+)7.9° (c=1, 100 mm, MeOH); The other enantiomer BB3b shows optical rotation α=(−) 3.8° (c 1, 100 mm, MeOH).

Cpd 28

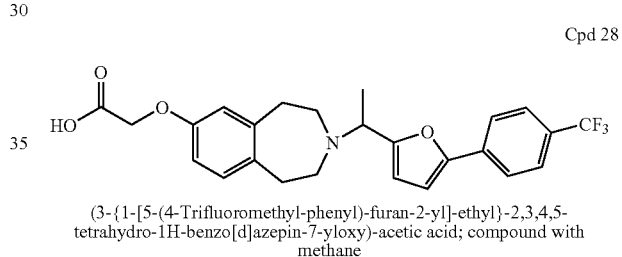

(3-{1-[5-(4-Trifluoromethyl-phenyl)-furan-2-yl]-ethyl}-2,3,4,5-tetrahydro-1H-benzo[d]azepin-7-yloxy)-acetic acid; compound with methane Cpd 28 was prepared according to a similar procedure as for cpd 26. Cpd 28 was obtained (30 mg) in quantitative yield: $^1$H NMR (300 MHz, DMSO) δ 7.82 (d, J=8.3 Hz, 2H), 7.74 (d, J=8.5 Hz, 2H), 7.06 (d, J=3.3 Hz, 1H), 6.96 (d, J=8.2 Hz, 1H), 6.65 (d, J=2.6 Hz, 1H), 6.55-6.57 (m, 1H), 6.41 (d, J=3.3 Hz, 1H), 4.56 (s, 2H), 4.07 (m, 1H), 2.69-2.79 (m, 8H), 1.41 (d, J=7.0 Hz, 3H); MS (ES) m/z: 460 (M+H$^+$). Cpd 28a: α(+)19.2° (c=0.4, MeOH); Cpd 28b: α=(−)25.4° (c=0.4, MeOH).

Example CC

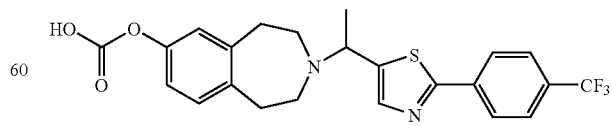

Compound 29: (3-{1-[2-(4-Trifluoromethyl-phenyl)-thiazol-5-yl]-ethyl}-2,3,4,5-tetrahydro-1H-benzo[d]azepin-7-yloxy)-acetic acid The title compound was made according to Scheme CC

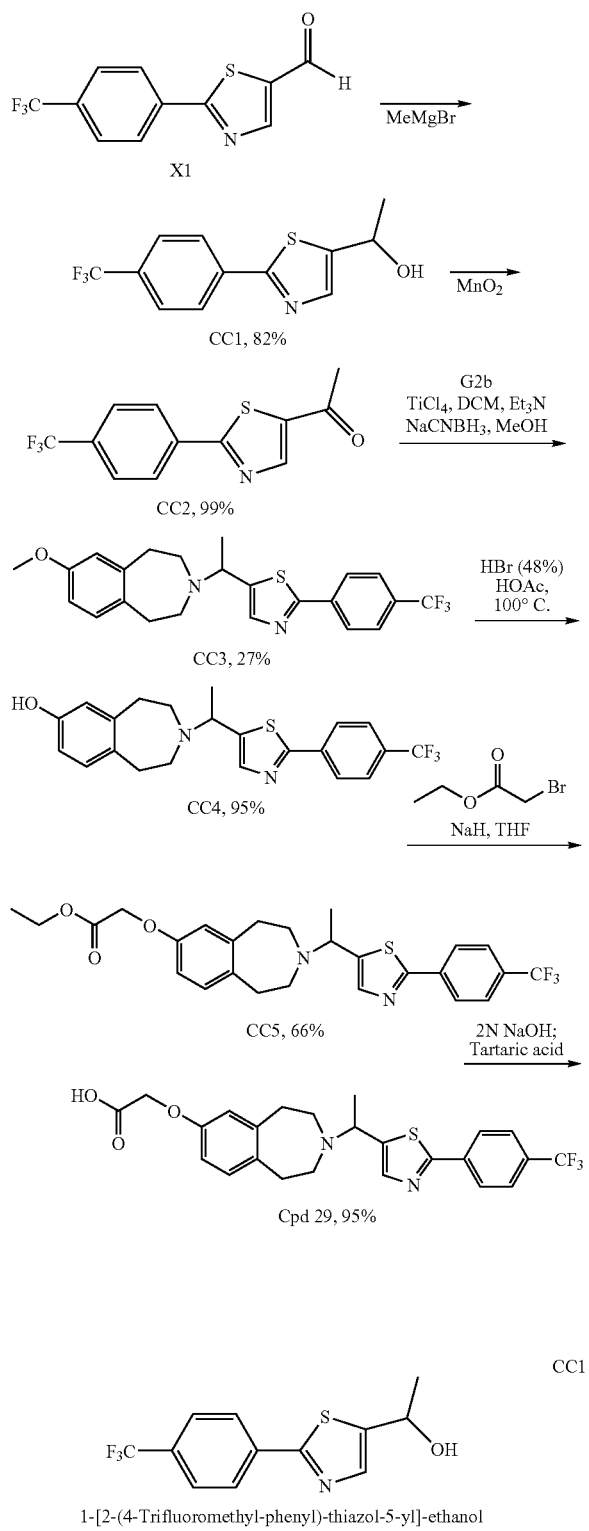

To a solution of cpd X1 (445 mg, 1.73 mmol) in THF (5 mL) was added MeMgBr (1.4 M, 1.48 mL, 2.078 mmol) at 0° C. After stirring at 0° C. for 2 h, the mixture was quenched with aqueous NH$_4$Cl and extracted with EtOAc. The organic extracts were dried and concentrated. The residue was purified by column chromatography to give cpd CC1 (307 mg) in 65% yield: $^1$H NMR (300 MHz, CDCl$_3$) δ 8.04 (d, J=8.1 Hz, 2H), 7.16 (s, 1H), 7.70 (d, J=8.2 Hz, 2H), 5.20-5.27 (q, J=6.3 Hz, 1H), 1.67 (d, J=6.4 Hz, 3H); MS (ES) m/z: 274 (M+H$^+$).

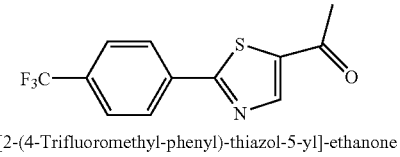

1-[2-(4-Trifluoromethyl-phenyl)-thiazol-5-yl]-ethanone

A mixture of cpd CC1 (302 mg, 1.106 mmol), MnO$_2$ (1.92 g, 22.12 mmol) in dichloromethane (20 mL) was stirred at room temperature for 7 h. It was filtered through celite and concentrated to give cpd CC2 (295 mg, 99%) as a white solid: $^1$H NMR (300 MHz, CDCl$_3$) δ 8.38 (s, 1H), 8.12 (d, J=8.2 Hz, 2H), 7.74 (d, J=8.2 Hz, 2H), 2.64 (s, 3H); MS (ES) m/z: 272 (M+H$^+$).

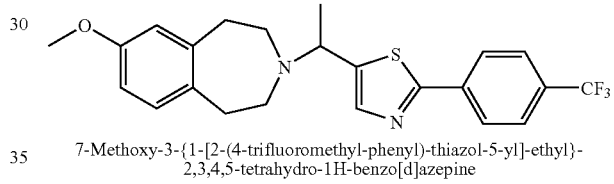

7-Methoxy-3-{1-[2-(4-trifluoromethyl-phenyl)-thiazol-5-yl]-ethyl}-2,3,4,5-tetrahydro-1H-benzo[d]azepine Cpd CC3 was prepared according to a similar procedure as for cpd AA2. Cpd CC3 was obtained (130 mg, 27%) as yellow slurry: $^1$H NMR (300 MHz, CDCl$_3$) δ 8.03 (d, J=8.2 Hz, 2H), 7.68 (d, J=8.2 Hz, 2H), 7.61 (s, 1 H), 6.99 (d, J=7.9 Hz, 1H), 6.62-6.65 (m, 2H), 4.21 (m, 1H), 3.77 (s, 3H), 2.85-2.90 (m, 4H), 2.70-2.76 (m, 4H), 1.44 (d, J=6.7 Hz, 3H); MS (ES) m/z: 433 (M+H$^+$).

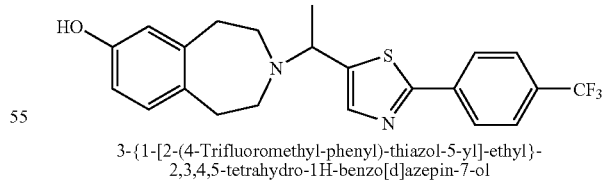

3-{1-[2-(4-Trifluoromethyl-phenyl)-thiazol-5-yl]-ethyl}-2,3,4,5-tetrahydro-1H-benzo[d]azepin-7-ol Cpd CC4 was prepared according to a similar procedure as for cpd Y2b. Cpd CC4 was obtained (38 mg) in 95% yield: $^1$H NMR (300 MHz, CDCl$_3$) δ 8.03 (d, J=8.2 Hz, 2H), 7.68 (d, J=8.3 Hz, 2H), 7.61 (s, 1H), 6.94 (d, J=7.9 Hz, 1H), 6.55-6.59 (m, 2H), 4.16-4.22 (m, 1H), 2.84 (m, 4H), 2.64-2.68 (m, 4H), 1.44 (d, J=6.6 Hz, 3H); MS (ES) m/z: 419 (M+H$^+$), 417 (M−H$^+$).

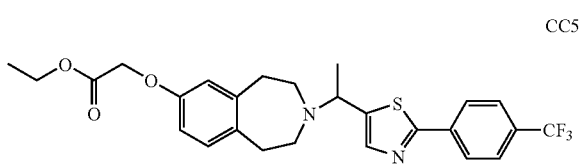

(3-{1-[2-(4-Trifluoromethyl-phenyl)-thiazol-5-yl]-ethyl}-2,3,4,5-tetrahydro-1H-benzo[d]azepin-7-yloxy)-acetic acid ethyl ester Cpd CC5 was prepared according to a similar procedure as for cpd Y2c. Cpd CC5 was obtained (23 mg) in 70% yield: $^1$H NMR (300 MHz, CDCl$_3$) δ 8.03 (d, J=8.2 Hz, 2H), 7.68 (d, J=8.2 Hz, 2H), 7.61 (s, 1H), 7.00 (d, J=8.1 Hz, 1H), 6.69 (d, J=2.5 Hz, 1H), 6.60-6.64 (dd, J=2.6, 8.2 Hz, 1H), 4.57 (s, 2H), 4.11-4.30 (m, 3H), 2.86 (m, 4H), 2.69 (m, 4H), 1.44 (d, J=6.6 Hz, 3H), 1.23-1.31 (m, 3H); MS (ES) m/z: 505 (M+H$^+$).

Cpd 29

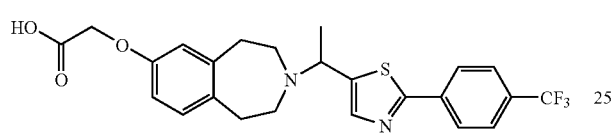

(3-{1-[2-(4-Trifluoromethyl-phenyl)-thiazol-5-yl]-ethyl}-2,3,4,5-tetrahydro-1H-benzo[d]azepin-7-yloxy)-acetic acid Cpd 29 was prepared according to a similar procedure as for cpd 27. Cpd 29 was obtained (18 mg, 95%) as a white solid: $^1$H NMR (300 MHz, CDCl$_3$) δ 8.03 (d, J=8.2 Hz, 2H), 7.75 (s, 1H), 7.68 (d, J=8.2 Hz, 2H), 6.90 (d, J=8.1 Hz, 1H), 6.72 (m, 1H), 6.60 (s, 1H), 5.15 (m, 1H), 4.61 (s, 2H), 3.00 (m, 8H), 1.90 (d, J=6.6 Hz, 3H); MS (ES) m/z: 477 (M+H$^+$).

Example DD

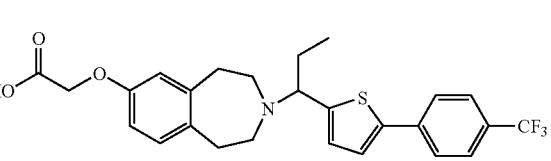

Compound 30: (3-{1-[5-(4-Trifluoromethyl-phenyl)-thiophen-2-yl]-propyl}-2,3,4,5-tetrahydro-1H-benzo[d]azepin-7-yloxy)-acetic acid The title compound was made according to Scheme DD.

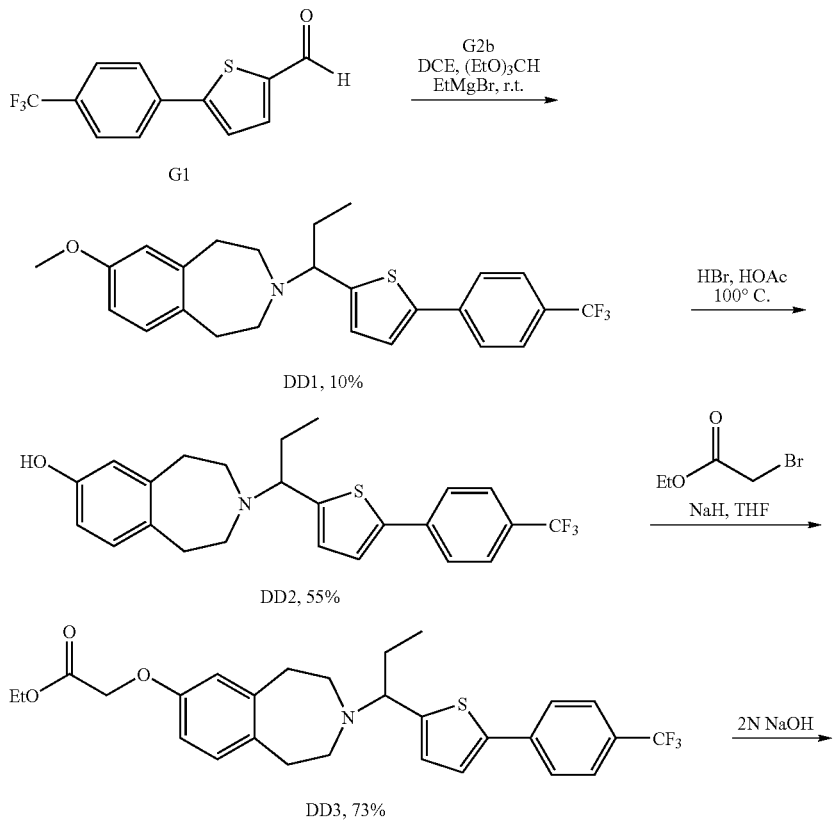

Scheme DD

-continued

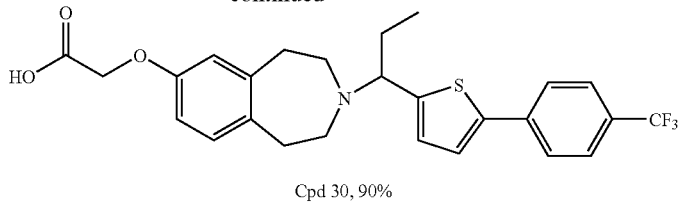

Cpd 30, 90%

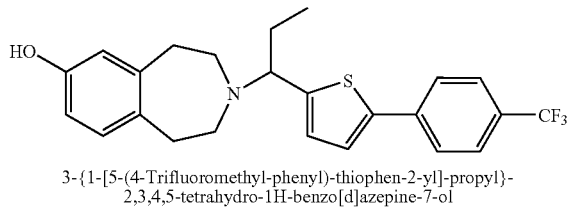

3-{1-[5-(4-Trifluoromethyl-phenyl)-thiophen-2-yl]-propyl}-
2,3,4,5-tetrahydro-1H-benzo[d]azepine-7-ol Cpd DD1 was prepared following a similar procedure as for cpd BB1. Crude cpd DD1 was subjected to the same reaction condition as for preparing cpd Z2 and cpd DD2 was obtained (64 mg, 55%) as brown oil: $^1$H NMR (300 MHz, CDCl$_3$) δ 7.56-7.64 (m, 4H), 7.21 (d, J=3.6 Hz, 1H), 6.91 (d, J=8.0 Hz, 1H), 6.80 (d, J=3.3 Hz, 1H), 6.49-6.56 (m, 2H), 3.83 (t, J=7.7 Hz, 1H), 2.83-2.92 (m, 4H), 2.70-2.80 (m, 2H), 2.54-2.61 (m, 2H), 1.83-1.99 (m, 2H), 1.24-1.28 (t, J=7.2 Hz, 3H); MS (ES) m/z: 432 (M+H$^+$).

DD3

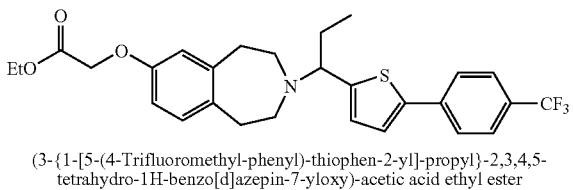

(3-{1-[5-(4-Trifluoromethyl-phenyl)-thiophen-2-yl]-propyl}-2,3,4,5-
tetrahydro-1H-benzo[d]azepin-7-yloxy)-acetic acid ethyl ester Cpd DD3 was prepared following the same procedure as for cpd Z3. Cpd DD3 was obtained (50 mg) in 73% yield: $^1$H NMR (300 MHz, CDCl$_3$) δ 7.56-7.64 (m, 4H), 7.21 (d, J=3.6 Hz, 1H), 6.96 (d, J=8.2 Hz, 1H), 6.80 (d, J=3.6 Hz, 1H), 6.66 (d, J=2.5 Hz, 1H), 6.56-6.60 dd, J=2.6, 8.2 Hz, 1H), 4.55 (s, 2H), 4.21-4.28 (q, J=7.1 Hz, 2H), 3.83 (m, 1H), 2.58-2.87 (m, 8H), 1.81-2.11 (m, 2H), 1.23-1.30 (q, J=7.0 Hz, 3H), 1.01 (t, J=7.3 Hz, 3H); MS (ES) m/z: 518 (M+H$^+$).

Cpd 30

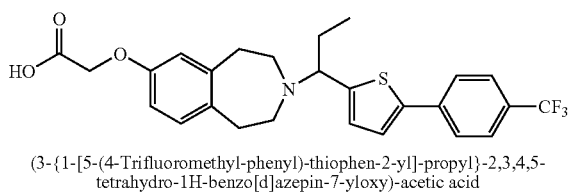

(3-{1-[5-(4-Trifluoromethyl-phenyl)-thiophen-2-yl]-propyl}-2,3,4,5-
tetrahydro-1H-benzo[d]azepin-7-yloxy)-acetic acid Cpd 30 was prepared according to the same procedure as for cpd 26. Cpd 30 was obtained (17 mg) in 45% yield: $^1$H NMR (300 MHz, CDCl$_3$) δ 7.52-7.62 (m, 5H), 7.12-7.16 (m, 1H), 6.91-6.97 (m, 1H), 6.67 (d, J=8.3 Hz, 1H), 6.62 (s, 1H), 4.65-4.76 (m, 1H), 4.61 (s, 2H), 3.56-3.85 (m, 4H), 2.64-2.75 (m, 4H), 1.90-2.09 (m, 2H), 0.95 (t, J=6.8 Hz, 3H); MS (ES) m/z: 490 (M+H$^+$).

Example EE

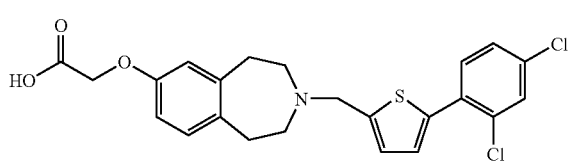

Compound 31: {3-[5-(2,4-Dichloro-phenyl)-thiophen-2-ylmethyl]-
2,3,4,5-tetrahydro-1H-benzo[d]azepin-7-yloxy)-acetic acid The title compound was made according to Scheme EE

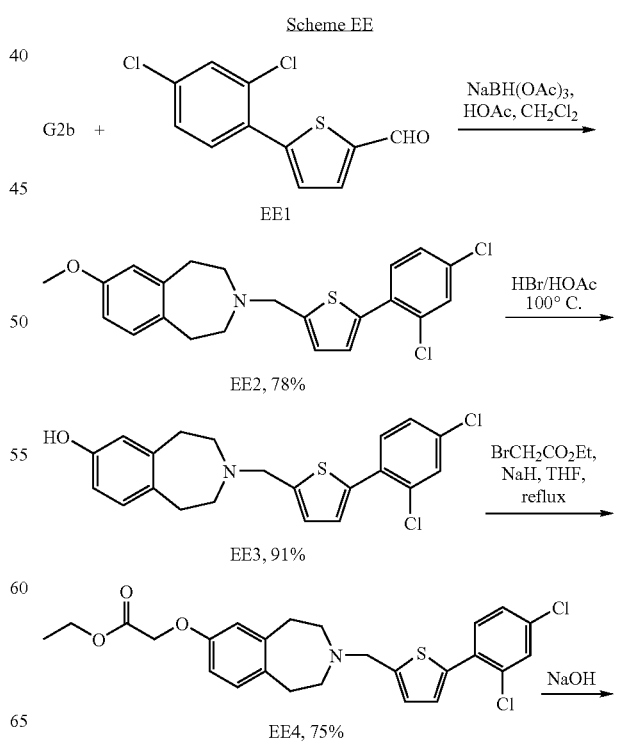

-continued

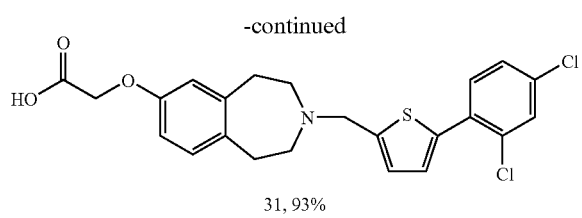

31, 93%

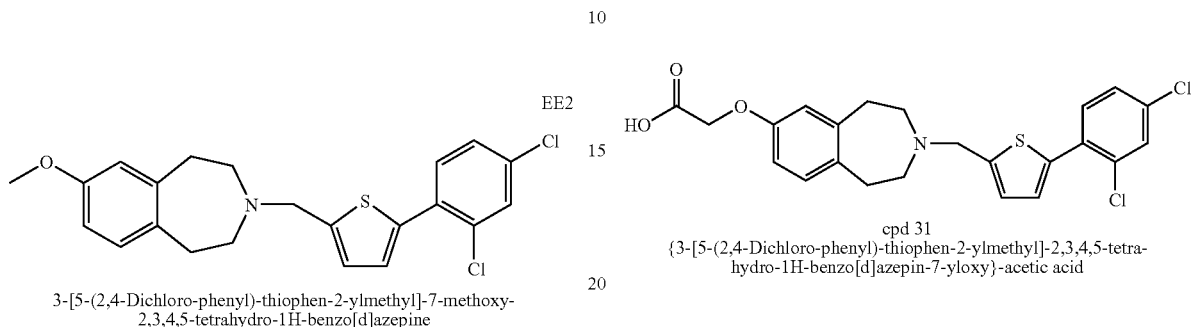

EE2

3-[5-(2,4-Dichloro-phenyl)-thiophen-2-ylmethyl]-7-methoxy-2,3,4,5-tetrahydro-1H-benzo[d]azepine To a mixture of cpd G2b (0.15 g, 0.85 mmol), 5-(dichlorophenyl)-thiophene-2-carbaldehyde (0.20 g, 0.78 mmol), CH$_2$Cl$_2$ (15 mL) and HOAc (0.05 mL, 0.87 mmol) at room temperature was added Na(OAc)$_3$BH (0.26 g, 1.17 mmol). The mixture was stirred for 2 days and additional Na(OAc)$_3$BH (0.13 g, 0.59 mmol) was added. After the mixture was continued stirring overnight, it was basified with aqueous NaHCO$_3$ and extracted with CH$_2$Cl$_2$. The organic extracts were dried (MgSO$_4$) and concentrated. The crude product was purified by column chromatography to give cpd EE2 (0.25 g, 78%): $^1$H NMR (300 MHz, CDCl$_3$) δ 7.39 (m, 2H), 7.17 (m, 2H), 6.92 (d, 1H, J=7.9 Hz), 6.85 (m, 1H), 6.60 (m, 2H), 3.84 (s, 2H), 3.70 (s, 3H), 2.85 (m, 4H), 2.67 (m, 4H); MS (ES) m/z: 418, 420 (M+H$^+$).

EE3

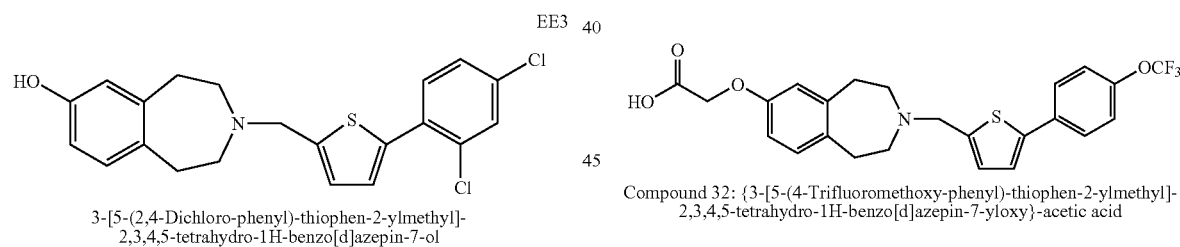

3-[5-(2,4-Dichloro-phenyl)-thiophen-2-ylmethyl]-2,3,4,5-tetrahydro-1H-benzo[d]azepin-7-ol Cpd EE3 was prepared according to the same procedure as for cpd X3. Cpd EE3 was obtained (0.22 g, 91%) as a brown solid: $^1$H NMR (300 MHz, CDCl$_3$) δ 7.35 (m, 2H), 7.15 (m, 2H), 6.83 (m, 2H), 6.50 (m, 2H), 3.81 (s, 2H), 2.80 (m, 4H), 2.64 (m, 4H); MS (ES) m/z: 404, 406 (M+H$^+$).

EE4

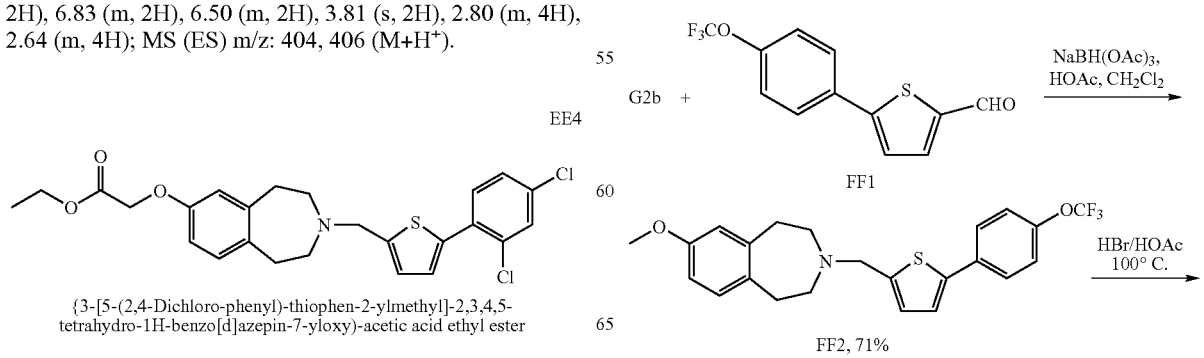

{3-[5-(2,4-Dichloro-phenyl)-thiophen-2-ylmethyl]-2,3,4,5-tetrahydro-1H-benzo[d]azepin-7-yloxy)-acetic acid ethyl ester Cpd EE4 was prepared according to the same procedure as for cpd X4. Cpd EE4 was obtained (0.17 g, 65%) as pale oil: $^1$H NMR (300 MHz, CDCl$_3$) δ 7.39 (s, 1H), 7.38 (d, J=11 Hz, 1H), 7.16 (m, 2H), 6.91 (d, J=8.2 Hz, 1H), 6.81 (d, J=3.6 Hz, 1H), 6.61 (d, J=2.7 Hz, 1H), 6.54 (dd, J=8.2, 2.7 Hz, 1H), 4.51 (s, 2H), 4.19 (q, J=7.1 Hz), 3.80 (s, 2H), 2.83 (m, 4H), 2.63 (m, 4H); 1.22 (t, J=7.1 Hz, 3H); MS (ES) m/z: 490, 492 (M+H$^+$).

cpd 31
{3-[5-(2,4-Dichloro-phenyl)-thiophen-2-ylmethyl]-2,3,4,5-tetrahydro-1H-benzo[d]azepin-7-yloxy}-acetic acid A solution of cpd EE4 (0.15 g, 0.31 mmol) in THF (2 mL) and methanol (2 mL) was treated with 1N aqueous NaOH (0.60 mL, 0.60 mmol). After stirring for 1 h, the mixture was concentrated to dryness. The residue was dissolved in H$_2$O, washed with Et$_2$O twice and then acidified with 1N HCl. The precipitates were collected and dried to give cpd 31 (0.13 g, 93%). $^1$H NMR (300 MHz, DMSO-d$_6$) δ 7.73 (d, J=2.1 Hz, 1H), 7.65 (d, J=8.5 Hz, 1H), 7.47 (dd, J=8.3, 2.2 Hz, 1H), 7.34 (d, J=3.6 Hz, 1H), 7.06 (d, J=6.5 Hz, 1H), 7.00 (d, J=8.3 Hz, 1H) 6.70 (d, J=2.5 Hz, 1H), 6.61 (dd, J=8.3, 2.6 Hz, 1H), 4.59 (s, 2H), 3.95 (s, 2H), 2.85 (m, 4H), 2.68 (m, 4H); MS (ES) m/z: 462, 464 (M+H$^+$).

Example FF

Compound 32: {3-[5-(4-Trifluoromethoxy-phenyl)-thiophen-2-ylmethyl]-2,3,4,5-tetrahydro-1H-benzo[d]azepin-7-yloxy}-acetic acid The title compound was made according to Scheme FF.

Scheme FF

G2b + [FF1 structure: F$_3$CO-phenyl-thiophene-CHO]  →(NaBH(OAc)$_3$, HOAc, CH$_2$Cl$_2$)

FF2, 71%  →(HBr/HOAc, 100° C.)

-continued

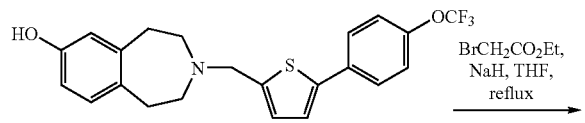

FF3, 74%

BrCH₂CO₂Et,
NaH, THF,
reflux

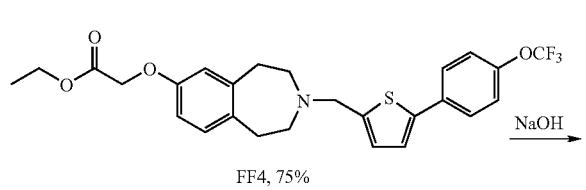

FF4, 75%

NaOH

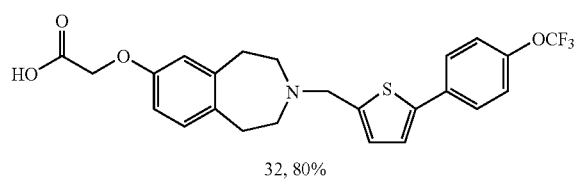

32, 80%

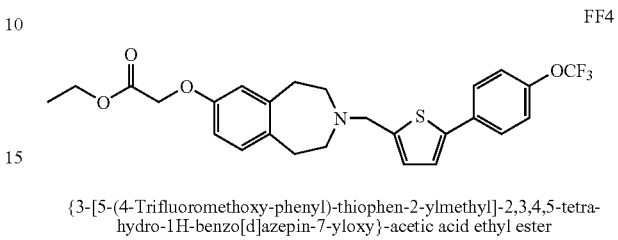

FF2

7-Methoxy-3-[5-(4-trifluoromethoxy-phenyl)-thiophen-2-ylmethyl]-
2,3,4,5-tetrahydro-1H-benzo[d]azepine Cpd FF2 was prepared according to the same procedure as for cpd EE2. Cpd FF2 was obtained (0.24 g, 71%) as a solid: $^1$H NMR (300 MHz, CDCl₃) δ 7.51 (d, J=8.8 Hz, 2H), 7.16 (m, 2H), 7.05 (d, J=3.6 Hz, 1H), 6.92 (d, J=3.6 Hz, 1H), 6.81 (s, 1H), 6.56 (m, 2H), 3.79 (s, 2H), 3.70 (s, 3H), 2.83 (m, 4H), 2.63 (m, 4H); MS (ES) m/z: 434 (M+H⁺).

FF3

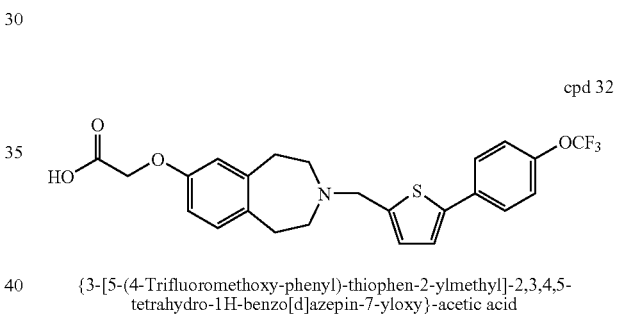

3-[5-(4-Trifluoromethoxy-phenyl)-thiophen-2-ylmethyl]-2,3,4,5-tetrahydro-
1H-benzo[d]azepin-7-ol Cpd FF3 was prepared according to the same procedure as for cpd EE3. Cpd FF3 was obtained (0.17 g, 74%) as white foam: $^1$H NMR (300 MHz, CDCl₃) δ 7.51 (d, J=8.8 Hz, 2H), 7.13 (d, J=8.1 Hz, 2H), 7.05 (d, J=3.6 Hz, 1H), 6.87 (d, J=7.8 Hz, 1H), 6.80 (d, J=3.3 Hz, 1H), 6.50 (m, 2H), 3.79 (s, 2H), 2.80 (m, 4H), 2.63 (m, 4H); MS (ES) m/z: 420 (M+H⁺).

FF4

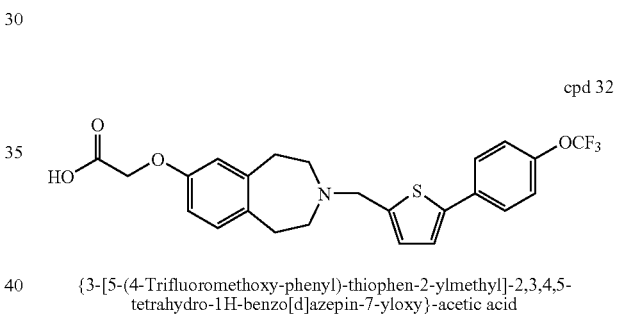

{3-[5-(4-Trifluoromethoxy-phenyl)-thiophen-2-ylmethyl]-2,3,4,5-tetra-
hydro-1H-benzo[d]azepin-7-yloxy}-acetic acid ethyl ester Cpd FF4 was prepared according to the same procedure as for cpd EE4. Cpd FF4 was obtained (0.15 g, 75%) as pale oil: $^1$H NMR (300 MHz, CDCl₃) δ 7.51 (d, J=8.8 Hz, 2H), 7.11 (d, J=8.0 Hz, 2H), 7.04 (d, J=3.6 Hz, 1H), 6.91 (d, J=8.2 Hz, 1H), 6.78 (d, J=3.6 Hz 1H), 6.61 (d, J=2.7 Hz, 1H), 6.54 (dd, J=8.2, 2.7 Hz, 1H), 4.50 (s, 2H), 4.17 (q, J=7.1 Hz), 3.77 (s, 2H), 2.81 (m, 4H), 2.62 (m, 4H), 1.21 (t, J=7.1 Hz); MS (ES) m/z: 492 (M+H⁺).

cpd 32

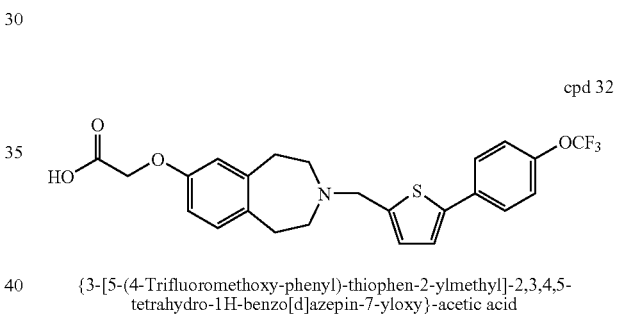

{3-[5-(4-Trifluoromethoxy-phenyl)-thiophen-2-ylmethyl]-2,3,4,5-
tetrahydro-1H-benzo[d]azepin-7-yloxy}-acetic acid Cpd 32 was prepared according to the same procedure as for cpd 31. Cpd 32 was obtained (0.08 g, 80%) as a white solid: $^1$H NMR (300 MHz, DMSO-d₆) δ 7.74 (d, J=7.7 Hz, 2H), 7.39 (m, 3H), 6.98 (d, J=2.7 Hz, 1H), 6.91 (d, J=8.1 Hz, 1H), 6.57 (s, 1H), 6.49 (d, J=8.1 Hz, 1H), 4.02 (s, 2H), 3.82 (s, 2H), 2.77 (m, 4H), 2.60 (m, 4H); MS (ES) m/z: 478 (M+H⁺).

Example GG

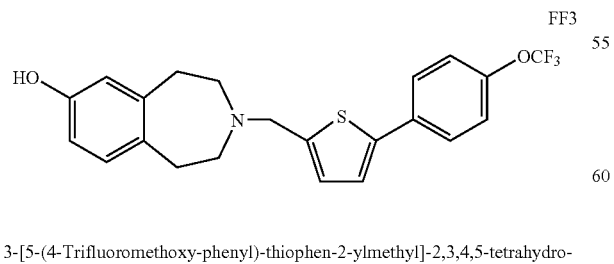

Compound 33: {3-[5-(2,4-Dichloro-phenyl)-furan-2-ylmethyl]-2,3,4,5-
tetrahydro-1H-benzo[d]azepin-7-yloxy}-acetic acid The title compound was made according to Scheme GG.

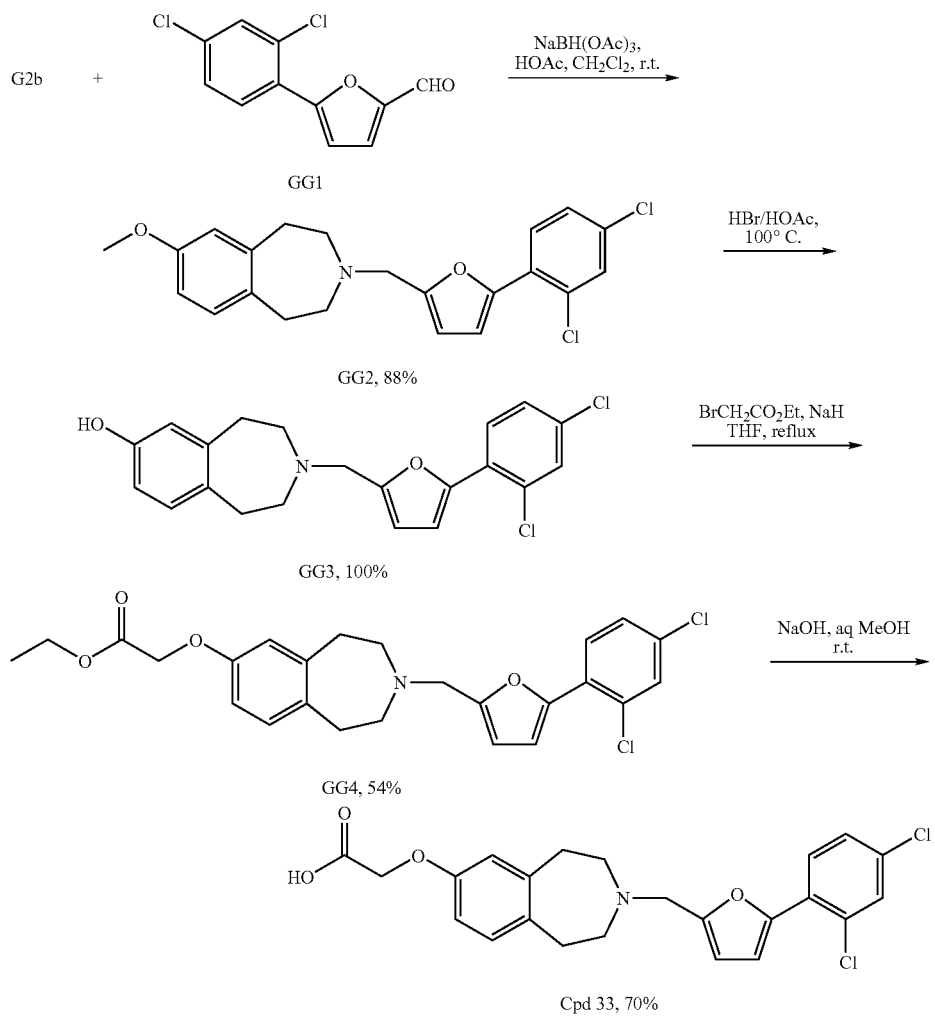

extracts were dried (MgSO$_4$) and concentrated. The crude product was purified by column chromatography to give cpd GG2 (0.29 g, 88%); $^1$H NMR (300 MHz, CDCl$_3$) δ 7.69 (d, J=8.6 Hz, 1H), 7.35 (d, J=2.1 Hz), 7.19n (m, 1H), 6.97 (d, =3.4 Hz, 1H), 6.91 (d, J=7.9 Hz, 1H), 6.56 (m, 2H), 6.26 (d, J=3.4 Hz, 1H), 3.74 (s, 2H), 3.69 (s, 3H), 2.84 (m, 4H), 2.66 (m, 4H), MS (ES) m/z: 402, 404 (M+H$^+$).

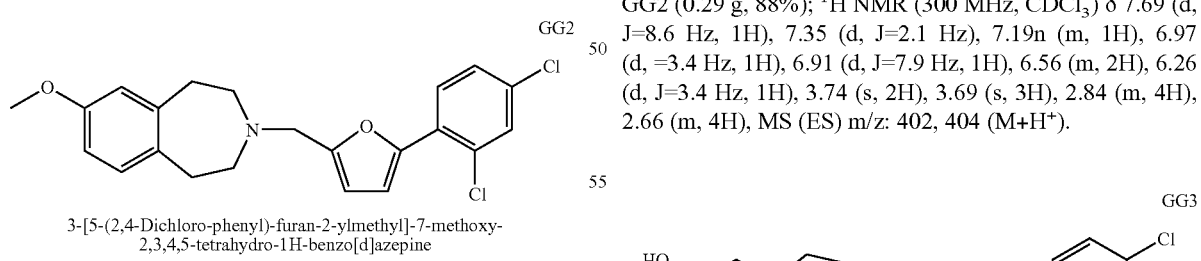

3-[5-(2,4-Dichloro-phenyl)-furan-2-ylmethyl]-7-methoxy-2,3,4,5-tetrahydro-1H-benzo[d]azepine To a mixture of cpd G2b (0.17 g, 0.96 mmol), 5-(2,4-dichlorophenyl)-furan-2-carbaldehyde (0.20 g, 0.83 mmol), CH$_2$Cl$_2$ (15 mL) and HOAc (0.05 mL, 0.87 mmol) at room temperature was added Na(OAc)$_3$BH (0.30 g, 1.37 mmol). After the mixture was stirred overnight, it was basified with aqueous NaHCO$_3$ and extracted with CH$_2$Cl$_2$. The organic

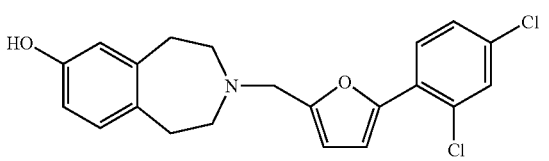

3-[5-(2,4-Dichloro-phenyl)-furan-2-ylmethyl]-2,3,4,5-tetrahydro-1H-benzo[d]azepin-7-ol A mixture of GG2 (0.28 g, 0.70 mmol), 48% HBr (0.80 mL, 7.07 mmol) and n-Bu$_4$NBr (30 mg, 0.09 mmol) in HOAc (0.8 mL) was heated at 100° C. under N$_2$ for 18 h. After cooled to room temperature, the reaction mixture was treated with aqueous K$_2$CO$_3$ till pH 9. The precipitates were collected, washed with water and dried to give cpd GG3 (0.27 g, 100%) as a beige solid: $^1$H NMR (300 MHz, DMSO-d$_6$) δ 9.30 (s, 1H), 7.91 (d, J=48.6 Hz, 1H), 7.77 (d, J=2.1 Hz, 1H), 7.60 (dd, J=8.1, 2.2 Hz, 1H), 7.20 (d, J=3.5 Hz, 1H), 6.97 (d, J=8.1 Hz, 1H), 6.88 (d, J=31 Hz, 1H), 6.60 (d, J=2.3 Hz, 1H), 6.56 (dd, J=8.1, 2.3 Hz, 1H), 4.56 (s, 2H), 3.10 (m, 4H), 2.94 (m, 4H); MS (ES) m/z: 388, 390 (M+H$^+$).

GG4

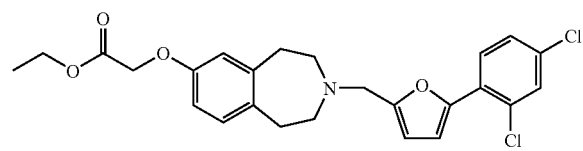

{3-[5-(2,4-Dichloro-phenyl)-furan-2-ylmethyl]-2,3,4,5-tetrahydro-1H-benzo[d]azepin-7-yloxy}-acetic acid ethyl ester Cpd GG4 was prepared according to the same procedure as for cpd X4. Cpd GG4 was obtained (65 mg, 54%) as pale oil: $^1$H NMR (300 MHz, CDCl$_3$) δ 7.69 (d, J=8.6 Hz, 1H), 7.36 (d, J=2.1 Hz, 1H), 7.24 (m, 1H), 6.97 (d, J=3.4 Hz, 1H), 6.91 (d, J=8.2 Hz, 1H), 6.65 (d, J=5.01 Hz), 6.57 (dd, J=8.2, 2.70 Hz, 1H), 6.29 (d, J=3.3 Hz, 1H), 4.50 (s, 2H), 4.19 (q, J=7.1 Hz, 2H), 3.77 (s, 2H), 2.85 (m, 4H), 2.68 (m, 4H); MS (ES) m/z: 474, 476 (M+H$^+$).

cpd 33

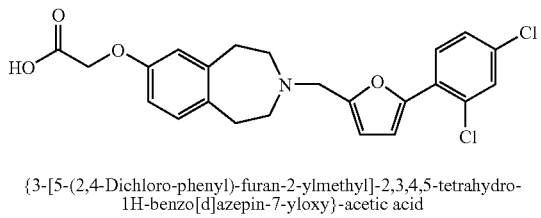

{3-[5-(2,4-Dichloro-phenyl)-furan-2-ylmethyl]-2,3,4,5-tetrahydro-1H-benzo[d]azepin-7-yloxy}-acetic acid A mixture of cpd GG4 (50 mg, 0.10 mmol) in methanol (2 mL) was treated with 1N aqueous NaOH (0.30 mL, 0.30 mmol). After stirring for 1 h, the mixture was concentrated to dryness. The residue was dissolved in H$_2$O and acidified with 1N HCl. A brown solid was collected and dried to give cpd 33 (32 mg, 70%): $^1$H NMR (300 MHz, DMSO-d$_6$) δ 7.83 (d, J=8.9 Hz, 1H), 7.72 (m, 1H), 7.55 (m, 1H), 7.13 (d, J=3.0 Hz, 1H), 7.03 (d, J=8.9 Hz, 1H), 6.72 (s, 1H), 6.63 (d, J=6.1 Hz), 4.60 (s, 2H), 4.61 (s, 2H), 3.32 (s, 2H), 2.80 (m, 8H); MS (ES) m/z: 446, 448 (M+H$^+$).

Example HH

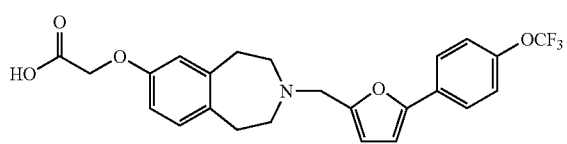

Compound 34: {3-[5-(4-Trifluoromethoxy-phenyl)-furan-2-ylmethyl]-2,3,4,5-tetrahydro-1H-benzo[d]azepin-7-yloxy}-acetic acid The title compound was made according to Scheme HH.

Scheme HH

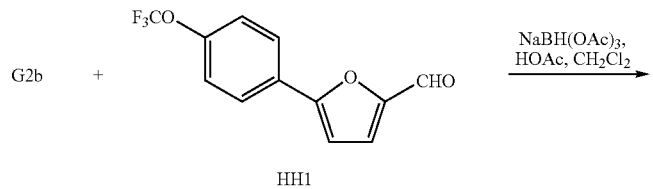

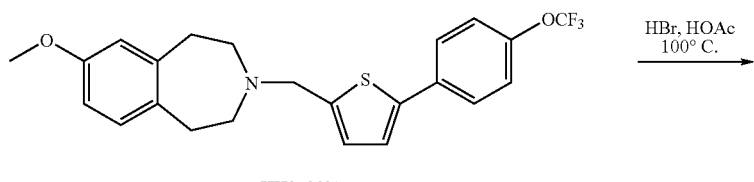

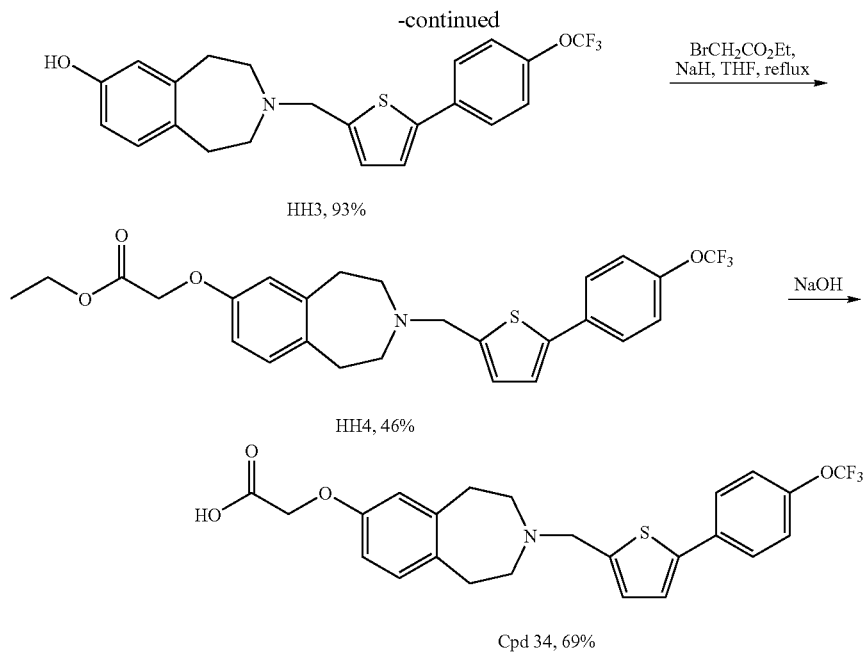

HH3, 93%

HH4, 46%

Cpd 34, 69%

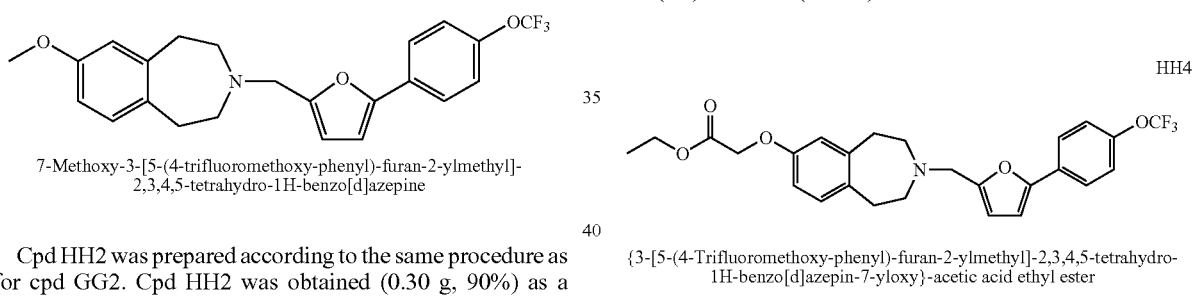

7-Methoxy-3-[5-(4-trifluoromethoxy-phenyl)-furan-2-ylmethyl]-2,3,4,5-tetrahydro-1H-benzo[d]azepine Cpd HH2 was prepared according to the same procedure as for cpd GG2. Cpd HH2 was obtained (0.30 g, 90%) as a yellow solid: $^1$H NMR (300 MHz, CDCl$_3$) δ 7.57 (d, J=8.8 Hz, 2H), 7.13 (d, J=8.2 Hz, 2H), 6.91 (d, J=8.2 Hz, 1H), 6.56 (m, 2H), 6.49 (d, J=3.39 Hz, 1H), 3.72 (s, 2H), 3.69 (s, 3H), 2.83 (m, 4H), 2.66 (m, 4H); MS (ES) m/z: 418 (M+H$^+$).

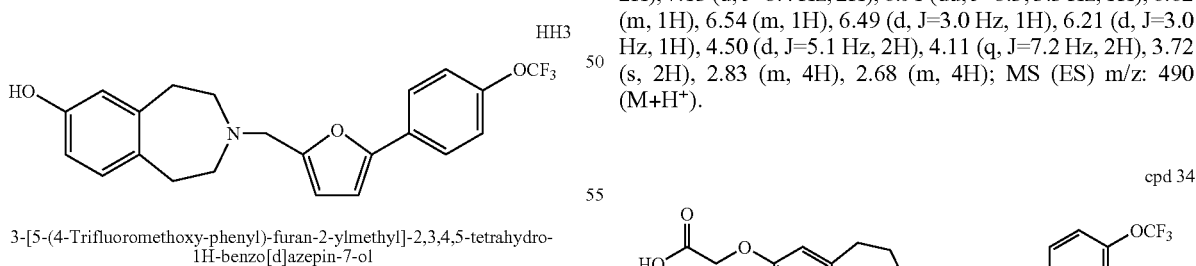

3-[5-(4-Trifluoromethoxy-phenyl)-furan-2-ylmethyl]-2,3,4,5-tetrahydro-1H-benzo[d]azepin-7-ol A mixture of cpd HH2 (0.28 g, 0.70 mmol), 48% HBr (0.80 mL, 7.07 mmol), n-Bu$_4$NBr (30 mg, 0.09 mmol) and HOAc (0.8 mL) was heated at 100° C. under N$_2$ for 18 h. After cooled to room temperature, the reaction mixture was treated with aqueous K$_2$CO$_3$ till pH 10 and extracted with EtOAc. The organic layer was dried (MgSO$_4$) and concentrated to provide cpd HH3 (0.26 g, 93%) as a brown solid: $^1$H NMR (300 MHz, DMSO-d$_6$) δ 9.04 (s, 1H), 7.76 (d, J=8.2 Hz, 2H), 7.39 (d, J=7.6 Hz, 2H), 6.93 (s, 1H), 6.85 (d, J=7.6 Hz, 1H), 6.50 (s, 1H), 6.41 (m, 2H), 3.71 (s, 2H), 2.78 (m, 4H), 2.53 (m, 4H); MS (ES) m/z: 404 (M+H$^+$).

{3-[5-(4-Trifluoromethoxy-phenyl)-furan-2-ylmethyl]-2,3,4,5-tetrahydro-1H-benzo[d]azepin-7-yloxy}-acetic acid ethyl ester Cpd HH4 was prepared according to the same procedure as for cpd X4. Cpd HH4 was obtained (55 mg, 46%) as light brown oil: $^1$H NMR (300 MHz, CDCl$_3$) δ 7.57 (d, J=8.7 Hz, 2H), 7.13 (d, J=8.4 Hz, 2H), 6.91 (dd, J=8.3, 3.3 Hz, 1H), 6.62 (m, 1H), 6.54 (m, 1H), 6.49 (d, J=3.0 Hz, 1H), 6.21 (d, J=3.0 Hz, 1H), 4.50 (d, J=5.1 Hz, 2H), 4.11 (q, J=7.2 Hz, 2H), 3.72 (s, 2H), 2.83 (m, 4H), 2.68 (m, 4H); MS (ES) m/z: 490 (M+H$^+$).

{3-[5-(4-Trifluoromethoxy-phenyl)-furan-2-ylmethyl]-2,3,4,5-tetrahydro-1H-benzo[d]azepin-7-yloxy}-acetic acid Cpd 34 was prepared according to the same procedure as for cpd 33. Cpd 34 was obtained (27 mg, 69%) as a light brown solid: $^1$H NMR (300 MHz, DMSO-d$_6$) δ 7.78 (d, J=6.1

Hz, 2H), 7.41 (d, J=6.1 Hz, 2H), 7.00 (d, J=6.0 Hz, 1H), 6.98 (d, J=3.0 Hz, 1H), 6.69 (s, 1H), 6.59 (m, 1H), 6.47 (s, 1H), 4.62 (s, 2H), 3.84 (s, 2H), 3.33 (m, 4H), 2.68 (m, 4H); MS (ES) m/z: 462 (M+H$^+$).

Example II

Compound 35:

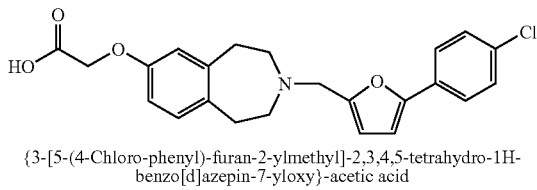

{3-[5-(4-Chloro-phenyl)-furan-2-ylmethyl]-2,3,4,5-tetrahydro-1H-benzo[d]azepin-7-yloxy}-acetic acid The title compound was made according to Scheme II.

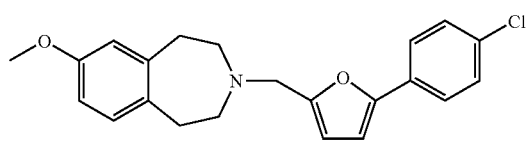

7-Methoxy-3-[5-(4-chlorophenyl)-furan-2-ylmethyl]-2,3,4,5-tetrahydro-1H-benzo[d]azepine Cpd II2 was prepared according to the same procedure as for cpd X2. Cpd II2 was obtained (0.26 g, 65%) as a brown oil: $^1$H NMR (300 MHz, CDCl$_3$) δ7.59 (d, J=8.9 Hz, 2H), 7.35 (d, J=8.9 Hz, 2H), 7.02 (d, J=9.1 Hz, 1H), 6.67 (m, 1H), 6.58 (m, 1H), 6.29 (d, J=2.1 Hz, 1H), 3.81 (s, 2H), 3.78 (s, 3H), 2.93 (m, 4H), 2.75 (m, 4H); MS (ES) m/z: 366, 368 (M+H$^+$).

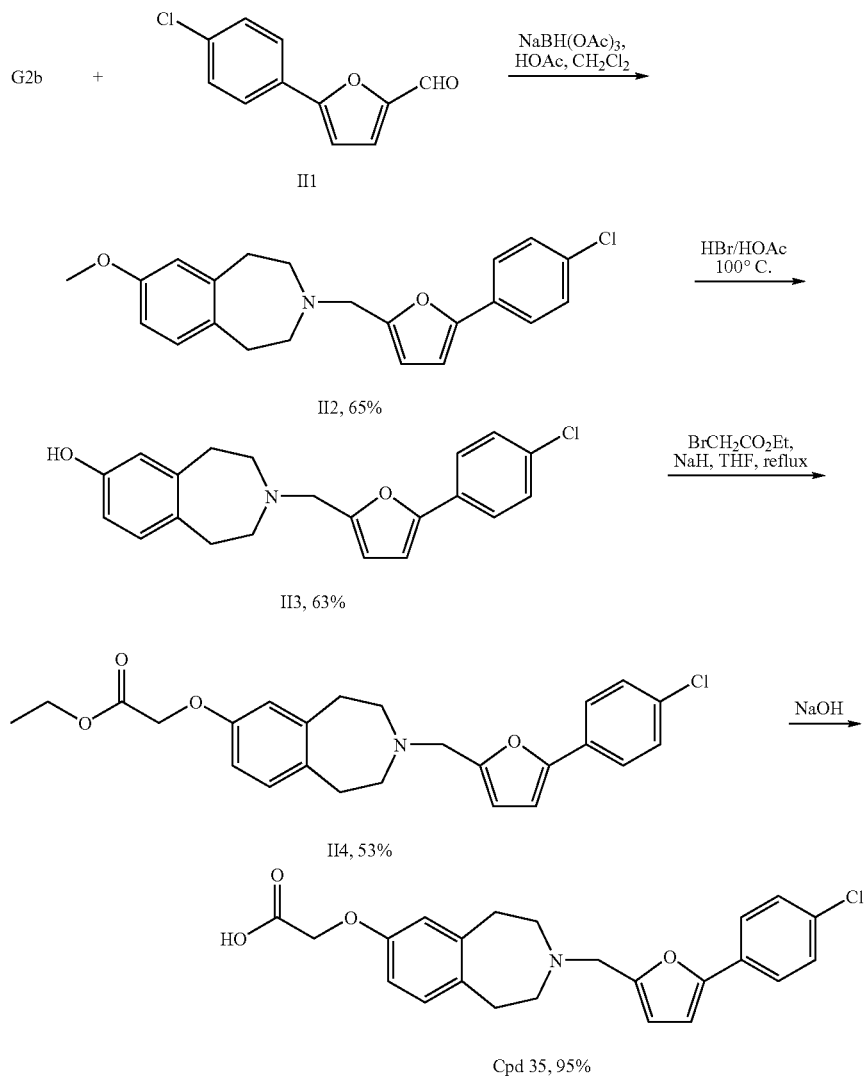

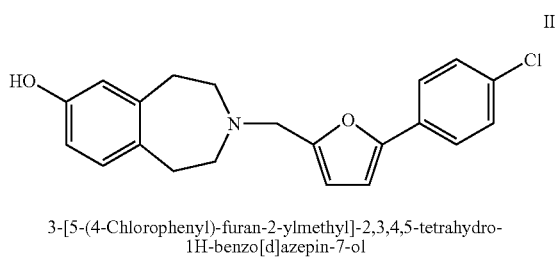

3-[5-(4-Chlorophenyl)-furan-2-ylmethyl]-2,3,4,5-tetrahydro-1H-benzo[d]azepin-7-ol A mixture of II2 (0.25 g, 0.68 mmol), 48% HBr (0.80 mL, 7.07 mmol) and n-Bu$_4$NBr (26 mg, 0.08 mmol) in HOAc (0.8 mL) was heated at 80° C. under N$_2$ overnight. After cooled to room temperature, the reaction mixture was treated with aqueous K$_2$CO$_3$ and a brown solid was collected and dried (0.11 g, 46%). The aqueous layer was then extracted with CH$_2$Cl$_2$. The CH$_2$Cl$_2$ solution was concentrated and purified by column chromatography to give a brown solid (0.04 g) as second batch of the product. Overall, cpd II3 was obtained (0.15 g) in 63% yield: $^1$H NMR (300 MHz, CD$_3$OD) δ 7.58 (d, J=8.8 Hz, 2H), 7.34 (d, J=9.0 Hz, 1H), 6.90 (d, J=6.1 Hz, 1H), 6.57 (m, 3H), 6.31 (d, J=2.5 Hz, 1H), 3.78 (s, 2H), 2.87 (m, 4H), 2.73 (m, 4H); MS (ES) m/z: 354, 356 (M+H$^+$).

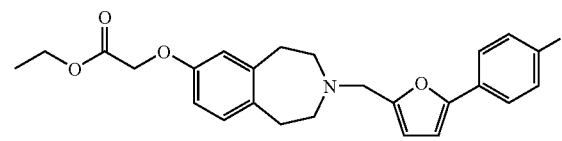

{3-[5-(4-Chlorophenyl)-furan-2-ylmehtyl]-2,3,4,5-tetrahydro-1H-benzo[d]azepin-7-yloxy}-acetic acid ethyl ester Cpd II4 was prepared according to the same procedure as for cpd X4. Cpd II4 was obtained (96 mg, 53%) as pale oil: $^1$H NMR (300 MHz, CDCl$_3$) δ 7.49 (d, J=8.4 Hz, 2H), 7.24 (d, J=8.4 Hz, 2H), 6.91 (d, J=8.0 Hz, 1H), 6.61 (d, J=2.4 Hz, 1H), 6.50 (dd, J=8.0, 2.5 Hz, 1H), 6.49 (d, J=2.4 Hz, 1H), 6.21 (s, 1H), 4.50 (s, 2H), 4.20 (q, J=7.1 Hz), 3.70 (s, 2H), 2.82 (m, 4H), 2.64 (m, 4H); MS (ES) m/z: 440, 442 (M+H$^+$).

35

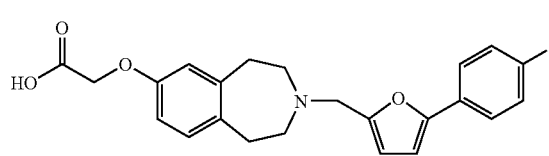

{3-[5-(4-Chlorophenyl)-furan-2-ylmethyl]-2,3,4,5-tetrahydro-1H-benzo[d]azepin-7-yloxy}-acetic acid Cpd 35 was prepared according to the same procedure as for cpd 33. Cpd 35 was obtained (70 mg, 95%) as a light yellow solid: $^1$H NMR (400 MHz, DMSO-d$_6$) δ 7.74 (d, J=8.5 Hz, 2H), 7.51 (d, J=8.5 Hz, 2H), 7.06 (d, J=8.2 Hz, 1H), 7.02 (d, J=2.8 Hz, 1H), 6.75 (s, 1H), 6.66 (m, 2H), 4.61 (s, 2H), 4.21 (bs, 2H), 3.00 (m, 8H); MS (ES) m/z: 412, 414 (M+H$^+$).

Example JJ

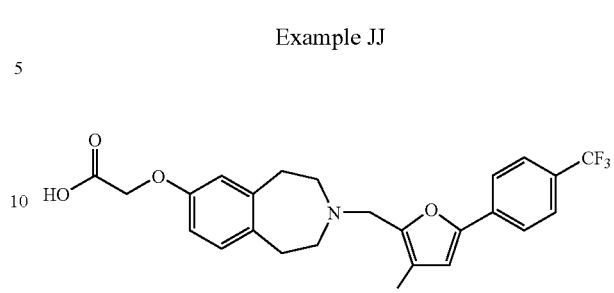

Compound 36: {3-[3-Methyl-5-(4-trifluoromethyl-phenyl)-furan-2-ylmethyl]-2,3,4,5-tetrahyd-1H-benzo[d]azepin-7-yloxy}-acetic acid The title compound was made according to Schemes JJ1 & JJ2.

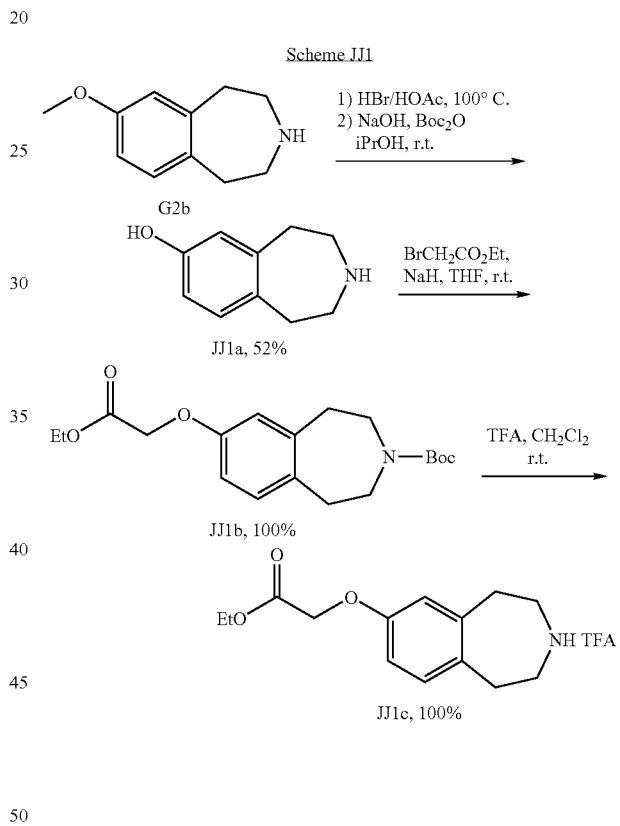

7-Hydroxy-1,2,4,5-tetrahydro-benzo[d]azepine-3-carboxylic acid tert-butyl ester

A mixture of G2b (0.26 g, 1.47 mmol), 48% HBr (1.7 mL, 15 mmol) and n-Bu$_4$NBr (50 mg, 0.16 mmol) in HOAc (1.7 mL) was heated at 100° C. under N$_2$ overnight. After cooled to room temperature, the reaction mixture was treated with solid NaOH to pH 9-10. To the resulting mixture was added H$_2$O (5 mL), iso-propanol (5 mL), followed by di-t-butyl dicarbonate (0.6 g, 2.8 mmol). The mixture was stirred at room temperature overnight and then extracted with EtOAc. The organic extracts were concentrated and the residue purified by column chromatography to give Cpd JJ1a as a white solid (0.20 g, 52%): ¹H NMR (300 MHz, CDCl₃) δ 6.90 (d, J=6.0 Hz, 1H), 6.54 (m, 2H), 4.52 (bs, 1H), 3.46 (m, 4H), 2.75 (m, 4H); MS (ES) m/z: 286 (M+Na).

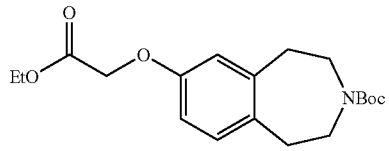

JJ1b

7-Ethoxycarbonylmethoxy-1,2,4,5-tetrahydro-benzo[d]azepine-3-carboxylic acid tert-butyl ester Cpd JJ1b was prepared according to the same procedure as for cpd EE4. Cpd JJ1b was obtained (0.26 g, 100%) as pale oil: ¹H NMR (300 MHz, CDCl₃) δ 6.95 (d, J=8.9 Hz, 1H), 6.65 (d, J=2.0 Hz, 1H), 6.56 (m, 1H), 6.50 (dd, J=8.0, 2.5 Hz, 1H), 4.52(s, 2H), 4.19 (q, J=7.1 Hz, 2H), 3.47 (m, 4H), 2.76 (m, 4H), 1.23 (t, J=7.1 Hz, 3H); MS (ES) m/z: 372 (M+Na).

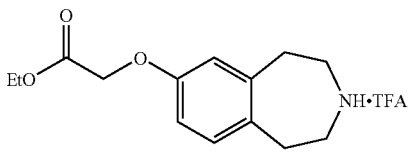

JJ1c

[3-(2,2,2-Trifluoro-acetyl)-2,3,4,5-tetrahydro-1H-benzo[d]azepin-7-yloxy]-acteic acid ethyl ester trifluoroacetate A mixture of cpd JJ1b (0.26 g, 0.76 mmol) and TFA (1.0 mL, 1.3 mmol) in CH₂Cl₂ (1 mL) was stirred at room temperature under N₂ for 1 h. The reaction mixture was concentrated and the resulting residue was washed with Et₂O, concentrated to give cpd JJ1c (0.17 g, 100% crude yield). ¹H NMR (300 MHz, CDCl₃) δ 6.99 (m, 1H), 6.62 (m, 2H), 6.56 (m, 1H), 5.56 (bs, 1H), 4.61 (s, 2H), 4.19 (m, 2H), 3.18 (m, 4H), 3.04 (m, 4H), 1.19 (m, 3H); MS (ES) m/z: 250 (M+H⁺).

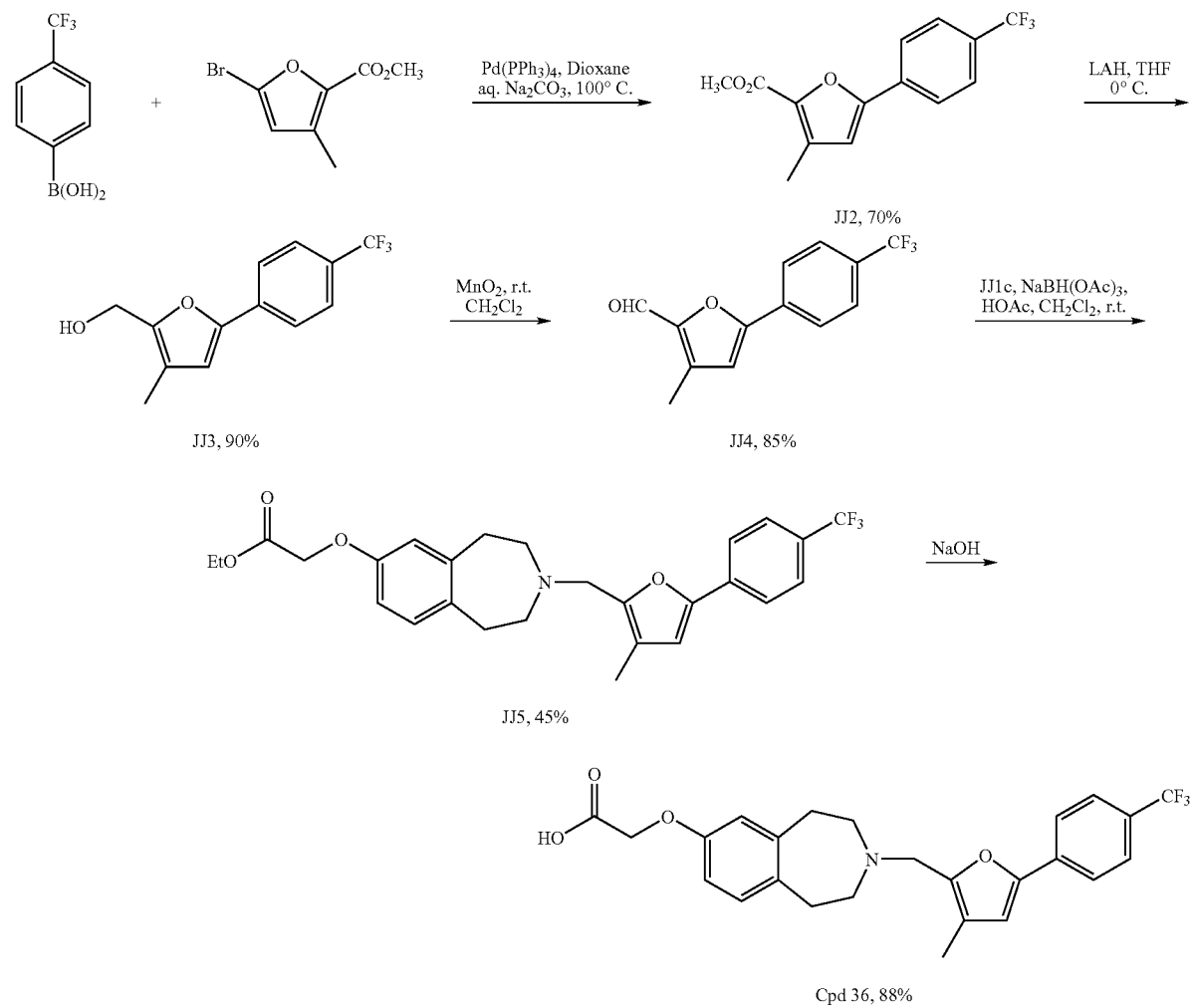

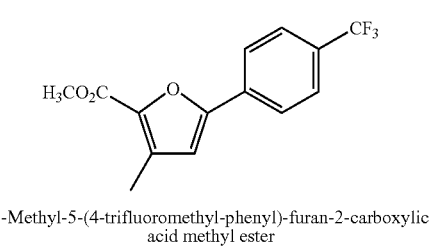

3-Methyl-5-(4-trifluoromethyl-phenyl)-furan-2-carboxylic acid methyl ester

Cpd JJ2 was prepared using a similar procedure as for cpd G1a. Cpd JJ2 was obtained (1.17 g, 70%) as a white solid: $^1$H NMR (300 MHz, CDCl$_3$) δ 7.78 (d, J=8.2 Hz, 2H), 7.58 (d, J=8.2 Hz, 2H), 6.65 (s, 1H), 3.86 (s, 3H), 2.34 (s, 3H); MS (ES) m/z: 285 (M+H$^+$).

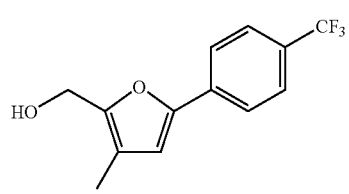

[3-Methyl-5-(4-trifluoromethyl-phenyl)-furan-2-yl]-methanol

To a solution of cpd JJ2 (1.17 g, 4.11 mmol) in THF (25 mL) at 0° C. under N$_2$ was added LiAlH$_4$ (1.0 M, 2.7 mL). After stirring for 1 h, the mixture was quenched with aqueous NH$_4$Cl solution and then extracted with EtOAc. The organic phase was dried (MgSO$_4$) and concentrated to provide cpd JJ3 (0.95 g, 91%) as a white solid: $^1$H NMR (300 MHz, CDCl$_3$) δ 7.65 (d, J=8.3 Hz, 2H), 7.53 (d, J=8.3 Hz, 2H), 6.54 (s, 1H), 4.58 (s, 2H), 2.04 (s, 3H); MS (ES) m/z: 239 (M−OH$^−$).

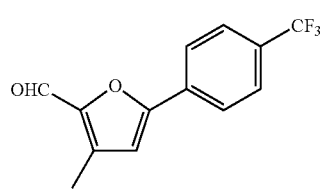

3-Methyl-5-(4-trifluoromethyl-phenyl)-furan-2-carbaldehyde

A mixture of cpd JJ3 (0.13 g, 0.51 mmol) and MnO$_2$ (0.87 g, 10.0 mmol) in CH$_2$Cl$_2$ (16 mL) was stirred at room temperature overnight. MnO$_2$ was removed by filtering the mixture through Celite. The filtrate was concentrated and purified by column chromatography to give cpd JJ4 (0.11 g, 85%) as a white solid. $^1$H NMR (300 MHz, CDCl$_3$) δ 9.76 (s, 1H), 7.82 (d, J=8.2 Hz, 2H), 7.62 (d, J=8.2 Hz, 2H), 6.72 (s, 1H), 2.38 (s, 3H).

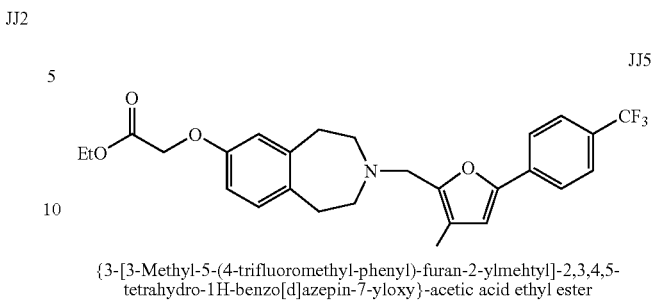

{3-[3-Methyl-5-(4-trifluoromethyl-phenyl)-furan-2-ylmehtyl]-2,3,4,5-tetrahydro-1H-benzo[d]azepin-7-yloxy}-acetic acid ethyl ester Cpd JJ5 was prepared according to the same procedure as for cpd X2. Cpd JJ5 was obtained (40 mg, 45%) as a brown oil: $^1$H NMR (300 MHz, CDCl$_3$) δ 7.71 (d, J=8.2 Hz, 2H), 7.61 (d, J=8.2 Hz, 2H), 7.00 (d, J=8.2 Hz), 6.71 (d, J=2.6 Hz, 1H), 6.63 (dd, J=8.2, 2.7 Hz, 1H), 6.60 (s, 1H), 4.59 (s, 2H), 4.27 (q, J=7.1 Hz, 2H), 3.80 (bs, 2H), 2.94 (m, 4H), 2.75 (m, 4H), 2.09 (3H), 1.30 (t, J=7.1 Hz, 3H); MS (ES) m/z: 488 (M+H$^+$).

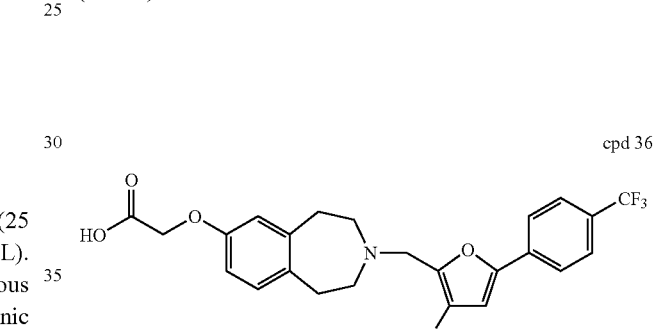

{3-[3-Methyl-5-(4-trifluoromethyl-phenyl)-furan-2-ylmethyl]-2,3,4,5-tetrahyd-1H-benzo[d]azepin-7-yloxy}-acetic acid Cpd 36 was prepared according to the same procedure as for cpd 31. Cpd 36 was obtained (25 mg, 68%) as a light brown solid: $^1$H NMR (300 MHz, DMSO-d$_6$) δ 7.83 (d, J=8.2 Hz, 2H), 7.75 (d, J=8.2 Hz, 2H), 7.00 (m, 1H), 6.69 (d, J=2.5 Hz, 1H), 6.60 (dd, J=8.2, 2.6 Hz, 1H), 4.58 (s, 2H), 3.75 (s, 2H), 2.82 (m, 4H), 2.64 (m, 4H), 2.05 (s, 3H); MS (ES) m/z: 460 (M+H$^+$).

Example KK

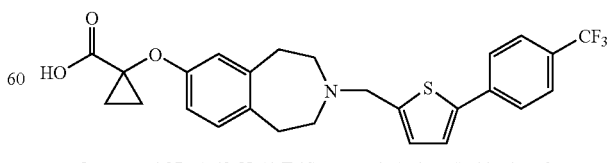

Compound 37: 1-{3-[5-(4-Trifluoromethyl-phenyl)-thiophen-2-ylmethyl]-2,3,4,5-tetrahydro-1H-benzo[d]azepin-7-yloxy}-cyclopropanecarboxylic acid The title compound was made according to Scheme KK.

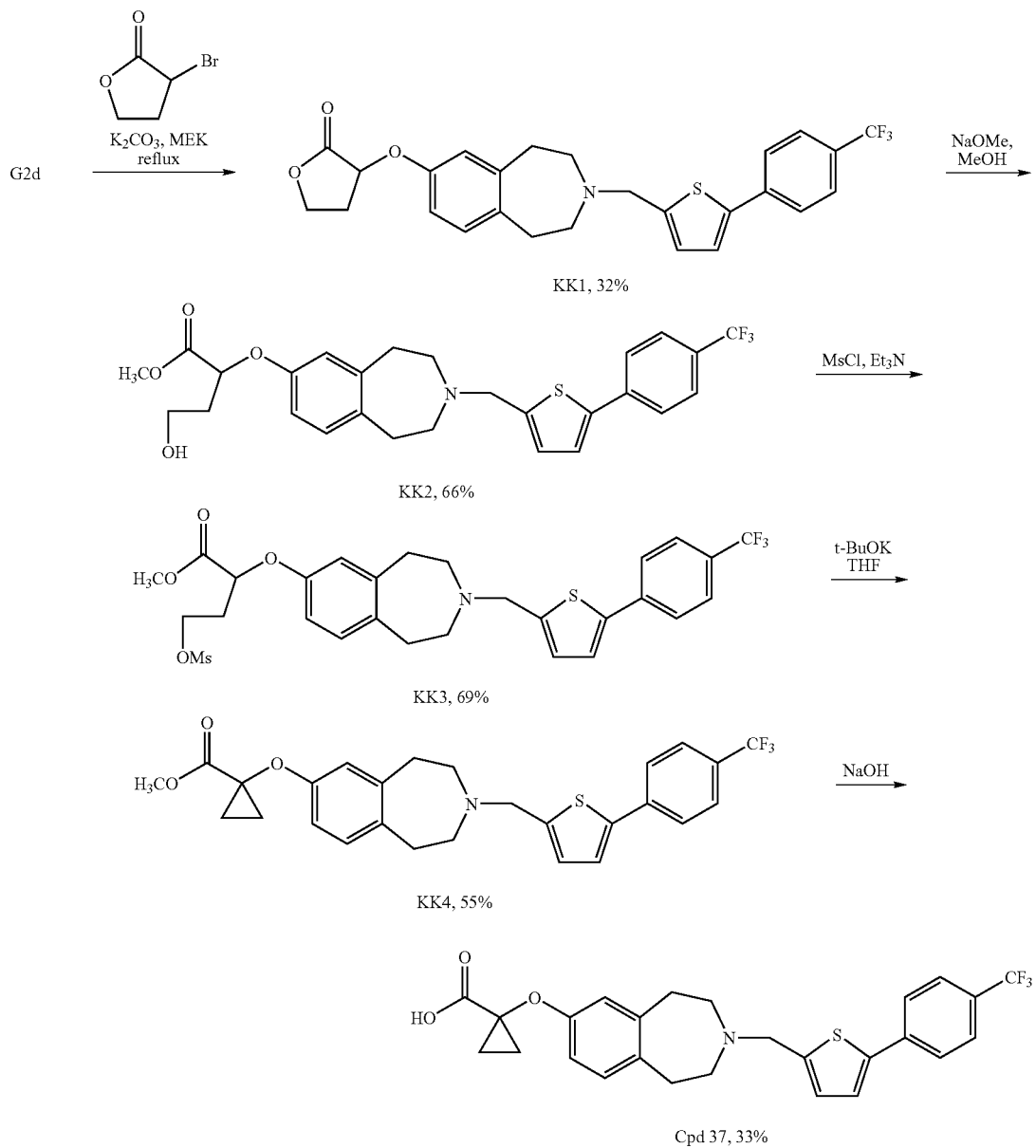

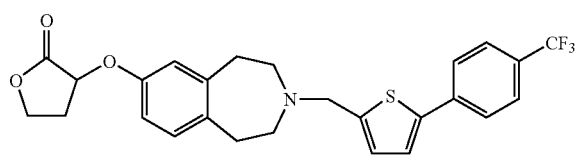

3-{3-[5-(4-Trifluoromethyl-phenyl)-thiophen-2-ylmethyl]-2,3,4,5-tetrahydro-1H-benzo[d]azepin-7-yloxy}-dihydro-furan-2-one A mixture of 3-bromo-dihydro-furan-2-one (0.62 mL, 6.45 mmol), cpd G2d (1.0 g, 2.48 mmol) and potassium carbonate (1.49 g, 9.33 mmol) in 2-butan-one (25 mL) was heated at reflux for 6 h. After removing solvents, the residue was partitioned between H₂O and EtOAc and the aqueous layer was extracted with EtOAc. The combined organic layers were dried (MgSO₄) and purified by column chromatography to give cpd KK1 (0.39 g, 32%) as a brown oil. 0.45 g of cpd G2d was recovered. ¹H NMR (300 MHz, CDCl₃) δ 7.70 (d, J=8.4 Hz, 2H), 7.62 (d, J=8.4 Hz, 2H), 7.27 (m, 2H), 7.03 (d, J=8.0 Hz, 1H), 6.92 (m, 1H), 6.79 (m, 2H), 4.92 (t, J=7.8 Hz, 1H), 4.53 (m, 1H), 4.37 (m, 1H), 3.89 (s, 2H), 2.92 (m, 4H), 2.72 (m, 4H), 2.66 (m, 1H), 2.46 (m, 1H); MS (ES) m/z: 404 (M+H⁺).

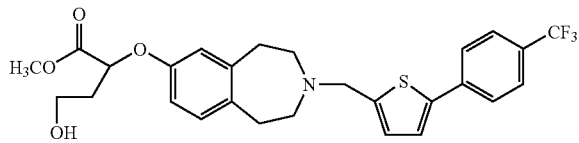

4-Hydoxy-2-{3-[5-(4-trifluoromethyl-phenyl)-thiophen-2-ylmethyl]-2,3,4,5-tetrahydro-1H-benzo[d]azepin-7-yloxy}-butyric acid methyl ester To a solution of cpd KK1 (0.35 g, 0.72 mmol) in MeOH (7.2 mL) at room temperature was added NaOMe (0.5 M in MeOH, 1.44 mL, 7.2 mmol). The resulting mixture was stirred at room temperature for 30 min and quenched with aqueous NH$_4$Cl. The mixture was extracted with EtOAc. The organic extracts were dried (MgSO$_4$) and concentrated. The crude product was purified by column chromatography to give cpd KK2 (0.25 g, 66%) as oil: $^1$H NMR (300 MHz, CDCl$_3$) δ 7.60 (d, J=8.3 Hz, 2H), 7.53 (d, J=8.3 Hz, 2H), 7.16 (d, J=3.6 Hz, 1H), 6.90 (d, J=8.2 Hz, 1H), 6.83 (m, 1H), 6.61 (s, J=2.6 Hz, 1H), 6.52 (dd, J=8.2, 2.7 Hz, 1H), 4.77 (t, J=6.2 Hz, 1H), 3.79 (m, 4H), 3.69 (s, 3H), 2.82 (m, 4H), 2.63 (m, 4H), 2.11 (m, 1H), 1.63 (m, 1H); MS (ES) m/z: 520 (M+H$^+$).

KK3

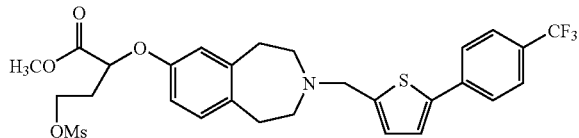

4-Methanesulfonyloxy-2-{3-[5-(4-trifluoromethyl-phenyl)-thiophen-2-ylmethyl]-2,3,4,5-tetrahhdro-1H-benzo[d]azepin-7-yloxy}-butyric acid methyl ester To a solution of cpd KK2 (0.23 g, 0.44 mmol), methanesulfonyl chloride (38 μL, 0.49 mmol) in CH$_2$Cl$_2$ (13 mL) at room temperature was added Et$_3$N (68 μL, 0.49 mmol) and the resulting mixture was stirred for 1 h. It was partitioned between H$_2$O and CH$_2$Cl$_2$ and the aqueous layer was extracted with CH$_2$Cl$_2$. The combined organic layers were dried (MgSO$_4$) and concentrated. The crude product was purified by column chromatography to give cpd KK3 (0.18 g, 69%) as pale oil: $^1$H NMR (300 MHz, CDCl$_3$) δ 7.60 (d, J=8.3 Hz, 2H), 7.53 (d, J=8.3 Hz, 2H), 7.17 (m, 2H), 6.90 (d, J=8.2 Hz, 1H), 6.83 (m, 1H), 6.61 (s, J=2.6 Hz, H), 6.52 (dd, J=8.2, 2.7 Hz, 1H), 4.77 (t, J=6.2 Hz, 1H), 3.79 (m, 4H), 3.69 (s, 3H), 2.82 (m, 4H), 2.63 (m, 4H), 2.11 (m, 1H), 1.63 (m, 1H); MS (ES) m/z: 520 (M+H$^+$).

KK4

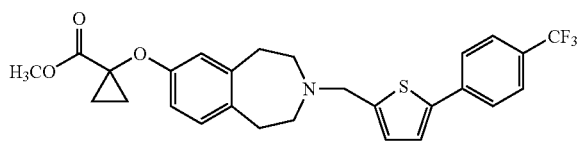

1-{3-[5-(4-Trifluoromethyl-phenyl)-thiophen-2-ylmethyl]-2,3,4,5-tetrahydro-1H-benzo[d]azepin-7-yloxy}-cyclopropanecarboxylic acid methyl ester To a solution of cpd KK3 (0.18 g, 0.30 mmol) in THF (10 mL) at 0° C. under N$_2$ was added t-BuOK (1 M in THF, 0.30 mL) in a dropwise fashion. The resulting mixture was stirred at 0° C. for 1 h, acidified with 1N HCl till pH 4 and extracted with EtOAc. The combined organic layers were dried (MgSO$_4$) and concentrated. The crude product was purified by column chromatography to give cpd KK4 (62 mg, 55%) as pale oil. $^1$H NMR (300 MHz, CDCl$_3$) δ 7.70 (d, J=8.4 Hz, 2H), 7.62 (d, J=8.4 Hz, 2H), 7.27 (m, 2 H), 6.99 (d, J=7.8 Hz, 1H), 6.65 (m, 2H), 3.89 (s, 2H), 3.74 (s, 3H), 2.91 (m, 4H), 2.73 (m, 4H), 1.61 (m, 2H), 1.32 (m, 2H); MS (ES) m/z: 502 (M+H$^+$).

cpd 37

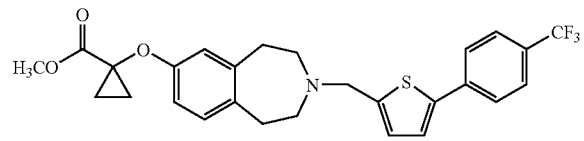

1-{3-[5-(4-Trifluoromethyl-phenyl)-thiophen-2-ylmethyl]-2,3,4,5-tetrahydro-1H-benzo[d]azepin-7-yloxy}-cyclopropanecarboxylic acid A mixture of cpd KK4 (38 mg, 0.76 mmol) and 1N NaOH (4.6 mL) in MeOH (1 mL) was stirred at room temperature overnight. The mixture was concentrated, the residue treated with tartaric acid to pH 3 and extracted with EtOAc. The organic layer was dried (MgSO$_4$) and concentrated. The residue was purified by column chromatography to give cpd 37 (12 mg, 33%) as beige solid. $^1$H NMR (300 MHz, DMSO-d$_6$) δ 7.79 (d, J=7.9 Hz, 2H), 7.68 (d, J=7.9 Hz, 2H), 7.48 (m, 1H), 6.96 (m, 2H), 6.56 (m, 2H), 3.78 (bs, 2H), 2.75 (m, 4H), 2.56 (m, 4H), 1.41 (m, 2H), 1.12 (m, 2H); MS (ES) m/z: 488 (M+H$^+$).

Example LL

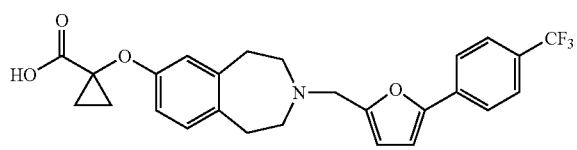

Compound 38: 1-{3-[5-(4-Trifluoromethyl-phenyl)-furan-2-ylmethyl]-2,3,4,5-tetrahydro-1H-benzo[d]azepin-7-yloxy}-cyclopropanecarboxylic acid The title compound was made according to Schemes LL1 & LL2.

Scheme LL1

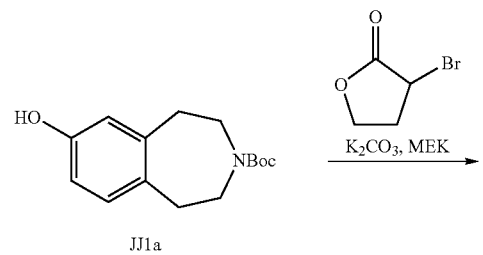

JJ1a

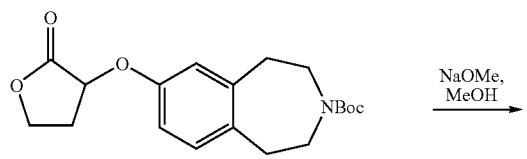

LL1, 54%

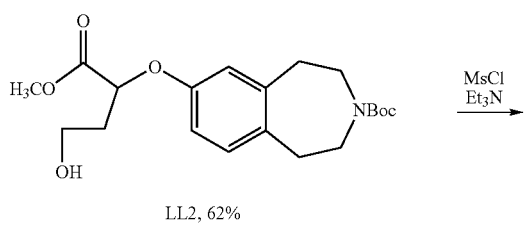

LL2, 62%

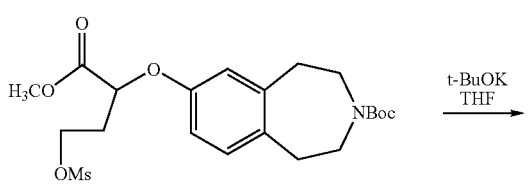

LL3, 100%

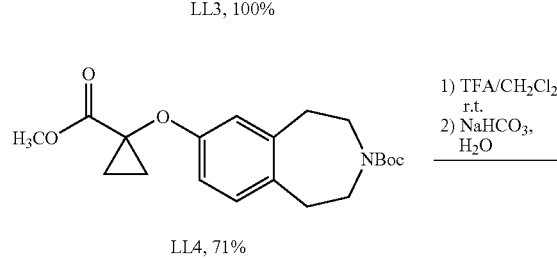

LL4, 71%

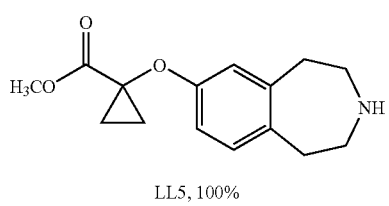

LL5, 100%

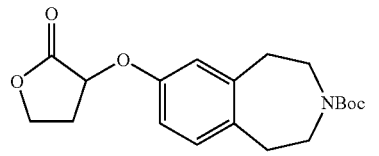

7-(2-Oxo-tetrahydro-furan-3-yloxy)-1,2,4,5-tetrahydro-
benzo[d]azepine-3-carboxylic acid tert-butyl ester Cpd LL1 was prepared according to the same procedure as for cpd KK1. Cpd LL1 was obtained (0.65 g, 54%) as a white solid: $^1$H NMR (300 MHz, CDCl$_3$) δ 7.06 (d, J=8.0 Hz, 1H), 6.82 (m, 2H), 4.93 (t, J=7.7 Hz, 1H), 4.53 (m, 1H), 4.36 (m, 1H), 3.55 (m, 4H), 2.87 (m, 4H), 2.73 (m, 1H), 2.49 (m, 1H), 1.50 (s, 9H); MS (ES) m/z: 370 (M+Na).

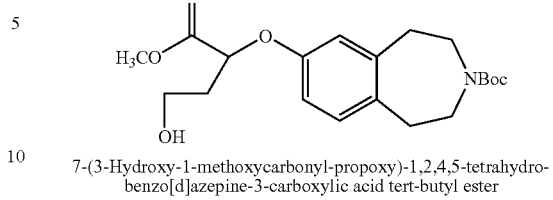

7-(3-Hydroxy-1-methoxycarbonyl-propoxy)-1,2,4,5-tetrahydro-
benzo[d]azepine-3-carboxylic acid tert-butyl ester Cpd LL2 was prepared according to the same procedure as for cpd KK2. Cpd LL2 was obtained (0.74 g, 62%): $^1$H NMR (300 MHz, CDCl$_3$) δ 7.01 (d, J=8.3 Hz, 1H), 6.71 (d, J=2.5 Hz, 1H), 6.63 (dd, J=8.3, 2.5 Hz, 1H), 4.87 (t, J=6.1 Hz, 1H), 3.89 (t, J=6.1 Hz, 2H), 3.78 (s, 3H), 3.54 (m, 4H), 2.85 (m, 4H), 2.21 (q, J=5.9 Hz, 2H), 1.50 (s, 9H); MS (ES) m/z: 402 (M+Na).

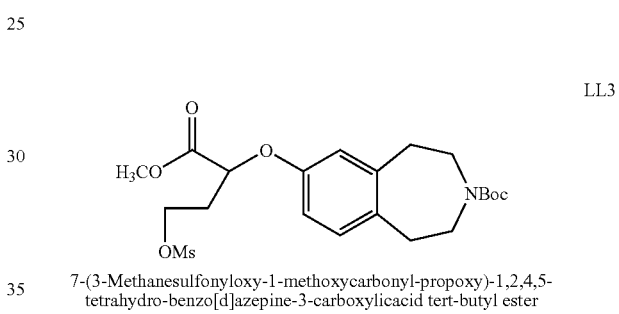

7-(3-Methanesulfonyloxy-1-methoxycarbonyl-propoxy)-1,2,4,5-
tetrahydro-benzo[d]azepine-3-carboxylicacid tert-butyl ester Cpd LL3 was prepared according to the same procedure as for cpd KK3. Cpd LL3 was obtained (0.86 g, 100%) as colorless oil: $^1$H NMR (300 MHz, CDCl$_3$) δ 7.03 (d, J=8.3 Hz, 1H), 6.71 (d, J=2.7 Hz, 1H), 6.63 (dd, J=8.3, 2.7 Hz, 1H), 4.81 (m, 1H), 4.47 (t, J=6.0 Hz, 2H), 3.79 (s, 3H), 3.53 (m, 4H), 2.99 (s, 3H), 2.85 (m, 4H), 2.39 (m, 2H), 1.50 (s, 9H); MS (ES) m/z: 480 (M+Na).

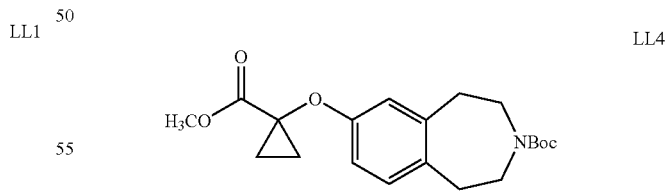

7-(1-Methoxycarbonyl-cyclopropoxy)-1,2,4,5-tetrahydro-
benzo[d]azepine-3-carboxylic acid tert-butyl ester Cpd LL4 was prepared according to the same procedure as for cpd KK4. Cpd LL4 was obtained (0.49 g, 71%) as a white solid: $^1$H NMR (300 MHz, CDCl$_3$) δ 7.05 (d, J=8.0 Hz, 1H), 6.80 (m, 2H), 4.93 (t, J=7.8 Hz, 1H), 4.53 (m, 1H), 4.36 (q, J=7.7 Hz, 2H), 3.54 (m, 4H), 2.86 (m, 4H), 2.71 (m, 1H), 2.46 (m, 1H), 1.50 (s, 9H); MS (ES) m/z: 384 (M+Na).

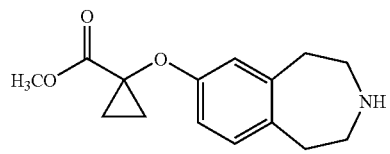

1-(2,3,4,5-Tetrahydro-1H-benzo[d]azepin-7-yloxy)-cyclopropane-
carboxylic acid methyl ester A mixture of cpd LL4 (0.50 g, 1.38 mmol) and TFA (0.5 mL) in CH$_2$Cl$_2$ (5 mL) was stirred at room temperature for 30 min. After the mixture was concentrated, the residue was treated with aqueous NaHCO$_3$ and extracted with EtOAc. The organic layer was dried (MgSO$_4$) and concentrated to dryness to give cpd LL5 (0.36 g, 100%) as a pale solid: $^1$H NMR (300 MHz, CDCl$_3$) δ 7.05 (d, J=8.0 Hz, 1H), 6.80 (m, 2H), 4.93 (t, J=7.8 Hz, 1H), 4.53 (m, 1H), 4.36 (q, J=7.7 Hz, 2H), 3.54 (m, 4H), 2.86 (m, 4H), 2.71 (m, 1H), 2.46 (m, 1H); MS (ES) m/z: 262 (M+H$^+$).

Scheme LL2

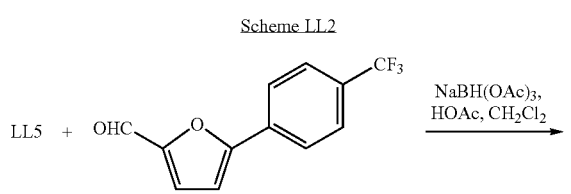

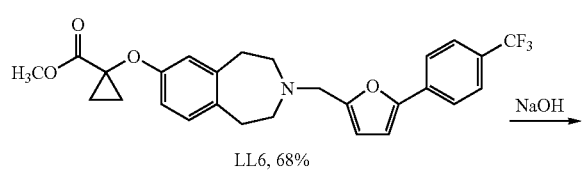

cpd 38, 79%

LL6

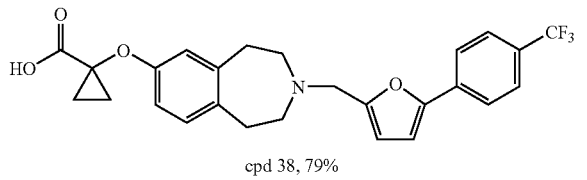

1-{3-[5-(4-Trifluoromethyl-phenyl)-furan-2-ylmethyl]-
2,3,4,5-tetrahydro-1H-benzo[d]azepin-7-yloxy}-
cyclopropanecarboxylic acid methyl ether Cpd LL6 was prepared according to the same procedure as for cpd X2. Cpd MM1 was obtained (25 mg, 68%) as a light brown solid: $^1$H NMR (300 MHz, CDCl$_3$) δ 7.75 (d, J=8.2 Hz, 2H), 7.62 (d, J=8.2 Hz, 2H), 6.98 (d, J=7.9 Hz, 1H), 6.71 (d, J=3.3 Hz, 1H), 6.64 (m, 2H), 6.33 (d, J=3.3 Hz), 3.83 (s, 2H), 3.73 (s, 3H), 2.92 (m, 4H), 2.75 (m, 4H), 1.60 (m, 2H), 1.31 (m, 2H); MS (ES) m/z: 486 (M+H$^+$).

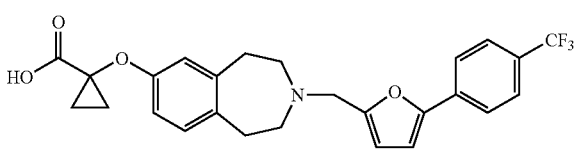

cpd 38

1-{3-[5-(4-Trifluoromethyl-phenyl)-furan-2-ylmethyl]-2,3,4,5-
tetrahydro-1H-benzo[d]azepin-7-yloxy}-cyclopropanecarboxylic acid A mixture of cpd MM1 (20 mg, 0.04 mmol) and 3N NaOH (0.15 mL) in MeOH (0.5 mL) was stirred at room temperature overnight. After the mixture was concentrated, the residue was dissolved in H$_2$O and washed with EtOAc. The aqueous layer was acidified with dilute tartaric acid till pH 3 and a brown solid was collected to give cpd 38 (15 mg, 79%): $^1$H NMR (400 MHz, DMSO-d$_6$) δ 7.87 (d, J=8.2 Hz, 2H), 7.77 (d, J=8.2 Hz, 2H), 7.11 (d, J=3.3 Hz, 1H), 7.00 (d, J=8.3 Hz, 1H), 6.65 (d, J=2.6 Hz, 1H), 6.59 (dd, J=8.2, 2.5 Hz, 1H), 6.49 (d, J=3.3 Hz, 1H), 3.79(s, 2H), 2.82 (m, 4H), 2.63 (m, 4H), 1.47 (m, 2H), 1.19 (m, 2H); MS (ES) m/z: 472 (M+H$^+$).

Example NN

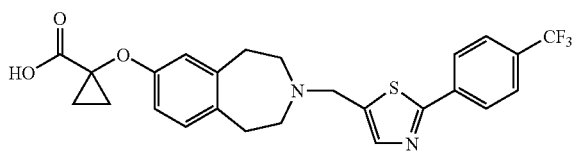

Compound 39: 1-{3-[2-(4-Trifluoromethyl-phenyl)-thiazol-5-ylmethyl]-
2,3,4,5-tetrahydro-1H-benzo[d]azepin-7-yloxy}-
cyclopropanecarboxylic acid The title compound was made according to Scheme NN.

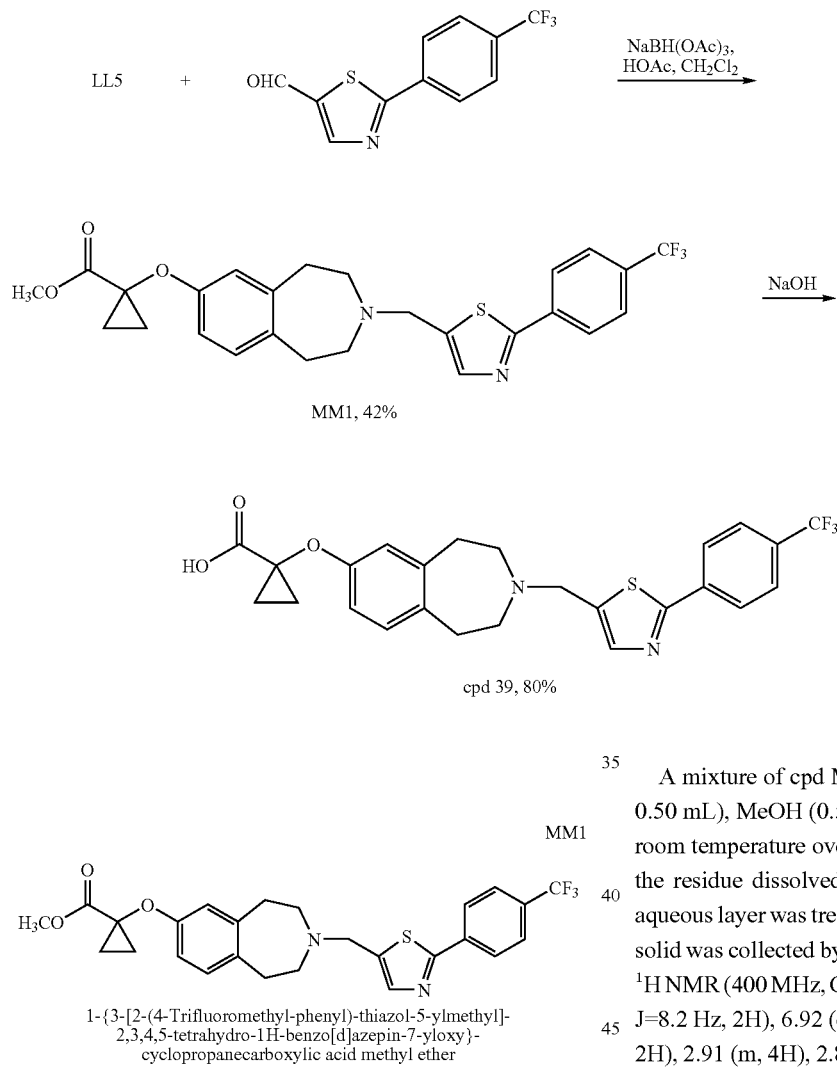

Cpd MM1 was prepared according to the same procedure as for cpd X2. Cpd MM1 was obtained (0.10 g, 53%) as a light brown solid: $^1$H NMR (300 MHz, CDCl$_3$) δ 8.06 (d, J=7.7 Hz, 2H), 7.71 (m, 3H), 6.99 (d, J=8.2 Hz, 1H), 6.67 (m, 2H), 3.92 (s, 2H), 3.74 (s, 3H), 2.89 (m, 4H), 2.71 (m, 4H), 1.63 (m, 2H), 1.32 (m, 2H); MS (ES) m/z: 502 (M+H$^+$).

A mixture of cpd MM1 (86 mg, 0.17 mmol), NaOH (3N, 0.50 mL), MeOH (0.5 mL) and THF (0.5 mL) was stirred at room temperature overnight. The mixture was concentrated, the residue dissolved in H$_2$O and washed with Et$_2$O. The aqueous layer was treated with tartaric acid to pH 3 and a pale solid was collected by filtration to give cpd 39 (66 mg, 80%): $^1$H NMR (400 MHz, CDCl$_3$) δ 8.02 (d, J=8.2 Hz, 2H), 7.74 (d, J=8.2 Hz, 2H), 6.92 (d, J=8.9 Hz, 1H), 6.75 (m, 2H), 4.21 (s, 2H), 2.91 (m, 4H), 2.84 (m, 4H), 1.59 (m, 2H), 1.25 (m, 2H); MS (ES) m/z: 489 (M+H$^+$).

Example OO

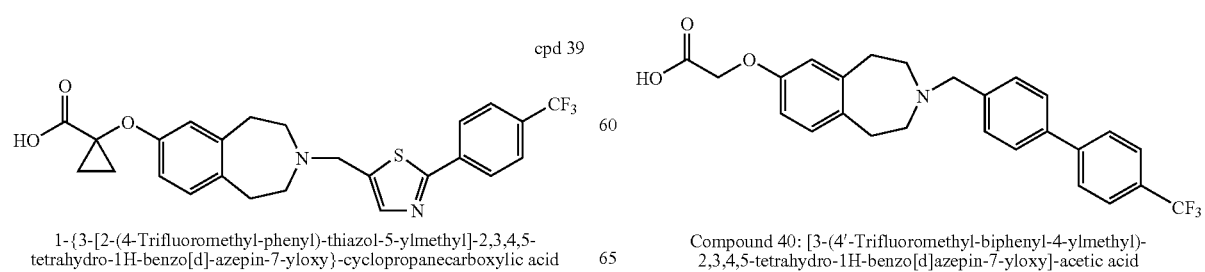

Compound 40: [3-(4'-Trifluoromethyl-biphenyl-4-ylmethyl)-2,3,4,5-tetrahydro-1H-benzo[d]azepin-7-yloxy]-acetic acid The title compound was made according to Scheme OO.
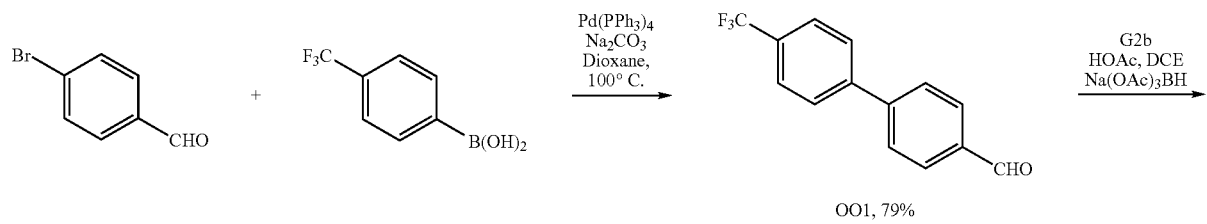
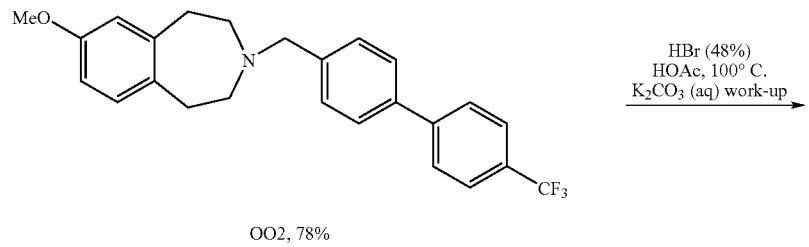
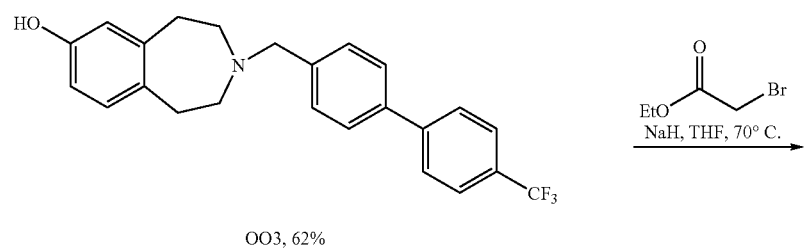
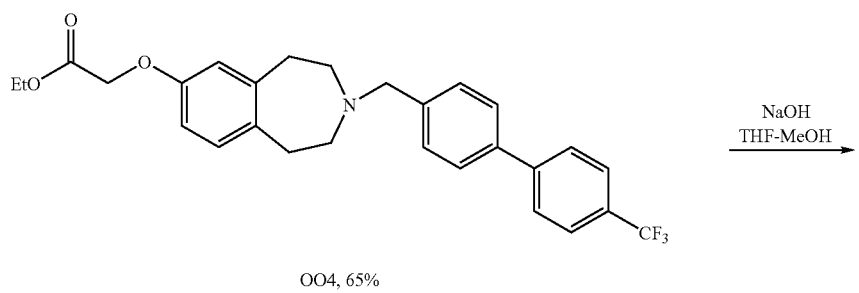
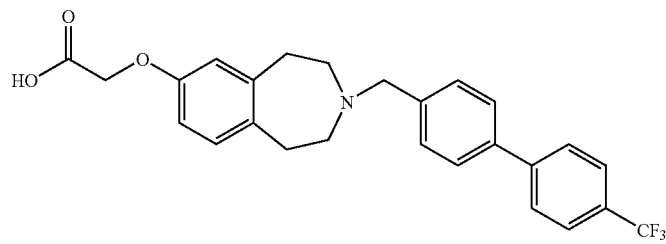

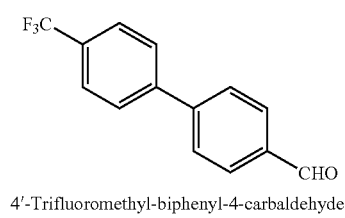

4'-Trifluoromethyl-biphenyl-4-carbaldehyde

Cpd OO1 (688 mg, 79%) was prepared according to a similar procedure as for cpd G1a: $^1$H NMR (300 MHz, CDCl$_3$) δ 10.09 (s, 1H), 7.99 (d, J=8.3 Hz, 2H), 7.76 (d, J=8.3 Hz, 2H), 7.74 (s, 4H).

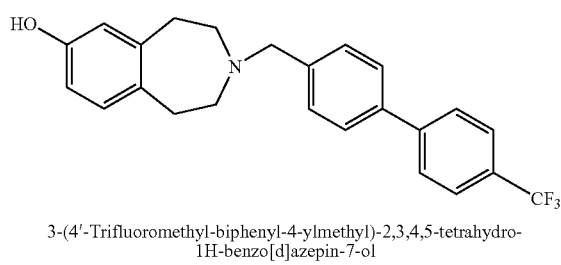

3-(4'-Trifluoromethyl-biphenyl-4-ylmethyl)-2,3,4,5-tetrahydro-1H-benzo[d]azepin-7-ol Cpd OO3 (62%) was prepared according to a similar procedure as for cpd G2d: $^1$H NMR (300 MHz, DMSO) δ 9.03 (s, 1H), 7.89 (d, J=8.2 Hz, 2H), 7.80 (d, J=8.3 Hz, 2H), 7.70 (d, J=8.1 Hz, 2H), 7.46 (d, J=8.1 Hz, 2H), 6.86 (d, J=8.0 Hz, 1H), 6.50 (d, J=2.3 Hz, 1H), 6.44-6.47 (dd, J=2.4, 8.0 Hz, 1H), 3.64 (s, 2H), 2.74 (br, s, 4H), 2.56 (br, s, 4H); MS (ES) m/z: 398.1 (M+H$^+$).

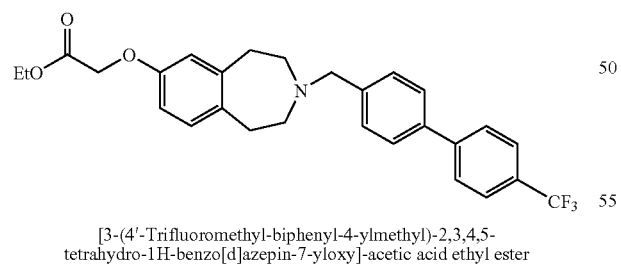

[3-(4'-Trifluoromethyl-biphenyl-4-ylmethyl)-2,3,4,5-tetrahydro-1H-benzo[d]azepin-7-yloxy]-acetic acid ethyl ester Cpd OO4 (138 mg, 65%) was prepared according to a similar procedure as for cpd G1b: $^1$H NMR (300 MHz, CDCl$_3$) δ 7.69 (s, 4H), 7.56 (d, J=8.1 Hz, 2H), 7.46 (d, J=8.1 Hz, 2H), 7.00 (d, J=8.2 Hz, 1H), 6.69 (d, J=2.6 Hz, 1H), 6.60-6.64 (dd, J=2.6, 8.1 Hz, 1H), 4.58 (s, 2H), 4.23-4.30 (q, J=7.1 Hz, 2H), 3.69 (s, 2H), 2.89 (s, br, 4H), 2.65 (s, br, 4H), 1.27-1.32 (t, J=7.1 Hz, 3H); MS (ES) m/z: 484.0 (M+H$^+$).

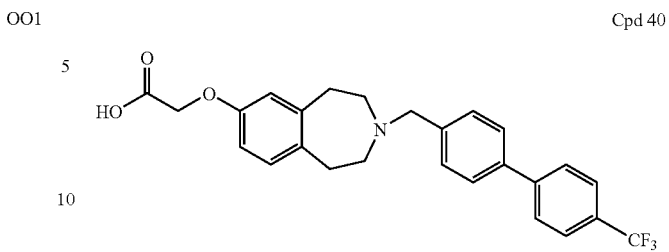

[3-(4'-Trifluoromethyl-biphenyl-4-ylmethyl)-2,3,4,5-tetrahydro-1H-benzo[d]azepin-7-yloxy]-acetic acid Cpd 40 (125 mg, 100%) was prepared according to a similar procedure as for cpd 7: $^1$H NMR (400 MHz, DMSO) δ 7.93 (d, J=8.2 Hz, 2H), 7.81-7.85 (m, 4H), 7.66 (d, J=7.9 Hz, 2H), 7.07 (d, J=8.3 Hz, 1H), 6.76 (d, J=2.4 Hz, 1H), 6.67-6.70 (dd, J=2.4, 8.2 Hz, 1H), 4.62 (s, 2H), 4.25 (s, 2H), 3.32 (s, br, 4H), 3.05 (s, br, 4H); MS (ES) m/z: 456.0 (M+H$^+$), 454.0 (M−H$^+$).

Example PP

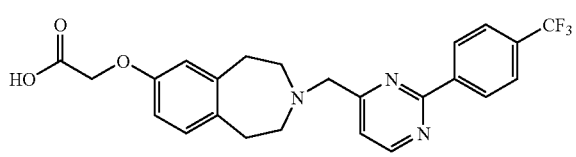

Compound 41: {3-[2-(4-Trifluoromethyl-phenyl)-pyrimidin-4-ylmethyl]-2,3,4,5-tetrahydro-1H-benzo[d]azepin-7-yloxy}-acetic acid The title compound was made according to Scheme PP.

Scheme PP

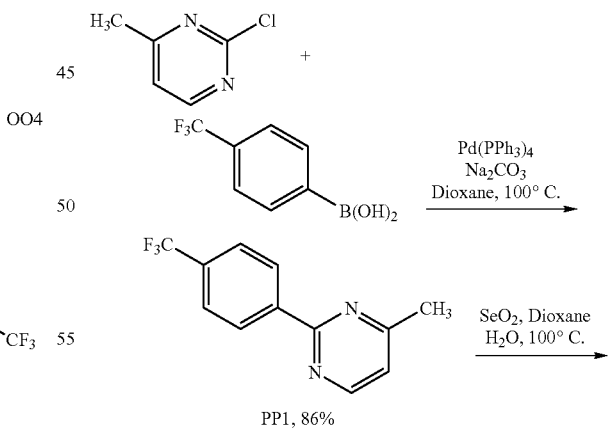

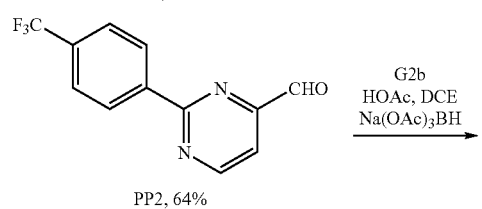

-continued

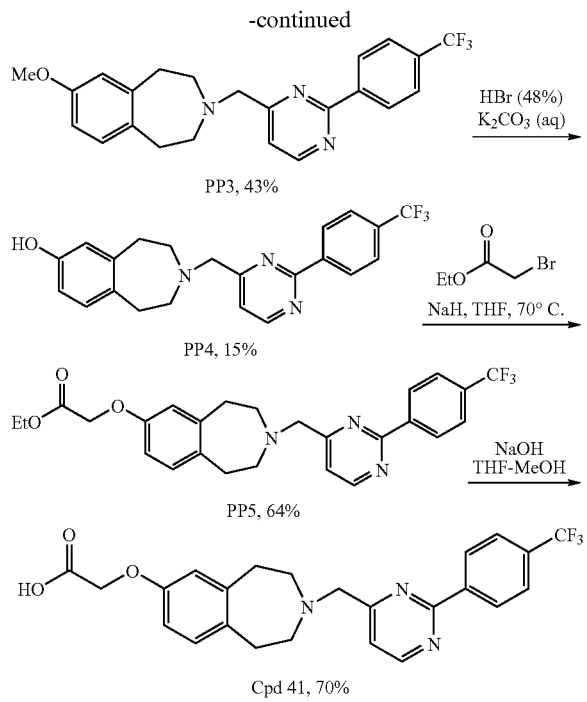

PP3, 43%

PP4, 15%

PP5, 64%

Cpd 41, 70%

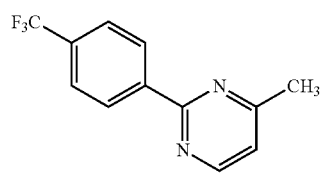

4-Methyl-2-(4-trifluoromethyl-phenyl)-pyrimidine

Cpd PP1 (1.507 g, 86%) was prepared according to similar procedure as for cpd G1a: $^1$H NMR (300 MHz, CDCl$_3$) δ 8.69 (d, J=5.0 Hz, 1H), 8.58 (d, J=8.2 Hz, 2H), 7.73 (d, J=8.2 Hz, 2H), 7.13 (d, J=5.0 Hz, 1H), 2.62 (s, 3H); MS (ES) m/z: 239.1 (M+H$^+$).

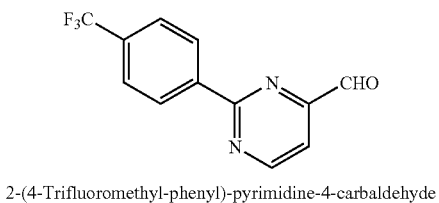

2-(4-Trifluoromethyl-phenyl)-pyrimidine-4-carbaldehyde

A mixture of cpd PP1 (428 mg, 1.798 mmol), SeO$_2$ (998 mg, 8.991 mmol), dioxane (5 mL) and water (0.16 mL) was stirred at 100° C. for 16 h. After the mixture was cooled to room temperature, it was filtered to remove solids and concentrated under vacuo. The residue was purified by column chromatography eluting with EtOAc/Hexane to give cpd PP2 (291 mg, 64%) as a white solid: $^1$H NMR (300 MHz, CDCl$_3$) δ 10.15 (s, 1H), 9.11 (d, J=4.8 Hz, 1H), 8.68 (d, J=8.1 Hz, 2H), 7.75-7.81 (m, 3H).

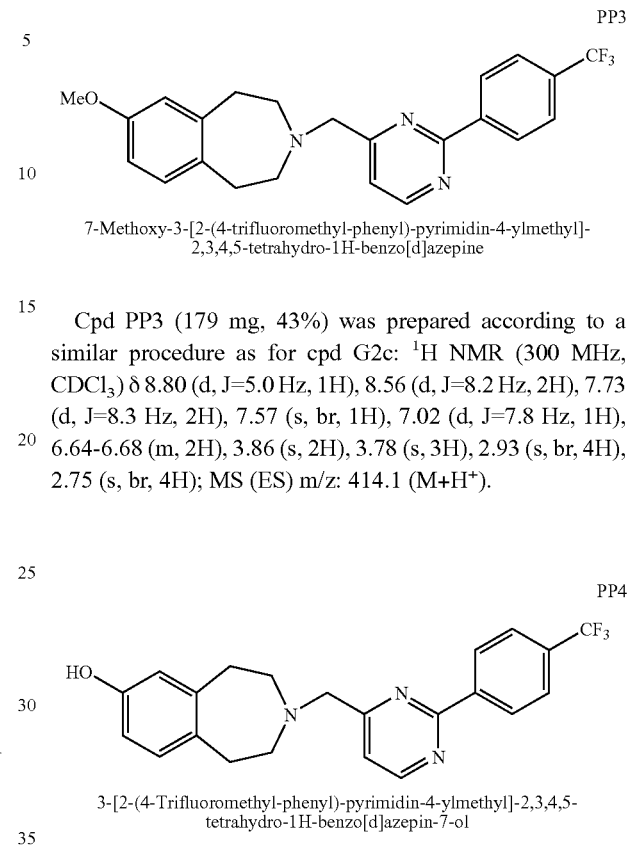

7-Methoxy-3-[2-(4-trifluoromethyl-phenyl)-pyrimidin-4-ylmethyl]-2,3,4,5-tetrahydro-1H-benzo[d]azepine Cpd PP3 (179 mg, 43%) was prepared according to a similar procedure as for cpd G2c: $^1$H NMR (300 MHz, CDCl$_3$) δ 8.80 (d, J=5.0 Hz, 1H), 8.56 (d, J=8.2 Hz, 2H), 7.73 (d, J=8.3 Hz, 2H), 7.57 (s, br, 1H), 7.02 (d, J=7.8 Hz, 1H), 6.64-6.68 (m, 2H), 3.86 (s, 2H), 3.78 (s, 3H), 2.93 (s, br, 4H), 2.75 (s, br, 4H); MS (ES) m/z: 414.1 (M+H$^+$).

3-[2-(4-Trifluoromethyl-phenyl)-pyrimidin-4-ylmethyl]-2,3,4,5-tetrahydro-1H-benzo[d]azepin-7-ol Cpd PP4 (26 mg, 20%) was prepared according to a similar procedure as for cpd G2d: $^1$H NMR (300 MHz, CDCl$_3$) δ 8.82 (d, J=5.0 Hz, 1H), 8.56 (d, J=8.2 Hz, 2H), 7.73 (d, J=8.3 Hz, 2H), 7.62 (s, br, 1H), 6.95 (d, J=7.8 Hz, 1H), 6.58-6.61 (m, 2H), 3.93 (s, br, 2H), 2.94 (s, br, 4H), 2.81 (s, br, 4H); MS (ES) m/z: 400.0 (M+H$^+$).

{3-[2-(4-Trifluoromethyl-phenyl)-pyrimidin-4-ylmethyl]-2,3,4,5-tetrahydro-1H-benzo[d]azepin-7-yloxy}-acetic acid ethyl ester Cpd PP5 (16 mg, 64%) was prepared according to a similar procedure as for cpd G1b: $^1$H NMR (300 MHz, CDCl$_3$) δ 8.85 (s, br, 1H), 8.54 (d, J=8.1 Hz, 2H), 7.73 (d, J=8.3 Hz, 2H), 7.61 (s, br, 1H), 7.03 (d, J=8.2 Hz, 1H), 6.72 (d, J=2.5 Hz, 1H), 6.64-6.67 (m, 1H), 4.59 (s, 2H), 4.23-4.30 (q, J=7.1 Hz, 2H), 3.92 (s, br, 2H), 2.80-2.93 (br, 8H), 1.29 (t, J=7.1 Hz, 3H); MS (ES) m/z: 486.1 (M+H$^+$).

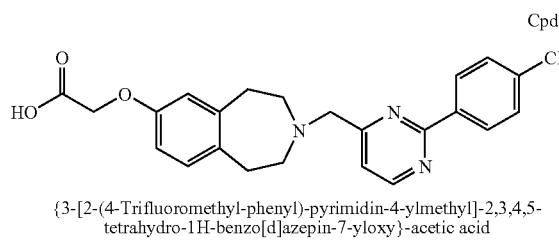

Cpd 41

{3-[2-(4-Trifluoromethyl-phenyl)-pyrimidin-4-ylmethyl]-2,3,4,5-tetrahydro-1H-benzo[d]azepin-7-yloxy}-acetic acid Cpd 41 (10 mg, 70%) was prepared according to a similar procedure as for cpd 7: $^1$H NMR (400 MHz, DMSO) δ 8.94 (d, J=5.0 Hz, 1H), 8.58 (d, J=8.3 Hz, 2H), 7.90 (d, J=8.5 Hz, 2H), 7.65 (d, J=5.1 Hz, 1H), 7.01 (d, J=8.3 Hz, 1H), 6.70 (d, J=2.6 Hz, 1H), 6.60-6.62 (dd, J=2.6, 8.2 Hz, 1H), 4.60 (s, 2H), 3.88 (s, 2H), 2.86 (s, br, 4H), 2.67 (s, br, 4H); MS (ES) m/z: 458.1 (M+H$^+$), 456.0 (M–H$^+$).

Example NN

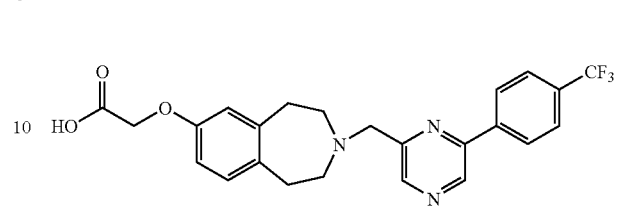

Compound 42: {3-[6-(4-Trifluoromethyl-phenyl)-pyrazin-2-ylmethyl]-2,3,4,5-tetrahydro-1H-benzo[d]azepin-7-yloxy}-acetic acid The title compound was made according to Scheme NN.

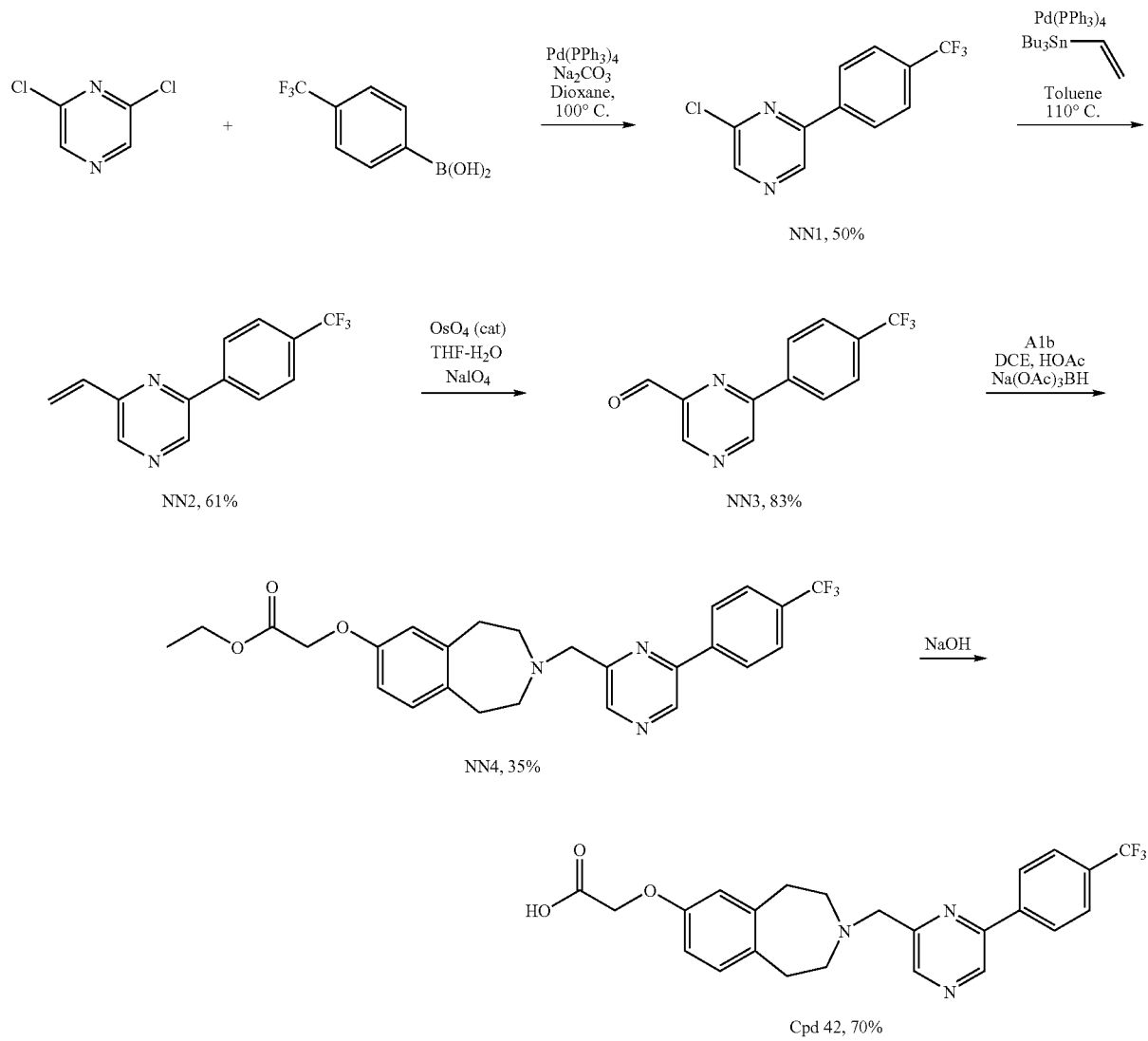

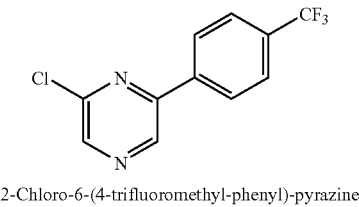

2-Chloro-6-(4-trifluoromethyl-phenyl)-pyrazine

Cpd NN1 (522 mg, 50%) was prepared according to a similar procedure as for cpd G1a. ¹H NMR (300 MHz, CDCl$_3$) δ 8.97 (s, 1H), 8.60 (s, 1H) 8.15 (d, J=8.2 Hz, 2H), 7.78 (d, J=8.3 Hz, 2H).

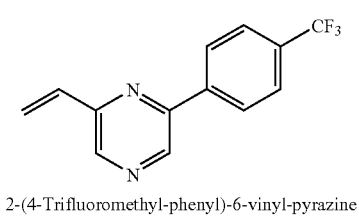

2-(4-Trifluoromethyl-phenyl)-6-vinyl-pyrazine

A mixture of cpd NN1 (106 mg, 0.411 mmol), Pd(PPh$_3$)$_4$ (47 mg, 0.041 mmol), tributylvinyltin (0.18 mL, 0.616 mmol) and toluene (2.0 mL) was refluxed under N$_2$ for 18 h. The mixture was cooled and concentrated. Cpd NN2 was obtained after column chromatography purification as clear oil (98 mg, 95%): ¹H NMR (300 MHz, CDCl$_3$) δ 8.92 (s, 1H), 8.58 (s, 1H), 8.20 (d, J=8.1 Hz, 2H), 7.78 (d, J=8.2 Hz, 2H), 6.87-6.97 (m, 1H), 6.49-6.55 (m, 1H), 5.70-5.74 (m, 1H).

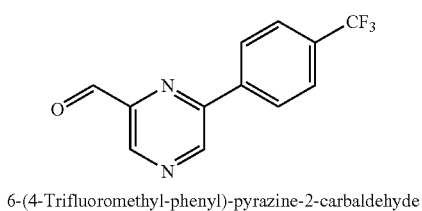

6-(4-Trifluoromethyl-phenyl)-pyrazine-2-carbaldehyde

A mixture of NN2 (72 mg, 0.288 mmol), THF (2.5 mL), water (2.5 mL), OsO$_4$ (2.5 wt %, 2 drops) and NaIO$_4$ (123 mg, 0.576 mmol) was stirred at r.t. for 18 h. The mixture was poured into aqueous NaHCO$_3$, extracted with CH$_2$Cl$_2$. The organic extracts were washed with water, brine, dried (Na$_2$SO$_4$) and concentrated. The residue was purified by column chromatography to give NN3 (60 mg, 83%) as beige solid: ¹H NMR (300 MHz, CDCl$_3$) δ 10.25 (s, 1H), 9.28 (s, 1H), 9.16 (s, 1H), 8.25 (d, J=8.1 Hz, 2H), 7.83 (d, J=8.2 Hz, 2H).

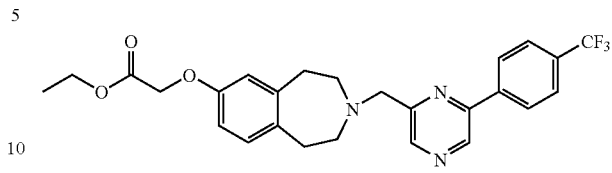

{3-[6-(4-Trifluoromethyl-phenyl)-pyrazin-2-ylmethyl]-2,3,4,5-tetrahydro-1H-benzo[d]azepin-7-yloxy}-acetic acid ethyl ester Cpd NN4 (38 mg, 35%) was prepared according to a similar procedure as for cpd G1b. ¹H NMR (300 MHz, CDCl$_3$) δ 8.94 (s, 1H), 8.81 (s, 1H), 8.14 (d, J=8.1 Hz, 2H), 7.76 (d, J=8.3 Hz, 2H), 7.00 (d, J=8.2 Hz, 1H), 6.70 (d, J=2.6 Hz, 1H), 6.61-6.65 (dd, J=2.7, 8.2 Hz, 1H), 4.58 (s, 2H), 4.23-4.30 (q, J=7.1 Hz, 2H), 3.94 (s, 2H), 2.91 (s, br, 4H), 2.75 (s, br, 4H), 1.27-1.32 (t, J=7.1 Hz, 3H); MS (ES) m/z: 486.1 (M+H⁺).

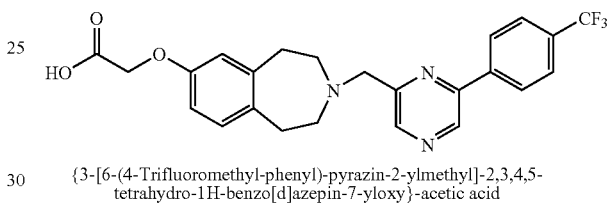

{3-[6-(4-Trifluoromethyl-phenyl)-pyrazin-2-ylmethyl]-2,3,4,5-tetrahydro-1H-benzo[d]azepin-7-yloxy}-acetic acid Cpd 42 (21 mg, 70%) was prepared according to a similar procedure as for cpd 7. ¹H NMR (400 MHz, DMSO-d$_6$) δ 9.40 (s, 1H), 8.89 (s, 1H), 8.43 (d, J=7.6 Hz, 2H), 7.95 (d, J=8.4 Hz, 2H), 7.09 (d, J=5.9 Hz, 1H), 6.78 (s, 1H), 6.68 (s, br, 1H), 5.76 (s, 2H), 4.62 (s, 2H), 3.00 (br, 8H); MS (ES) m/z: 458.1 (M+H⁺)

Example QQ

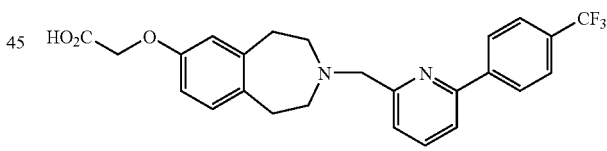

Compound 43: {3-[6-(4-Trifluoromethyl-phenyl)-pyridin-2-ylmethyl]-2,3,4,5-tetra-hydro-1H-benzo[d]azepin-7-yloxy}-acetic acid The title compound was made according to Scheme QQ.

Scheme QQ

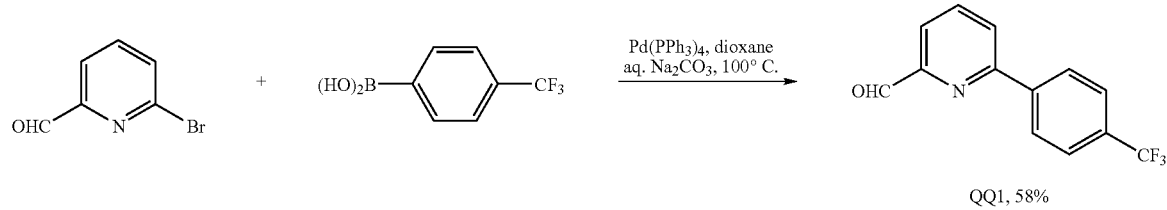

QQ1, 58%

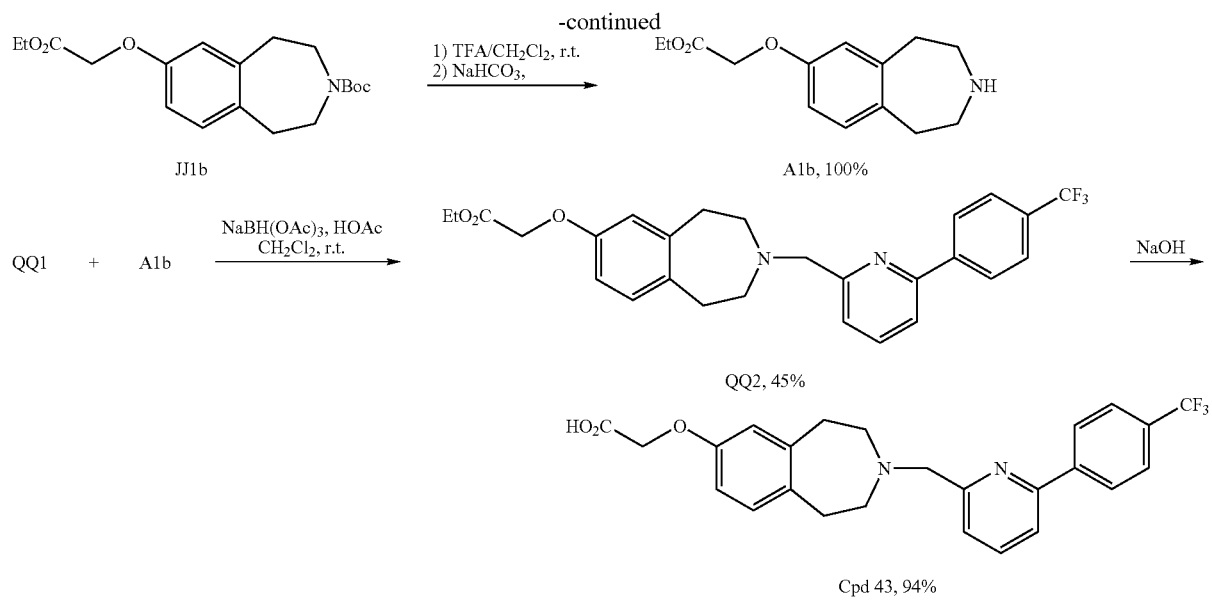

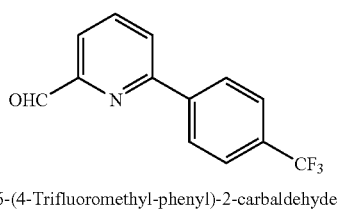

6-(4-Trifluoromethyl-phenyl)-2-carbaldehyde

Cpd QQ1 (0.78 g, 58%) was prepared according to the same procedure as for cpd G1a: ¹H NMR (300 MHz, CDCl₃) δ 10.2 (s, 1H), 8.25 (d, J=8.2 Hz, 2H), 8.02 (m, 3H), 7.80 (d, J=8.2 Hz, 2H); MS (ES) m/z: 284 (M+Na).

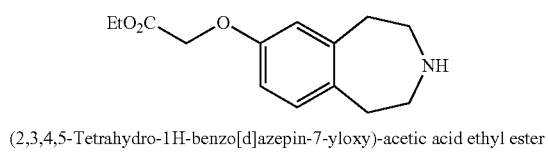

(2,3,4,5-Tetrahydro-1H-benzo[d]azepin-7-yloxy)-acetic acid ethyl ester

A mixture of cpd JJ1b (0.93 g, 2.66 mmol) an TFA (1.10 mL, 14.8 mmol) in CH₂Cl₂ (1.5 mL) was stirred at room temperature under N₂ for 21 h. After the mixture was concentrated, the residue was treated with aqueous NaHCO₃ and extracted with EtOAc. The organic layer was dried (MgSO₄) and concentrated to give cpd A1b (0.66 g, 100%) as oil: ¹H NMR (300 MHz, CDCl₃) δ 7.09 (d, J=8.2 Hz, 1H), 6.77 (d, J=2.5 Hz, 1H), 6.71 (dd, J=8.2, 2.6 Hz, 1H), 4.62 (s, 2H), 4.30 (q, J=7.1 Hz, 2H), 3.27 (m, 4H), 3.16 (m, 4H), 1.30 (t, J=7.1 Hz, 3H); MS (ES) m/z: 250 (M+H⁺).

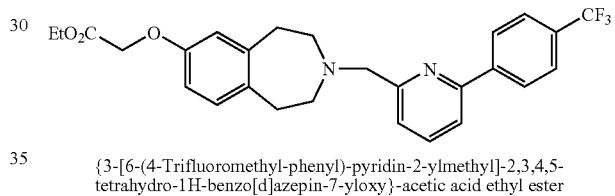

{3-[6-(4-Trifluoromethyl-phenyl)-pyridin-2-ylmethyl]-2,3,4,5-tetrahydro-1H-benzo[d]azepin-7-yloxy}-acetic acid ethyl ester Cpd QQ2 was prepared according to the same procedure as for cpd X2. Cpd QQ2 was obtained (43 mg, 45%) as an oil: ¹H NMR (300 MHz, CDCl₃) δ 8.13 (d, J=8.1 Hz, 2H), 7.81 (t, J=7.70 Hz, 1H), 7.73 (d, J=8.1 Hz, 2H), 7.65 (d, J=7.6 Hz, 1H), 7.58 (d, J=7.6 Hz, 1H), 7.02 (d, J=8.2 Hz, 1H), 6.72 (d, J=2.5 Hz, 1H), 6.64 (dd, J=8.1, 2.6 Hz, 1H), 4.60 (s, 2H), 4.28 (q, J=7.2 Hz, 2H), 3.93 (s, 2H), 2.94 (m, 4H), 2.78 (m, 4H), 2.09 (3H), 1.30 (t, J=7.2 Hz, 3H); MS (ES) m/z: 485 (M+H⁺).

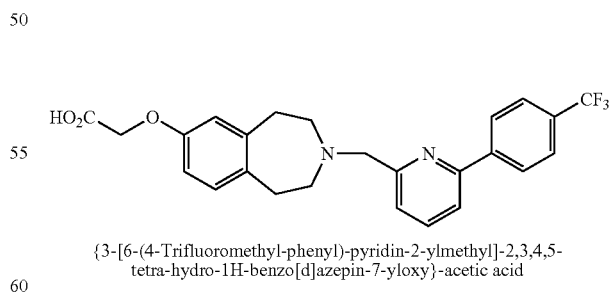

{3-[6-(4-Trifluoromethyl-phenyl)-pyridin-2-ylmethyl]-2,3,4,5-tetra-hydro-1H-benzo[d]azepin-7-yloxy}-acetic acid Cpd 43 was prepared according to the same procedure as for cpd 7. Cpd 43 was obtained (31 mg, 94%) as an off-white solid: ¹H NMR (400 MHz, DMSO-d₆) δ 8.30 (d, J=8.1 Hz, 2H), 7.95 (m, 2H), 7.86 (d, J=8.2 Hz, 1H), 7.58 (m, 1H), 7.00 (d, J=8.2 Hz, 1H), 6.69 (d, J=2.3 Hz, 1H), 6.61 (dd, J=8.2, 2.5

Hz, 1H), 4.60 (s, 2H), 3.87 (s, 2H), 2.84 (m, 4H), 2.67 (m, 4H); MS (ES) m/z: 457 (M+H+).

Example RR

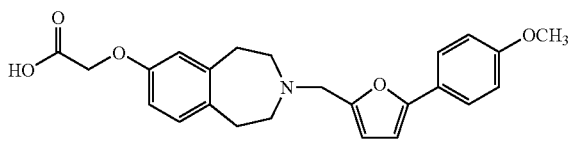

Compound 44: {3-[5-(4-Methoxy-phenyl)-furan-2-ylmethyl]-2,3,4,5-tetrahydro-1H-benzo[d]azepin-7-yloxy}-acetic acid The title compound was made according to Scheme RR.

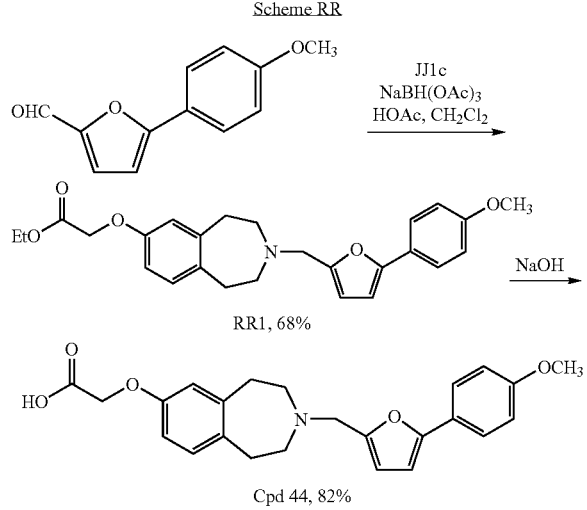

Cpd RR1 was prepared according to the same procedure as for cpd X4. Cpd RR1 was obtained (65 mg, 68%) as yellow oil: $^1$H NMR (400 MHz, CDCl$_3$) δ 7.49 (d, J=8.9 Hz, 2H), 6.90 (d, J=8.2 Hz, 1H), 6.82 (d, J=8.9 Hz, 2H), 6.60 (d, J=2.7 Hz, 1H), 6.57 (dd, J=8.2, 2.7 Hz, 1H), 6.35 (d, J=3.2 Hz, 1H), 6.17 (d, J=3.2 Hz, 1H) 4.49 (s, 2H), 4.18 (q, J=7.2 Hz, 2H), 3.75 (s, 3H), 3.71 (s, 2H), 2.83 (m, 4H), 2.65 (m, 4H), 1.22 (t, J=7.2 Hz, 3H); MS (ES) m/z: 436 (M+H+).

44

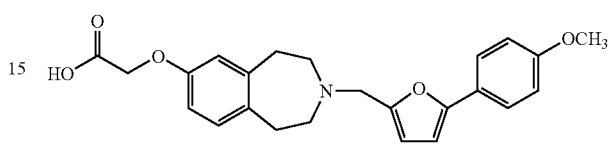

{3-[5-(4-Methoxy-phenyl)-furan-2-ylmethyl]-2,3,4,5-tetrahydro-1H-benzo[d]azepin-7-yloxy}-acetic acid A solution of cpd RR1 (55 mg, 0.13 mmol) in methanol (2 mL) was treated with 1N aqueous NaOH (0.26 mL, 0.26 mmol). After stirring overnight, the mixture was concentrated to dryness. The residue was dissolved in H$_2$O, washed with Et$_2$O twice and then acidified with 1N HCl. The acidic solution was extracted with EtOAc. The organic extracts were dried and concentrated to give cpd 44 (42 mg, 82%) as a yellow solid: $^1$H NMR (300 MHz, CDCl$_3$) δ 7.46 (d, J=8.8 Hz, 2H), 6.92 (d, J=7.3 Hz, 1H), 6.85 (d, J=8.8 Hz, 2H), 6.62 (m, 2H), 6.57 (d, J=3.3 Hz, 1H), 6.43 (d, =3.3 Hz, 1H), 4.56 (s, 2H), 4.34 (s, 2H), 3.76 (s, 3H), 3.63 (m, 4H), 2.70 (m, 4H); MS (ES) m/z: 408 (M+H+).

Example SS

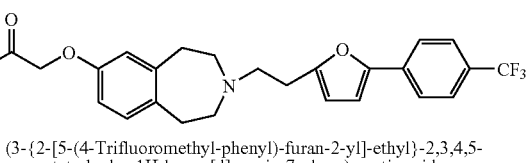

cpd 45

(3-{2-[5-(4-Trifluoromethyl-phenyl)-furan-2-yl]-ethyl}-2,3,4,5-tetrahydro-1H-benzo[d]azepin-7-yloxy)-acetic acid

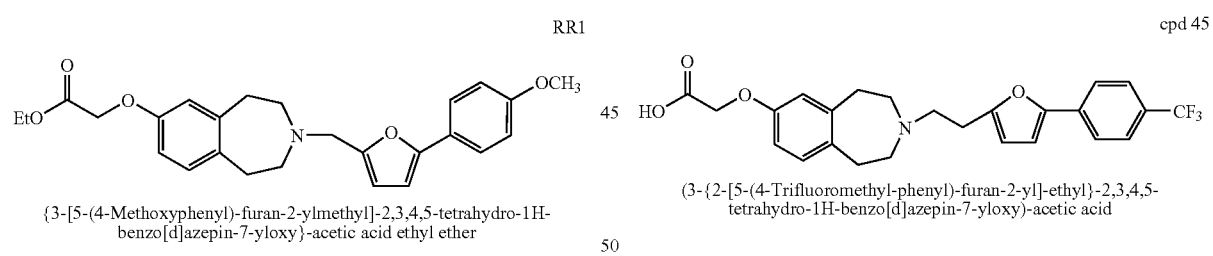

{3-[5-(4-Methoxyphenyl)-furan-2-ylmethyl]-2,3,4,5-tetrahydro-1H-benzo[d]azepin-7-yloxy}-acetic acid ethyl ether The title compound was made according to Scheme SS.

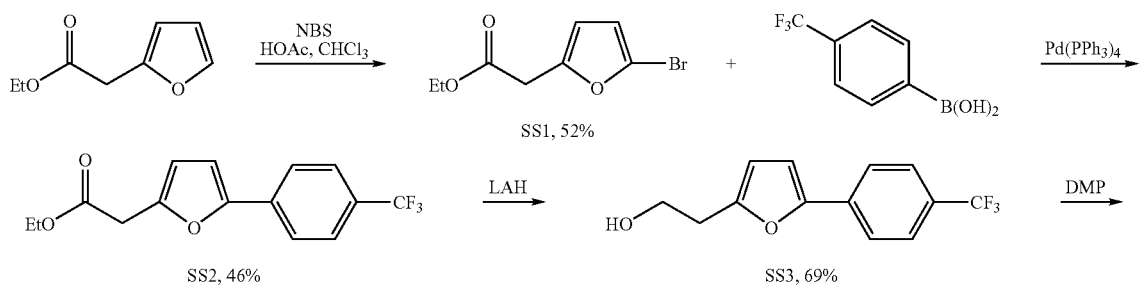

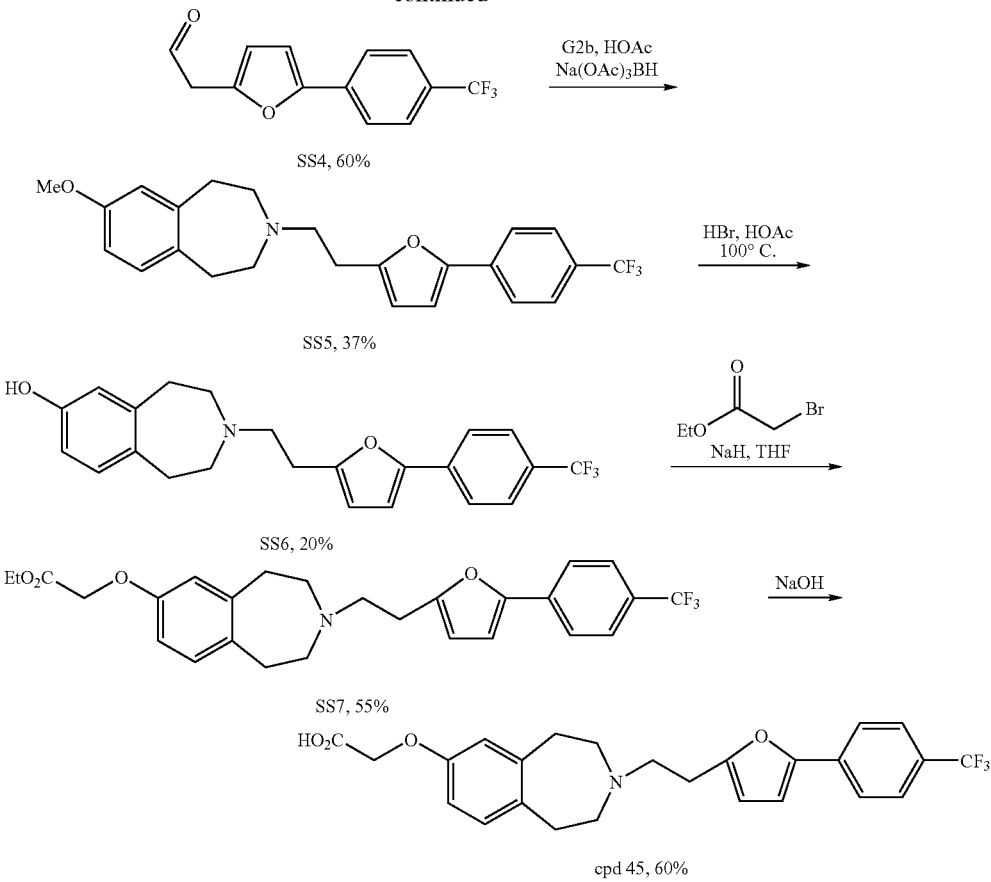

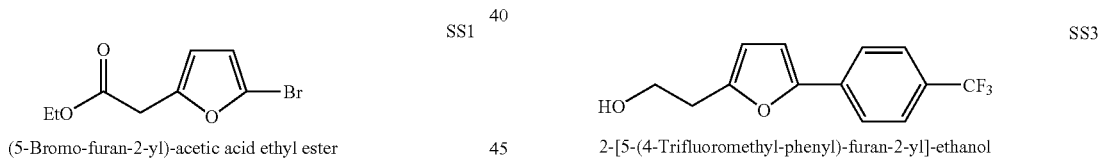

(5-Bromo-furan-2-yl)-acetic acid ethyl ester

Cpd SS1 (765 mg, 52%) was prepared using the same procedure as for cpd V1. $^1$H NMR (400 MHz, CDCl$_3$) δ 6.25 (d, J=3.2 Hz, 1H), 6.22 (d, J=3.2 Hz, 1H), 4.16-4.22 (q, J=7.1 Hz, 2H), 3.65 (s, 2H), 1.24-1.29 (t, J=7.2 Hz, 3H).

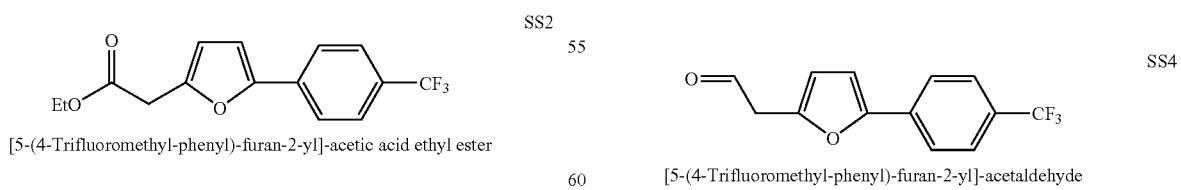

[5-(4-Trifluoromethyl-phenyl)-furan-2-yl]-acetic acid ethyl ester

Cpd SS2 (448 mg, 46%) was prepared using the same procedure as for cpd V2. $^1$H NMR (300 MHz, CDCl$_3$) δ 7.72 (d, J=8.2 Hz, 2H), 7.60 (d, J=8.3 Hz, 2H), 6.71 (d, J=3.3 Hz, 1H), 6.35 (d, J=3.3 Hz, 1H), 4.18-4.25 (q, J=7.2 Hz, 2H), 3.76 (s, 2H), 1.27-1.31 (t, J=7.1 Hz, 3H); MS (ES) m/z: 299.1 (M+H$^+$).

2-[5-(4-Trifluoromethyl-phenyl)-furan-2-yl]-ethanol

Cpd SS3 (249 mg, 69%) was prepared using the same procedure as for cpd V3. $^1$H NMR (400 MHz, CDCl$_3$) δ 7.71 (d, J=8.1 Hz, 2H), 7.61 (d, J=8.1 Hz, 2H), 6.70 (d, J=3.3 Hz, 1H), 6.24-6.25 (m, 1H), 3.96 (t, J=6.2 Hz, 2H), 2.99 (t, J=6.2 Hz, 2H).

[5-(4-Trifluoromethyl-phenyl)-furan-2-yl]-acetaldehyde

Cpd SS4 (144 mg, 60%) was prepared using the same procedure as for cpd V4. $^1$H NMR (300 MHz, CDCl$_3$) δ 9.79 (t, J=2.0 Hz, 1H), 7.73 (d, J=8.2 Hz, 2H), 7.62 (d, J=8.4 Hz, 2H), 6.75 (d, J=3.3 Hz, 1H), 6.38 d, J=3.3 Hz, 1H), 3.81 (d, J=1.9 Hz, 2H).

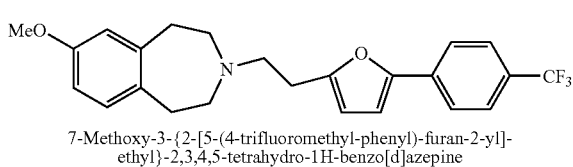

7-Methoxy-3-{2-[5-(4-trifluoromethyl-phenyl)-furan-2-yl]-ethyl}-2,3,4,5-tetrahydro-1H-benzo[d]azepine Cpd SS5 (81 mg, 37%) was prepared using the same procedure as for cpd G2c. $^1$H NMR (300 MHz, DMSO-$d_6$) δ 7.84 (d, J=8.2 Hz, 2H), 7.74 (d, J=8.4 Hz, 2H), 7.05 (d, J=3.3 Hz, 1H), 7.01 (d, J=8.2 Hz, 1H), 6.70 (d, J=2.6 Hz, 1H), 6.62-6.65 (d, J=8.1 Hz, 1H), 6.34 (d, J=3.2 Hz, 1H), 3.70 (s, 3H), 2.76-2.88 (m, 8H), 2.51-2.65 (m, 4H); MS (ES) m/z: 416.2 (M+H$^+$).

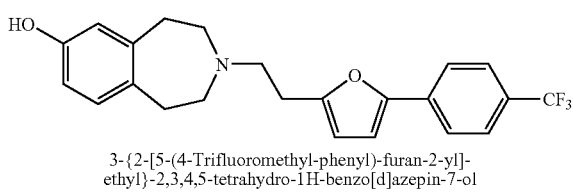

3-{2-[5-(4-Trifluoromethyl-phenyl)-furan-2-yl]-ethyl}-2,3,4,5-tetrahydro-1H-benzo[d]azepin-7-ol Cpd SS6 (15 mg, 20%) was prepared using the same procedure as for cpd G2d. $^1$H NMR (400 MHz, CDCl$_3$) δ 7.60-7.68 (m, 4H), 6.97-7.00 (m, 1H), 6.63-6.69 (m, 3H), 6.32 (d, J=3.1 Hz, 1H), 3.70-3.91 (m, 4H), 3.41-3.49 (m, 4H), 2.78-2.86 (m, 4H); MS (ES) m/z: 402.1 (M+H$^+$).

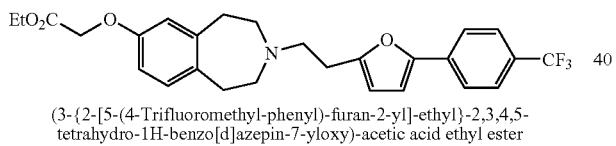

(3-{2-[5-(4-Trifluoromethyl-phenyl)-furan-2-yl]-ethyl}-2,3,4,5-tetrahydro-1H-benzo[d]azepin-7-yloxy)-acetic acid ethyl ester Cpd SS7 (10 mg, 55%) was prepared using the same procedure as for cpd G1b. $^1$H NMR (300 MHz, CDCl$_3$) δ 7.68 (d, J=8.6 Hz, 2H), 7.59-7.62 (m, 2H), 7.04 (d, J=7.9 Hz, 1H), 6.72 (s, 1H), 6.68 (d, J=3.3 Hz, 2H), 6.28 (br, 1H), 4.59 (s, 2H), 4.23-4.31 (q, J=7.1 Hz, 2H), 2.87-3.41 (m, 12H), 1.30 (t, J=7.1 Hz, 3H); MS (ES) m/z: 488.1 (M+H$^+$).

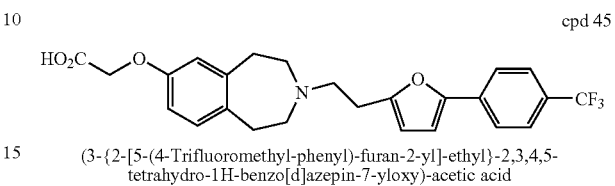

cpd 45

(3-{2-[5-(4-Trifluoromethyl-phenyl)-furan-2-yl]-ethyl}-2,3,4,5-tetrahydro-1H-benzo[d]azepin-7-yloxy)-acetic acid Cpd 45 (6 mg, 60%) was prepared using the same procedure as for cpd 7. $^1$H NMR (400 MHz, MeOD) δ 7.83 (d, J=8.3 Hz, 2H), 7.67 (d, J=8.2 Hz, 2H), 7.11 (d, J=8.2 Hz, 1H), 6.91 (d, J=3.2 Hz, 1H), 6.76-6.81 (m, 2H), 6.42 (d, J=3.0 Hz, 1H), 4.57 (s, 2H), 3.53-3.59 (m, 2H), 3.43 (m, 2H), 3.09-3.15 (m, 8H); MS (ES) m/z: 460.0 (M+H$^+$), 458.1 (M−H$^+$).

Example TT

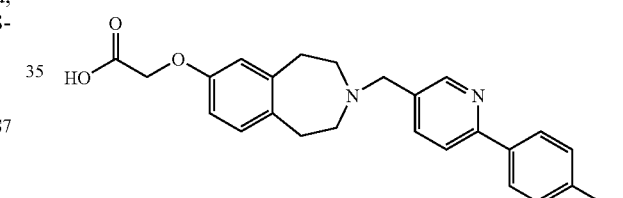

Compound 46: {3-[6-(4-Trifluoromethyl-phenyl)-pyridin-3-ylmethyl]-2,3,4,5-tetrahydro-1H-benzo[d]azepin-7-yloxy}-acetic acid The title compound was made according to Scheme TT.

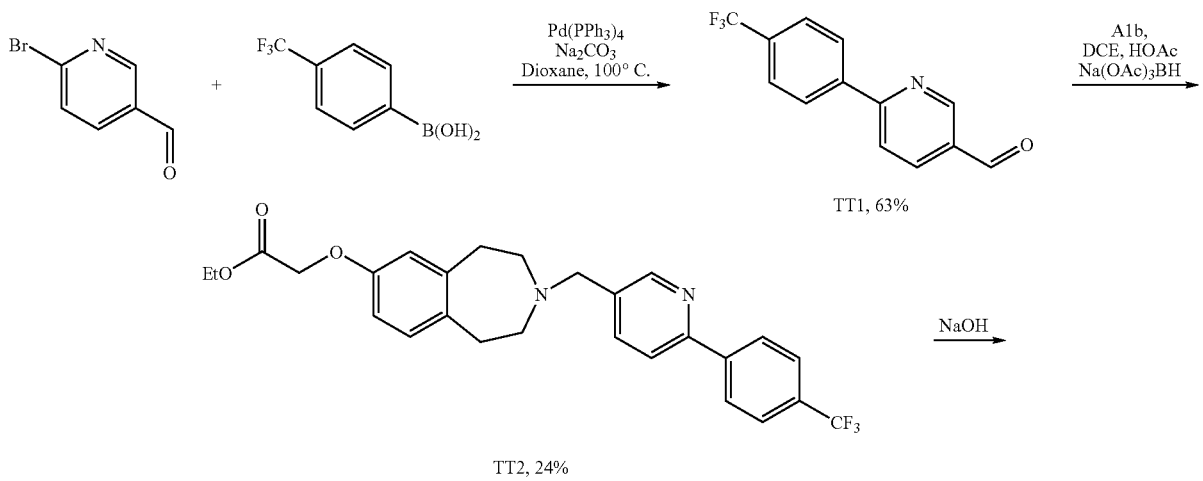

Scheme TT

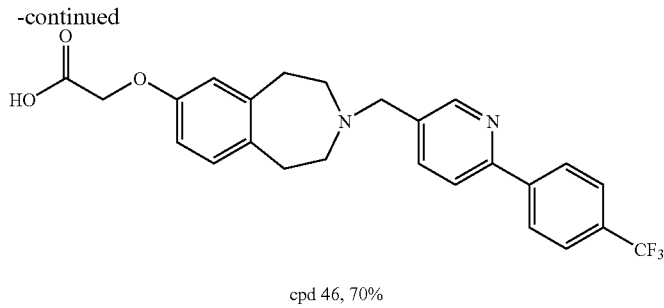

cpd 46, 70%

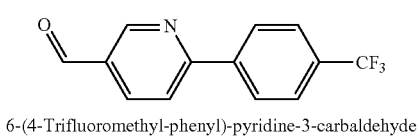

6-(4-Trifluoromethyl-phenyl)-pyridine-3-carbaldehyde

Cpd TT1 (498 mg, 63%) was prepared using the same procedure as cpd G1a. $^1$H NMR (300 MHz, CDCl$_3$) δ 10.18 (s, 1H), 9.18 (d, J=1.5 Hz, 1H), 8.29-8.33 (dd, J=2.1, 8.2 Hz, 1H), 8.22 (d, J=8.1 Hz, 2H), 7.97 (d, 8.2 Hz, 1H), 7.78 (d, J=8.2 Hz, 2H).

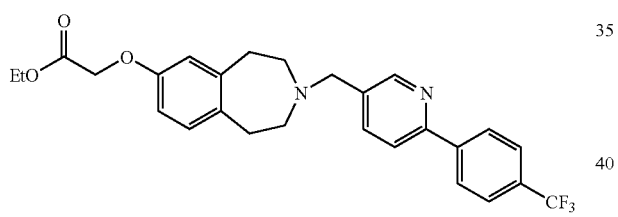

{3-[6-(4-Trifluoromethyl-phenyl)-pyridin-3-ylmethyl]-2,3,4,5-tetrahydro-1H-benzo[d]azepin-7-yloxy}-acetic acid ethyl ester Cpd TT2 (47 mg, 24%) was prepared using the same procedure as cpd G1b. $^1$H NMR (300 MHz, CDCl$_3$) δ 8.66 (s, 1H), 8.12 (d, J=8.2 Hz, 2H), 7.71-7.82 (m, 4H), 6.99 (d, J=8.1 Hz, 1H), 6.69 (d, J=2.5 Hz, 1H), 6.61-6.65 (dd, J=2.5, 8.2 Hz, 1H), 4.58 (s, 2H), 4.23-4.30 (q, J=7.1 Hz, 2H), 3.70 (s, br, 2H), 2.88 (s, br, 4H), 2.65 (s, br, 4H), 1.29 (t, J=7.1 Hz, 3H); MS (ES) m/z: 485.1 (M+H$^+$).

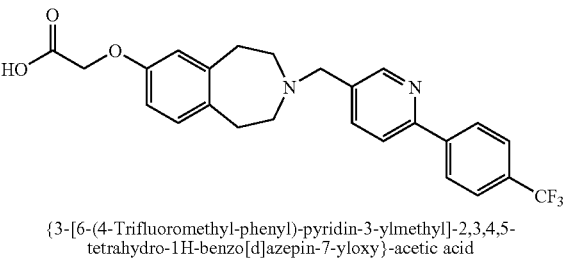

{3-[6-(4-Trifluoromethyl-phenyl)-pyridin-3-ylmethyl]-2,3,4,5-tetrahydro-1H-benzo[d]azepin-7-yloxy}-acetic acid Cpd 46 (28 mg, 70%) was prepared using the same procedure as for cpd 7. $^1$H NMR (400 MHz, DMSO-d$_6$) δ 8.87 (s, 1H), 8.35 (d, J=8.2 Hz, 2H), 8.20 (s, 2H), 7.89 (d, J=8.3 Hz, 2H), 7.09 (d, J=8.3 Hz, 1H), 6.79 (d, J=2.4 Hz, 1H), 6.69-6.72 (dd, J=2.5, 8.3 Hz, 1H), 4.63 (s, 2H), 4.45 (s, br, 2H), 2.98 (br, 8H); MS (ES) m/z: 457.0 (M+H$^+$), 455.1 (M-H$^+$).

Example UU

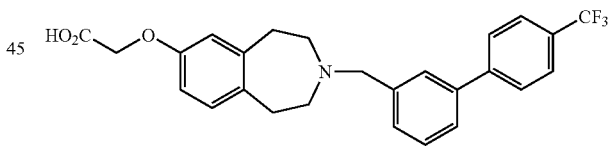

Compound 47: [3-(4'-Trifluoromethyl-biphenyl-3-ylmethyl)-2,3,4,5-tetrahydro-1H-benzo[d]azepin-7-yloxy]-acetic acid The title compound was made according to Scheme UU.

Scheme UU

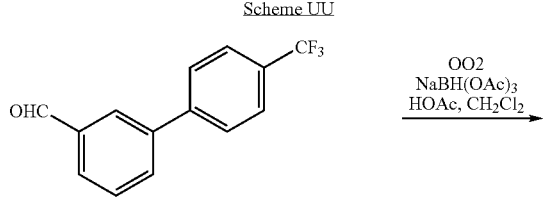

OO2
NaBH(OAc)$_3$
HOAc, CH$_2$Cl$_2$

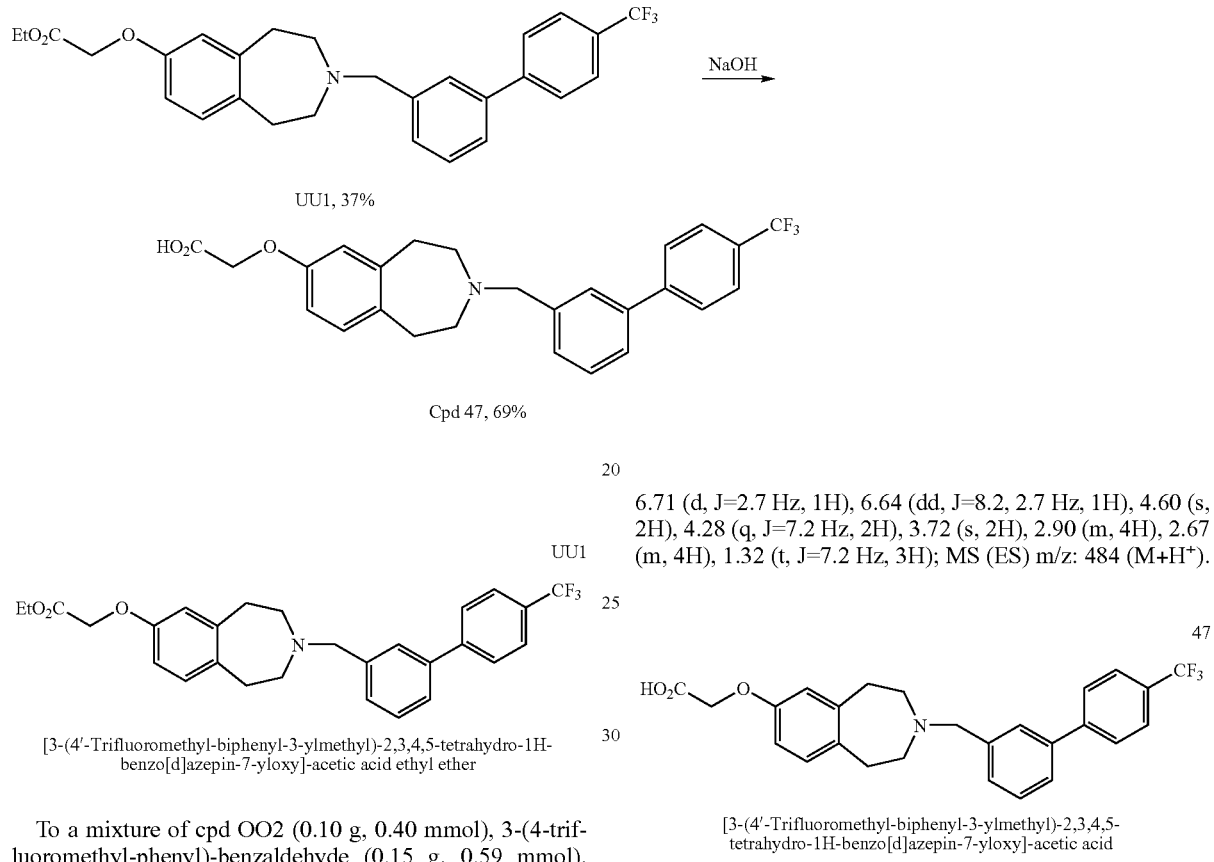

[3-(4'-Trifluoromethyl-biphenyl-3-ylmethyl)-2,3,4,5-tetrahydro-1H-benzo[d]azepin-7-yloxy]-acetic acid ethyl ether To a mixture of cpd OO2 (0.10 g, 0.40 mmol), 3-(4-trifluoromethyl-phenyl)-benzaldehyde (0.15 g, 0.59 mmol), CH$_2$Cl$_2$ (10 mL) and HOAc (0.02 mL, 0.35 mmol) at room temperature was added Na(OAc)$_3$BH (0.13 g, 0.58 mmol). After the mixture was stirred overnight, additional Na(OAc)$_3$BH (0.06 g, 0.27 mmol) was added. The mixture was stirred at r.t. overnight and heated at reflux for 30 min. After cooled to room temperature, it was basified with aqueous NaHCO$_3$ and extracted with EtOAc. The organic extracts were dried (MgSO$_4$) and concentrated. The crude product was purified by column chromatography to give cpd UU1 (70 mg, 37%): $^1$H NMR (300 MHz, CDCl$_3$) δ7.72 (m, 4H), 7.61 (s, 1H), 7.51 (m, 1H), 7.43 (m, 2H), 7.01 (d, J=8.2 Hz, 1H), 6.71 (d, J=2.7 Hz, 1H), 6.64 (dd, J=8.2, 2.7 Hz, 1H), 4.60 (s, 2H), 4.28 (q, J=7.2 Hz, 2H), 3.72 (s, 2H), 2.90 (m, 4H), 2.67 (m, 4H), 1.32 (t, J=7.2 Hz, 3H); MS (ES) m/z: 484 (M+H$^+$).

[3-(4'-Trifluoromethyl-biphenyl-3-ylmethyl)-2,3,4,5-tetrahydro-1H-benzo[d]azepin-7-yloxy]-acetic acid Cpd 47 was prepared according to the same procedure as for cpd 31. Cpd 47 was obtained (41 mg, 69%) as a beige solid: $^1$H NMR (300 MHz, DMSO-d$_6$) δ 7.92 (d, J=8.2 Hz, 2H), 7.84 (m, 3H), 7.72 (d, J=7.3 Hz, 1H), 7.55 (m, 2H), 7.04 (d, J=8.3 Hz, 1H), 6.72 (d, J=2.1 Hz, 1H), 6.65 (d, J=8.3 Hz, 1H), 4.61 (s, 2H), 3.99 (bs, 2H), 2.81 (m, 8H); MS (ES) m/z: 456 (M+H$^+$).

Compounds 1 through 47 of Formula (I) in Table 1 were prepared according to the methods described by the Schemes and Examples described herein.

TABLE 1

Representative Compounds

| Cpd No. | Structure |
|---|---|
| 1 | 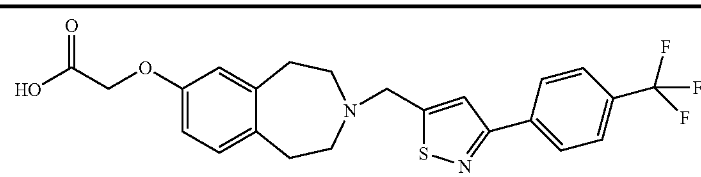 |
| 2 | 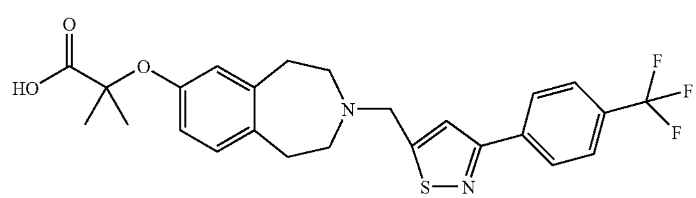 |

TABLE 1-continued

Representative Compounds

| Cpd No. | Structure |
|---|---|
| 3 | (chemical structure) |
| 4 | (chemical structure) |
| 5 | (chemical structure) |
| 6 | (chemical structure) |
| 7 | (chemical structure) |
| 8 | (chemical structure) |
| 9 | (chemical structure) |
| 10 | (chemical structure) |

TABLE 1-continued

Representative Compounds

| Cpd No. | Structure |
|---|---|
| 11 | 2-((3-((5-(4-(trifluoromethyl)phenyl)isoxazol-3-yl)methyl)-2,3,4,5-tetrahydro-1H-benzo[d]azepin-7-yl)oxy)acetic acid |
| 12 | 2-methyl-2-((3-((5-(4-(trifluoromethyl)phenyl)isoxazol-3-yl)methyl)-2,3,4,5-tetrahydro-1H-benzo[d]azepin-7-yl)oxy)propanoic acid |
| 13 | 2-((3-((3-methyl-5-(4-(trifluoromethyl)phenyl)thiophen-2-yl)methyl)-2,3,4,5-tetrahydro-1H-benzo[d]azepin-7-yl)oxy)acetic acid |
| 14 | 2-methyl-2-((3-((3-methyl-5-(4-(trifluoromethyl)phenyl)thiophen-2-yl)methyl)-2,3,4,5-tetrahydro-1H-benzo[d]azepin-7-yl)oxy)propanoic acid |
| 15 | 2-((3-((3-methyl-4-(4-(trifluoromethyl)phenyl)thiophen-2-yl)methyl)-2,3,4,5-tetrahydro-1H-benzo[d]azepin-7-yl)oxy)acetic acid |
| 16 | 2-methyl-2-((3-((3-methyl-4-(4-(trifluoromethyl)phenyl)thiophen-2-yl)methyl)-2,3,4,5-tetrahydro-1H-benzo[d]azepin-7-yl)oxy)propanoic acid |
| 17 | 2-((3-((2-(4-(trifluoromethyl)phenyl)thiazol-4-yl)methyl)-2,3,4,5-tetrahydro-1H-benzo[d]azepin-7-yl)oxy)acetic acid |
| 18 | 2-((3-((4-methyl-2-(4-(trifluoromethyl)phenyl)oxazol-5-yl)methyl)-2,3,4,5-tetrahydro-1H-benzo[d]azepin-7-yl)oxy)acetic acid |

TABLE 1-continued

Representative Compounds

| Cpd No. | Structure |
|---|---|
| 19 | |
| 20 | |
| 21 | |
| 22 | |
| 23 | |
| 24 | |
| 25 | |
| 26 | |
| 27 | |

TABLE 1-continued
Representative Compounds
| Cpd No. | Structure |
|---|---|
| 27a | 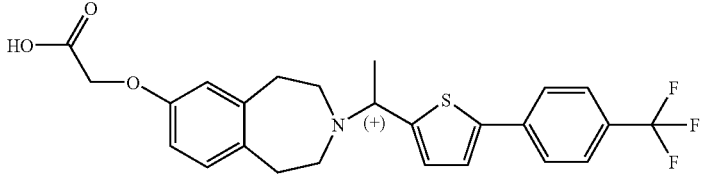 |
| 27b | 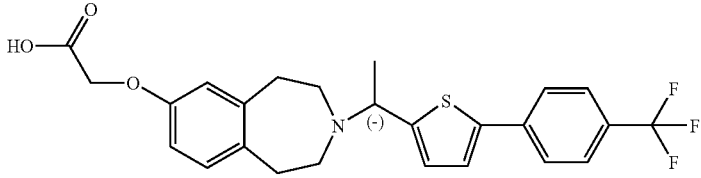 |
| 28 | 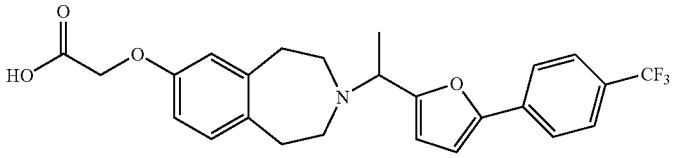 |
| 28a | 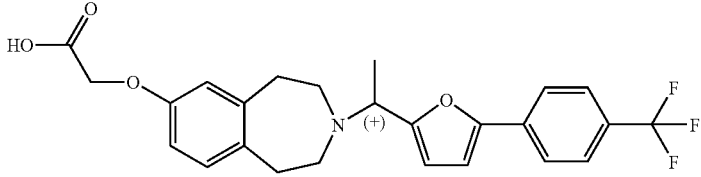 |
| 28b | 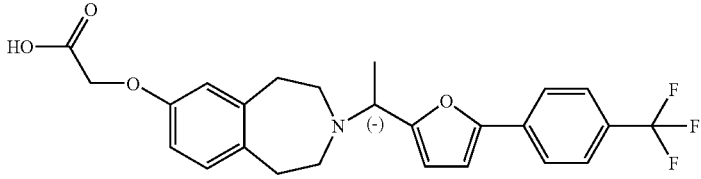 |
| 29 | 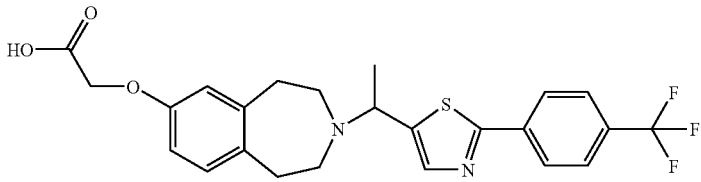 |
| 30 | 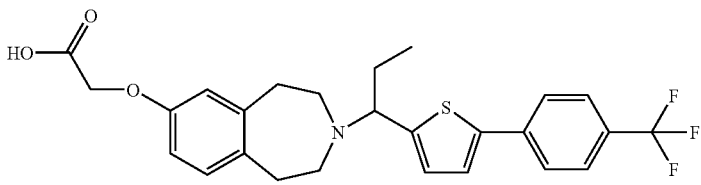 |
| 31 | 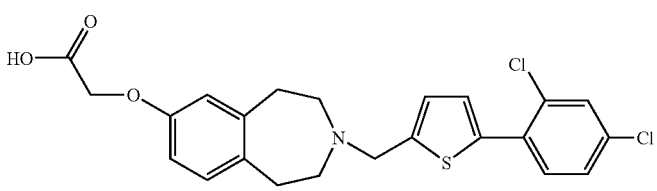 |

TABLE 1-continued

Representative Compounds

| Cpd No. | Structure |
|---|---|
| 32 | 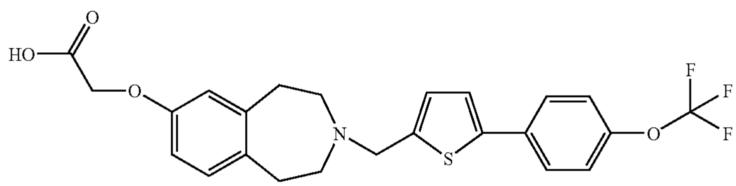 |
| 33 | 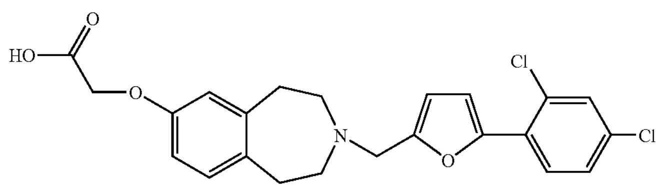 |
| 34 | 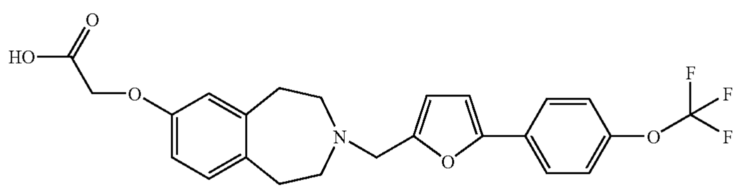 |
| 35 | 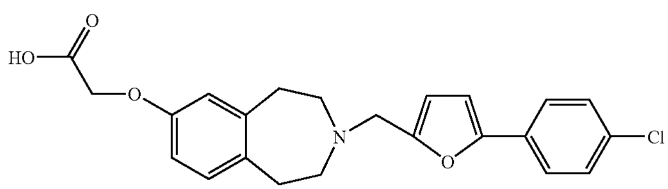 |
| 36 | 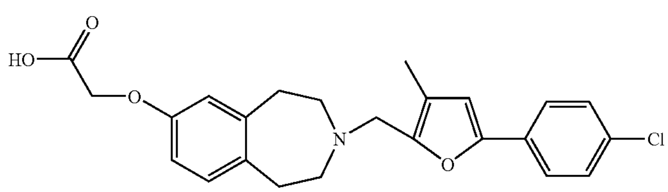 |
| 37 | 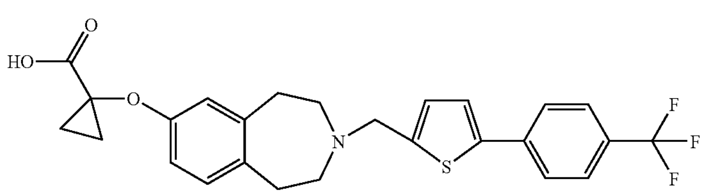 |
| 38 | 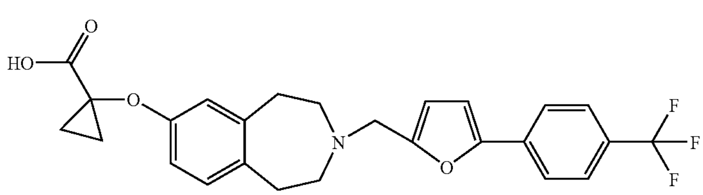 |

TABLE 1-continued

Representative Compounds

| Cpd No. | Structure |
|---|---|
| 39 | 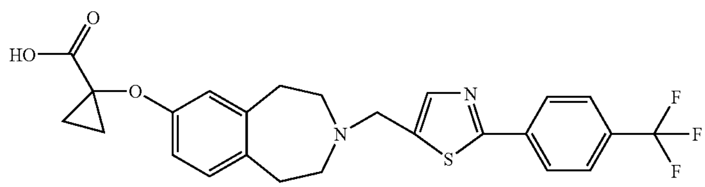 |
| 40 | 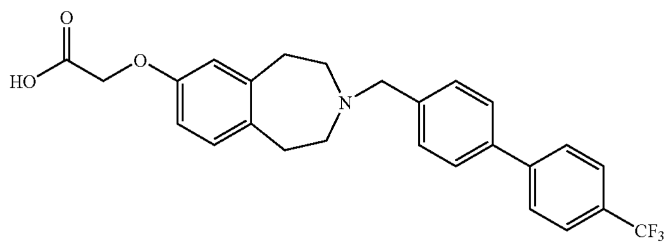 |
| 41 | 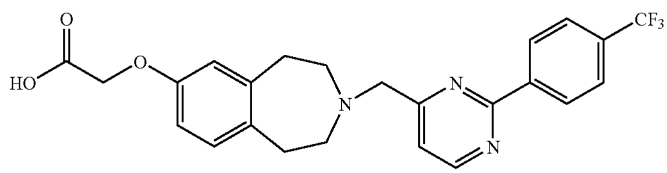 |
| 42 | 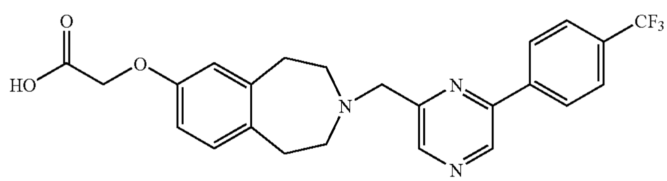 |
| 43 | 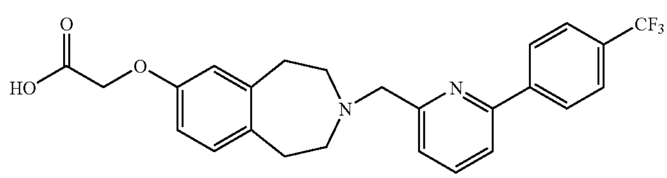 |
| 44 | 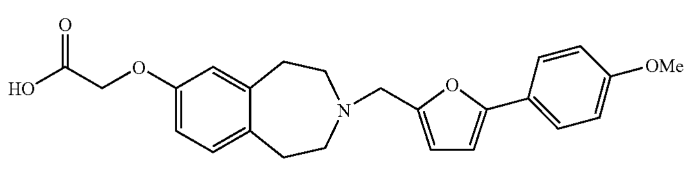 |
| 45 | 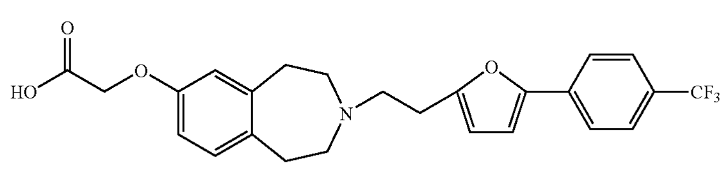 |

TABLE 1-continued

Representative Compounds

| Cpd No. | Structure |
|---|---|
| 46 | [Structure: HO-C(=O)-CH2-O-[benzazepine]-N-CH2-pyridyl-phenyl-CF3] |
| 47 | [Structure: HO-C(=O)-CH2-O-[benzazepine]-N-CH2-phenyl-phenyl-CF3] |

Biological Examples

Example 1

Transfection Assay Method for PPAR α, γ or δ Receptors

HEK293 cells were grown in DMEM/F12 medium supplemented with 10% FBS and glutamine (Invitrogen) and incubated in a 5% $CO_2$ incubator at 37° C. The cells were co-transfected using DMRIE-C reagent (Invitrogen) in serum free medium (Opti-MEM, Invitrogen) with two mammalian expression plasmids, one containing the DNA sequence coding for the ligand binding domains of either PPARα, γ or δ fused to the yeast GAL4 DNA binding domain and the other containing the promoter sequence of the yeast GAL4 (UAS) fused to the firefly luciferase cDNA reporter. The next day, the medium was changed to DMEM/F12 medium supplemented with 5% charcoal treated serum (Hyclone) and glutamine. After 6 hrs the cells were trypsinized and seeded at a density of 50,000 cells/well into 96 well plates and incubated overnight as above. The cells were then treated with test compounds or vehicle and incubated for 18-24 hrs as above. Luciferase reporter activity was measured using the Steady-Glo Luciferase Assay Kit from Promega. DMRIE-C Reagent was purchased from GIBCO Cat. No. 10459-014. OPTI-MEM I Reduced Serum Medium was purchased from GIBCO (Cat. No. 31985). Steady-Glo Luciferase Assay Kit was purchased from Promega (Part# E254B).

A variety of example compounds have been made and tested, with a range of in vitro results. Below, in Table 2, are representative compounds and data; in some cases, where multiple $EC_{50}$'s are shown, multiple measurements were taken. Naturally, different compounds in Formula (I) may have not activities identical to any one compound below.

TABLE 2

In vitro data of PPARdelta agonists

| Cpd No. | PPARδ $EC_{50}$ (nM) | PPARγ $EC_{50}$ (nm) | PPARα $EC_{50}$ (nM) |
|---|---|---|---|
| 1 | 34.1 | >3000 | 546 758 |
|  | 66.6 | >3000 |  |
| 2 | 161.8 | >3000 | >3000 |
| 3 | 142.9 | >3000 | >3000 |
| 4 | 95.2 | >3000 | >3000 |
| 5 | 51.6 | >3000 | >3000 |
| 6 | 243.1 | >3000 | >1000 |
| 7 | 14.5 | >3000 | >3000 |
|  | 18.9 | >3000 |  |
| 8 | 85.9 | >3000 | >1000 |
|  | 122.7 |  |  |
| 9 | 74.2 | >3000 | >3000 |
|  | 70.9 | >3000 |  |
| 10 | 53.0 | >3000 | >3000 |
|  | 87.7 | >3000 |  |
| 11 | 135.8 | >3000 | >1000 |
| 12 | 121.7 | >3000 | >1000 |
| 13 | 174.3 | >3000 | >3000 |
|  | 193 | >3000 |  |
| 14 | 397.8 | >3000 | >3000 |
| 15 | 103.6 | >3000 | >3000 |
|  | 104 |  |  |
| 16 | 375.4 | >3000 | >3000 |
| 17 | 439.2 | >3000 | >3000 |
| 18 | 174.4 | >3000 | >3000 |
| 19 | 230.6 | >3000 | >3000 |
| 20 | >1000 | >3000 | >3000 |
| 21 | 421.7 | >3000 | >3000 |
| 22 | >3000 | >3000 | >3000 |
| 23 | 109.3 | >3000 | >3000 |
|  | 70.2 | >3000 |  |
| 24 | 27.1 | >3000 | >1000 |
|  | 22.0 | >3000 |  |
| 25 | 11.0 | >3000 | >1000 |
|  | 10.8 | >3000 |  |
| 26 | 15.8 | >3000 | >3000 |
| 27 | <3 | >3000 | >3000 |
|  | 1.4 | >3000 |  |
| 27a | 0.92 | >1000 | >3000 |
| 27b | 12.6 | >3000 | >3000 |
|  | 13.9 | >3000 |  |
| 28 | <3 | >3000 | >3000 |
| 28a | 1.8 | >3000 | >3000 |

TABLE 2-continued

In vitro data of PPARdelta agonists

| Cpd No. | PPARδ $EC_{50}$ (nM) | PPARγ $EC_{50}$ (nm) | PPARα $EC_{50}$ (nM) |
|---|---|---|---|
| 28b | 5.4 | >3000 | >3000 |
|  | 9.8 | >3000 | >3000 |
| 29 | <3 | 622 | >3000 |
| 30 | 0.9 | >3000 | >3000 |
| 31 | 237 | >3000 | >3000 |
| 32 | 157.0 | >3000 | >3000 |
| 33 | 147.9 | >3000 | >3000 |
|  | 167 | >3000 | >3000 |
| 34 | 372.8 | >3000 | >3000 |
|  |  | >3000 | >3000 |
| 35 | 169.2 | >3000 | >3000 |
| 36 | 29.2 | >3000 | >3000 |
| 37 | 5.3 | >3000 | >3000 |
| 38 | 18 | >1000 | 31 |
| 39 | 12 | >1000 | >1000 |
| 40 | >1000 | >3000 | >3000 |
| 41 | >1000 | >3000 | >3000 |
| 42 | >1000 | >3000 | >3000 |
| 43 | >3000 | >3000 | >3000 |
| 44 | >1000 | >3000 | >3000 |

TABLE 2-continued

In vitro data of PPARdelta agonists

| Cpd No. | PPARδ $EC_{50}$ (nM) | PPARγ $EC_{50}$ (nm) | PPARα $EC_{50}$ (nM) |
|---|---|---|---|
| 45 | >1000 | >3000 | >3000 |
| 46 | 312.3 | >3000 | >1000 |
| 47 | >3000 | >3000 | >3000 |

Example 2

Rat Study of Compound 7

Compound 7

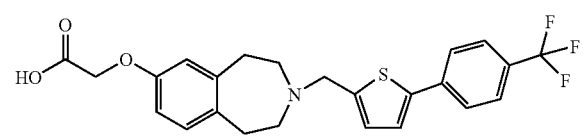

Rats carry the majority of serum cholesterol in the HDL lipoprotein fraction while humans carry the majority of serum cholesterol in LDL and VLDL lipoproteins. To mimic a human hypercholesterolemic state in a rodent model, Sprague Dawley rats were fed a diet high in cholesterol (Research Diets, C13002) for 6 days before treatment with the compounds for another 8 days while remaining on the diet. Under this dietary regimen, the vehicle controls (HC: High Cholesterol) typically have serum total cholesterol and LDL-C levels that are increased by 3-8 fold and serum HDL-C is decreased by approximately 30-50% compared with chow diet (lean) controls.

Treatment of Sprague Dawley rats fed the high cholesterol diet with Compound 7 for 8 days significantly increased HDL-C levels, achieving the levels of the chow fed controls (Chow). There were also significant decreases in serum total cholesterol and LDL-C levels. Compound 7 had no effect on serum triglycerides or liver weights. There were dose-related increases in drug plasma levels (Cmax and AUC) and there may be accumulation after multiple doses as evidenced by the differences in Cmax and AUC between the single and multiple doses at 3 mg/kg. Data from this study are shown in Tables 3 and 4 below.

TABLE 3

Compound 7 in vivo data (I)

| Dose (mg/kg) | HDL-C (mg/dL) | LDL-C (mg/dL) | Total Cholesterol (mg/dL) | Triglycerides (mg/dL) | Liver Weights |
|---|---|---|---|---|---|
| Veh (Chow) | 38.0 ± 1.1 | 10.4 ± 0.8 | 59.0 ± 2.3 | 168.9 ± 13.0 |  |
| Veh (HC) | 23.7 ± 3.3 | 35.8 ± 7.3 | 260.0 ± 32.1 | 263.7 ± 21.3 | 25.1 ± 0.4 |
| 0.1 | 24.2 ± 2.9 | 32.7 ± 4.7 | 239.0 ± 22.4 | 269.8 ± 27.8 | 24.9 ± 20.8 |
| 0.3 | 29.6 ± 1.4 | 31.2 ± 1.5 | 233.2 ± 9.5 | 264.7 ± 29.8 | 25.0 ± 0.8 |
| 1 | 31.8 ± 0.9* | 24.4 ± 1.3 | 173.3 ± 7.9* | 237.7 ± 25.4 | 23.9 ± 0.5 |
| 3 | 39.6 ± 1.6** | 20.6 ± 1.5* | 152.0 ± 8.5** | 299.5 ± 35.9 | 27.2 ± 0.9 |

*$p < 0.05$
**$p < 0.001$

TABLE 4

Compound 7 in vivo data (II)

| Dose | Dose Interval | $t^{1/2}$ (hr) | $T_{max}$ (ng/mL) | $C_{max}$ (ng/mL) | $AUC_{0-24}$ (ng · hr/mL) |
|---|---|---|---|---|---|
| $0.1^b$ | Multiple | ~13 | 2.5 | 57.0 | 772 |
| 0.3 | Multiple | ~22 | 3.0 | 124 | 1640 |
| $1^b$ | Multiple | ND | 4.0 | 595 | 10875 |
| 3 | Multiple | ~36 | 5.0 | 2030 | 37100 |
| $3^b$ | Single | ~29 | 5.5 | 733 | 14200 |

ND - $t^{1/2}$ could not be determined
$^b$n = 2

REFERENCES

Auboeuf et al., 1997, Diabetes 46(8):1319-1327
Braissant et al., 1996, Endocrinology 137(1): 354-366
Barak et al, 2002, Proc. Natl. Acad. Sci. USA 99(1):303-308
Lawn et al., 1999, J. Clin. Investigation 104(8): R25-R31
Leibowitz et al., 2000, FEBS Lett. 473(3):333-336
Oliver et al., 2001, Proc. Natl. Acad. Sci. USA 98(9):5306-5311
Tanaka et al, 2003, Proc. Natl. Acad. Sci. USA 100(26): 15924-15929
Wang et al., 2003, Cell 113:159-170

What is claimed is:

1. A compound of Formula (I)

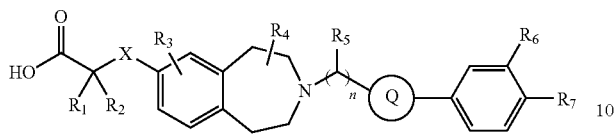

Formula (I)

wherein:

X is a covalent bond, O, or S;

$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;

$R_3$ is H;

$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, cyano substituted $C_{1-4}$alkyl, and hydroxy substituted $C_{1-4}$alkyl;

$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;

n is 1; and

Q is selected from the group consisting of

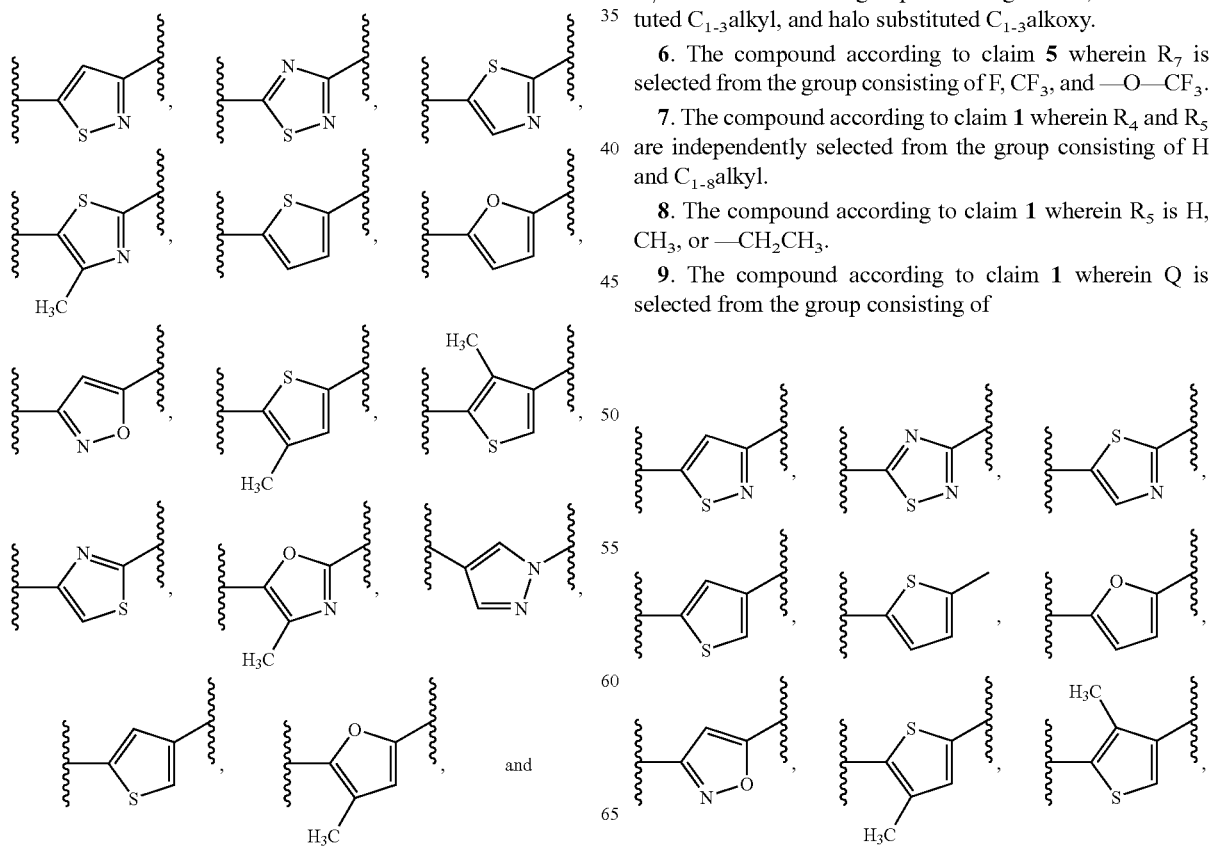

-continued

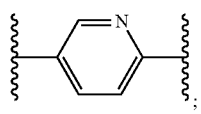

and enantiomers, diastereomers, tautomers, or pharmaceutically acceptable salts thereof.

2. The compound according to claim 1 wherein $R_1$ and $R_2$ are independently selected from the group consisting of H and $C_{1-8}$alkyl, or $R_1$, $R_2$ and the carbon atom to which they are attached together may form $C_{3-5}$cycloalkyl.

3. The compound according to claim 1 wherein $R_1$ and $R_2$ are independently selected from the group consisting of H and $CH_3$, or $R_1$, $R_2$ and the carbon atom to which they are attached together may form

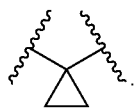

4. The compound according to claim 1 wherein $R_6$ and $R_7$ are independently selected from the group consisting of H, halo, halo substituted $C_{1-3}$alkyl, $C_{1-3}$alkoxy, and halo substituted $C_{1-3}$alkoxy.

5. The compound according to claim 1 wherein $R_6$ is H and $R_7$ is selected from the group consisting of halo, halo substituted $C_{1-3}$alkyl, and halo substituted $C_{1-3}$alkoxy.

6. The compound according to claim 5 wherein $R_7$ is selected from the group consisting of F, $CF_3$, and —O—$CF_3$.

7. The compound according to claim 1 wherein $R_4$ and $R_5$ are independently selected from the group consisting of H and $C_{1-8}$alkyl.

8. The compound according to claim 1 wherein $R_5$ is H, $CH_3$, or —$CH_2CH_3$.

9. The compound according to claim 1 wherein Q is selected from the group consisting of

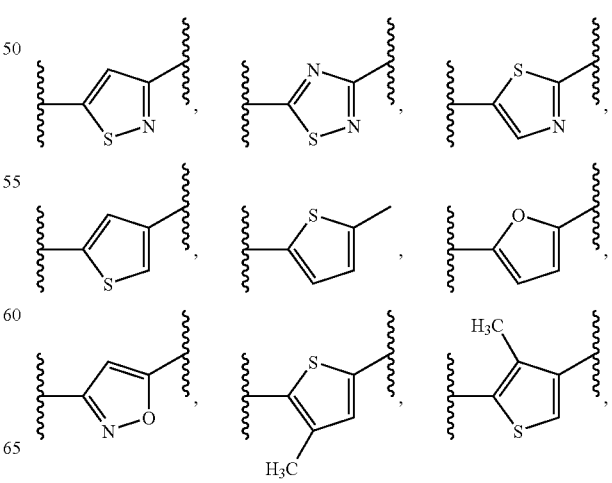

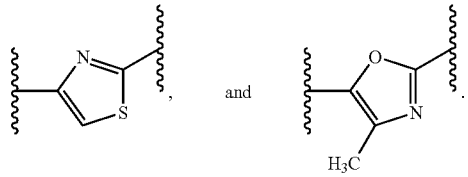

10. The compound according to claim 1 wherein Q is selected from the group consisting of

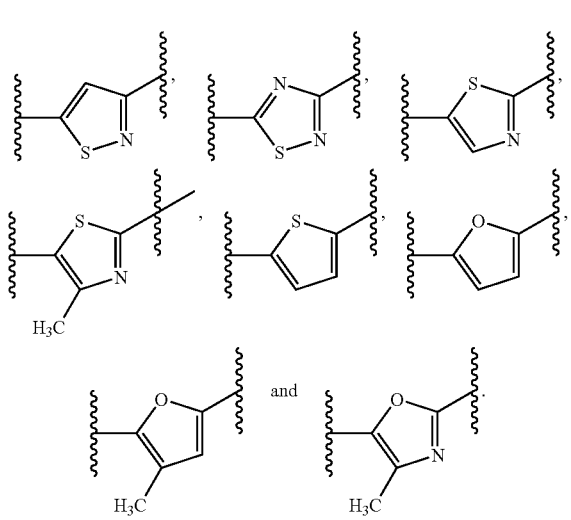

11. The compound according to claim 1 wherein X is O.
12. A compound according to claim 1 wherein
X is O;
$R_1$, $R_2$, $R_4$, and $R_5$ are independently selected from the group consisting of H and $C_{1-3}$alkyl, or $R_1$, $R_2$ and the carbon atom to which they are attached may form

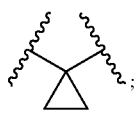

and
$R_6$ and $R_7$ are independently selected from the group consisting of H, halo, $C_{1-3}$alkoxy, and halo substituted $C_{1-3}$alkyl, and halo substituted $C_{1-3}$alkoxy;
and enantiomers, diastereomers, tautomers, or pharmaceutically acceptable salts thereof.
13. A compound of Formula (Ia)

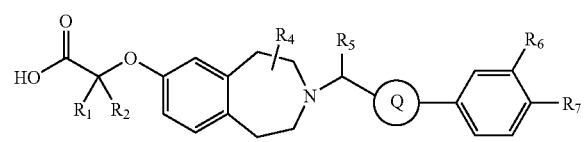

Formula (Ia)

wherein
$R_1$ and $R_2$ are independently selected from the group consisting of H and $C_{1-8}$alkyl, or $R_1$, $R_2$ and the carbon atom to which they are attached together may form $C_{3-5}$cycloalkyl;
$R_6$ and $R_7$ are independently selected from the group consisting of H, $C_{1-3}$alkyl, halo, and halo substituted $C_{1-3}$alkyl;
$R_4$ and $R_5$ are independently selected from the group consisting of H and $C_{1-8}$alkyl; and
Q is selected from the group consisting of

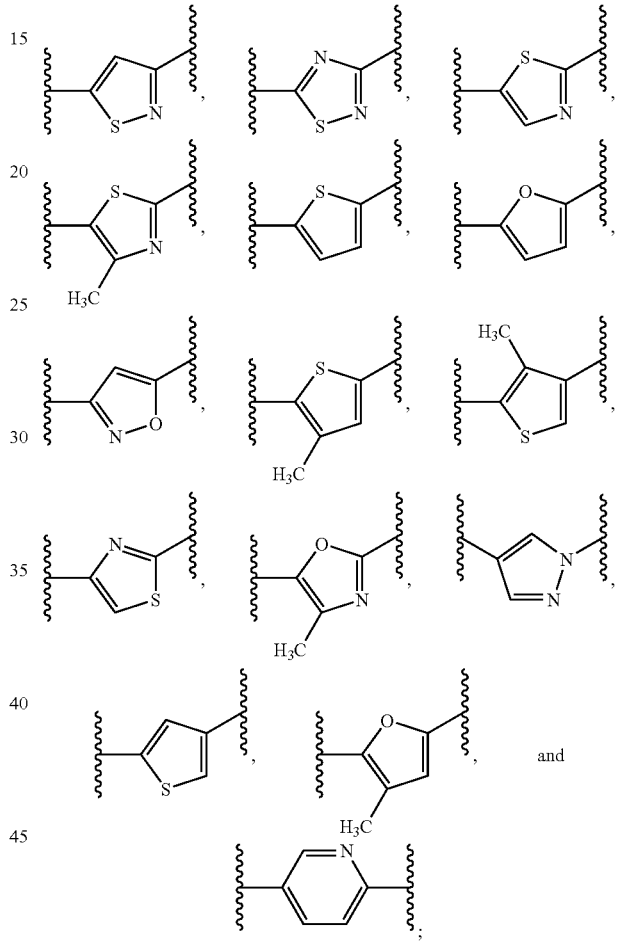

and enantiomers, diastereomers, tautomers, or pharmaceutically acceptable salts thereof.
14. A compound of Formula (Ib)

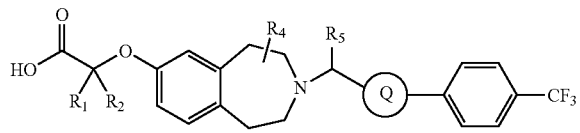

Formula (Ib)

wherein
$R_1$ and $R_2$ are independently selected from the group consisting of H and $CH_3$, or $R_1$, $R_2$ and the carbon atom to which they may form

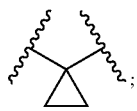

$R_4$ and $R_5$ are independently selected from the group consisting of H, $CH_3$, and $—CH_2CH_3$; and Q is selected from the group consisting of

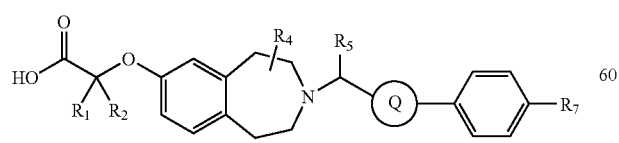

and enantiomers, diastereomers, tautomers, or pharmaceutically acceptable salts thereof.

15. A compound of Formula (Ic)

Formula (Ic)

$R_1$, $R_2$, and $R_4$, are independently selected from the group consisting of H and $CH_3$, or $R_1$, $R_2$ and the carbon atom to which they are attached together may form

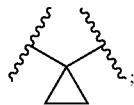

$R_5$ is selected from the group consisting of H, $CH_3$, and $—CH_2CH_3$;

$R_7$ is halo or halo substituted $C_{1-3}$alkyl; and

Q is selected from the group consisting of and enantiomers, diastereomers, tautomers, or pharmaceutically acceptable salts thereof.

16. A compound according to claim 15 wherein:
(a) $R_1$ or $R_2$ is H;
(b) $R_1$ and $R_2$ are both H;
(c) $R_1$ or $R_2$ is $CH_3$;
(d) $R_1$ and $R_2$ are both $CH_3$;
(e) $R_1$, $R_2$ and the carbon atom to which they are attached together form

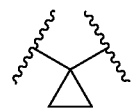

(f) $R_4$ is H or $CH_3$;
(g) $R_5$ is H, $CH_3$, or $—CH_2CH_3$;
(h) $R_1$ or $R_2$ is H and $R_4$ is H or $CH_3$;
(i) $R_1$ and $R_2$ are both H and $R_4$ is H or $CH_3$;
(j) $R_1$ or $R_2$ is H and $R_5$ is H, $CH_3$, or $—CH_2CH_3$;
(k) $R_1$ and $R_2$ are both H and $R_5$ is H, $CH_3$, or $—CH_2CH_3$;
(l) $R_1$ or $R_2$ is $CH_3$ and $R_5$ is H, $CH_3$, or $—CH_2CH_3$;
(m) $R_1$ and $R_2$ are both $CH_3$ and $R_5$ is H, $CH_3$, or $—CH_2CH_3$;
(n) $R_1$ or $R_2$ is H, $R_4$ is H, and $R_5$ is H, $CH_3$, or $—CH_2CH_3$;
(o) $R_1$ and $R_2$ are both H, $R_4$ is H, and $R_5$ is H, $CH_3$, or $—CH_2CH_3$;
(p) $R_1$ or $R_2$ is $CH_3$, $R_4$ is H, and $R_5$ is H, $CH_3$, or $—CH_2CH_3$;
(q) $R_1$ and $R_2$ are both $CH_3$, $R_4$ is H, and $R_5$ is H, $CH_3$, or $—CH_2CH_3$;

(r) $R_1$, $R_2$ and the carbon atom to which they are attached together form

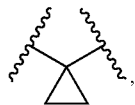

$R_4$ is H, and $R_5$ is H, $CH_3$, or $-CH_2CH_3$;
  (s) $R_7$ is $CF_3$;
  (t) $R_7$ is Cl;
  (u) $R_1$ or $R_2$ is H, $R_7$ is $CF_3$, and $R_4$ is H or $CH_3$;
  (v) $R_1$ and $R_2$ are both H, $R_7$ is $CF_3$, and $R_4$ is H or $CH_3$;
  (w) $R_1$ or $R_2$ is H, $R_7$ is $CF_3$, and $R_5$ is H, $CH_3$, or $-CH_2CH_3$;
  (x) $R_1$ and $R_2$ are both H, $R_7$ is $CF_3$, and $R_5$ is H, $CH_3$, or $-CH_2CH_3$;
  (y) $R_1$ or $R_2$ is $CH_3$, $R_7$ is $CF_3$, and $R_5$ is H, $CH_3$, or $-CH_2CH_3$;
  (z) $R_1$ and $R_2$ are both $CH_3$, $R_7$ is $CF_3$, and $R_5$ is H, $CH_3$, or $-CH_2CH_3$;
  (aa) $R_1$ or $R_2$ is H, $R_4$ is H, $R_7$ is $CF_3$, and $R_5$ is H, $CH_3$, or $-CH_2CH_3$;
  (bb) $R_1$ and $R_2$ are both H, $R_4$ is H, $R_7$ is $CF_3$, and $R_5$ is H, $CH_3$, or $-CH_2CH_3$;
  (cc) $R_1$ or $R_2$ is $CH_3$, $R_4$ is H, $R_7$ is $CF_3$, and $R_5$ is H, $CH_3$, or $-CH_2CH_3$;
  (dd) $R_1$ and $R_2$ are both $CH_3$, $R_4$ is H, $R_7$ is $CF_3$, and $R_5$ is H, $CH_3$, or $-CH_2CH_3$;
  (ee) $R_1$, $R_2$ and the carbon atom to which they are attached together form

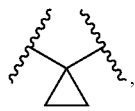

$R_4$ is H, $R_7$ is $CF_3$, and $R_5$ is H, $CH_3$, or $-CH_2CH_3$;
  (ff) Q is selected from the group consisting of

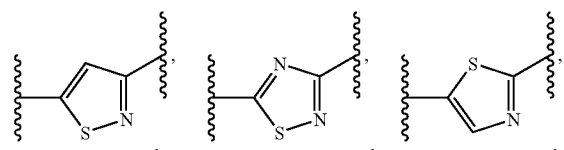

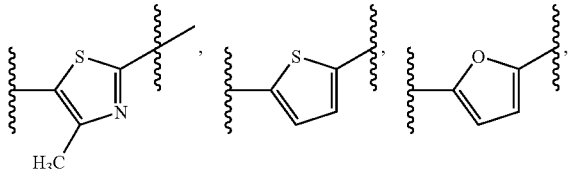

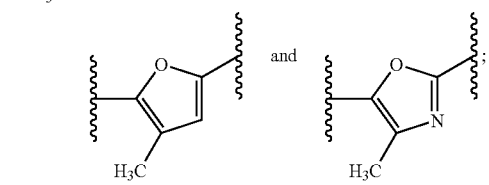

(gg) $R_1$ or $R_2$ is H and Q is selected from the group consisting of

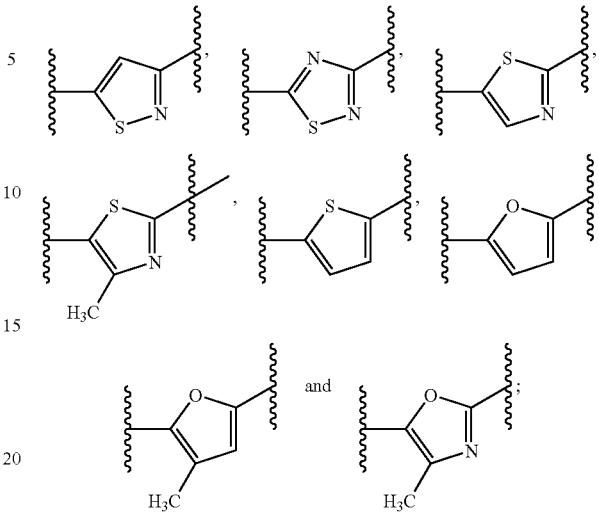

(hh) $R_1$ and $R_2$ are both H and Q is selected from the group consisting of

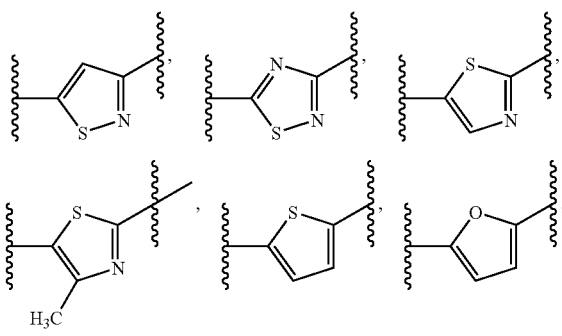

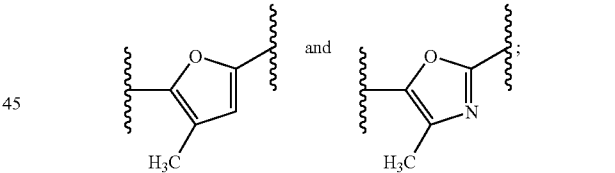

(ii) $R_1$ or $R_2$ is $CH_3$ and Q is selected from the group consisting of

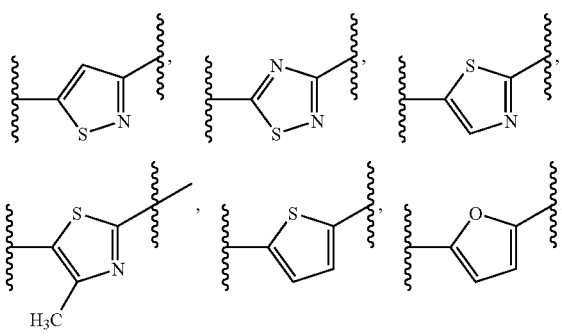

-continued

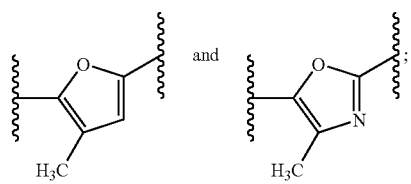

(jj) $R_1$ and $R_2$ are both $CH_3$ and Q is selected from the group consisting of

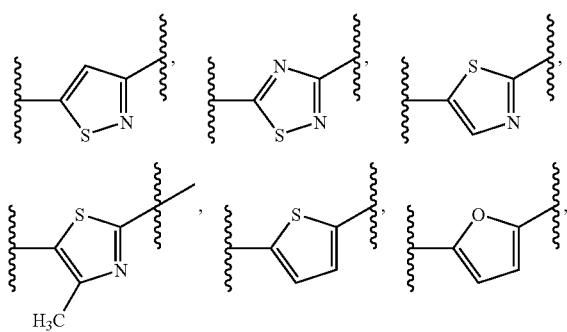

(kk) $R_4$ is H or $CH_3$ and Q is selected from the group consisting of

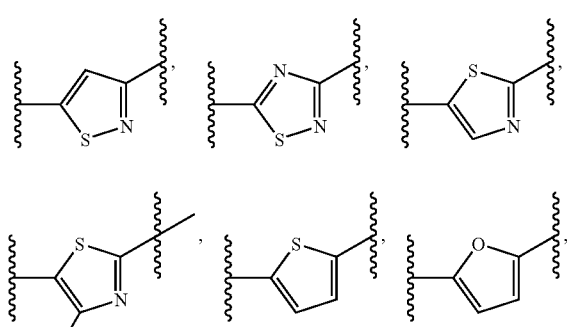

(ll) $R_5$ is H, $CH_3$, or —$CH_2CH_3$ and Q is selected from the group consisting of

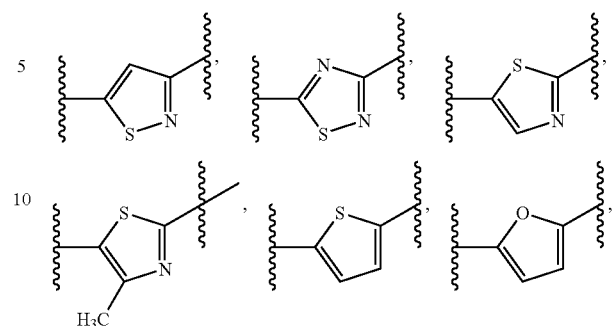

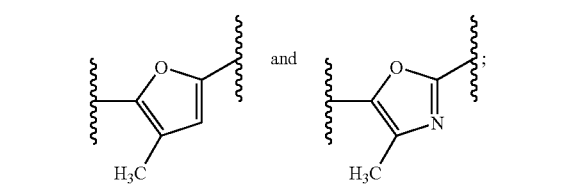

(mm) $R_1$ or $R_2$ is H and $R_4$ is H or $CH_3$ and Q is selected from the group consisting of

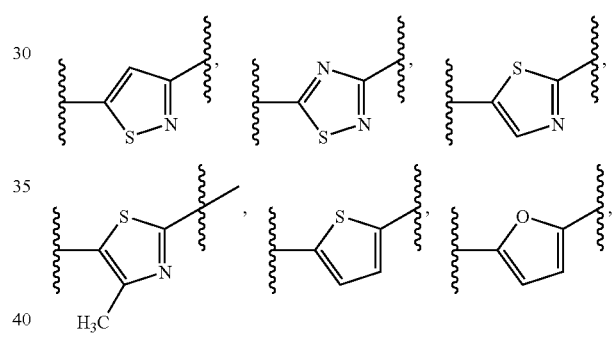

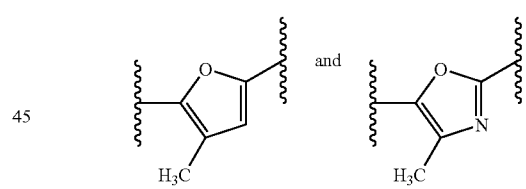

(nn) $R_1$ and $R_2$ are both H and $R_4$ is H or $CH_3$ and Q is selected from the group consisting of

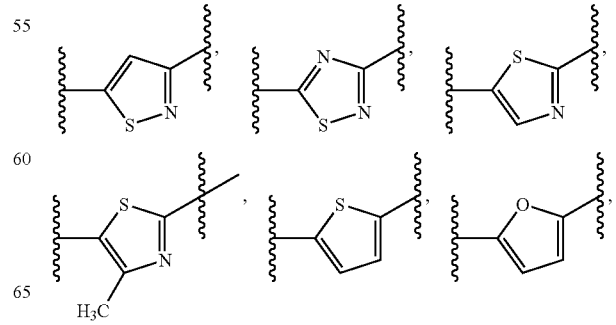

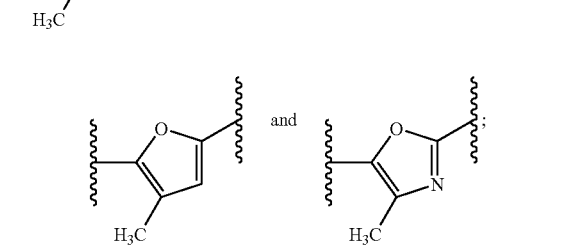

-continued

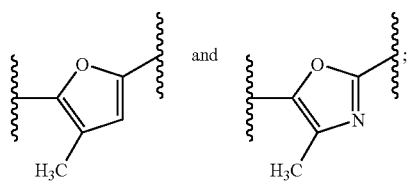

(oo) $R_1$ or $R_2$ is H and $R_5$ is H, $CH_3$, or —$CH_2CH_3$ and Q is selected from the group consisting of

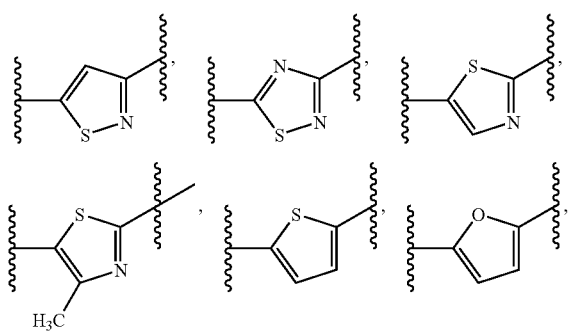

(pp) $R_1$ and $R_2$ are both H and $R_5$ is H, $CH_3$, or —$CH_2CH_3$ and Q is selected from the group consisting of

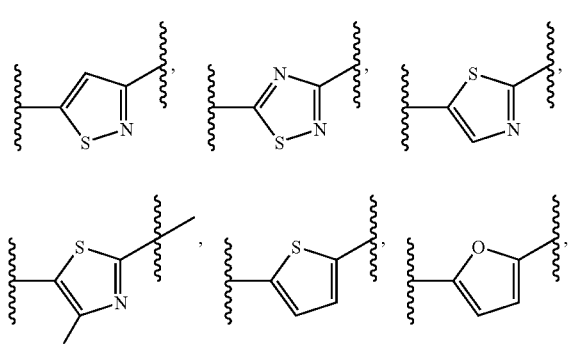

(qq) $R_1$ or $R_2$ is $CH_3$ and $R_5$ is H, $CH_3$, or —$CH_2CH_3$ and Q is selected from the group consisting of

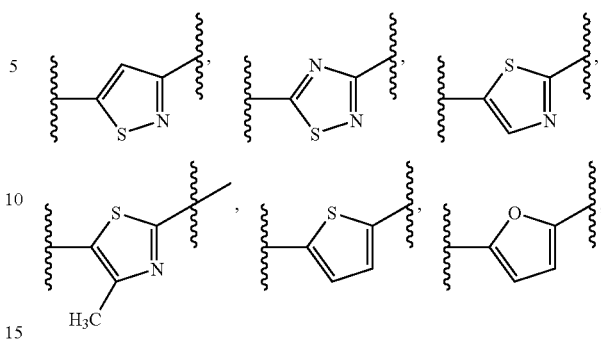

(rr) $R_1$ and $R_2$ are both $CH_3$, $R_5$ is H, $CH_3$, or —$CH_2CH_3$, and Q is selected from the group consisting of

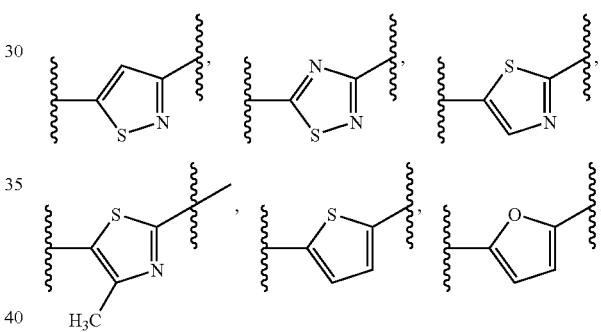

(ss) $R_1$ or $R_2$ is H, $R_4$ is H, $R_5$ is H, $CH_3$, or —$CH_2CH_3$, and Q is selected from the group consisting of

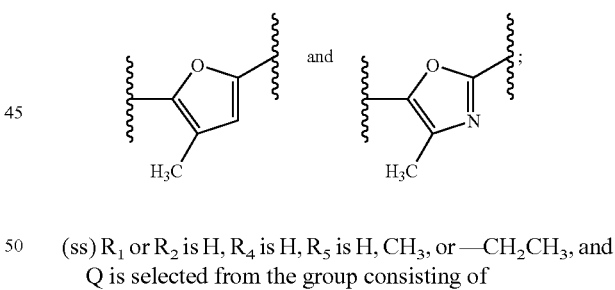

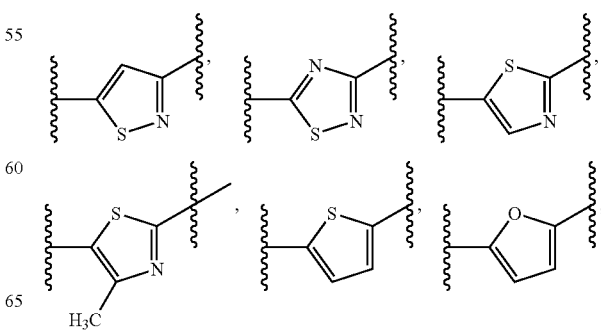

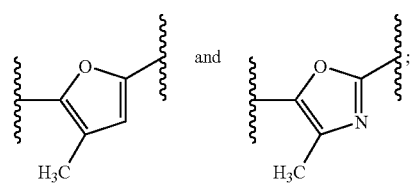

(tt) R₁ and R₂ are both H, R₄ is H, R₅ is H, CH₃, or —CH₂CH₃, and Q is selected from the group consisting of

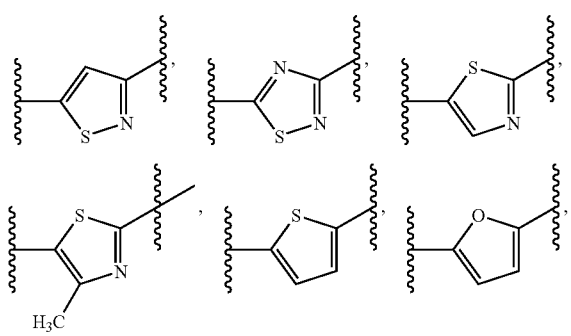

(uu) R₁ or R₂ is CH₃, R₄ is H, R₅ is H, CH₃, or —CH₂CH₃, and Q is selected from the group consisting of

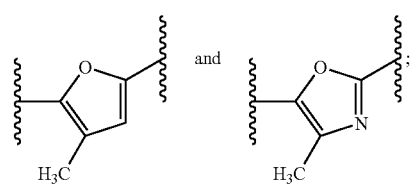

(vv) R₁ and R₂ are both CH₃, R₄ is H, R₅ is H, CH₃, or —CH₂CH₃, and Q is selected from the group consisting of

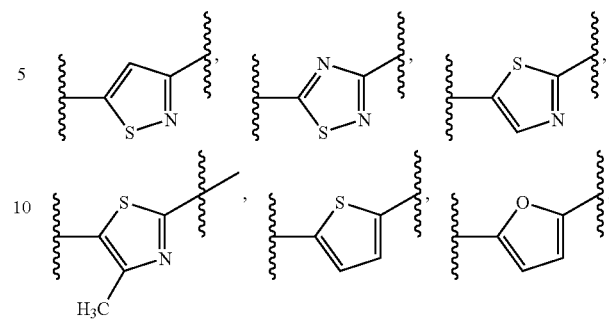

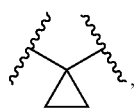

(ww) R₁, R₂ and the carbon atom to which they are attached together form

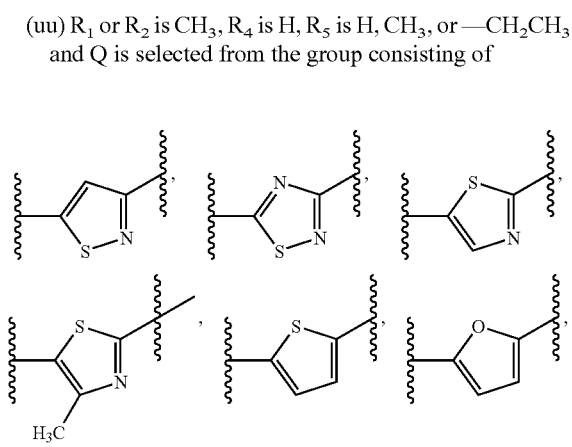

R₄ is H, R₅ is H, CH₃, or —CH₂CH₃, and Q is selected from the group consisting of

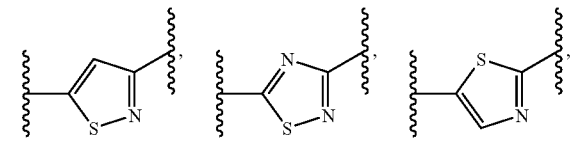

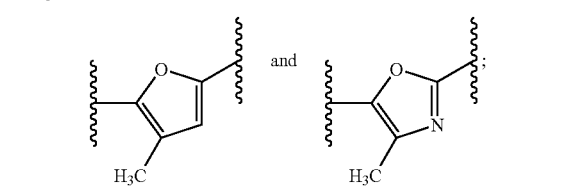

(xx) R₇ is CF₃ and Q is selected from the group consisting of

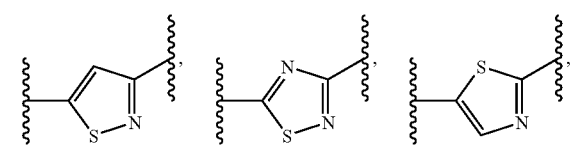

-continued
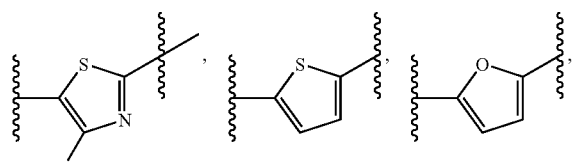
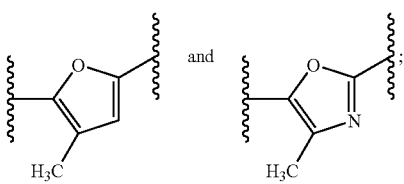
(yy) R₇ is Cl and Q is selected from the group consisting of
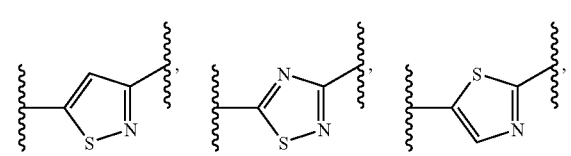
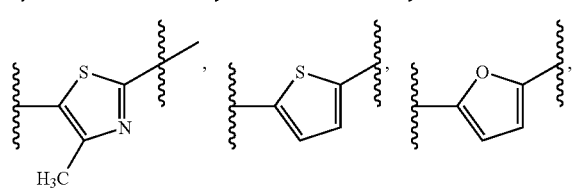
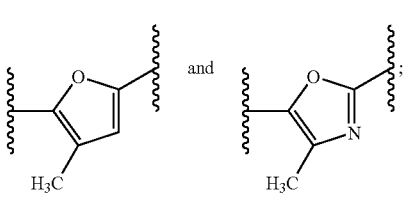
(zz) R₁ or R₂ is H, R₇ is CF₃, R₄ is H or CH₃, and Q is selected from the group consisting of
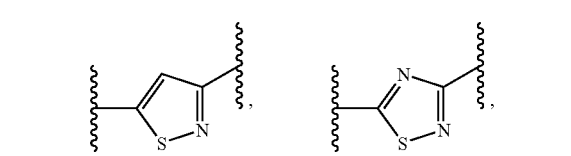
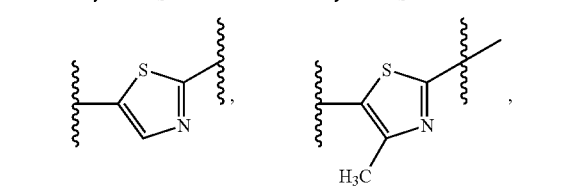
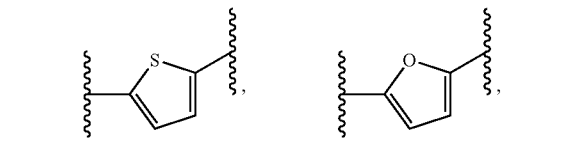
-continued
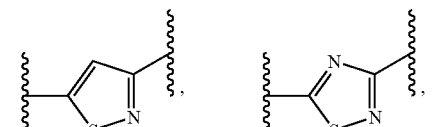 and 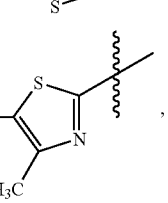;
(aaa) R₁ and R₂ are both H, R₇ is CF₃, R₄ is H or CH₃, and Q is selected from the group consisting of
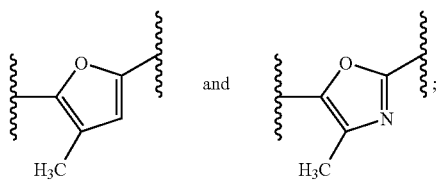
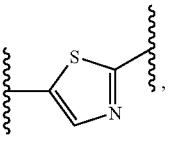, 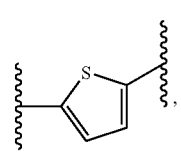,
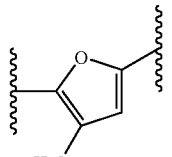 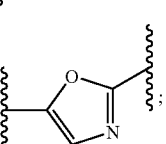
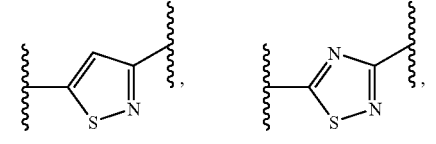
(bbb) R₁ or R₂ is H, R₇ is CF₃, R₅ is H, CH₃, or —CH₂CH₃, and Q is selected from the group consisting of
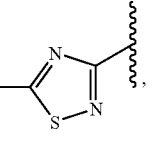
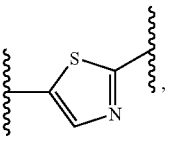 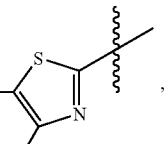
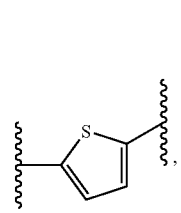 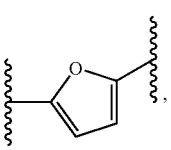

-continued

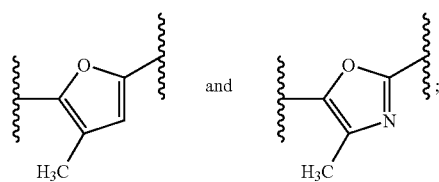

(ccc) $R_1$ and $R_2$ are both H, $R_7$ is $CF_3$, $R_5$ is H, $CH_3$, or —$CH_2CH_3$, and Q is selected from the group consisting of

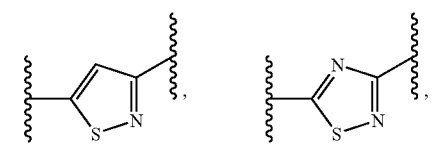

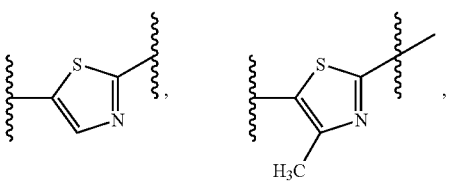

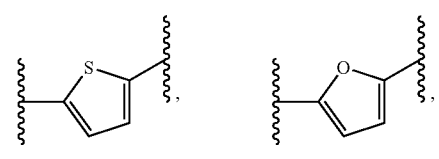

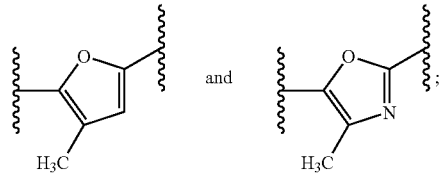

(ddd) $R_1$ or $R_2$ is $CH_3$, $R_7$ is $CF_3$, $R_5$ is H, $CH_3$, or —$CH_2CH_3$, and Q is selected from the group consisting of

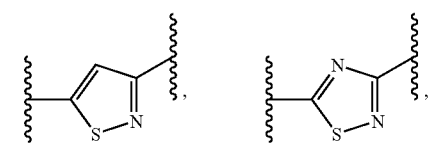

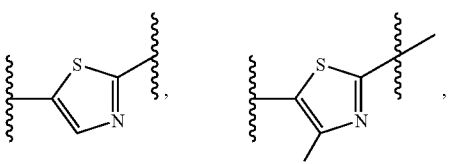

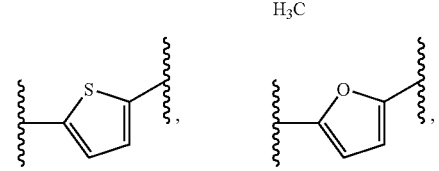

-continued

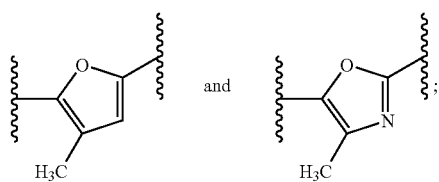

(eee) $R_1$ and $R_2$ are both $CH_3$, $R_7$ is $CF_3$, $R_5$ is H, $CH_3$, or —$CH_2CH_3$, and Q is selected from the group consisting of

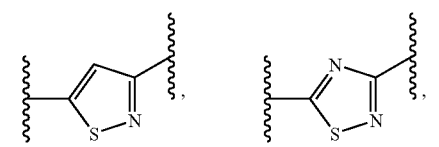

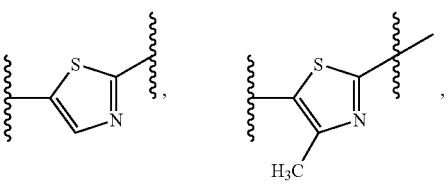

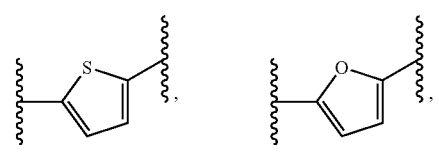

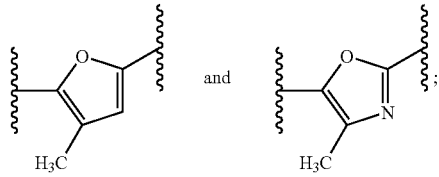

(fff) $R_1$ or $R_2$ is H, $R_4$ is H, $R_7$ is $CF_3$, $R_5$ is H, $CH_3$, or —$CH_2CH_3$, and Q is selected from the group consisting of

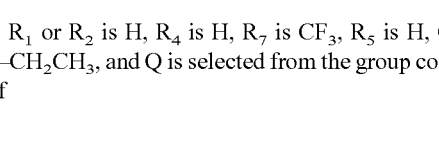

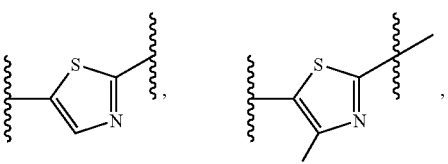

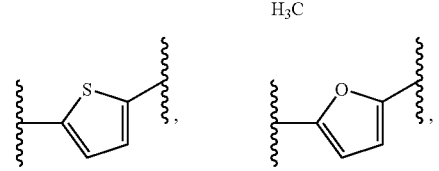

-continued

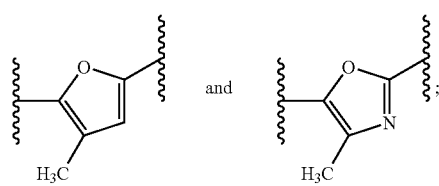

(ggg) $R_1$ and $R_2$ are both H, $R_4$ is H, $R_7$ is $CF_3$, $R_5$ is H, $CH_3$, or —$CH_2CH_3$, and Q is selected from the group consisting of

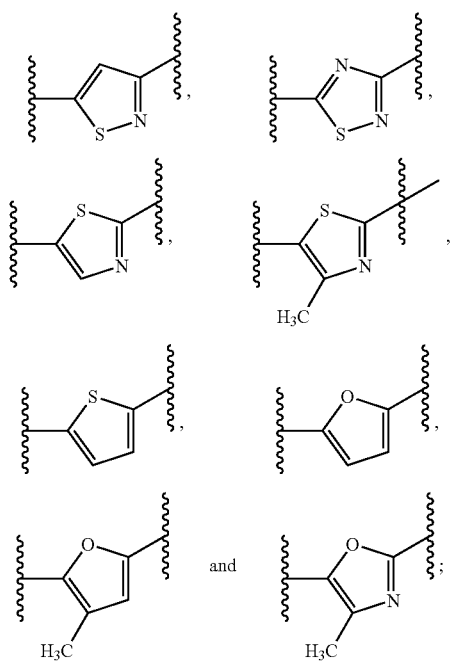

(hhh) $R_1$ or $R_2$ is $CH_3$, $R_4$ is H, $R_7$ is $CF_3$, $R_5$ is H, $CH_3$, or —$CH_2CH_3$, and Q is selected from the group consisting of

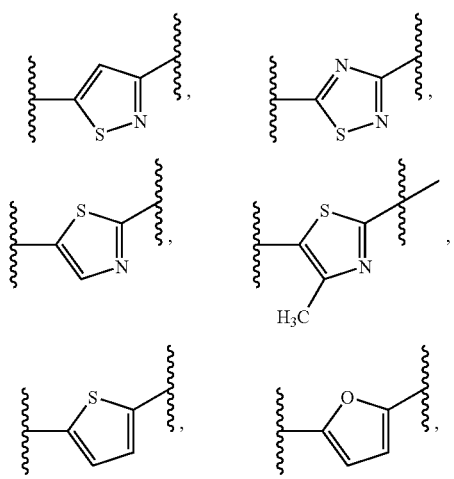

-continued

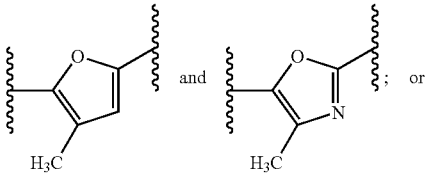

(iii) $R_1$ and $R_2$ are both $CH_3$, $R_4$ is H, $R_7$ is $CF_3$, $R_5$ is H, $CH_3$, or —$CH_2CH_3$, and Q is selected from the group consisting of

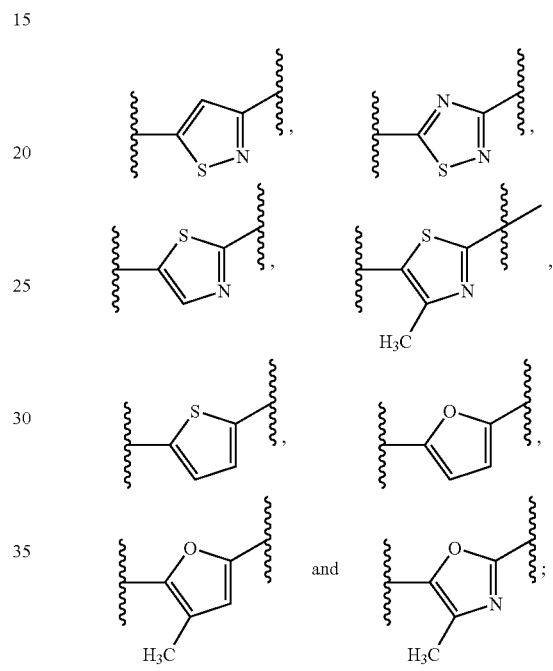

and enantiomers, diastereomers, tautomers, or pharmaceutically acceptable salts thereof.

17. A compound selected from the group consisting of

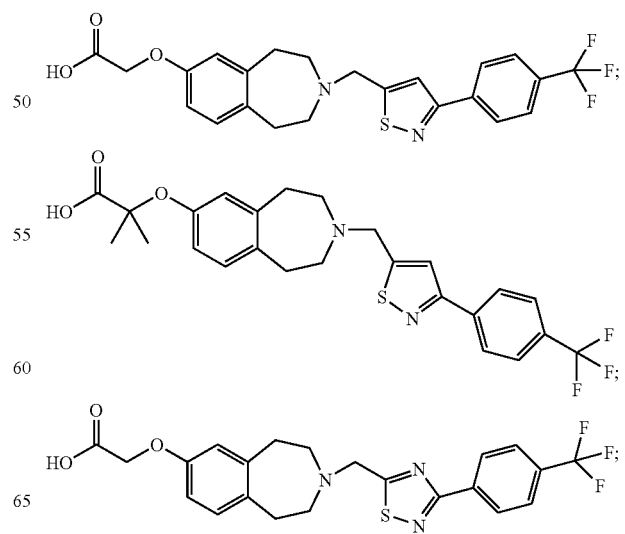

211
-continued
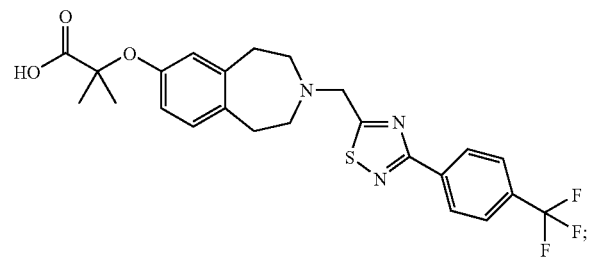
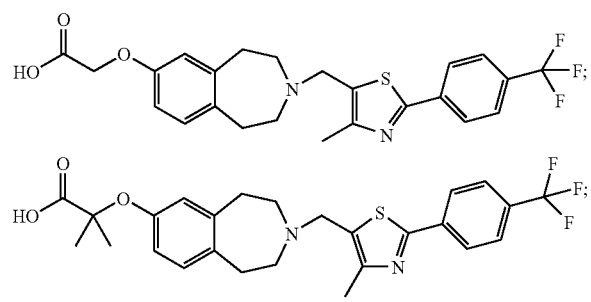
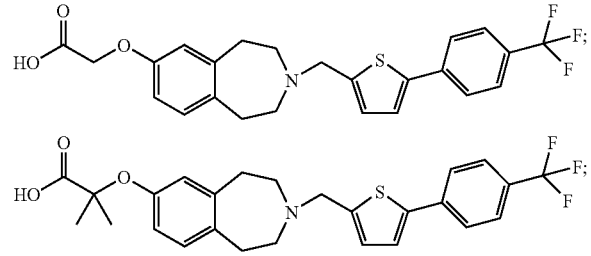
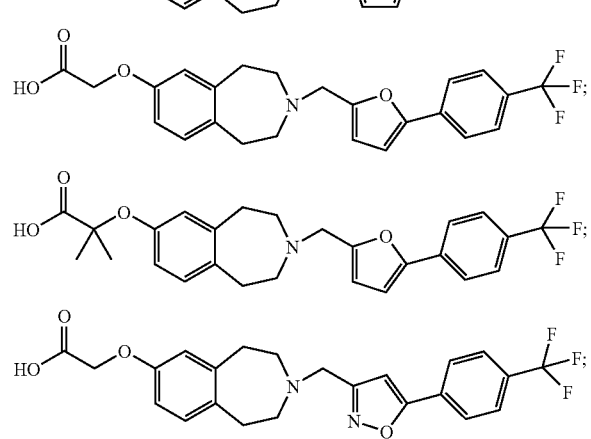
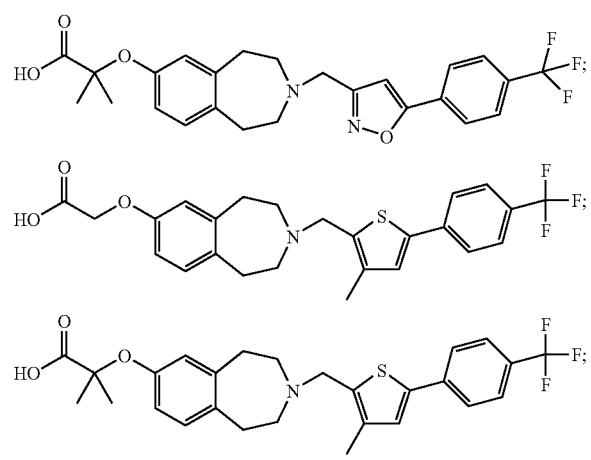
212
-continued
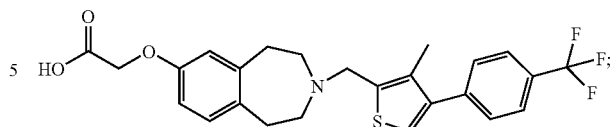
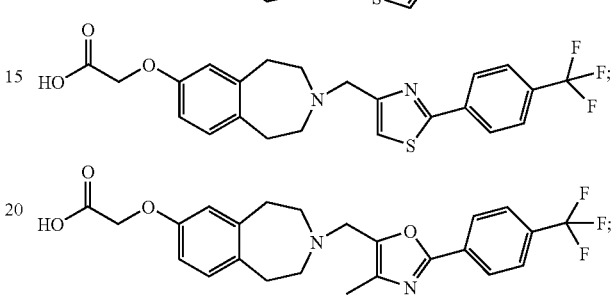
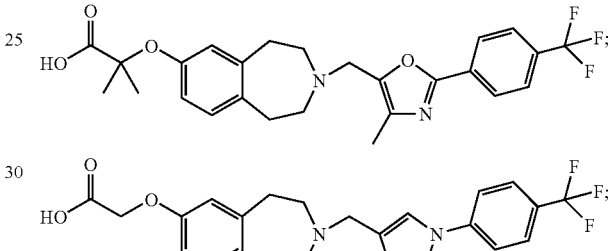
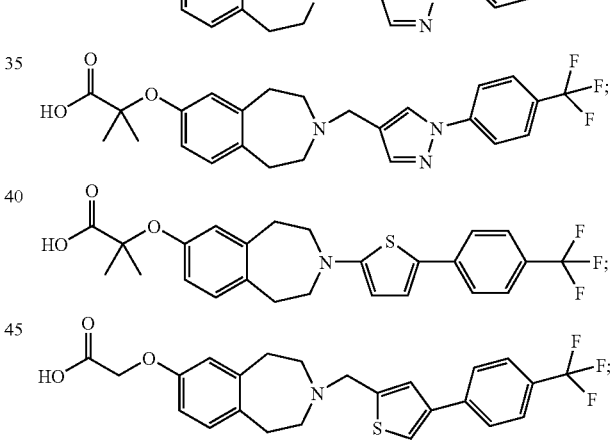
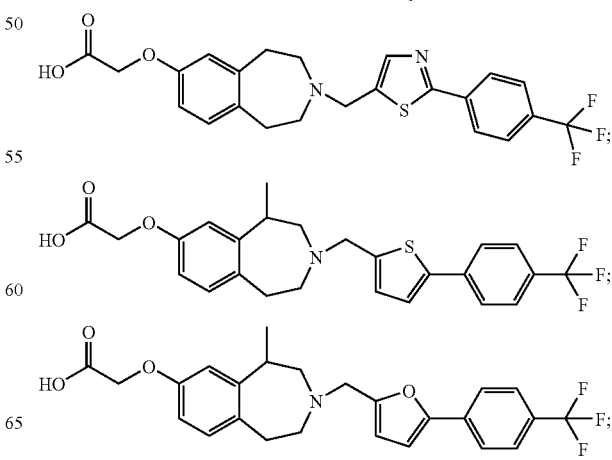

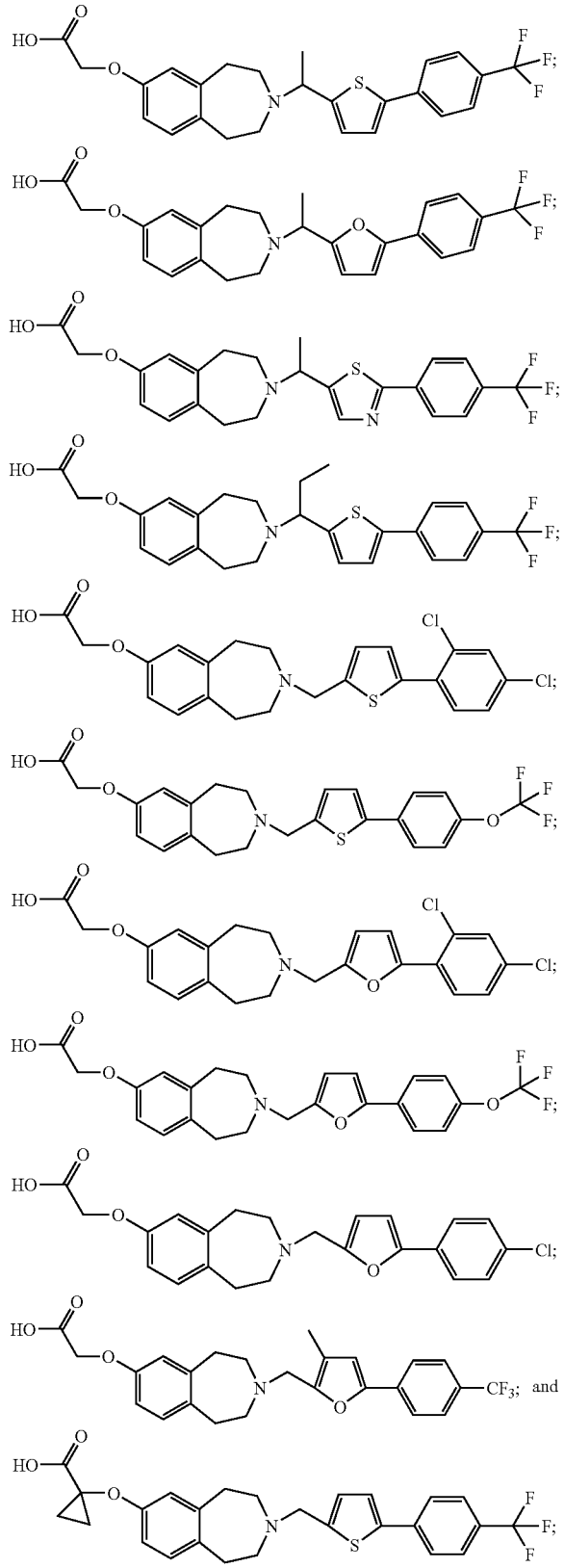

and enantiomers, diastereomers, tautomers, or pharmaceutically acceptable salts thereof.

18. A compound selected from the group consisting of

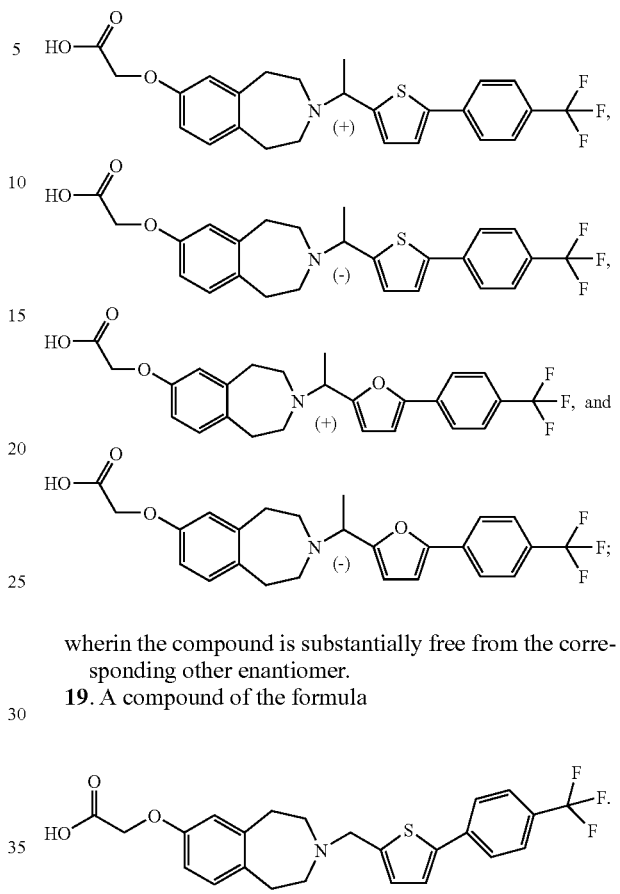

wherin the compound is substantially free from the corresponding other enantiomer.

19. A compound of the formula

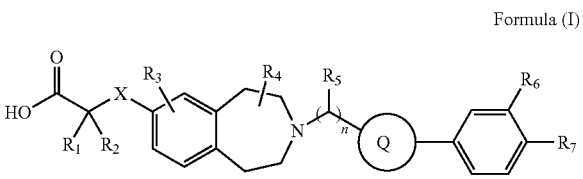

20. A pharmaceutical composition comprising a compound, or salt according to claim 1 admixed with a pharmaceutically acceptable carrier, excipient or diluent.

21. A compound of Formula (I)

Formula (I)

wherein:

X is a covalent bond, O, or S;

$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;

$R_3$ is H;

$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$ alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, heteroaryl substituted $C_{1-4}$alkyl, cyano substituted $C_{1-4}$alkyl, and hydroxy substituted $C_{1-4}$alkyl;

$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;

n is 1; and

Q is $C_{6-10}$aryl;

and enantiomers, diastereomers, tautomers, or pharmaceutically acceptable salts thereof.

22. A compound of Formula (I)

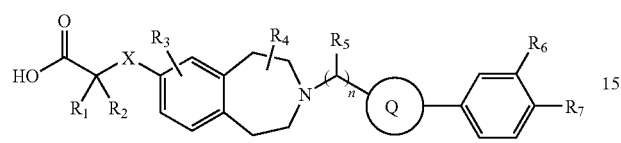

Formula (I)

wherein:

X is a covalent bond, O, or S;

$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;

$R_3$ is H;

$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy-$C_{1-4}$ alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, heteroaryl substituted $C_{1-4}$alkyl, cyano substituted $C_{1-4}$alkyl, and hydroxy substituted $C_{1-4}$alkyl;

$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;

n is 1 or 2; and

Q is selected from the group consisting of

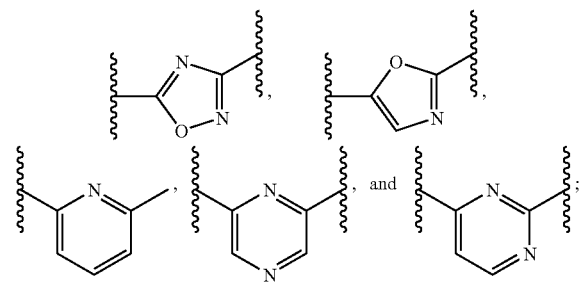

and enantiomers, diastereomers, tautomers, or pharmaceutically acceptable salts thereof.

23. A compound of Formula (I)

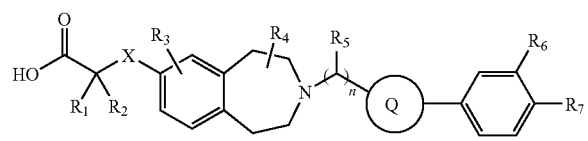

Formula (I)

wherein:

X is a covalent bond, O, or S;

$R_1$ and $R_2$ are independently selected from the group consisting of H, $C_{1-8}$alkyl, and substituted $C_{1-8}$alkyl, or $R_1$, $R_2$ and the carbon atom to which they are attached together may form $C_{3-7}$cycloalkyl;

$R_3$ is H;

$R_4$ and $R_5$ are independently selected from the group consisting of H, halo, $C_{1-8}$alkyl, $C_{3-7}$cycloalkyl, $C_{3-7}$cycloalkyl-$C_{1-4}$alkyl, $C_{3-7}$cycloalkyloxy-$C_{1-4}$alkyl, $C_{1-6}$alkoxy $C_{1-4}$ alkyl, $C_{6-10}$aryl, heteroaryl, halo substituted $C_{1-4}$alkyl, amino substituted $C_{1-4}$alkyl, $C_{6-10}$aryl substituted $C_{1-4}$alkyl, cyano substituted $C_{1-4}$alkyl, and hydroxy substituted $C_{1-4}$alkyl;

$R_6$ and $R_7$ are independently selected from the group consisting of H, halo, $C_{1-3}$alkyl, halo substituted $C_{1-3}$alkyl, $C_{1-3}$alkoxy, and halo substituted $C_{1-3}$alkoxy;

n is 2; and

Q is selected from the group consisting of

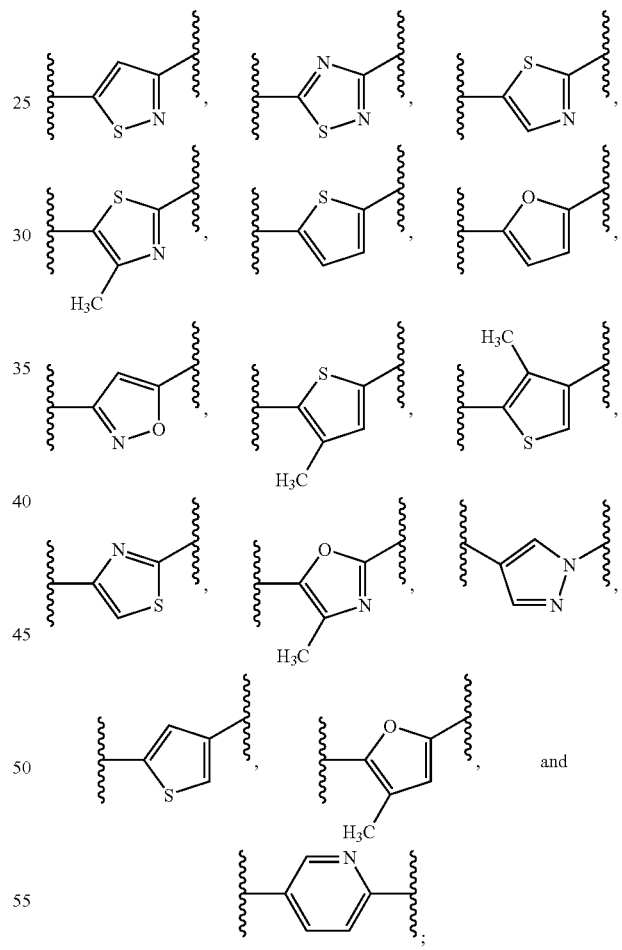

and enantiomers, diastereomers, tautomers, or pharmaceutically acceptable salts thereof.

24. A compound selected from the group consisting of

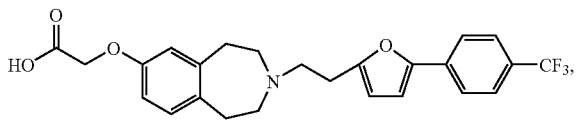

-continued
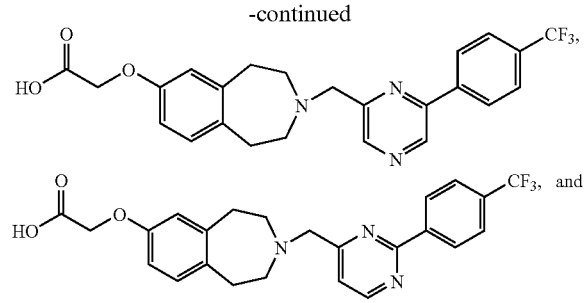
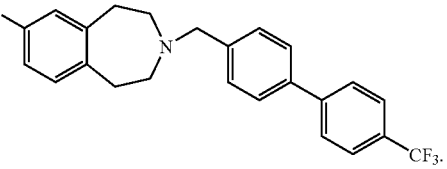
* * * * *